United States Patent
Benning et al.

(10) Patent No.: US 11,286,494 B2
(45) Date of Patent: Mar. 29, 2022

(54) ENHANCED LIPID BIOSYNTHESIS VIA ENGINEERED PLASTID LIPASES

(71) Applicant: Board of Trustees of Michigan State University, East Lansing, MI (US)

(72) Inventors: Christoph Benning, East Lansing, MI (US); Kun Wang, East Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 22 days.

(21) Appl. No.: 16/498,663

(22) PCT Filed: Mar. 29, 2018

(86) PCT No.: PCT/US2018/025234
§ 371 (c)(1),
(2) Date: Sep. 27, 2019

(87) PCT Pub. No.: WO2018/183734
PCT Pub. Date: Oct. 4, 2018

(65) Prior Publication Data
US 2020/0040351 A1    Feb. 6, 2020

Related U.S. Application Data

(60) Provisional application No. 62/479,599, filed on Mar. 31, 2017.

(51) Int. Cl.
*C12N 15/82* (2006.01)
*C12N 9/02* (2006.01)
*C12N 9/20* (2006.01)

(52) U.S. Cl.
CPC ....... *C12N 15/8247* (2013.01); *C12N 9/0071* (2013.01); *C12N 9/20* (2013.01); *C12Y 114/19* (2013.01); *C12Y 301/01032* (2013.01)

(58) Field of Classification Search
None
See application file for complete search history.

(56) References Cited

U.S. PATENT DOCUMENTS

| | | |
|---|---|---|
| 2013/0089916 A1 | 4/2013 | Franklin et al. |
| 2015/0089683 A1 | 3/2015 | Abad et al. |

FOREIGN PATENT DOCUMENTS

WO    WO-2018183734 A1    10/2018

OTHER PUBLICATIONS

Padham et al, Plant Physiol 143(3): 1372-1384, 2007 (Year: 2007).*
Sequence Accession D7LSD7_ARALL, Aug. 10, 2010 (Year: 2010), sequence alignment is attached to the office action.*
"International Application Serial No. PCT/US2018/025234, International Preliminary Report on Patentability dated Oct. 10, 2019", 8 pgs.
Brady, L., et al., "A serine protease triad forms the catalytic centre of a triacylglycerol lipase", *Nature* 343(6260), (1990), 767-770.
Browse, J., et al., "A Mutant of *Arabidopsis* Lacking a Chloroplast-Specific Lipid", *Science* 227(4688), (1985), 763-765.
Browse, J., et al., "Mutants of *Arabidopsis* Deficient in the Synthesis of α-Linolenate. Biochemical and genetic characterization of the endoplasmic reticulum linoleoyl desaturase", *J Biol Chem* 268(22), (1993), 16345-16351.
Kelly, A. A., et al., "Oil is on the agenda: Lipid turnover in higher plants", *Biochim Biophys Acta (BBA)—Molecular and Cell Biology of Lipids*, vol. 1861, Issue 9, Part B, (Sep. 2016), 1253-1268.
Li, N., "FAX1, a novel membrane protein mediating plastid fatty acid export", *PLoS Biol* 13, e1002053, (2015), 37 pgs.
Li, X., et al., "A Galactoglycerolipid Lipase Is Required for Triacylglycerol Accumulation and Survival Following Nitrogen Deprivation in *Chlamydomonas reinhardtii*", *The Plant Cell*, 24(11), (Nov. 2012), 4670-4686.
Richmond, G. S., et al., "Phospholipases $A_1$", *Int J Mol Sci* 12(1), (2011), 588-612.
Scherer, G. F., et al., "Patatin-related phospholipase A: nomenclature, subfamilies and functions in plants", *Trends Plant Sci* 15(12), (2010), 693-700.
Wang, G., et al., "Chapter 8—Plant phospholipases: an overview", *Methods Mol Biol*, vol. 861—*Lipases and Phospholipases: Methods and Protocols*, (2012), 123-137.
"Application Serial No. PCT/US2018/025234, Invitation to Pay Additional Fees, and, Where Applicable, Protest Fee", 2 pgs.
"International Application Serial No. PCT/US2018/025234, International Search Report dated Aug. 24, 2018", 5 pgs.
"International Application Serial No. PCT/US2018/025234, Written Opinion dated Aug. 24, 2018", 6 pgs.
"UniProtKB accession No. Q7Y220", [Online] Retrieved from the internet: <http//www.uniprot.org/uniprotJQ7y22o.txt>, (Oct. 1, 2003), 3 pgs.

* cited by examiner

*Primary Examiner* — Elizabeth F Mcelwain
(74) *Attorney, Agent, or Firm* — Schwegman Lundberg & Woessner, P.A.

(57) ABSTRACT

Described herein are transgenic plants with increased oil content that exhibit enhanced expression of plastid-specific lipases (e.g., PLIP1). The manufacture of lipids can be enhanced by expression of FAD4.

16 Claims, 26 Drawing Sheets
Specification includes a Sequence Listing.

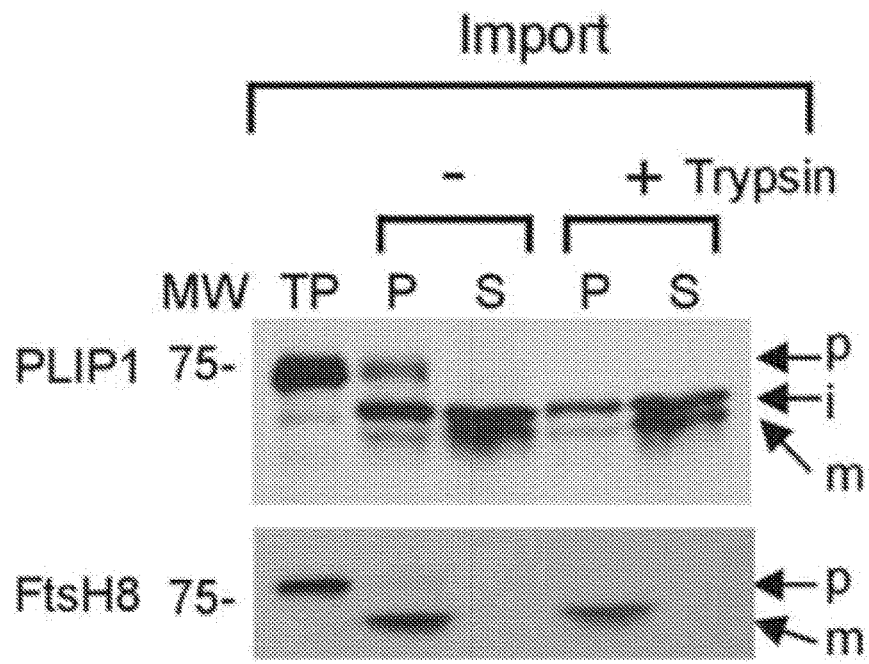
FIG. 1D
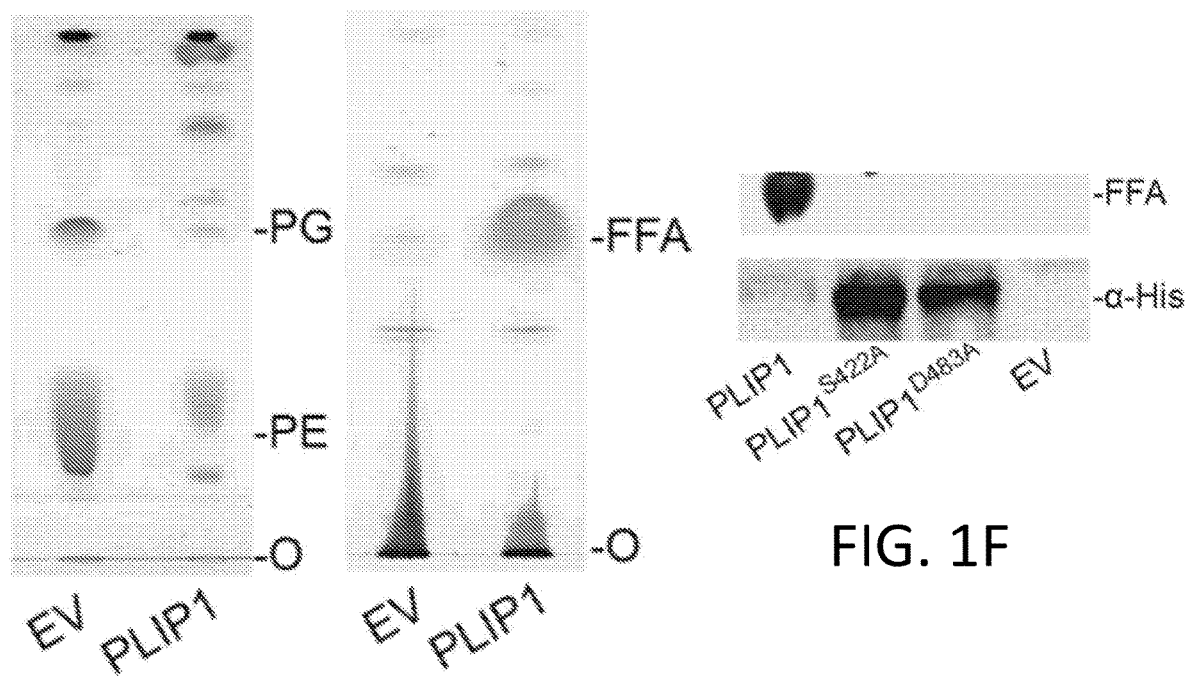
FIG. 1E
FIG. 1F

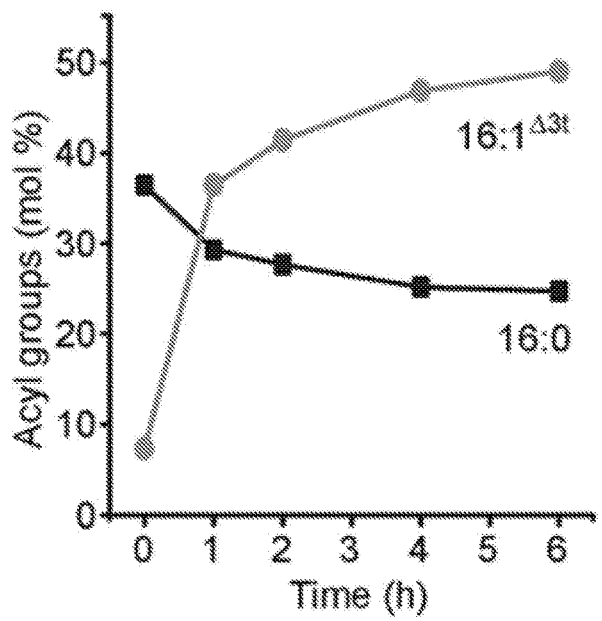
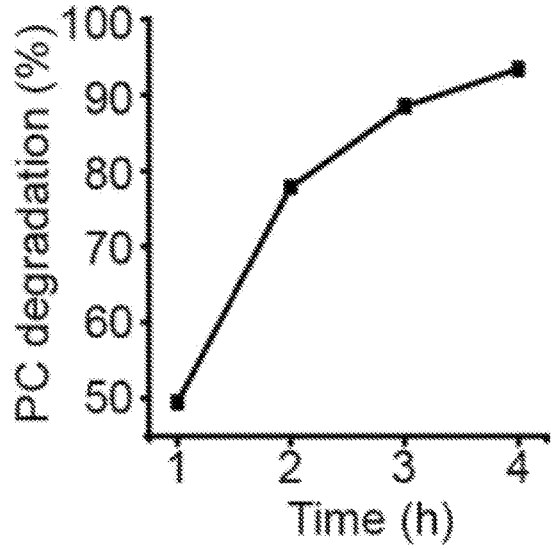
FIG. 2F
FIG. 2G
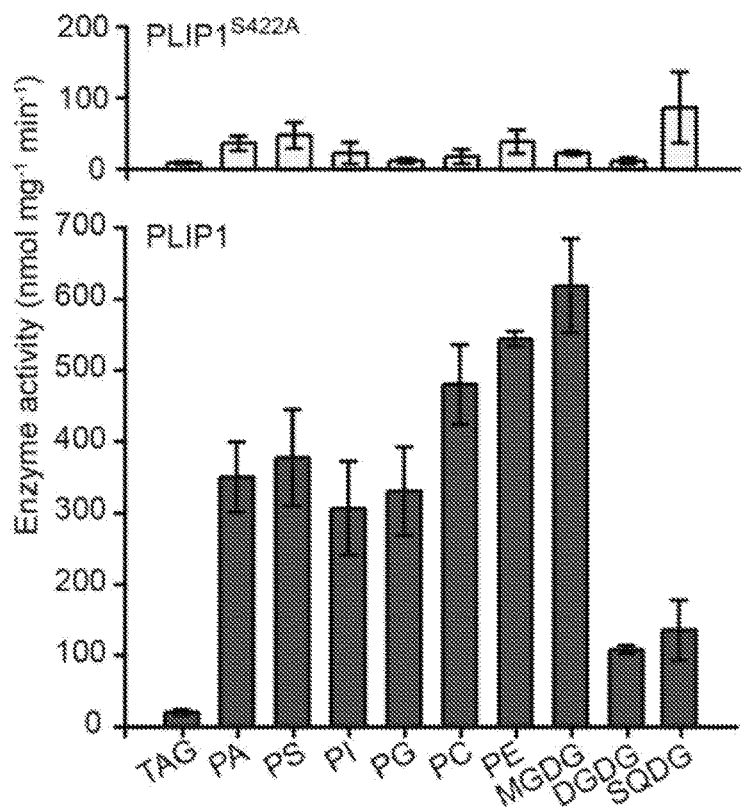
FIG. 2H

SEQUENCE LISTING

<160> NUMBER OF SEQ ID NOS: 71

<210> SEQ ID NO 1
<211> LENGTH: 649
<212> TYPE: PRT
<213> ORGANISM: Arabidopsis thaliana

<400> SEQUENCE: 1

```
Met Ala Phe Asn Thr Ala Met Ala Ser Thr Ser Pro Ala Ala Ala Asn
1               5                   10                  15

Asp Val Leu Arg Glu His Ile Gly Leu Arg Arg Ser Leu Ser Gly Gln
            20                  25                  30

Asp Leu Val Leu Lys Gly Gly Ile Arg Arg Ser Ser Ser Asp Asn
        35                  40                  45

His Leu Cys Cys Arg Ser Gly Asn Asn Asn Arg Ile Leu Ala Val
    50                  55                  60

Ser Val Arg Pro Gly Met Lys Thr Ser Arg Ser Val Gly Val Phe Ser
65                  70                  75                  80

Phe Gln Ile Ser Ser Ser Ile Ile Pro Ser Pro Ile Lys Thr Leu Leu
                85                  90                  95

Phe Glu Thr Asp Thr Ser Gln Asp Glu Gln Glu Ser Asp Glu Ile Glu
            100                 105                 110
```

```
Ile Glu Thr Glu Pro Asn Leu Asp Gly Ala Lys Lys Ala Asn Trp Val
            115                 120                 125

Glu Arg Leu Leu Glu Ile Arg Arg Gln Trp Lys Arg Glu Gln Lys Thr
130                 135                 140

Glu Ser Gly Asn Ser Asp Val Ala Glu Ser Val Asp Val Thr Cys
145                 150                 155                 160

Gly Cys Glu Glu Glu Gly Cys Ile Ala Asn Tyr Gly Ser Val Asn
                165                 170                 175

Gly Asp Trp Gly Arg Glu Ser Phe Ser Arg Leu Leu Val Lys Val Ser
            180                 185                 190

Trp Ser Glu Ala Lys Lys Leu Ser Gln Leu Ala Tyr Leu Cys Asn Leu
        195                 200                 205

Ala Tyr Thr Ile Pro Glu Ile Lys Gly Glu Asp Leu Arg Arg Asn Tyr
        210                 215                 220

Gly Leu Lys Phe Val Thr Ser Ser Leu Glu Lys Lys Ala Lys Ala Ala
225                 230                 235                 240

Ile Leu Arg Glu Lys Leu Glu Gln Asp Pro Thr His Val Pro Val Ile
                245                 250                 255

Thr Ser Pro Asp Leu Glu Ser Glu Lys Gln Ser Gln Arg Ser Ala Ser
            260                 265                 270

Ser Ser Ala Ser Ala Tyr Lys Ile Ala Ala Ser Ala Ala Ser Tyr Ile
        275                 280                 285

His Ser Cys Lys Glu Tyr Asp Leu Ser Glu Pro Ile Tyr Lys Ser Ala
        290                 295                 300

Ala Ala Ala Gln Ala Ala Ala Ser Thr Met Thr Ala Val Val Ala Ala
305                 310                 315                 320

Gly Glu Glu Glu Lys Leu Glu Ala Ala Arg Glu Leu Gln Ser Leu Gln
                325                 330                 335

Ser Ser Pro Cys Glu Trp Phe Val Cys Asp Asp Pro Asn Thr Tyr Thr
            340                 345                 350

Arg Cys Phe Val Ile Gln Gly Ser Asp Ser Leu Ala Ser Trp Lys Ala
        355                 360                 365

Asn Leu Phe Phe Glu Pro Thr Lys Phe Glu Asp Thr Asp Val Leu Val
        370                 375                 380

His Arg Gly Ile Tyr Glu Ala Ala Lys Gly Ile Tyr Glu Gln Phe Leu
385                 390                 395                 400

Pro Glu Ile Thr Glu His Leu Ser Arg His Gly Asp Arg Ala Lys Phe
                405                 410                 415

Gln Phe Thr Gly His Ser Leu Gly Gly Ser Leu Ser Leu Ile Val Asn
            420                 425                 430

Leu Met Leu Ile Ser Arg Gly Leu Val Ser Ser Glu Ala Met Lys Ser
        435                 440                 445

Val Val Thr Phe Gly Ser Pro Phe Val Phe Cys Gly Gly Glu Lys Ile
450                 455                 460

Leu Ala Glu Leu Gly Leu Asp Glu Ser His Val His Cys Val Met Met
465                 470                 475                 480

His Arg Asp Ile Val Pro Arg Ala Phe Ser Cys Asn Tyr Pro Asp His
                485                 490                 495

Val Ala Leu Val Leu Lys Arg Leu Asn Gly Ser Phe Arg Thr His Pro
            500                 505                 510

Cys Leu Asn Lys Asn Lys Leu Leu Tyr Ser Pro Met Gly Lys Val Tyr
        515                 520                 525

Ile Leu Gln Pro Ser Glu Ser Val Ser Pro Thr His Pro Trp Leu Pro
```

```
                530              535              540
Pro Gly Asn Ala Leu Tyr Ile Leu Glu Asn Ser Asn Glu Gly Tyr Ser
545                      550                  555                  560

Pro Thr Ala Leu Arg Ala Phe Leu Asn Arg Pro His Pro Leu Glu Thr
                565                  570                  575

Leu Ser Gln Arg Ala Ala Tyr Gly Ser Glu Gly Ser Val Leu Arg Asp
                580                  585                  590

His Asp Ser Lys Asn Tyr Val Lys Ala Val Asn Gly Val Leu Arg Gln
                595                  600                  605

His Thr Lys Leu Ile Val Arg Lys Ala Arg Ile Gln Arg Arg Ser Val
                610                  615                  620

Trp Pro Val Leu Thr Ser Ala Gly Arg Gly Leu Asn Glu Ser Leu Thr
625                      630                  635                  640

Thr Ala Glu Glu Ile Met Thr Arg Val
                645

<210> SEQ ID NO 2
<211> LENGTH: 2374
<212> TYPE: DNA
<213> ORGANISM: Arabidopsis thaliana

<400> SEQUENCE: 2
```

| | | | | | |
|---|---|---|---|---|---|
| cgtatatatt | aatctggctc | catctacatc | tgtgaaagag | agagagagat | tcatgaatct | 60 |
| ttttacagaa | acacgaacaa | gtttcagaat | ctggtctgac | tctttgtaac | cttctcgttt | 120 |
| aagattcatt | gtacgtattc | aaatctacat | ttctttgcca | ttgttggaat | ctccgcctcg | 180 |
| atcgtttctt | atcaaaggat | ctggtattcg | attttttgcta | tcgtttcaaa | gcatggtcta | 240 |
| atgatgatcc | tgatctccga | ctgatccaat | aacggttaag | caacgctgtt | tttgatcctc | 300 |
| cattgttgtt | tgccatcgat | caacactcag | aaataagttg | gagttttgtt | cataaagaat | 360 |
| ggcgtttaat | acggctatgg | cgtctacatc | tccagcggcg | gcaaatgacg | ttttaagaga | 420 |
| acatattggc | ctccgtagat | cgttgtccgg | tcaagatctc | gtcttaaaag | gcggtggtat | 480 |
| acggagatcg | agttccgaca | atcacttgtg | ttgtcgctcc | ggtaataata | ataatcgcat | 540 |
| tcttgctgtg | tctgttcgtc | cggggatgaa | acgagtcga | tctgtgggag | tgttctcgtt | 600 |
| tcagatatcg | agttctataa | tcccaagtcc | gataaaaacg | ttgctatttg | aaacggacac | 660 |
| gtctcaagac | gagcaagaga | gcgatgagat | tgagattgag | acagagccaa | atctagatgg | 720 |
| agccaagaag | gcaaattggg | tcgagaggct | gcttgagata | aggagacagt | ggaagagaga | 780 |
| gcaaaaaaca | gagagtggaa | acagtgacgt | tgcagaggaa | agtgttgacg | ttacgtgtgg | 840 |
| ttgtgaagaa | gaagaaggtt | gcattgcgaa | ttacggatct | gtaaatggtg | attggggacg | 900 |
| agaatcgttc | tctagattgc | ttgtgaaggt | tccttggtct | gaggctaaaa | agctttctca | 960 |
| gttagcttat | ttgtgtaact | tggcttacac | gataccgag | atcaagggtg | aggatttgag | 1020 |
| aagaaactat | gggttaaagt | ttgtgacatc | ttcattggaa | agaaagcta | aagcagcgat | 1080 |
| acttagagag | aaactagagc | aagatccaac | acatgtccct | gttattacat | ccccggattt | 1140 |
| agaatccgag | aagcagtctc | aacgatcagc | ttcatcttct | gcttctgctt | acaagattgc | 1200 |
| tgcttcagct | gcgtcttaca | ttcactcttg | caaagagtat | gatctttcag | aaccaattta | 1260 |
| taaatcagct | gctgctgctc | aggctgcagc | gtctaccatg | accgcggtgg | ttgctgcggg | 1320 |
| tgaggaggag | aagctagaag | cggcaaggga | gttacagtcg | ctacaatcat | ctccttgtga | 1380 |
| gtggtttgtt | tgtgatgatc | caaacacata | cactaggtgc | tttgtgattc | agggatctga | 1440 |

```
ttctttagct tcttggaaag caaacctttt cttcgagcca actaagtttg aggacacaga    1500
tgtattagtc cacagaggaa tctacgaggc agcaaaagga atatacgaac agttcttacc    1560
agaaataaca gagcatttgt ctagacatgg agatagagct aagtttcagt tcacgggtca    1620
ttctcttgga ggcagtctct cattaatagt gaatttgatg cttatctcta gaggactcgt    1680
tagctctgaa gctatgaaat ccgttgtcac gttcggttca ccgtttgtgt tttgtggtgg    1740
tgagaagatt ctagcggagc ttggtcttga cgagagtcat gttcactgtg tgatgatgca    1800
tagagatatc gtcccacgag cctttcgtg taattatcct gaccatgttg ctctcgttct    1860
caagcgtttg aatggctcct tccgtacaca tccttgtctc aacaaaaata aactgttgta    1920
ttcaccgatg gggaaagtat atattctaca gccgagtgag agcgtctcgc cgacgcaccc    1980
atggcttcca ccgggaaacg ctctgtacat tttagaaaat agcaacgaag gttactctcc    2040
tacggcgtta cgagcatttt taaaccgccc tcacccgctc gaaacgctga gtcaacgcgc    2100
agcttatggc tcggaaggtt cagtcttgag ggaccacgac tccaagaact acgttaaggc    2160
cgtgaacgga gttctcaggc agcacacgaa gctcatagtt aggaaagcca ggatacaaag    2220
gaggagtgtt tggcccgtgc tgacatcagc aggacgtgga ttaaacgaga gcctgacgac    2280
ggccgaggag atcatgacac gtgtctaatg aaggaaaatg tacggttgta tataagtgga    2340
atcacttctg attatgcgtt tatttacatt tctt                                 2374
```

<210> SEQ ID NO 3
<211> LENGTH: 658
<212> TYPE: PRT
<213> ORGANISM: Arabidopsis thaliana
<400> SEQUENCE: 3

```
Met Ala Phe Asn Thr Ala Met Ala Ser Thr Ser Pro Ala Ala Ala Asn
1               5                   10                  15

Asp Val Leu Arg Glu His Ile Gly Leu Arg Arg Ser Leu Ser Gly Gln
            20                  25                  30

Asp Leu Val Leu Lys Gly Gly Gly Ile Arg Arg Ser Ser Ser Asp Asn
        35                  40                  45

His Leu Cys Cys Arg Ser Gly Asn Asn Asn Arg Ile Leu Ala Val
    50                  55                  60

Ser Val Arg Pro Gly Met Lys Thr Ser Arg Ser Val Gly Val Phe Ser
65                  70                  75                  80

Phe Gln Ile Ser Ser Ile Ile Pro Ser Pro Ile Lys Thr Leu Leu
                85                  90                  95

Phe Glu Thr Asp Thr Ser Gln Asp Glu Gln Ser Asp Glu Ile Glu
            100                 105                 110

Ile Glu Thr Glu Pro Asn Leu Asp Gly Ala Lys Lys Ala Asn Trp Val
        115                 120                 125

Glu Arg Leu Leu Glu Ile Arg Arg Gln Trp Lys Arg Glu Gln Lys Thr
    130                 135                 140

Glu Ser Gly Asn Ser Asp Val Ala Glu Ser Val Asp Val Thr Cys
145                 150                 155                 160

Gly Cys Glu Glu Glu Gly Cys Ile Ala Asn Tyr Gly Ser Val Asn
                165                 170                 175

Gly Asp Trp Gly Arg Glu Ser Phe Ser Arg Leu Leu Val Lys Val Ser
            180                 185                 190

Trp Ser Glu Ala Lys Lys Leu Ser Gln Leu Ala Tyr Leu Cys Asn Leu
        195                 200                 205
```

-continued

Ala Tyr Thr Ile Pro Glu Ile Lys Gly Glu Asp Leu Arg Arg Asn Tyr
210                 215                 220

Gly Leu Lys Phe Val Thr Ser Ser Leu Glu Lys Lys Ala Lys Ala Ala
225                 230                 235                 240

Ile Leu Arg Glu Lys Leu Glu Gln Asp Pro Thr His Val Pro Val Ile
            245                 250                 255

Thr Ser Pro Asp Leu Glu Ser Glu Lys Gln Ser Gln Arg Ser Ala Ser
        260                 265                 270

Ser Ser Ala Ser Ala Tyr Lys Ile Ala Ala Ser Ala Ala Ser Tyr Ile
        275                 280                 285

His Ser Cys Lys Glu Tyr Asp Leu Ser Glu Pro Ile Tyr Lys Ser Ala
    290                 295                 300

Ala Ala Ala Gln Ala Ala Ala Ser Thr Met Thr Ala Val Val Ala Ala
305                 310                 315                 320

Gly Glu Glu Glu Lys Leu Glu Ala Ala Arg Glu Leu Gln Ser Leu Gln
                325                 330                 335

Ser Ser Pro Cys Glu Trp Phe Val Cys Asp Asp Pro Asn Thr Tyr Thr
            340                 345                 350

Arg Cys Phe Val Ile Gln Gly Ser Asp Ser Leu Ala Ser Trp Lys Ala
        355                 360                 365

Asn Leu Phe Phe Glu Pro Thr Lys Phe Glu Val Lys Ile Leu Ile Leu
    370                 375                 380

Ala Arg Asp Asp Thr Asp Val Leu Val His Arg Gly Ile Tyr Glu Ala
385                 390                 395                 400

Ala Lys Gly Ile Tyr Glu Gln Phe Leu Pro Glu Ile Thr Glu His Leu
                405                 410                 415

Ser Arg His Gly Asp Arg Ala Lys Phe Gln Phe Thr Gly His Ser Leu
            420                 425                 430

Gly Gly Ser Leu Ser Leu Ile Val Asn Leu Met Leu Ile Ser Arg Gly
        435                 440                 445

Leu Val Ser Ser Glu Ala Met Lys Ser Val Val Thr Phe Gly Ser Pro
    450                 455                 460

Phe Val Phe Cys Gly Gly Glu Lys Ile Leu Ala Glu Leu Gly Leu Asp
465                 470                 475                 480

Glu Ser His Val His Cys Val Met Met His Arg Asp Ile Val Pro Arg
                485                 490                 495

Ala Phe Ser Cys Asn Tyr Pro Asp His Val Ala Leu Val Leu Lys Arg
            500                 505                 510

Leu Asn Gly Ser Phe Arg Thr His Pro Cys Leu Asn Lys Asn Lys Leu
        515                 520                 525

Leu Tyr Ser Pro Met Gly Lys Val Tyr Ile Leu Gln Pro Ser Glu Ser
    530                 535                 540

Val Ser Pro Thr His Pro Trp Leu Pro Pro Gly Asn Ala Leu Tyr Ile
545                 550                 555                 560

Leu Glu Asn Ser Asn Glu Gly Tyr Ser Pro Thr Ala Leu Arg Ala Phe
                565                 570                 575

Leu Asn Arg Pro His Pro Leu Glu Thr Leu Ser Gln Arg Ala Ala Tyr
            580                 585                 590

Gly Ser Glu Gly Ser Val Leu Arg Asp His Asp Ser Lys Asn Tyr Val
        595                 600                 605

Lys Ala Val Asn Gly Val Leu Arg Gln His Thr Lys Leu Ile Val Arg
    610                 615                 620

Lys Ala Arg Ile Gln Arg Arg Ser Val Trp Pro Val Leu Thr Ser Ala

```
                625                 630                 635                 640
Gly Arg Gly Leu Asn Glu Ser Leu Thr Thr Ala Glu Glu Ile Met Thr
                    645                 650                 655
Arg Val

<210> SEQ ID NO 4

<400> SEQUENCE: 4

000

<210> SEQ ID NO 5
<211> LENGTH: 677
<212> TYPE: PRT
<213> ORGANISM: Zea mays

<400> SEQUENCE: 5

Met Val Ala Thr Val Ala Ala Gly Ala Ala Ala Ala Ser
1               5                   10                  15

Gly Arg Arg Gly Ala Arg Arg Glu Pro Ala Thr Met His Ala Gly
                20                  25                  30

Ile Arg Arg Ser Arg Ser Glu Pro His Leu Arg Cys Pro Arg Arg Gly
                35                  40                  45

Gly Ala Ala Gly Ala Ala Leu Thr Thr Ser Arg Ser Ile Gly Val Phe
    50                  55                  60

Pro Phe Gln Phe Gly Ala Ala Pro Leu Arg Pro Pro Leu Pro Asp
65                  70                  75                  80

Gly Gly Gly Asp Gly Ser Arg Leu Leu Thr Val Ala Asp Asp Ala Asp
                85                  90                  95

Pro Pro Glu Pro Cys Pro Glu Met Pro Pro Ala Arg Arg Pro Glu Ala
                100                 105                 110

His Trp Leu Asp Arg Leu Leu Glu Val Arg Ser Arg Phe His Asp Pro
            115                 120                 125

Thr Trp Arg Asp Val Leu Asp His Asp Asp Asp Asp Asp Glu Asp
    130                 135                 140

Leu Tyr Arg Leu Asp Ala Asp His His His Asp Gly Gly Cys Gly Val
145                 150                 155                 160

Ser Tyr Glu Asp Asp Gly Glu Glu Asp Ala Arg Trp Asp Arg Asp
                165                 170                 175

Ser Phe Ala Lys Leu Leu Ala Arg Ala Pro Leu Gly Glu Ala Arg Leu
                180                 185                 190

Phe Ala Gln Leu Ala Phe Leu Cys Asn Met Ala Tyr Val Ile Pro Glu
            195                 200                 205

Ile Lys Val Glu Glu Leu Lys Arg His Tyr Gly Leu Arg Phe Val Thr
    210                 215                 220

Ser Ser Leu Glu Lys Lys Ala Glu Ala Gly Ile Ile Ser Ala Lys Leu
225                 230                 235                 240

Asp Ala Asp Ser Thr Arg Pro Arg Thr Ala Pro Ala Tyr Glu Val Ala
                245                 250                 255

Ser Gly Pro Gln Pro Arg Arg Pro Ile Arg Ser Ser His Leu Ala Tyr
                260                 265                 270

Glu Val Ala Ala Ser Ala Ala Ser Tyr Val His Ala Arg Ala Arg Gly
            275                 280                 285

Leu Leu Ser Phe Gly Ala Pro Thr Arg Gln Gln Gln Ala Ala Gly
    290                 295                 300
```

```
Gln Gly Arg Leu Tyr Asn Ser Gly Val Ala Ala Tyr Met Ala Ala Ser
305                 310                 315                 320

Thr Val Thr Ala Val Ala Ala Glu Asp Glu Ala Arg Gln Glu Ala
            325                 330                 335

Ala Arg Asp Leu Arg Ser Pro Leu Ser Ser Pro Cys Glu Trp Phe Val
                340                 345                 350

Cys Asp Glu Ala Asp Ala Arg Thr Arg Cys Leu Val Ile Gln Gly Ser
                355                 360                 365

Asp Ser Leu Ala Ser Trp Gln Ala Asn Leu Leu Phe Glu Pro Thr Glu
    370                 375                 380

Phe Glu Gly Thr Gly Val Leu Val His Arg Gly Ile Tyr Glu Ala Ala
385                 390                 395                 400

Lys Gly Ile Tyr Glu Gln Val Met Pro Glu Ile Glu Ala His Leu Arg
                405                 410                 415

Ala His Ala Gly Arg Ala Pro Pro Arg Leu Arg Leu Thr Gly His Ser
                420                 425                 430

Leu Gly Gly Ser Leu Ala Val Leu Val Ser Leu Met Leu Leu Ala Arg
            435                 440                 445

Gly Val Val Thr Pro Asp Ala Leu His Pro Val Thr Phe Gly Ala
450                 455                 460

Pro Ser Val Phe Cys Gly Gly Asn Arg Val Leu Glu Ala Leu Gly Val
465                 470                 475                 480

Gly Glu Ala His Val Arg Ser Val Ala Met His Arg Asp Ile Val Pro
                485                 490                 495

Arg Ala Phe Ser Cys Arg Tyr Pro Gly His Ala Ile Ala Leu Leu Lys
                500                 505                 510

Arg Leu Asn Gly Val Leu Arg Thr His Pro Cys Leu Asn Thr His Lys
            515                 520                 525

Ala Leu Tyr Thr Pro Met Gly Ser Thr Tyr Ile Leu Gln Pro Asp Ser
530                 535                 540

Ser Val Ser Pro Arg His Pro Phe Leu Pro Glu Gly Ala Ala Leu Phe
545                 550                 555                 560

Arg Leu Asp Ser Asp Ala Gly Leu Arg Gly Gly Ala Glu Arg Pro
                565                 570                 575

Pro Arg Ala Leu Val Ala Ser Ala Leu Arg Ala Phe Leu Asn Ser Pro
            580                 585                 590

His Pro Leu Glu Thr Leu Ser Asp Leu Ser Ala Tyr Gly Ala Gly Gly
                595                 600                 605

Ala Ile Leu Arg Asp His Glu Ser Ser Asn Tyr Phe Arg Ala Leu Ser
610                 615                 620

Ala Leu Ala Arg Ala Pro Pro Arg Arg Arg Lys Gln Pro Glu Val Val
625                 630                 635                 640

Trp Gln Leu Pro Gly Val Glu Arg Leu Gln Gln Tyr Trp Trp Pro Gly
                645                 650                 655

Ile Ala Ser Thr Val Ile Pro Ala Pro Leu Ala Val Ser Lys Lys Glu
            660                 665                 670

Leu Val Ser Glu Ala
        675

<210> SEQ ID NO 6
<211> LENGTH: 690
<212> TYPE: PRT
<213> ORGANISM: Zea mays

<400> SEQUENCE: 6
```

```
Met Asp Val Leu Arg Phe Val Pro Gly Val Arg Pro Leu Pro Thr
1               5                   10                  15

Phe Ala Thr Pro Val Ser Pro Ala Thr Ala Pro Ser Pro His Ala Ala
            20                  25                  30

Ala Ala Ala Ala Ala Pro Gly Pro Gly Phe His Ser Gly Met Leu Gly
        35                  40                  45

Leu Trp Pro Arg Arg Ala Gly Glu Asn Ala Leu Gly Ala Ala Ala Glu
    50                  55                  60

Ala Ala Gly Val Glu Glu Ala Arg Glu Arg Arg Arg Arg Ala Val
65                  70                  75                  80

Glu Ala Glu Asp Gly Arg Gly Gly Asn Trp Val Leu Gln Ile Leu Arg
                85                  90                  95

Val Gln Ser Ser Pro Pro Ser Pro Ser Arg Asp Asp Gly Arg Cys
            100                 105                 110

Gly Val Asp Asp Gly Gly Ser Val Pro Gly Ser Gly Glu Gly Asp Gly
        115                 120                 125

Ser Ser Gln Arg Cys Val Glu Arg Gly Val Gly Pro Asp Ser Glu
    130                 135                 140

Glu Gly Cys Ser Val Ala Asp Gly Glu Glu Leu Asp Arg Ala Ala Phe
145                 150                 155                 160

Ser Arg Leu Leu Arg Lys Val Ser Leu Ala Glu Ala Lys Leu Phe Ser
            165                 170                 175

Glu Met Ser Gly Leu Cys Asn Leu Ala Tyr Met Val Pro Arg Ile Lys
            180                 185                 190

Pro Arg Tyr Leu His Lys Tyr Asn Met Thr Phe Val Thr Ser Ser Val
        195                 200                 205

Glu Glu Arg Ala Lys Leu Pro Asn Pro Cys Asn Gln Glu Asp Gln Asn
210                 215                 220

Leu Asn Gly Arg Lys Asn Ala Asn Ile Ser Thr Ser Ser Arg His Ser
225                 230                 235                 240

Asp Glu Gln Glu Ser Thr Tyr Gly Ala Thr Ser Glu His Glu Arg Met
            245                 250                 255

Gln Glu Asn Gln Ser Gly Gln Gly Ile Asn Pro Leu Ala Ala Tyr Arg
            260                 265                 270

Ile Ala Ala Ser Ala Ala Ser Tyr Met Gln Ser Arg Ala Met Glu Val
        275                 280                 285

Leu Pro Phe Gly Ser Gln Asn Glu Ala Arg Arg Asp Arg Thr Ile Gln
    290                 295                 300

Ala Ile Val Asn Ala Gln Thr Glu Gly Leu Thr Met Asp Glu Ala Ser
305                 310                 315                 320

Phe Val Ala Thr Thr Asn Ser Met Thr Ser Met Val Ala Ala Lys Glu
            325                 330                 335

Glu Thr Lys Gln Ala Val Ala Asp Asp Leu Asn Ser Ser Arg Ser Cys
            340                 345                 350

Pro Cys Glu Trp Phe Ile Cys Asp Gly Asn Arg Asn Ser Thr Arg Tyr
        355                 360                 365

Phe Val Ile Gln Gly Ser Glu Thr Ile Ala Ser Trp Gln Ala Asn Leu
    370                 375                 380

Leu Phe Glu Pro Ile Lys Phe Glu Gly Leu Asp Val Leu Val His Arg
385                 390                 395                 400

Gly Ile Tyr Glu Ala Ala Lys Gly Ile Tyr Gln Gln Met Leu Pro Tyr
                405                 410                 415
```

```
Val Lys Ser His Phe Ile Val His Gly Glu Ser Ala Arg Leu Arg Phe
            420                 425                 430

Thr Gly His Ser Leu Gly Gly Ser Leu Ala Leu Leu Val Asn Leu Met
                435                 440                 445

Phe Leu Ile Arg Gly Val Ala Pro Ala Ala Ser Leu Leu Pro Val Ile
        450                 455                 460

Thr Phe Gly Ser Pro Ser Val Met Cys Gly Gly Asp Tyr Leu Leu Gln
465                 470                 475                 480

Lys Leu Gly Leu Pro Lys Ser His Val Gln Ser Val Thr Leu His Arg
                485                 490                 495

Asp Ile Val Pro Arg Ala Phe Ser Cys His Tyr Pro Asp His Ile Ala
            500                 505                 510

Ser Ile Leu Lys Leu Val Asn Gly Asn Phe Arg Ser His Pro Cys Leu
        515                 520                 525

Thr Asn Gln Lys Leu Leu Tyr Ala Pro Met Gly Glu Val Phe Ile Leu
530                 535                 540

Gln Pro Asp Glu Lys Leu Ser Pro His His Leu Leu Pro Ala Gly
545                 550                 555                 560

Ser Gly Leu Tyr Leu Ile Gly Gly Gln Thr Val Asp Ser Gly Thr Ser
                565                 570                 575

Ser Thr Ala Leu Arg Ser Ala Leu Ser Ala Phe Phe Asn Ser Pro His
            580                 585                 590

Pro Leu Glu Ile Leu Arg Asp Ala Gly Ala Tyr Gly Pro Lys Gly Thr
        595                 600                 605

Val Tyr Arg Asp His Asp Val His Ser Tyr Leu Arg Ser Ile Arg Ala
610                 615                 620

Val Val Arg Lys Glu Met Arg Ala Glu Lys Glu Arg Arg Leu Leu
625                 630                 635                 640

Arg Trp Pro Ile Glu Val Tyr Gly Ala Leu Ala Thr Ile Asp Arg Arg
                645                 650                 655

Gln Val Leu Arg Gln Leu Arg Arg His Ala His Leu Leu Val Val Phe
            660                 665                 670

Leu Leu Pro Ala Lys Leu Leu Phe Leu Gly Val Leu Ser Leu Ile Arg
        675                 680                 685

Pro Thr
    690

<210> SEQ ID NO 7
<211> LENGTH: 705
<212> TYPE: PRT
<213> ORGANISM: Glycine max

<400> SEQUENCE: 7

Met Gln Gln Val Ser Asn Thr Gly Ile Ser Met Ala Tyr Thr Ala Val
1               5                   10                  15

Ala Met Pro Thr Ser Pro Ala Ala Thr Ser Ala Thr Met Asp Ile Ala
            20                  25                  30

Lys Glu His Asn Gly Leu Arg Arg Ser Gln Ser Ser Lys Glu Leu Cys
        35                  40                  45

Thr Arg Ser Ile Met Arg Arg Ser Tyr Ser Asp Asn His Leu Cys Cys
    50                  55                  60

Ser Ile Asn Arg Ile Gln Ala Thr Ser Val Pro Pro Lys Leu Lys Ser
65                  70                  75                  80

Asn Arg Ser Met Gly Ile Ser Pro Phe Gln Phe Ser Gly Ser Met Leu
                85                  90                  95
```

-continued

```
Pro Asn Ser Leu Arg Ser Phe Leu Phe Asp Pro Glu Thr Ser Lys Asp
            100                 105                 110

Val Ser Val Glu Glu Lys Val Ser Ile Glu Asn Met Val Glu
            115                 120             125

Ser Ser Lys Glu Glu Ile Ala Asn Arg Ala Asn Trp Val Glu Arg Leu
            130                 135                 140

Met Glu Ile Lys Lys His Trp Arg Asn Arg Leu Pro Lys Glu Ser Met
145                 150                 155                 160

Asp Pro Asp Ala Ile Cys Asn Glu Asn Thr Tyr Asp Cys Glu Cys
                165                 170                 175

Asp Gly Asp Gly Asp Asn Val Cys Val Gly Glu Asp Glu Asp
            180                 185                 190

Glu Gln Glu Val Thr Tyr Asp Cys Asp Ser Phe Ser Asn Phe Leu Val
            195                 200                 205

Gln Val Pro Trp Ser Asp Thr Lys Leu Tyr Ser Gln Leu Ala Phe Leu
            210                 215                 220

Cys Asn Met Ala Tyr Val Ile Pro Gln Ile Lys Ala Lys Asp Leu Arg
225                 230                 235                 240

Arg Tyr Tyr Ser Leu Gln Phe Ile Thr Ser Leu Glu Lys Lys Val
            245                 250                 255

Glu Val Ala Lys Leu Lys Val Lys Leu Asp Gln Asp Ser Thr Arg Val
            260                 265                 270

Pro Ile Asp Asp Ser Asp Val Ser Glu Lys Gly Lys Asp Ser Ile Lys
            275                 280                 285

Lys Pro Gln Ile Lys Leu Ala Tyr Asp Ile Ala Ser Ala Ala Ser
            290                 295                 300

Tyr Val Gln Leu Arg Ala Lys Asp Leu Leu His Arg Ala Ala Lys Ser
305                 310                 315                 320

Arg Asp Thr Gln Gln Thr Glu Asn Glu Asp Ser Asn Gly Arg Gly Asp
            325                 330                 335

Ser Pro Arg Glu Glu Leu Glu Ser Thr Ser Arg Gly Tyr Lys Ser Glu
            340                 345                 350

Val Ala Ala Tyr Val Ala Ala Ser Thr Met Thr Ala Val Val Ala Ala
            355                 360                 365

Gly Glu Lys Glu Lys Gln Glu Ala Ala Asn Asp Leu Gln Ser Leu His
            370                 375                 380

Ser Ser Pro Cys Glu Trp Phe Val Cys Asp Asp Pro Gly Asn Tyr Thr
385                 390                 395                 400

Arg Cys Phe Val Ile Gln Gly Ser Asp Ser Leu Ala Ser Trp Gln Ala
                405                 410                 415

Asn Leu Phe Phe Glu Pro Thr Lys Phe Glu Asp Thr Asp Val Leu Val
            420                 425                 430

His Arg Gly Ile Tyr Glu Ala Ala Lys Gly Ile Tyr Lys Gln Phe Met
            435                 440                 445

Pro Glu Ile Met Glu His Leu Lys Arg His Gly Asp Arg Ala Lys Leu
            450                 455                 460

Gln Phe Thr Gly His Ser Leu Gly Gly Ser Leu Ser Leu Leu Val His
465                 470                 475                 480

Leu Met Leu Leu Thr Asn Lys Val Val Ser Pro Ser Thr Leu Arg Pro
                485                 490                 495

Val Val Thr Phe Gly Ser Pro Phe Val Phe Cys Gly Gly Gln Gln Ile
            500                 505                 510
```

-continued

```
Ile Asn Glu Leu Gly Leu Asp Glu Ser Gln Ile His Cys Val Met Met
            515                 520                 525

His Arg Asp Ile Val Pro Arg Ala Phe Ser Cys Asn Tyr Pro Asn His
530                 535                 540

Val Ala Val Val Leu Lys Arg Leu Asn Ser Ser Phe Arg Ser His Pro
545                 550                 555                 560

Cys Leu Leu Lys Asn Lys Leu Leu Tyr Ser Pro Leu Gly Lys Ile Phe
                565                 570                 575

Ile Leu Gln Pro Asp Glu Lys Thr Ser Pro Pro His Pro Leu Leu Pro
            580                 585                 590

Arg Gly Ser Ala Phe Tyr Ala Leu Asp Asn Thr Lys Gly Gly Tyr Ser
        595                 600                 605

Pro Ser Val Leu Arg Thr Phe Leu Asn Gln Pro His Pro Ile Asp Thr
    610                 615                 620

Leu Ser Asp Pro Thr Ala Tyr Gly Ser Glu Gly Thr Ile Leu Arg Asp
625                 630                 635                 640

His Asp Ser Ser Asn Tyr Leu Lys Ala Ile Asn Gly Val Leu Arg Lys
                645                 650                 655

His Ser Lys Ile Thr Val Gly Arg Met Arg Lys Gln Arg Ile Asn Gln
            660                 665                 670

Leu Trp Pro Leu Leu Thr Ser Pro Ser Pro His Ser Trp Ser His Glu
        675                 680                 685

Gln Asn Leu Glu Arg Cys Ser Leu Arg Thr Lys Glu Ile Val Thr Gly
    690                 695                 700

Val
705

<210> SEQ ID NO 8
<211> LENGTH: 688
<212> TYPE: PRT
<213> ORGANISM: Glycine max

<400> SEQUENCE: 8

Met Pro Thr Ser Pro Ala Ala Thr Ser Ala Thr Met Asp Ile Ala Lys
1               5                   10                  15

Glu His Asn Gly Leu Arg Arg Ser Gln Ser Ser Lys Glu Leu Cys Thr
            20                  25                  30

Arg Ser Ile Met Arg Arg Ser Tyr Ser Asp Asn His Leu Cys Cys Ser
        35                  40                  45

Ile Asn Arg Ile Gln Ala Thr Ser Val Pro Pro Lys Leu Lys Ser Asn
    50                  55                  60

Arg Ser Met Gly Ile Ser Pro Phe Gln Phe Ser Gly Ser Met Leu Pro
65                  70                  75                  80

Asn Ser Leu Arg Ser Phe Leu Phe Asp Pro Glu Thr Ser Lys Asp Val
                85                  90                  95

Ser Val Glu Glu Lys Val Val Ser Ile Glu Glu Asn Met Val Glu Ser
            100                 105                 110

Ser Lys Glu Glu Ile Ala Asn Arg Ala Asn Trp Val Glu Arg Leu Met
        115                 120                 125

Glu Ile Lys Lys His Trp Arg Asn Arg Leu Pro Lys Glu Ser Met Asp
    130                 135                 140

Pro Asp Ala Ile Cys Asn Glu Asn Thr Tyr Asp Glu Cys Glu Cys Asp
145                 150                 155                 160

Gly Asp Gly Asp Asp Asn Val Cys Val Val Gly Glu Asp Glu Asp Glu
                165                 170                 175
```

```
Gln Glu Val Thr Tyr Asp Cys Asp Ser Phe Ser Asn Phe Leu Val Gln
            180                 185                 190

Val Pro Trp Ser Asp Thr Lys Leu Tyr Ser Gln Leu Ala Phe Leu Cys
            195                 200                 205

Asn Met Ala Tyr Val Ile Pro Gln Ile Lys Ala Lys Asp Leu Arg Arg
210                 215                 220

Tyr Tyr Ser Leu Gln Phe Ile Thr Ser Leu Glu Lys Lys Val Glu
225                 230                 235                 240

Val Ala Lys Leu Lys Val Lys Leu Asp Gln Asp Ser Thr Arg Val Pro
                245                 250                 255

Ile Asp Asp Ser Asp Val Ser Glu Lys Gly Lys Asp Ser Ile Lys Lys
            260                 265                 270

Pro Gln Ile Lys Leu Ala Tyr Asp Ile Ala Ala Ser Ala Ala Ser Tyr
            275                 280                 285

Val Gln Leu Arg Ala Lys Asp Leu Leu His Arg Ala Ala Lys Ser Arg
            290                 295                 300

Asp Thr Gln Gln Thr Glu Asn Glu Asp Ser Asn Gly Arg Gly Asp Ser
305                 310                 315                 320

Pro Arg Glu Glu Leu Glu Ser Thr Ser Arg Gly Tyr Lys Ser Glu Val
                325                 330                 335

Ala Ala Tyr Val Ala Ala Ser Thr Met Thr Ala Val Val Ala Ala Gly
            340                 345                 350

Glu Lys Glu Lys Gln Glu Ala Ala Asn Asp Leu Gln Ser Leu His Ser
            355                 360                 365

Ser Pro Cys Glu Trp Phe Val Cys Asp Asp Pro Gly Asn Tyr Thr Arg
            370                 375                 380

Cys Phe Val Ile Gln Gly Ser Asp Ser Leu Ala Ser Trp Gln Ala Asn
385                 390                 395                 400

Leu Phe Phe Glu Pro Thr Lys Phe Glu Asp Thr Asp Val Leu Val His
                405                 410                 415

Arg Gly Ile Tyr Glu Ala Ala Lys Gly Ile Tyr Lys Gln Phe Met Pro
            420                 425                 430

Glu Ile Met Glu His Leu Lys Arg His Gly Asp Arg Ala Lys Leu Gln
            435                 440                 445

Phe Thr Gly His Ser Leu Gly Gly Ser Leu Ser Leu Leu Val His Leu
            450                 455                 460

Met Leu Leu Thr Asn Lys Val Val Ser Pro Ser Thr Leu Arg Pro Val
465                 470                 475                 480

Val Thr Phe Gly Ser Pro Phe Val Phe Cys Gly Gly Gln Gln Ile Ile
                485                 490                 495

Asn Glu Leu Gly Leu Asp Glu Ser Gln Ile His Cys Val Met Met His
            500                 505                 510

Arg Asp Ile Val Pro Arg Ala Phe Ser Cys Asn Tyr Pro Asn His Val
            515                 520                 525

Ala Val Val Leu Lys Arg Leu Asn Ser Ser Phe Arg Ser His Pro Cys
            530                 535                 540

Leu Leu Lys Asn Lys Leu Leu Tyr Ser Pro Leu Gly Lys Ile Phe Ile
545                 550                 555                 560

Leu Gln Pro Asp Glu Lys Thr Ser Pro Pro His Pro Leu Leu Pro Arg
                565                 570                 575

Gly Ser Ala Phe Tyr Ala Leu Asp Asn Thr Lys Gly Gly Tyr Ser Pro
            580                 585                 590
```

-continued

```
Ser Val Leu Arg Thr Phe Leu Asn Gln Pro His Pro Ile Asp Thr Leu
        595                 600             605

Ser Asp Pro Thr Ala Tyr Gly Ser Glu Gly Thr Ile Leu Arg Asp His
610                 615                 620

Asp Ser Ser Asn Tyr Leu Lys Ala Ile Asn Gly Val Leu Arg Lys His
625                 630                 635                 640

Ser Lys Ile Thr Val Gly Arg Met Arg Lys Gln Arg Ile Asn Gln Leu
                645                 650                 655

Trp Pro Leu Leu Thr Ser Pro Ser Pro His Ser Trp Ser His Glu Gln
                660                 665                 670

Asn Leu Glu Arg Cys Ser Leu Arg Thr Lys Glu Ile Val Thr Gly Val
            675                 680                 685

<210> SEQ ID NO 9
<211> LENGTH: 697
<212> TYPE: PRT
<213> ORGANISM: Glycine max

<400> SEQUENCE: 9

Met Ala Tyr Thr Ala Val Ala Met Pro Thr Ser Pro Ala Ala Thr Ser
1               5                   10                  15

Ala Thr Val Asp Ile Ala Lys Glu His Asn Gly Leu Arg Arg Ser Gln
                20                  25                  30

Ser Ser Lys Glu Leu His Thr Arg Ala Val Met Arg Arg Ser Tyr Ser
            35                  40                  45

Asp Asn His Leu Cys Cys Ser Ile Asn Arg Val Gln Ala Thr Ser Val
        50                  55                  60

Pro Pro Lys Leu Lys Ser Asn Gln Pro Met Gly Ile Ser Pro Phe Gln
65                  70                  75                  80

Phe Ser Gly Ser Ile Leu Pro Asn Ser Leu Arg Ser Phe Leu Phe Asp
                85                  90                  95

Pro Glu Thr Ser Asn Asp Leu Val Val Glu Glu Lys Val Val Ser Ile
                100                 105                 110

Glu Glu Asn Met Val Glu Ser Ser Lys Glu Glu Ile Val Asn Arg Ala
            115                 120                 125

Asn Trp Val Glu Arg Leu Met Glu Ile Lys Lys His Trp Arg Asn Arg
        130                 135                 140

Leu Pro Lys Glu Ser Met Asn Thr Asp Ala Ile Cys Asn Asp Asn Thr
145                 150                 155                 160

Tyr Asp Glu Cys Glu Cys Asp Gly Asp Gly Asp Asn Val Cys Val
                165                 170                 175

Val Gly Glu Asp Glu Asp Glu Gln Glu Val Thr Tyr Asp Arg Asp Ser
                180                 185                 190

Phe Ser Ser Phe Leu Val Gln Val Pro Trp Ser Asp Thr Lys Leu Tyr
            195                 200                 205

Ser Gln Leu Ala Phe Leu Cys Asn Met Ala Tyr Val Ile Pro Gln Ile
        210                 215                 220

Lys Ala Lys Asp Leu Arg Arg Tyr Tyr Ser Leu Gln Phe Ile Thr Ser
225                 230                 235                 240

Ser Leu Glu Lys Lys Ala Glu Val Ala Lys Leu Lys Val Gln Leu Asn
                245                 250                 255

Gln Asp Ser Thr Cys Val Pro Val Asp Asp Ser Val Ala Ser Gln Asp
                260                 265                 270

Val Ser Lys Lys Asp Lys Asp Asn Thr Lys Lys Pro Gln Ile Lys Leu
            275                 280                 285
```

```
Ala Tyr Asp Ile Ala Ala Ser Ala Ser Tyr Val Gln Leu Arg Ala
    290                 295                 300

Lys Asp Leu Leu His Arg Ala Ala Lys Ser Gln Asp Thr Gln Gln Thr
305                 310                 315                 320

Glu Asn Glu Asp Ser Asn Glu Arg Glu Asp Leu Pro Gly Arg Glu Glu
                325                 330                 335

Leu Glu Gly Thr Ser Arg Gly Tyr Lys Ser Glu Val Ala Ala Tyr Val
            340                 345                 350

Ala Ala Ser Thr Met Thr Ala Val Val Ala Ala Gly Glu Lys Glu Lys
        355                 360                 365

Gln Glu Thr Ala Asn Asp Leu Gln Ser Leu His Ser Ser Pro Cys Glu
    370                 375                 380

Trp Phe Val Cys Asp Asp Pro Gly Asn Tyr Thr Arg Cys Phe Val Ile
385                 390                 395                 400

Gln Gly Ser Asp Ser Leu Ala Ser Trp Gln Ala Asn Leu Phe Phe Glu
                405                 410                 415

Pro Thr Lys Phe Glu Gly Thr Asp Val Leu Val His Arg Gly Ile Tyr
            420                 425                 430

Glu Ala Ala Lys Gly Ile Tyr Lys Gln Phe Met Pro Glu Ile Met Glu
        435                 440                 445

His Leu Lys Arg His Gly Asp Arg Ala Lys Leu Gln Phe Thr Gly His
    450                 455                 460

Ser Leu Gly Gly Ser Leu Ser Leu Leu Val His Leu Met Leu Leu Thr
465                 470                 475                 480

Asn Lys Val Val Ser Pro Ser Thr Leu Gly Pro Ile Val Thr Phe Gly
                485                 490                 495

Ser Pro Phe Val Phe Cys Gly Gly Gln Gln Ile Ile Asp Glu Leu Gly
            500                 505                 510

Leu Asp Glu Ser Gln Ile His Cys Val Met Met His Arg Asp Ile Val
        515                 520                 525

Pro Arg Ala Phe Ser Cys Asn Tyr Pro Asn His Val Ala Leu Val Leu
    530                 535                 540

Lys Arg Leu His Thr Ser Phe Arg Ser His Pro Cys Leu Leu Lys Asn
545                 550                 555                 560

Lys Leu Leu Tyr Ser Pro Leu Gly Lys Ile Phe Ile Leu Gln Pro Asp
                565                 570                 575

Glu Lys Thr Ser Pro Pro His Pro Leu Leu Pro Arg Gly Ser Ala Phe
            580                 585                 590

Tyr Ala Leu Asp Asn Thr Lys Cys Pro Ser Val Leu Arg Thr Phe Leu
        595                 600                 605

Asn Gln Pro His Pro Ile Asp Thr Leu Ser Asp Pro Thr Ala Tyr Gly
    610                 615                 620

Ser Glu Gly Thr Ile Leu Arg Asp His Asp Ser Ser Asn Tyr Leu Lys
625                 630                 635                 640

Ala Ile Asn Gly Val Leu Arg Lys His Ser Lys Ile Ile Val Gly Arg
                645                 650                 655

Val Arg Lys Gln Arg Ile Asn Gln Leu Trp Pro Leu Leu Thr Ser Pro
            660                 665                 670

Ser Pro His Ser Arg Ser His Glu Gln Asn Ser Glu Arg Cys Ser Leu
        675                 680                 685

Arg Thr Lys Glu Ile Val Thr Gly Val
    690                 695
```

<210> SEQ ID NO 10
<211> LENGTH: 644
<212> TYPE: PRT
<213> ORGANISM: Brassica napus

<400> SEQUENCE: 10

```
Met Ala Phe Asn Ala Ala Met Ala Ser Pro Pro Ala Ala Ala
1               5                   10                  15

Asn Asp Val Phe Lys Glu His Phe Gly Leu Arg Arg Ser Leu Ser Gly
            20                  25                  30

Gln Asp Leu Val Val Lys Ala Gly Ile Arg Arg Ser Ser Ser Asp
        35                  40                  45

Asn His Leu Cys Cys Asn Asn Arg Ile Arg Ala Val Ser Val Arg Pro
    50                  55                  60

Gly Gln Gly Met Lys Ser Ser Arg Ser Val Gly Val Phe Ser Phe Gln
65                  70                  75                  80

Ile Ser Ser Ser Ile Ile Pro Ser Pro Ile Lys Thr Leu Leu Phe Glu
                85                  90                  95

Thr Glu Asp Asp Lys Asp Ser Asp Asp Glu Pro Glu Val Gln Pro Asn
            100                 105                 110

Leu Asp Gly Val Lys Lys Ala Asn Trp Val Gln Arg Leu Leu Glu Ile
        115                 120                 125

Arg Arg Gln Trp Lys Lys Glu Thr Lys Thr Glu Asn Val Asn Gly Asp
130                 135                 140

Val Val Ser Glu His Glu Asn Val Thr Cys Gly Cys Glu Asp Gly Glu
145                 150                 155                 160

Gly Cys Val Ala Asp Tyr Glu Asn Gly Asp Trp Glu Arg Glu Ser Phe
                165                 170                 175

Ser Lys Leu Leu Val Arg Val Ser Trp Ser Asp Ala Lys Gln Leu Ser
            180                 185                 190

Gln Leu Ala Tyr Leu Cys Asn Val Ala Tyr Thr Ile Pro Glu Ile Lys
        195                 200                 205

Gly Glu Asp Leu Arg Arg Asn Tyr Gly Leu Lys Phe Val Thr Ser Ser
    210                 215                 220

Leu Glu Lys Lys Ala Lys Ala Ala Leu Leu Arg Glu Lys Leu Glu Gln
225                 230                 235                 240

Asp Ser Thr Arg Val Pro Val Val Thr Ser Pro Glu Ser Glu Ser Glu
                245                 250                 255

Lys Pro Gln Gln Arg Ser Ser Ser Ser Ala Tyr Asn Ile Ala Ala
            260                 265                 270

Ser Ala Ala Ser Tyr Ile His Ser Cys Lys Glu Val Asp Ser Ser Asp
        275                 280                 285

Leu Ser Asn Pro Tyr Lys Ser Ala Ala Ala Gln Ala Ala Ala Ser
    290                 295                 300

Thr Met Thr Ala Val Val Ala Gly Glu Asp Glu Lys Leu Glu Ala
305                 310                 315                 320

Ala Arg Glu Leu Gln Ser Leu Gln Ser Ser Pro Cys Glu Trp Phe Val
                325                 330                 335

Cys Asp Asp Leu Ser Ser Tyr Thr Arg Cys Phe Val Ile Gln Gly Ser
            340                 345                 350

Asp Ser Leu Ala Ser Trp Lys Ala Asn Leu Phe Phe Glu Pro Thr Lys
        355                 360                 365

Phe Glu Asp Thr Asp Val Leu Val His Arg Gly Ile Tyr Glu Ala Ala
    370                 375                 380
```

Lys Gly Ile Tyr Glu Gln Phe Leu Pro Glu Ile Thr Glu His Leu Ser
385                 390                 395                 400

Leu His Gly Asp Arg Ala Arg Phe Gln Phe Thr Gly His Ser Leu Gly
            405                 410                 415

Gly Ser Leu Ser Leu Ile Val Asn Leu Met Leu Leu Ser Arg Gly Leu
            420                 425                 430

Val Ser Ser Glu Ala Met Lys Pro Val Val Thr Phe Gly Ser Pro Phe
            435                 440                 445

Val Phe Cys Gly Gly Glu Lys Ile Leu Glu Glu Leu Gly Leu Asp Glu
        450                 455                 460

Ser His Val His Cys Val Met Met His Arg Asp Ile Val Pro Arg Ala
465                 470                 475                 480

Phe Ser Cys Asn Tyr Pro Asp His Val Ala Leu Val Leu Lys Arg Leu
                485                 490                 495

Asn Gly Thr Phe Arg Thr His Pro Cys Leu Asn Lys Asn Lys Leu Leu
            500                 505                 510

Tyr Ser Pro Met Gly Lys Val Phe Ile Leu Gln Pro Ser Glu Ser Val
            515                 520                 525

Ser Pro Thr His Pro Trp Leu Pro Pro Gly Asn Ala Leu Tyr Val Leu
            530                 535                 540

Asp Lys Asn Asn Glu Asp Tyr Ser Pro Thr Ala Leu Arg Gly Phe Leu
545                 550                 555                 560

Asn Arg Pro His Pro Leu Glu Thr Leu Ser Gln Arg Ala Ala Tyr Gly
                565                 570                 575

Ser Glu Gly Ser Val Leu Arg Asp His Asp Ser Lys Asn Tyr Val Lys
            580                 585                 590

Ala Val Asn Gly Val Ile Arg Gln His Thr Lys Leu Ile Val Arg Lys
            595                 600                 605

Val Arg Arg Gln Arg Ser Thr Ile Trp Pro Val Leu Thr Ser Ala Glu
            610                 615                 620

Pro Asn Ser Ser Val Asn Asp Trp Ser Leu Thr Ala Thr Glu Glu Ile
625                 630                 635                 640

Met Thr Arg Ala

<210> SEQ ID NO 11
<211> LENGTH: 645
<212> TYPE: PRT
<213> ORGANISM: Brassica napus

<400> SEQUENCE: 11

Met Ser Phe Asn Ala Ala Met Ala Ser Pro Ser Pro Pro Ala Ala Asn
1               5                   10                  15

Asp Val Phe Lys Glu His Phe Gly Leu Arg Arg Ser Leu Ser Gly Gln
                20                  25                  30

Asp Leu Val Val Lys Ala Gly Gly Ile Arg Arg Ser Ser Ser Asp Asn
            35                  40                  45

His Leu Cys Cys Lys Asn Arg Ile Arg Ala Val Ser Val Arg Pro Gly
        50                  55                  60

Gln Gly Met Lys Ser Ser Arg Ser Val Gly Val Phe Ser Phe Gln Ile
65                  70                  75                  80

Ser Ser Ser Ile Ile Pro Ser Pro Ile Lys Thr Leu Leu Phe Glu Thr
                85                  90                  95

Glu Asp Asp Thr Asp Ser Asp Asp Glu Pro Glu Val Glu Pro Asn Leu
            100                 105                 110

```
Asp Gly Ala Lys Lys Ala Asn Trp Val Gln Arg Leu Leu Glu Ile Arg
        115                 120                 125

Arg Gln Trp Lys Lys Glu Thr Arg Thr Glu Asn Ser Asn Gly Asp Val
130                 135                 140

Val Ser Glu His Glu Asn Val Thr Cys Gly Cys Glu Asp Gly Glu Gly
145                 150                 155                 160

Cys Val Ala Asp Tyr Glu Asn Gly Asp Trp Glu Arg Glu Ser Phe Ser
                165                 170                 175

Lys Leu Leu Val Arg Val Ser Trp Ser Asp Ala Lys Gln Leu Ser Gln
                180                 185                 190

Leu Ala Tyr Leu Cys Asn Val Ala Tyr Thr Ile Pro Glu Ile Lys Gly
            195                 200                 205

Glu Asp Leu Arg Arg Asn Tyr Gly Leu Lys Phe Val Thr Ser Ser Leu
210                 215                 220

Glu Lys Lys Ala Lys Ala Ala Leu Leu Arg Glu Lys Leu Glu Gln Asp
225                 230                 235                 240

Ser Thr Arg Val Pro Val Thr Ser Pro Glu Ser Glu Ser Asp Lys
                245                 250                 255

Phe Gln Gln Arg Ser Ser Ser Ser Ala Tyr Lys Ile Ala Ala
            260                 265                 270

Ser Ala Ala Ser Tyr Ile His Ser Cys Lys Glu Tyr Glu Ser Ser Asp
            275                 280                 285

Leu Asn Asn Pro Tyr Lys Ser Ala Ala Ala Gln Ala Ala Ala Ser
            290                 295                 300

Thr Met Thr Ala Val Ala Ala Gly Glu Asp Glu Lys Leu Glu Ala
305                 310                 315                 320

Ala Arg Glu Leu Gln Ser Leu Gln Ser Ser Pro Cys Glu Trp Phe Val
            325                 330                 335

Cys Asp Glu Pro Asn Ser Tyr Thr Arg Cys Phe Val Ile Gln Gly Ser
            340                 345                 350

Asp Ser Leu Ala Ser Trp Lys Ala Asn Leu Phe Phe Glu Pro Thr Arg
            355                 360                 365

Phe Glu Asp Thr Asp Val Leu Val His Arg Gly Ile Tyr Glu Ala Ala
370                 375                 380

Lys Gly Ile Tyr Glu Gln Phe Leu Pro Glu Ile Thr Glu His Leu Ser
385                 390                 395                 400

Leu His Gly Asp Arg Ala Lys Phe Gln Phe Thr Gly His Ser Leu Gly
                405                 410                 415

Gly Ser Leu Ser Leu Ile Val Asn Leu Met Leu Leu Ser Arg Gly Leu
            420                 425                 430

Val Ser Ser Glu Ala Met Lys Pro Val Val Thr Phe Gly Ser Pro Phe
            435                 440                 445

Val Phe Cys Gly Gly Glu Lys Ile Leu Glu Glu Leu Gly Leu Glu Glu
450                 455                 460

Ser His Val His Cys Val Met Met His Arg Asp Ile Val Pro Arg Ala
465                 470                 475                 480

Phe Ser Cys Asn Tyr Pro Asp His Val Ala Leu Val Leu Lys Arg Leu
                485                 490                 495

Asn Gly Thr Phe Arg Thr His Pro Cys Leu Asn Lys Asn Lys Leu Leu
            500                 505                 510

Tyr Ser Pro Met Gly Lys Val Phe Ile Leu Gln Pro Ser Glu Ser Val
            515                 520                 525
```

```
Ser Pro Thr His Pro Trp Leu Pro Pro Gly Asn Ala Leu Tyr Val Leu
    530                 535                 540

Asp Lys Asn Asn Glu Gly Tyr Ser Pro Thr Ala Leu Arg Gly Phe Leu
545                 550                 555                 560

Asn Arg Pro His Pro Leu Glu Thr Leu Ser Gln Arg Ala Ala Tyr Gly
                565                 570                 575

Ser Glu Gly Ser Val Leu Arg Asp His Asp Ser Lys Asn Tyr Val Lys
            580                 585                 590

Ala Val Asn Gly Val Ile Arg Gln His Thr Lys Leu Ile Val Arg Lys
        595                 600                 605

Val Arg Arg Gln Arg Arg Ser Thr Val Trp Pro Val Leu Thr Pro Ala
610                 615                 620

Glu Pro Asn Ser Val Asn Asp Trp Ser Leu Thr Ala Thr Glu Glu
625                 630                 635                 640

Ile Met Thr Arg Ala
            645

<210> SEQ ID NO 12
<211> LENGTH: 713
<212> TYPE: PRT
<213> ORGANISM: Arabidopsis thaliana

<400> SEQUENCE: 12

Met Asp Ser Leu Cys Leu Asn Ser Gly Leu His Gly Val Ile Pro Ala
1               5                   10                  15

Ile Thr Ala Val Gly Asn Gly Gly Cys Gly Val Val Glu Val Arg
            20                  25                  30

Ala Thr Ala Ser Ala Pro Ser Gln Lys Arg Gly Pro Phe Gly Phe Ser
        35                  40                  45

Phe Lys Tyr Pro Leu Thr Pro Phe Trp Ser Arg Gly Gly Gly Gly Gly
    50                  55                  60

Ile Ala Ser Arg Arg Arg Ser Gly Leu Cys Leu Asp Asp Ala Val Leu
65                  70                  75                  80

Val Asp Ser Gly Asp Ser Arg Lys Pro Ile Ala Glu Thr Ala Val
                85                  90                  95

Glu Met Asp Thr Glu Arg Arg Asn Gly Ser Trp Val Leu Lys Ile Leu
            100                 105                 110

Asp Val Gln Ser Thr Trp Lys His Glu Glu Glu Asp Asp Asp Glu
        115                 120                 125

Val Glu Asp Glu Asp Gly Asp Glu Asp Glu Val Glu Leu Asp Asp
    130                 135                 140

Ala Val Val Ser Glu Asp Asp Gly Gly Cys Asp Val Cys Ser Val Leu
145                 150                 155                 160

Glu Asp Asp Gly Asn Glu Ala Asn Lys Phe Gln Leu Asp Arg Glu Ser
                165                 170                 175

Phe Ser Lys Leu Leu Arg Arg Val Thr Leu Pro Glu Ser Lys Leu Tyr
            180                 185                 190

Ala Gln Leu Ser Tyr Leu Gly Asn Leu Ala Tyr Ser Ile Ser Lys Ile
        195                 200                 205

Lys Pro Ala Asn Leu Ser Lys Tyr Tyr Gly Leu Arg Phe Val Thr Ser
    210                 215                 220

Ser Ala Glu Lys Thr Glu Ser Ala Leu Lys Ala Glu Asn Gly Glu Val
225                 230                 235                 240

Ser Gly Glu Thr Lys Pro Ile Val Glu Ala Glu Glu Val Glu Glu
                245                 250                 255
```

```
Glu Glu Lys Asn Lys Ser Arg Lys Ile Ser Ala Ser Ala Ala Tyr Glu
            260                 265                 270

Ile Val Ala Ser Ala Ala Ser Tyr Leu His Ser Arg Thr Asn Asn Ile
            275                 280                 285

Leu Pro Phe Asn Ser Ser Lys Ala Glu Asn Ser Asp Lys His Asp
290                 295                 300

Val Asn Leu Thr Asn Ala Glu Ser Ser Asp Val Ala Tyr Ser Val
305                 310                 315                 320

Thr Ser Val Val Ala Glu Glu Asp Val Lys Gln Ala Val Ala Asp
            325                 330                 335

Asp Leu Lys Ser Thr Ile Ser Ser Pro Cys Asp Trp Phe Ile Cys Asp
            340                 345                 350

Asp Asp Gln Ser His Thr Arg Phe Val Val Ile Gln Gly Ser Glu Ser
            355                 360                 365

Leu Ala Ser Trp Gln Ala Asn Leu Leu Phe Glu Pro Ile Glu Phe Glu
        370                 375                 380

Gly Leu Gly Ala Ile Val His Arg Gly Ile Tyr Glu Ala Ala Lys Gly
385                 390                 395                 400

Met Tyr Glu Gln Met Leu Pro Glu Val Lys Ala His Ile Lys Thr His
            405                 410                 415

Gly Thr Ser Ala Lys Phe Arg Phe Thr Gly His Ser Leu Gly Gly Ser
            420                 425                 430

Leu Ser Leu Leu Leu Asn Leu Met Leu Leu Val Arg Gly Glu Val Pro
            435                 440                 445

Ala Ser Ser Leu Leu Pro Val Ile Thr Tyr Gly Ala Pro Phe Val Leu
450                 455                 460

Cys Gly Asp Arg Leu Leu Lys Lys Leu Gly Leu Pro Lys Ser His
465                 470                 475                 480

Val Gln Ala Ile Val Met His Arg Asp Ile Val Pro Arg Ala Phe Ser
                485                 490                 495

Cys Asn Tyr Pro Tyr His Val Ala Glu Leu Leu Lys Ala Val Asn Gly
            500                 505                 510

Asn Phe Arg Ser His Pro Cys Leu Asn Lys Gln Ser Met Leu Tyr Ser
            515                 520                 525

Pro Met Gly Glu Leu Leu Ile Leu Gln Pro Asp Glu Thr Phe Ser Pro
530                 535                 540

Gly His Glu Leu Leu Pro Ser Gly Asn Gly Leu Tyr Leu Leu Thr Ser
545                 550                 555                 560

Asp Phe Glu Ser Pro Asp Ile Glu Asp Ser Asp Glu Glu Arg Leu Arg
                565                 570                 575

Ala Ala Gln Thr Val Phe Leu Asn Thr Pro His Pro Leu Asp Ile Leu
            580                 585                 590

Ser Asp Arg Ser Ala Tyr Gly Ser Gly Thr Ile Gln Arg Asp His
            595                 600                 605

Asp Met Asn Ser Tyr Leu Lys Ala Val Arg Ser Val Ile Arg Lys Glu
            610                 615                 620

Val Asn Gln Ile Arg Arg Ala Lys Arg Glu His Arg Ser Leu Trp
625                 630                 635                 640

Trp Pro Ile Leu Val Ala Arg Glu Ser Gly Ser Gly Ile Ala Val
            645                 650                 655

Ser Asn Gly Gln Ile Asn Gly Gln Asp Phe Ser Gly Met Met Gln Thr
            660                 665                 670
```

```
Gly Arg Lys Ser Leu Gln Arg Phe Ser Arg Leu Val Ala Ser Gln His
         675                 680                 685

Met Pro Leu Ile Val Val Met Leu Phe Pro Val Lys Leu Leu Phe Leu
         690                 695                 700

Gly Ala Phe Asn Val Phe Ser Phe Arg
705                 710

<210> SEQ ID NO 13
<211> LENGTH: 2142
<212> TYPE: DNA
<213> ORGANISM: Arabidopsis thaliana

<400> SEQUENCE: 13
atggacagtt tgtgtttgaa tagcggttta cacggtgtaa ttccagcgat cactgcggtt      60
ggaaacggcg gttgcggtgg agttgttgaa gtccgagcaa ctgcgtcggc accatcgcaa     120
aaaagaggac ctttcgggtt ctcatttaag tacccactga cgccgttttg gtctcgcggc     180
ggtggaggag gaattgcgtc gaggagacga agtggattgt gtttagacga cgccgttttg     240
gttgattccg gcgattcgag aaagccgatc gcggaggaga cggcggtgga aatggatacg     300
gagaggcgaa atgggagctg gttttgaag atcttggatg tacaatctac gtggaaacac     360
gaagaagaag aagatgatga tgaagtagaa gatgaagacg gagacgaaga cgaggaggtt     420
gaattagacg acgccgtagt atctgaagat gatggtggat gcgatgtatg ttcagttttg     480
gaagatgatg gcaacgaagc aaacaaattt caactcgata gagaatcgtt ctccaaattg     540
ctaaggaggg ttacgttacc cgaatcaaaa ctctatgccc aactatcgta tttgggaaac     600
ttggcttatt caatttcaaa aatcaagcct gcgaatctgt cgaaatatta cggcctgaga     660
tttgtaactt catcagctga gaaaacagaa tcggcgttaa aagctgagaa tggtgaagtt     720
tcaggtgaga ctaagccaat tgtggaagca gaagaagaag ttgaagaaga agagaagaac     780
aaaagtcgca agattagtgc ttctgctgca tatgagattg ttgcatcagc tgcttcttac     840
cttcactctc gtaccaacaa catacttcct ttcaactctt catcgaaagc cgagaattcg     900
gacaaacatg atgtaaattt gactaatgcg gagtcatcat cagatgttgc ttattctgtt     960
acttctgttg ttgctgctga ggaagatgtg aagcaagcag ttgcagacga tttgaaatcc    1020
acgatttcgt ctccctgcga ttggtttata tgtgatgatg atcagagtca cactagattc    1080
gttgtgattc agggatctga atctctagct tcttggcaag caaatttact ctttgagcct    1140
attgaatttg agggccttgg tgcgatcgta cacagaggaa tatacgaagc tgcaaaagga    1200
atgtatgaac aaatgctacc tgaagttaaa gcccatatta aaacccatgg gaccagcgct    1260
aaattccgtt tcaccggtca ttcattaggt ggaagcttat cgctattact aaacctcatg    1320
ttactcgttc gaggcgaagt acctgcgtct tctttacttc cggttataac atatggtgca    1380
ccatttgtgc tatgtggagg tgaccgtctt cttaagaaac tcggattgcc taaaagccat    1440
gttcaagcta ttgttatgca ccgtgacatt gttccgagag cttttttcttg taactatccg    1500 taccatgttg ctgagcttct caaagctgtt aatggaaact tccgtagcca tccttgtctt    1560
aacaaacaga gtatgttgta ttctccgatg ggcgagcttc tgattcttca accagatgag    1620
acattctccc ccgggcatga acttcttcct tccggaaacg gttataacct tctaactagt    1680
gattttgaat cgccggatat tgaagattcg gatgaggagc ggttaagagc cgcgcagacg    1740
gttttcttga acaccccgca tcctctcgac attctcagcg acagatcggc ttatgggtcc    1800
agcggaacaa tccaaagaga ccatgatatg aactcgtatc tgaaagcggt taggagtgta    1860
```

-continued

```
ataagaaagg aagtgaatca gataaggaga gcaaaaggg agcatcgccg gagtctttgg    1920
tggccaattc tggtggctag agaaagtgga agctcaggga ttgcggtcag taacggccaa    1980
atcaacggtc aggatttctc cgggatgatg cagacaggaa gaaagtcgtt gcagaggttt    2040
agccgccttg tggcgtctca acatatgccg ttgatcgttg ttatgttgtt tccggttaag    2100
ttgttgttcc ttggagcttt caacgtcttt agtttccgtt ga                      2142
```

<210> SEQ ID NO 14
<211> LENGTH: 713
<212> TYPE: PRT
<213> ORGANISM: Arabidopsis thaliana

<400> SEQUENCE: 14

```
Met Asp Ser Leu Cys Leu Asn Ser Gly Leu His Gly Val Ile Pro Ala
1               5                   10                  15

Ile Thr Ala Val Gly Asn Gly Cys Gly Gly Val Val Glu Val Arg
                20                  25                  30

Ala Thr Ala Ser Ala Pro Ser Gln Lys Arg Gly Pro Phe Gly Phe Ser
            35                  40                  45

Phe Lys Tyr Pro Leu Thr Pro Phe Trp Ser Arg Gly Gly Gly Gly
    50                  55                  60

Ile Ala Ser Arg Arg Arg Ser Gly Leu Cys Leu Asp Asp Ala Val Leu
65                  70                  75                  80

Val Asp Ser Gly Asp Ser Arg Lys Pro Ile Ala Glu Glu Thr Ala Val
                85                  90                  95

Glu Met Asp Thr Glu Arg Arg Asn Gly Ser Trp Val Leu Lys Ile Leu
            100                 105                 110

Asp Val Gln Ser Thr Trp Lys His Glu Glu Glu Glu Asp Asp Asp Glu
        115                 120                 125

Val Glu Asp Glu Asp Gly Asp Glu Asp Glu Val Glu Leu Asp Asp
    130                 135                 140

Ala Val Val Ser Glu Asp Asp Gly Gly Cys Asp Val Cys Ser Val Leu
145                 150                 155                 160

Glu Asp Asp Gly Asn Glu Ala Asn Lys Phe Gln Leu Asp Arg Glu Ser
                165                 170                 175

Phe Ser Lys Leu Leu Arg Arg Val Thr Leu Pro Glu Ser Lys Leu Tyr
            180                 185                 190

Ala Gln Leu Ser Tyr Leu Gly Asn Leu Ala Tyr Ser Ile Ser Lys Ile
        195                 200                 205

Lys Pro Ala Asn Leu Ser Lys Tyr Tyr Gly Leu Arg Phe Val Thr Ser
    210                 215                 220

Ser Ala Glu Lys Thr Glu Ser Ala Leu Lys Ala Glu Asn Gly Glu Val
225                 230                 235                 240

Ser Gly Glu Thr Lys Pro Ile Val Glu Ala Glu Glu Val Glu Glu
                245                 250                 255

Glu Glu Lys Asn Lys Ser Arg Lys Ile Ser Ala Ser Ala Ala Tyr Glu
            260                 265                 270

Ile Val Ala Ser Ala Ala Ser Tyr Leu His Ser Arg Thr Asn Asn Ile
        275                 280                 285

Leu Pro Phe Asn Ser Ser Lys Ala Glu Asn Ser Asp Lys His Asp
    290                 295                 300

Val Asn Leu Thr Asn Ala Glu Ser Ser Ser Asp Val Ala Tyr Ser Val
305                 310                 315                 320

Thr Ser Val Val Ala Ala Glu Glu Asp Val Lys Gln Ala Val Ala Asp
```

```
            325                 330                 335
Asp Leu Lys Ser Thr Ile Ser Ser Pro Cys Asp Trp Phe Ile Cys Asp
            340                 345                 350

Asp Asp Gln Ser His Thr Arg Phe Val Val Ile Gln Gly Ser Glu Ser
            355                 360                 365

Leu Ala Ser Trp Gln Ala Asn Leu Leu Phe Glu Pro Ile Glu Phe Glu
            370                 375                 380

Gly Leu Gly Ala Ile Val His Arg Gly Ile Tyr Glu Ala Ala Lys Gly
385                 390                 395                 400

Met Tyr Glu Gln Met Leu Pro Glu Val Lys Ala His Ile Lys Thr His
            405                 410                 415

Gly Thr Ser Ala Lys Phe Arg Phe Thr Gly His Ser Leu Gly Gly Ser
            420                 425                 430

Leu Ser Leu Leu Leu Asn Leu Met Leu Leu Val Arg Gly Glu Val Pro
            435                 440                 445

Ala Ser Ser Leu Leu Pro Val Ile Thr Tyr Gly Ala Pro Phe Val Leu
            450                 455                 460

Cys Gly Gly Asp Arg Leu Leu Lys Lys Leu Gly Leu Pro Lys Ser His
465                 470                 475                 480

Val Gln Ala Ile Val Met His Arg Asp Ile Val Pro Arg Ala Phe Ser
            485                 490                 495

Cys Asn Tyr Pro Tyr His Val Ala Glu Leu Leu Lys Ala Val Asn Gly
            500                 505                 510

Asn Phe Arg Ser His Pro Cys Leu Asn Lys Gln Ser Met Leu Tyr Ser
            515                 520                 525

Pro Met Gly Glu Leu Leu Ile Leu Gln Pro Asp Glu Thr Phe Ser Pro
            530                 535                 540

Gly His Glu Leu Leu Pro Ser Gly Asn Gly Leu Tyr Leu Leu Thr Ser
545                 550                 555                 560

Asp Phe Glu Ser Pro Asp Ile Glu Asp Ser Asp Glu Glu Arg Leu Arg
            565                 570                 575

Ala Ala Gln Thr Val Phe Leu Asn Thr Pro His Pro Leu Asp Ile Leu
            580                 585                 590

Ser Asp Arg Ser Ala Tyr Gly Ser Gly Thr Ile Gln Arg Asp His
            595                 600                 605

Asp Met Asn Ser Tyr Leu Lys Ala Val Arg Ser Ile Arg Lys Glu
            610                 615                 620

Val Asn Gln Ile Arg Arg Ala Lys Arg Glu His Arg Arg Ser Leu Trp
625                 630                 635                 640

Trp Pro Ile Leu Val Ala Arg Glu Ser Gly Ser Ser Val Ile Ala Val
            645                 650                 655

Ser Asn Gly Gln Ile Asn Gly Gln Asp Phe Ser Gly Met Met Gln Thr
            660                 665                 670

Gly Arg Lys Ser Leu Gln Arg Phe Ser Arg Leu Val Ala Ser Gln His
            675                 680                 685

Met Pro Leu Ile Val Val Met Leu Phe Pro Val Lys Leu Leu Phe Leu
            690                 695                 700

Gly Ala Phe Asn Val Phe Ser Phe Arg
705                 710

<210> SEQ ID NO 15
<211> LENGTH: 693
<212> TYPE: PRT
<213> ORGANISM: Arabidopsis thaliana
```

<400> SEQUENCE: 15

```
Met Asp Ser Leu Cys Leu Asn Ser Gly Leu His Gly Val Ile Pro Ala
1               5                   10                  15

Ile Thr Ala Val Gly Asn Gly Gly Cys Gly Val Val Glu Val Arg
            20                  25                  30

Ala Thr Ala Ser Ala Pro Ser Gln Lys Arg Gly Pro Phe Gly Phe Ser
            35                  40                  45

Phe Lys Tyr Pro Leu Thr Pro Phe Trp Ser Arg Gly Gly Gly Gly
 50                  55                  60

Ile Ala Ser Arg Arg Ser Gly Leu Cys Leu Asp Asp Ala Val Leu
 65              70                  75                  80

Val Asp Ser Gly Asp Ser Arg Lys Pro Ile Ala Glu Glu Thr Ala Val
                85                  90                  95

Glu Met Asp Thr Glu Arg Arg Asn Gly Ser Trp Val Leu Lys Ile Leu
                100                 105                 110

Asp Val Gln Ser Thr Trp Lys His Glu Glu Glu Asp Asp Asp Glu
            115                 120                 125

Val Glu Asp Glu Asp Gly Asp Glu Asp Glu Val Glu Leu Asp Asp
130                 135                 140

Ala Val Val Ser Glu Asp Asp Gly Gly Cys Asp Val Cys Ser Val Leu
145                 150                 155                 160

Glu Asp Asp Gly Asn Glu Ala Asn Lys Phe Gln Leu Asp Arg Glu Ser
                165                 170                 175

Phe Ser Lys Leu Leu Arg Arg Val Thr Leu Pro Glu Ser Lys Leu Tyr
            180                 185                 190

Ala Gln Leu Ser Tyr Leu Gly Asn Leu Ala Tyr Ser Ile Ser Lys Ile
            195                 200                 205

Lys Pro Ala Asn Leu Ser Lys Tyr Tyr Gly Leu Arg Phe Val Thr Ser
            210                 215                 220

Ser Ala Glu Lys Thr Glu Ser Ala Leu Lys Ala Glu Asn Gly Glu Val
225                 230                 235                 240

Ser Gly Glu Thr Lys Pro Ile Val Glu Ala Glu Glu Val Glu Glu
                245                 250                 255

Glu Glu Lys Asn Lys Ser Arg Lys Ile Ser Ala Ser Ala Ala Tyr Glu
                260                 265                 270

Ile Val Ala Ser Ala Ala Ser Tyr Leu His Ser Arg Thr Asn Asn Ile
                275                 280                 285

Leu Pro Phe Asn Ser Ser Lys Ala Glu Asn Ser Asp Lys His Asp
            290                 295                 300

Val Asn Leu Thr Asn Ala Glu Ser Ser Ser Asp Val Ala Tyr Ser Val
305                 310                 315                 320

Thr Ser Val Val Ala Ala Glu Glu Asp Val Lys Gln Ala Val Ala Asp
                325                 330                 335

Asp Leu Lys Ser Thr Ile Ser Ser Pro Cys Asp Trp Phe Ile Cys Asp
            340                 345                 350

Asp Asp Gln Ser His Thr Arg Phe Val Val Ile Gln Gly Leu Gly Ala
            355                 360                 365

Ile Val His Arg Gly Ile Tyr Glu Ala Ala Lys Gly Met Tyr Glu Gln
            370                 375                 380

Met Leu Pro Glu Val Lys Ala His Ile Lys Thr His Gly Thr Ser Ala
385                 390                 395                 400

Lys Phe Arg Phe Thr Gly His Ser Leu Gly Gly Ser Leu Ser Leu Leu
```

```
                    405                 410                 415
Leu Asn Leu Met Leu Leu Val Arg Gly Glu Val Pro Ala Ser Ser Leu
                420                 425                 430

Leu Pro Val Ile Thr Tyr Gly Ala Pro Phe Val Leu Cys Gly Gly Asp
            435                 440                 445

Arg Leu Leu Lys Lys Leu Gly Leu Pro Lys Ser His Val Gln Ala Ile
        450                 455                 460

Val Met His Arg Asp Ile Val Pro Arg Ala Phe Ser Cys Asn Tyr Pro
465                 470                 475                 480

Tyr His Val Ala Glu Leu Leu Lys Ala Val Asn Gly Asn Phe Arg Ser
                485                 490                 495

His Pro Cys Leu Asn Lys Gln Ser Met Leu Tyr Ser Pro Met Gly Glu
            500                 505                 510

Leu Leu Ile Leu Gln Pro Asp Glu Thr Phe Ser Pro Gly His Glu Leu
        515                 520                 525

Leu Pro Ser Gly Asn Gly Leu Tyr Leu Leu Thr Ser Asp Phe Glu Ser
    530                 535                 540

Pro Asp Ile Glu Asp Ser Asp Glu Glu Arg Leu Arg Ala Ala Gln Thr
545                 550                 555                 560

Val Phe Leu Asn Thr Pro His Pro Leu Asp Ile Leu Ser Asp Arg Ser
                565                 570                 575

Ala Tyr Gly Ser Ser Gly Thr Ile Gln Arg Asp His Asp Met Asn Ser
            580                 585                 590

Tyr Leu Lys Ala Val Arg Ser Val Arg Lys Glu Val Asn Gln Ile
        595                 600                 605

Arg Arg Ala Lys Arg Glu His Arg Arg Ser Leu Trp Trp Pro Ile Leu
    610                 615                 620

Val Ala Arg Glu Ser Gly Ser Ser Gly Ile Ala Val Ser Asn Gly Gln
625                 630                 635                 640

Ile Asn Gly Gln Asp Phe Ser Gly Met Met Gln Thr Gly Arg Lys Ser
                645                 650                 655

Leu Gln Arg Phe Ser Arg Leu Val Ala Ser Gln His Met Pro Leu Ile
            660                 665                 670

Val Val Met Leu Phe Pro Val Lys Leu Leu Phe Leu Gly Ala Phe Asn
        675                 680                 685

Val Phe Ser Phe Arg
    690

<210> SEQ ID NO 16
<211> LENGTH: 690
<212> TYPE: PRT
<213> ORGANISM: Zea mays

<400> SEQUENCE: 16

Met Asp Val Leu Arg Phe Val Pro Gly Val Arg Pro Pro Leu Pro Thr
1               5                   10                  15

Phe Ala Thr Pro Val Ser Pro Ala Thr Ala Pro Ser Pro His Ala Ala
            20                  25                  30

Ala Ala Ala Ala Ala Pro Gly Pro Gly Phe His Ser Gly Met Leu Gly
        35                  40                  45

Leu Trp Pro Arg Arg Ala Gly Glu Asn Ala Leu Gly Ala Ala Ala Glu
    50                  55                  60

Ala Ala Gly Val Glu Glu Ala Arg Glu Arg Arg Arg Arg Ala Val
65                  70                  75                  80
```

```
Glu Ala Glu Asp Gly Arg Gly Gly Asn Trp Val Leu Gln Ile Leu Arg
                85                  90                  95
Val Gln Ser Ser Pro Pro Ser Pro Ser Arg Asp Asp Gly Arg Cys
        100                 105                 110
Gly Val Asp Asp Gly Gly Ser Val Pro Gly Ser Gly Glu Gly Asp Gly
        115                 120                 125
Ser Ser Gln Arg Cys Val Glu Arg Gly Gly Val Gly Pro Asp Ser Glu
130                 135                 140
Glu Gly Cys Ser Val Ala Asp Gly Glu Glu Leu Asp Arg Ala Ala Phe
145                 150                 155                 160
Ser Arg Leu Leu Arg Lys Val Ser Leu Ala Glu Ala Lys Leu Phe Ser
                165                 170                 175
Glu Met Ser Gly Leu Cys Asn Leu Ala Tyr Met Val Pro Arg Ile Lys
                180                 185                 190
Pro Arg Tyr Leu His Lys Tyr Asn Met Thr Phe Val Thr Ser Ser Val
                195                 200                 205
Glu Glu Arg Ala Lys Leu Pro Asn Pro Cys Asn Gln Glu Asp Gln Asn
        210                 215                 220
Leu Asn Gly Arg Lys Asn Ala Asn Ile Ser Thr Ser Ser Arg His Ser
225                 230                 235                 240
Asp Glu Gln Glu Ser Thr Tyr Gly Ala Thr Ser Glu His Glu Arg Met
                245                 250                 255
Gln Glu Asn Gln Ser Gly Gln Gly Ile Asn Pro Leu Ala Ala Tyr Arg
                260                 265                 270
Ile Ala Ala Ser Ala Ala Ser Tyr Met Gln Ser Arg Ala Met Glu Val
                275                 280                 285
Leu Pro Phe Gly Ser Gln Asn Glu Ala Arg Arg Asp Arg Thr Ile Gln
        290                 295                 300
Ala Ile Val Asn Ala Gln Thr Glu Gly Leu Thr Met Asp Glu Ala Ser
305                 310                 315                 320
Phe Val Ala Thr Thr Asn Ser Met Thr Ser Met Val Ala Ala Lys Glu
                325                 330                 335
Glu Thr Lys Gln Ala Val Ala Asp Asp Leu Asn Ser Ser Arg Ser Cys
        340                 345                 350
Pro Cys Glu Trp Phe Ile Cys Asp Gly Asn Arg Asn Ser Thr Arg Tyr
        355                 360                 365
Phe Val Ile Gln Gly Ser Glu Thr Ile Ala Ser Trp Gln Ala Asn Leu
370                 375                 380
Leu Phe Glu Pro Ile Lys Phe Glu Gly Leu Asp Val Leu Val His Arg
385                 390                 395                 400
Gly Ile Tyr Glu Ala Ala Lys Gly Ile Tyr Gln Gln Met Leu Pro Tyr
                405                 410                 415
Val Lys Ser His Phe Ile Val His Gly Glu Ser Ala Arg Leu Arg Phe
                420                 425                 430
Thr Gly His Ser Leu Gly Gly Ser Leu Ala Leu Leu Val Asn Leu Met
                435                 440                 445
Phe Leu Ile Arg Gly Val Ala Pro Ala Ala Ser Leu Leu Pro Val Ile
450                 455                 460
Thr Phe Gly Ser Pro Ser Val Met Cys Gly Gly Asp Tyr Leu Leu Gln
465                 470                 475                 480
Lys Leu Gly Leu Pro Lys Ser His Val Gln Ser Val Thr Leu His Arg
                485                 490                 495
Asp Ile Val Pro Arg Ala Phe Ser Cys His Tyr Pro Asp His Ile Ala
```

```
                500             505             510
Ser Ile Leu Lys Leu Val Asn Gly Asn Phe Arg Ser His Pro Cys Leu
            515                 520                 525

Thr Asn Gln Lys Leu Leu Tyr Ala Pro Met Gly Glu Val Phe Ile Leu
            530                 535                 540

Gln Pro Asp Glu Lys Leu Ser Pro His His His Leu Leu Pro Ala Gly
545                 550                 555                 560

Ser Gly Leu Tyr Leu Ile Gly Gly Gln Thr Val Asp Ser Gly Thr Ser
                565                 570                 575

Ser Thr Ala Leu Arg Ser Ala Leu Ser Ala Phe Phe Asn Ser Pro His
            580                 585                 590

Pro Leu Glu Ile Leu Arg Asp Ala Gly Ala Tyr Gly Pro Lys Gly Thr
            595                 600                 605

Val Tyr Arg Asp His Asp Val His Ser Tyr Leu Arg Ser Ile Arg Ala
            610                 615                 620

Val Val Arg Lys Glu Met Arg Ala Glu Lys Glu Arg Arg Leu Leu
625                 630                 635                 640

Arg Trp Pro Ile Glu Val Tyr Gly Ala Leu Ala Thr Ile Asp Arg Arg
                645                 650                 655

Gln Val Leu Arg Gln Leu Arg Arg His Ala His Leu Leu Val Val Phe
            660                 665                 670

Leu Leu Pro Ala Lys Leu Leu Phe Leu Gly Val Leu Ser Leu Ile Arg
            675                 680                 685

Pro Thr
    690

<210> SEQ ID NO 17
<211> LENGTH: 688
<212> TYPE: PRT
<213> ORGANISM: Zea mays

<400> SEQUENCE: 17

Met Asp Val Leu Arg Phe Val Arg Ala Ala Ala Pro Gln Pro Ala
1               5                   10                  15

Val Ala Pro Pro Ala Ser Ala Ala Thr Val Pro Ala Gln Arg Gln Arg
                20                  25                  30

Leu Arg Met Trp Pro Arg Gly Gly Gly Asp Gln Pro Pro Val Gly
            35                  40                  45

Ala Ala Ser Thr Arg Gly Ala Glu Pro Arg Ser Pro Pro Asp Glu Glu
        50                  55                  60

Arg Lys Ala Glu Gly Ala Gln Arg Gly Gln Gly Asn Trp Val Leu Gln
65                  70                  75                  80

Met Leu Arg Val Gln Pro Arg Trp Val Asp Ala Asp Ala Glu Ala
                85                  90                  95

Thr Gly Gly Gly Gln Glu Pro Asp Glu Glu Thr Ala Ala Ala Ala
            100                 105                 110

Ala Gly Ala Gly Gly Val Glu Glu Cys Ala Ser Cys Gly Cys Glu
            115                 120                 125

Asp Asp Glu Gly Cys Ala Val Gly Tyr Gly Asp Gly Asp Gly Glu Val
    130                 135                 140

Phe Asp Arg Ala Ser Phe Ser Arg Leu Leu Arg Lys Ala Ser Leu Gly
145                 150                 155                 160

Glu Ala Lys Glu Tyr Ser Met Met Ser Tyr Leu Cys Asn Ile Ala Tyr
                165                 170                 175
```

```
Met Ile Pro Arg Ile Gln Pro Lys Cys Leu Arg Arg Tyr Asn Leu Arg
                180                 185                 190

Phe Val Thr Ser Ser Val Gln Asp Lys Ala Gly Val Ser Asn Pro Asp
        195                 200                 205

Gln Lys Gln Glu Arg Ser Thr Lys Lys Asp Glu Ser Gly Asp Gln Ala
    210                 215                 220

Ser Glu Ala Val Asp Asp Ala Val Pro Arg Arg Gly Leu Gly Thr Ile
225                 230                 235                 240

Lys Pro Phe Gly Ala Tyr His Val Val Ser Ser Ala Ala Ser Tyr Leu
                245                 250                 255

His Ser Arg Ala Met Gly Val Met Pro Phe Gly Pro Gly Asn Gly Val
                260                 265                 270

Lys Asp Asp His Pro Ala Ala Val Thr Ser Leu Val Ser Gly Ala Ser
            275                 280                 285

Gly Asp Gly Leu Ser Val Asp Glu Ala Ser Phe Val Ala Thr Thr Ser
        290                 295                 300

Ser Val Thr Ser Met Val Ala Ala Lys Glu Glu Thr Arg Gln Ala Val
305                 310                 315                 320

Ala Asp Asp Leu Asn Ser Ser Arg Ser Cys Pro Cys Glu Trp Phe Val
                325                 330                 335

Cys Glu Asp Asp Gln Asn Ser Thr Ile Tyr Phe Val Val Gln Gly Ser
                340                 345                 350

Glu Ser Ile Ala Ser Trp Gln Ala Asn Leu Leu Phe Glu Pro Val Lys
            355                 360                 365

Phe Glu Glu Val Asp Val Leu Val His Arg Gly Ile Tyr Glu Ala Ala
        370                 375                 380

Lys Gly Met Tyr His Gln Met Leu Pro Tyr Val Lys Ala His Leu Lys
385                 390                 395                 400

Ser Trp Gly Lys Ser Ala Arg Leu Arg Phe Thr Gly His Ser Leu Gly
                405                 410                 415

Gly Ser Leu Ala Leu Leu Val Asn Leu Met Leu Leu Val Arg Gly Glu
            420                 425                 430

Ala Pro Ala Ser Ser Leu Leu Pro Val Ile Thr Phe Gly Ala Pro Cys
        435                 440                 445

Ile Met Cys Gly Gly Asp His Leu Leu Arg Arg Leu Gly Leu Pro Arg
450                 455                 460

Ser His Val Gln Ser Val Thr Met His Arg Asp Ile Val Pro Arg Val
465                 470                 475                 480

Phe Ser Cys His Tyr Pro Asp His Val Ala Asn Ile Leu Lys Leu Ala
                485                 490                 495

Asn Gly Asn Phe Arg Ser His Pro Cys Leu Ala Asn Gln Lys Leu Leu
            500                 505                 510

Tyr Ala Pro Met Gly Glu Val Leu Ile Leu Gln Pro Asp Glu Arg Leu
        515                 520                 525

Ser Pro His His His Leu Leu Pro Pro Asp Ser Gly Ile Tyr His Leu
        530                 535                 540

Gly Gly Gly Gly Gly Gly Gly Ala Gly Thr Ala Ala Asn Ala Gly
545                 550                 555                 560

Glu Gly Ser Leu Pro Gln Leu Arg Ser Ala Leu Ser Ala Phe Phe Asn
                565                 570                 575

Ser Pro His Pro Leu Glu Ile Leu Lys Asp Gly Ala Ala Tyr Gly Pro
            580                 585                 590

Arg Gly Ser Val Tyr Arg Asp His Asp Val Asn Ser Tyr Leu Arg Ser
```

-continued

```
                595                 600                 605
Val Arg Ala Val Val Arg Lys Glu Ala Arg Arg Ala Arg Glu Ala Glu
    610                 615                 620

Arg Glu Arg Trp Arg Leu Leu Leu Trp Trp Pro Phe Gly Val His Gly
625                 630                 635                 640

Val Ser Ser Ala Ser Ala Gly Arg Arg Gly Gly Leu Val Asp Ala Val
                645                 650                 655

Ser Glu Ala Ala Arg Arg Ala His Leu Leu Leu Val Val Leu Leu Pro
            660                 665                 670

Ala Glu Leu Leu Ala Leu Gly Ala Leu Leu Ala Val Ile Arg Phe Arg
        675                 680                 685

<210> SEQ ID NO 18
<211> LENGTH: 703
<212> TYPE: PRT
<213> ORGANISM: Glycine max

<400> SEQUENCE: 18

Met Glu Thr Met Cys Leu Lys Ser Gly Ile Val Pro Thr Ile Ser Ile
1               5                   10                  15

Ser Gly Ser Leu Asp Ala Arg Ala Asn Pro Ser Gln Val Ser Thr Val
            20                  25                  30

Gly Arg Ser Ala Ser Asp Lys Pro Pro Gln Arg Ser Val Phe Ser Arg
        35                  40                  45

Phe Ser Phe Trp Tyr Pro Leu Glu Ser Leu Trp Pro Arg Gly Asn Asn
    50                  55                  60

Ser Arg Tyr Lys Gly Leu Ala Leu Asp Asp Ala Val Leu Ser Asp Asn
65                  70                  75                  80

Asn Ala Glu Ala Lys Ala Val Gly Asp Asp Gly Thr Glu Arg Gln Thr
                85                  90                  95

Gly Asn Trp Val Leu Lys Ile Leu His Val Lys Ser Leu Trp Glu Gly
            100                 105                 110

Lys Gln Arg Asp Glu Glu Glu Gly Ser Val Arg Asp Gln Thr Gln Thr
        115                 120                 125

Asn Tyr Glu Glu Glu Glu Val Cys Glu Cys Asp Ala Cys Asp Glu
    130                 135                 140

Val Glu Ala Gln Phe Asp Arg Gly Ser Phe Ser Arg Met Leu Arg
145                 150                 155                 160

Arg Val Ser Leu Ala Glu Ser Arg Leu Tyr Ala Gln Met Ser His Leu
                165                 170                 175

Gly Asn Leu Ala Tyr Asp Ile Pro Arg Ile Lys Pro Gly Lys Leu Leu
            180                 185                 190

Lys His Tyr Gly Leu Arg Phe Val Thr Ser Ser Ile Glu Lys Lys Glu
        195                 200                 205

Leu Ala Val Ala Ala Thr Ala Glu Lys Asp Pro Gln Lys Val Gln Thr
    210                 215                 220

Asp Glu Lys Val Asp Glu Lys Glu Arg Lys Asp Pro Lys Asn Gly
225                 230                 235                 240

Glu Tyr Lys Ile Ser Ala Thr Ala Ala Tyr Asn Ile Ala Ala Ser Ala
                245                 250                 255

Ala Thr Tyr Leu His Ser Gln Thr Arg Ser Ile Phe Pro Leu Lys Ser
            260                 265                 270

Ser Asn Ala Val Ala Gly Glu Gly Ser Leu Ala Gly Asn Asn Glu Ser
        275                 280                 285
```

```
Leu Asp Ser Val Asn Met Leu Asn Thr Glu Val Ala Ser Leu Met Ala
290                 295                 300

Thr Thr Asp Ser Val Thr Ala Val Val Ala Ala Lys Glu Glu Val Lys
305                 310                 315                 320

Gln Ala Val Ala Asp Asp Leu Asn Ser Ser His Ser Thr Pro Cys Glu
                325                 330                 335

Trp Phe Val Cys Asp Asn Asp Gln Ser Gly Thr Arg Phe Phe Val Ile
                340                 345                 350

Gln Gly Ser Glu Thr Leu Ala Ser Trp Gln Ala Asn Leu Leu Phe Glu
            355                 360                 365

Pro Ile Lys Phe Glu Gly Leu Asp Val Leu Val His Arg Gly Ile Tyr
370                 375                 380

Glu Ala Ala Lys Gly Ile Tyr Gln Gln Met Leu Pro Glu Val His Ala
385                 390                 395                 400

His Leu Lys Ser Arg Gly Ser Arg Ala Thr Phe Arg Phe Thr Gly His
                405                 410                 415

Ser Leu Gly Gly Ser Leu Ala Leu Leu Val Asn Leu Met Leu Leu Ile
            420                 425                 430

Arg His Glu Val Pro Ile Ser Ser Leu Leu Pro Val Ile Thr Phe Gly
                435                 440                 445

Ser Pro Ser Ile Met Cys Gly Gly Asp Ser Leu Leu Glu Lys Leu Gly
450                 455                 460

Leu Pro Lys Ser His Val Gln Ala Ile Thr Met His Arg Asp Ile Val
465                 470                 475                 480

Pro Arg Ala Phe Ser Cys Asn Tyr Pro Asn His Val Ala Glu Leu Leu
                485                 490                 495

Lys Ala Val Asn Gly Asn Phe Arg Ser His Pro Cys Leu Asn Lys Gln
                500                 505                 510

Lys Leu Leu Tyr Ala Pro Met Gly Asn Leu Leu Ile Leu Gln Pro Asp
            515                 520                 525

Glu Lys Phe Ser Pro Ser His His Leu Leu Pro Ser Gly Ser Gly Leu
                530                 535                 540

Tyr Leu Leu Cys Cys Pro Leu Ser Glu Ser Asn Asp Thr Glu Lys Gln
545                 550                 555                 560

Leu Arg Ala Ala Gln Met Val Phe Leu Asn Ser Pro His Pro Leu Glu
                565                 570                 575

Ile Leu Ser Asp Arg Ser Ala Tyr Gly Ser Gly Ser Val Gln Arg
                580                 585                 590

Asp His Asp Met Asn Ser Tyr Leu Lys Ser Val Arg Thr Val Ile Arg
            595                 600                 605

Gln Glu Leu Asn Gln Ile Arg Lys Ala Lys Arg Glu Gln Arg Arg Lys
610                 615                 620

Val Trp Trp Pro Leu Leu Pro Arg Gly Val Asp Thr Ser Ile Val
625                 630                 635                 640

Ala Gly Arg Ser Met Ile Ser Ile Asn Val Gly Gln Arg Gln Ser Pro
                645                 650                 655

Phe Ser Gly Val Gln Thr Gly Arg Glu Ser Leu Lys Arg Phe Ser Arg
                660                 665                 670

Val Val Thr Ser Gln His Met His Leu Phe Val Leu Leu Phe Pro
                675                 680                 685

Ala Arg Leu Leu Leu Leu Gly Thr Tyr Ser Val Ile Asn Leu Lys
690                 695                 700
```

```
<210> SEQ ID NO 19
<211> LENGTH: 755
<212> TYPE: PRT
<213> ORGANISM: Glycine max

<400> SEQUENCE: 19

Met Glu Thr Val Cys Leu Lys Ser Gly Met Val Pro Thr Ile Ser Ile
1               5                   10                  15

Ser Gly Ser Leu Asp Ala Arg Ala Asn Pro Ser Gln Val Ser Thr Val
            20                  25                  30

Gly Arg Ala Ala Gly Asp Lys Pro Pro Gln Arg Ser Val Phe Ser Arg
        35                  40                  45

Phe Ser Phe Trp Tyr Pro Leu Glu Ser Leu Trp Pro Arg Gly Asn Asn
    50                  55                  60

Ser Arg Tyr Lys Gly Leu Ala Leu Asp Asp Ala Val Leu Ala Asp Asn
65                  70                  75                  80

Asn Ala Glu Ala Lys Ala Val Arg Asp Gly Gln Gly Asp Gly Thr
                85                  90                  95

Glu Arg Gln Thr Gly Asn Trp Val Leu Lys Ile Leu His Val Lys Ser
            100                 105                 110

Val Trp Glu Gly Lys Gln Arg Asn Glu Glu Asp Gly Val His Asp
        115                 120                 125

Gln Thr Gln Thr Asn Phe Asp Glu Glu Val Cys Glu Cys Asp Ala
    130                 135                 140

Cys Gly Val Asp Glu Asp Asp Gly Tyr Cys Glu Glu Glu Ala Glu
145                 150                 155                 160

Phe Asp Arg Gly Ser Phe Ser Arg Met Leu Arg Arg Val Ser Leu Gly
                165                 170                 175

Glu Ala Arg Leu Tyr Ala Gln Met Ser His Leu Gly Asn Leu Ala Tyr
            180                 185                 190

Asp Ile Pro Arg Ile Lys Pro Gly Lys Leu Leu Lys His His Gly Leu
        195                 200                 205

Arg Phe Val Ile Ser Ser Ile Glu Lys Lys Glu Leu Ala Val Ala Ala
    210                 215                 220

Thr Ala Glu Lys Asp Pro Gln Lys Val Gly Ser Ser Ile Glu Lys Lys
225                 230                 235                 240

Glu Phe Ala Ala Ile Ala Glu Lys Asp Pro Gln Lys Val Gly Ser Ser
                245                 250                 255

Thr Glu Lys Lys Glu Phe Ala Ala Ile Ala Glu Lys Asp Pro Gln Lys
            260                 265                 270

Val Glu Thr Asp Glu Lys Val Glu Lys Glu Thr Lys Asp Pro
        275                 280                 285

Lys Asn Ala Gly Tyr Lys Ile Ser Ala Thr Ala Ala Tyr Asn Ile Ala
    290                 295                 300

Ala Ser Ala Ala Thr Tyr Leu His Ser Gln Thr Ser Ser Ile Phe Pro
305                 310                 315                 320

Phe Lys Ser Ser Asn Ala Val Thr Gly Glu Gly Ser Leu Glu Gly Ser
                325                 330                 335

Asn Glu Ser Leu Asp Thr Val Asn Met Leu Asn Thr Glu Val Ala Ser
            340                 345                 350

Leu Met Ala Thr Thr Asp Ser Val Thr Ala Val Val Ala Ala Lys Glu
        355                 360                 365

Glu Val Lys Gln Ala Val Ala Asp Asp Leu Asn Ser Ala His Ser Thr
    370                 375                 380
```

Pro Cys Glu Trp Phe Val Cys Asp Asp Asp Gln Ser Ala Thr Arg Phe
385                 390                 395                 400

Phe Val Ile Gln Gly Ser Glu Thr Leu Ala Ser Trp Gln Ala Asn Leu
            405                 410                 415

Leu Phe Glu Pro Ile Lys Phe Glu Gly Leu Asp Val Leu Val His Arg
        420                 425                 430

Gly Ile Tyr Glu Ala Ala Lys Gly Ile Tyr Gln Gln Met Leu Pro Glu
    435                 440                 445

Val Arg Ala His Leu Lys Ser Arg Gly Ser Arg Ala Thr Phe Arg Phe
450                 455                 460

Thr Gly His Ser Leu Gly Gly Ser Leu Ala Leu Leu Val Asn Leu Met
465                 470                 475                 480

Leu Leu Ile Arg Asn Glu Val Pro Val Ser Ser Leu Leu Pro Val Ile
            485                 490                 495

Thr Phe Gly Ser Pro Ser Ile Met Cys Gly Gly Asp Ser Leu Leu Lys
        500                 505                 510

Lys Leu Gly Leu Pro Arg Ser His Val Gln Ala Ile Thr Met His Arg
    515                 520                 525

Asp Ile Val Pro Arg Ala Phe Ser Cys Asn Tyr Pro Asn His Val Ala
530                 535                 540

Glu Leu Leu Lys Ala Val Asn Gly Asn Phe Arg Ser His Pro Cys Leu
545                 550                 555                 560

Asn Lys Gln Lys Leu Leu Tyr Ala Pro Met Gly Asn Leu Leu Ile Leu
            565                 570                 575

Gln Pro Asp Glu Lys Phe Ser Pro Ser His His Leu Leu Pro Ser Gly
        580                 585                 590

Ser Gly Leu Tyr Leu Leu Cys Cys Pro Leu Ser Glu Ser Asp Asp Thr
    595                 600                 605

Glu Lys Arg Leu Arg Ala Ala Gln Met Val Phe Leu Asn Ser Pro His
610                 615                 620

Pro Leu Glu Ile Leu Ser Asp Arg Ser Ala Tyr Gly Ser Gly Gly Ser
625                 630                 635                 640

Ile Gln Arg Asp His Asp Met Asn Ser Tyr Leu Lys Ser Leu Arg Thr
            645                 650                 655

Val Ile Arg Lys Glu Leu Asn Gln Ile Arg Lys Ala Lys Arg Glu Gln
        660                 665                 670

Arg Arg Lys Val Trp Trp Pro Leu Leu Ser Arg Gly Ala Asp Thr
    675                 680                 685

Ser Ile Val Ala Gly Arg Ser Met Ile Ser Ile Asn Val Gly Gln Arg
690                 695                 700

Gln Ser Pro Phe Ser Ser Val Ile Gln Thr Gly Arg Glu Ser Leu Lys
705                 710                 715                 720

Arg Phe Ser Arg Ile Val Thr Ser Gln His Met His Leu Phe Val Leu
            725                 730                 735

Leu Leu Phe Pro Ala Arg Leu Leu Leu Gly Thr Tyr Ser Val Ile
        740                 745                 750

Asn Leu Lys
    755

<210> SEQ ID NO 20
<211> LENGTH: 675
<212> TYPE: PRT
<213> ORGANISM: Brassica napus

<400> SEQUENCE: 20

```
Met Asp Ser Leu Cys Leu Asn Pro Gly Val Ile Pro Ala Ile Lys Ala
1               5                   10                  15
Val Gly Ser Gly Cys Gly Gly Val Val Glu Val Arg Ala Asn Ala Ser
                20                  25                  30
Gln Lys Arg Arg Pro Ser Gly Ser Ser Phe Lys His Pro Leu Thr Pro
            35                  40                  45
Phe Trp Ser Arg Gly Gly Ile Ala Ser Arg Arg Ser Gly Leu
        50                  55                  60
Gly Leu Asp Asp Ala Val Leu Val Asp Ser Gly Asp Ser Arg Lys Pro
65                  70                  75                  80
Ile Ala Glu Glu Glu Pro Ser Ala Val Glu Met Glu Thr Glu Arg Arg
                85                  90                  95
Asn Gly Ser Trp Ile Leu Lys Ile Leu Asp Val His Ser Met Trp Arg
                100                 105                 110
Asp Glu Glu Ile Glu Glu Glu Glu Glu Glu Leu Asn Asp Ala Val
                115                 120                 125
Leu Pro Glu Asp Asp Gly Val Cys Ser Val Leu Glu Asp Gly Asp Glu
        130                 135                 140
Glu Asn Lys Phe Gln Met His Arg Glu Ser Phe Ser Lys Leu Leu Lys
145                 150                 155                 160
Arg Val Ser Leu Ser Glu Ser Lys Leu Tyr Ala Gln Met Ser Tyr Leu
                165                 170                 175
Gly Asn Leu Ala Tyr Ser Ile Ser Lys Ile Lys Pro Ala Asn Leu Ser
                180                 185                 190
Lys Tyr Tyr Gly Leu Arg Phe Val Thr Ser Ser Ala Glu Lys Thr Glu
                195                 200                 205
Leu Ala Leu Lys Ala Gln Val Ser Ala Glu Thr Lys Pro Lys Glu Glu
210                 215                 220
Asp Glu Glu Val Glu Asp Glu Asn Lys Gly Ala Ser Ala Ala Tyr
225                 230                 235                 240
Glu Val Val Ala Ser Ala Ser Tyr Leu Gln Ser Arg Thr Thr Asn
                245                 250                 255
Ile Leu Pro Phe Pro Ser Ser Lys Asn Asp Asp Glu Glu Glu Ser
                260                 265                 270
Ser Ser Ser Ser Ser Ser Leu Thr Ser Ser Val Thr Cys Val Val Ala
        275                 280                 285
Ala Glu Glu Asp Val Lys Gln Ala Val Ala Asp Asp Leu Lys Phe Thr
        290                 295                 300
Ile Ser Ser Pro Cys Asp Trp Phe Ile Cys Asp Asp Gln Thr Leu
305                 310                 315                 320
Thr Arg Phe Phe Val Ile Gln Gly Ser Glu Ser Leu Ala Ser Trp Gln
                325                 330                 335
Ala Asn Leu Leu Phe Glu Pro Ile Glu Phe Glu Glu Leu Asp Asp Gly
                340                 345                 350
Ala Ile Val His Arg Gly Ile Tyr Glu Ala Ala Lys Gly Met Tyr Glu
                355                 360                 365
Gln Met Leu Pro Glu Val Lys Ala His Ile Lys Ala His Gly Asn Arg
        370                 375                 380
Ala Lys Phe Arg Phe Thr Gly His Ser Leu Gly Gly Ser Leu Ser Leu
385                 390                 395                 400
Leu Leu Asn Leu Met Leu Leu Val Arg Gly Glu Val Pro Ala Ser Ser
                405                 410                 415
```

```
Leu Leu Pro Val Ile Thr Phe Gly Ala Pro Phe Val Leu Cys Gly Gly
            420                 425                 430

Asp Ser Leu Leu Lys Met Leu Gly Leu Pro Lys Ser His Val Gln Ala
        435                 440                 445

Ile Ile Met His Arg Asp Ile Val Pro Arg Ala Phe Ser Cys Asn Tyr
    450                 455                 460

Pro Tyr His Val Ala Glu Leu Leu Lys Ala Val Asn Gly His Phe Arg
465                 470                 475                 480

Ser His Pro Cys Leu Asn Lys Gln Ser Met Leu Tyr Ser Pro Met Gly
                485                 490                 495

Glu Leu Leu Ile Leu Gln Pro Asp Glu Ser Phe Ser Pro Gly His Asp
            500                 505                 510

Leu Leu Pro Ile Gly Asn Gly Leu Tyr Leu Leu Thr Gly Gly Gly Phe
        515                 520                 525

Glu Ser Leu Asp Asp Glu Glu Gln Arg Leu Arg Ala Ala Gln Thr
    530                 535                 540

Val Phe Leu Asn Thr Pro His Pro Leu Asp Ile Leu Ser Asp Arg Ser
545                 550                 555                 560

Ala Tyr Gly Ser Ser Gly Thr Ile Gln Arg Asp His Asp Met Asn Ser
                565                 570                 575

Tyr Leu Lys Ala Val Arg Ser Val Ile Arg Lys Glu Val Ser Gln Ile
            580                 585                 590

Arg Arg Leu Lys Arg Glu His Arg Ser Leu Trp Trp Pro Ile Leu
        595                 600                 605

Val Ala Arg Glu Ser Gly Arg Ser Ser Gly Thr Ala Ile Gly Asn Asn
610                 615                 620

Gly Gln Asp Phe Ser Gly Met Met Lys Thr Gly Arg Lys Ser Leu Gln
625                 630                 635                 640

Arg Phe Ser Arg Leu Val Ala Ser Gln His Met Pro Leu Ile Val Val
                645                 650                 655

Leu Leu Phe Pro Val Lys Leu Leu Phe Leu Glu Ala Phe Asn Val Leu
            660                 665                 670

Ser Phe Arg
        675

<210> SEQ ID NO 21
<211> LENGTH: 649
<212> TYPE: PRT
<213> ORGANISM: Arabidopsis thaliana

<400> SEQUENCE: 21

Met Glu Gly Val Phe Leu Lys Met Ser Val Val Gly Val Ser Pro Met
1               5                   10                  15

Ile Pro Val Gly Pro Ser Ser Phe Ile Cys Ala Ile Gly Gly Ser Val
                20                  25                  30

Glu Glu Lys Ser Thr Ala Ala Ser Leu Pro Arg Trp Val Ser Leu Arg
            35                  40                  45

Arg Leu Arg Pro Leu Glu Phe Leu Arg Ile Gly Gly Lys Arg Glu Glu
        50                  55                  60

Lys Gly Thr Val Arg Asp Asp Asp Ala Val Leu Leu Gly Arg Arg Asp
65                  70                  75                  80

Arg Asn Arg Asn Glu Asn Asp Asn Gly Asn Trp Val Leu Lys Ile Leu
                85                  90                  95

Glu Val Gly Ser Ile Trp Lys Gly Lys Arg Gln Arg Ser Gly Gly Gly
            100                 105                 110
```

```
Gly Gly Gly Glu Glu Asp Glu Glu Glu Val Ala Glu Pro Lys Lys
            115                 120                 125

Lys Glu Asp Leu Cys Glu Cys Asp Phe Cys Arg Ile Asp Asp Asp
        130                 135                 140

Asp Glu Asp Glu Glu Lys Glu Lys Thr Val Phe Glu Phe Ser Glu Met
145                 150                 155                 160

Leu Ser Lys Ile Pro Val Glu Asp Ala Gln Met Phe Ala Lys Leu Ser
                165                 170                 175

Phe Leu Gly Asn Leu Ala Tyr Ser Ile Pro Lys Ile Lys Pro Glu Asn
            180                 185                 190

Leu Leu Lys Tyr Gln Lys Leu Arg Phe Val Thr Ser Ser Ile Glu Lys
            195                 200                 205

Arg Met Ser Leu Lys Val Glu Glu Asn Asn Asn Gly Glu Glu Asp Glu
210                 215                 220

Glu Lys Lys Lys Leu Ile Asn Pro Ala Val Ala Tyr Arg Ile Ala Ala
225                 230                 235                 240

Ser Ala Ala Ser Arg Leu Phe Ser His Ser Lys Ser Val Leu Pro Phe
                245                 250                 255

Gly Ser Ser Lys Arg Gln Asp Asn Glu Glu Ala Ser Leu Leu Ala Thr
            260                 265                 270

Ala Asp Ser Val Thr Ala Val Ala Ala Lys Glu Glu Val Lys Gln
            275                 280                 285

Ala Val Ala Asp Asp Leu Lys Ser Asn Arg Ser Pro Pro Cys Glu Trp
            290                 295                 300

Phe Val Cys Asp Asp Asp Lys Ser Gly Thr Arg Phe Phe Ile Gln
305                 310                 315                 320

Gly Ser Asp Ser Leu Ala Ser Trp Gln Ala Asn Leu Leu Phe Glu Pro
            325                 330                 335

Val Pro Phe Glu Asp Leu Asp Val Leu Val His Arg Gly Ile Tyr Glu
            340                 345                 350

Ala Ala Lys Gly Ile Tyr Glu Gln Met Leu Pro Glu Val His Ala His
            355                 360                 365

Leu Asn Ser Arg Gly Lys Asn Arg Ala Phe Leu Arg Phe Ser Gly His
    370                 375                 380

Ser Leu Gly Gly Ser Leu Ser Leu Leu Val Asn Leu Met Leu Leu Ile
385                 390                 395                 400

Arg Gly Gln Val Pro Ala Ser Ser Leu Leu Pro Val Ile Thr Phe Gly
            405                 410                 415

Ser Pro Cys Ile Met Cys Gly Gly Asp Arg Leu Leu Gln Lys Leu Gly
            420                 425                 430

Leu Pro Lys Ser His Leu Leu Gly Ile Ser Met His Arg Asp Ile Val
    435                 440                 445

Pro Arg Ala Phe Ser Cys Asn Tyr Pro Asn Arg Ala Ala Lys Leu Leu
    450                 455                 460

Lys Ala Leu Asn Gly Asn Phe Arg Asn His Pro Cys Leu Asn Asn Gln
465                 470                 475                 480

Asn Val Leu Tyr Ser Pro Met Gly Lys Leu Leu Ile Leu Gln Pro Ser
                485                 490                 495

Glu Arg Phe Ser Pro Pro His Pro Leu Leu Pro Pro Gly Ser Gly Leu
            500                 505                 510

Tyr Leu Leu Ala Ser Lys Asn Thr Asp Glu Thr Glu Lys Ser Leu Arg
            515                 520                 525
```

```
Ala Ala Lys Ile Leu Phe Phe Asn Ser Pro His Pro Leu Glu Ile Leu
        530                 535                 540

Ser Asp Arg Arg Ser Tyr Gly Ser Glu Gly Lys Ile Lys Arg Asn His
545                 550                 555                 560

Asp Met Ser Ser Tyr Leu Lys Ala Leu Arg His Val Ile Arg Lys Glu
                565                 570                 575

Leu Lys Gln Met Lys Ala Glu Arg Asp Gln Trp Leu Arg Lys Phe Phe
            580                 585                 590

Ile Ile Asn Ile Leu Phe Ser Gly Arg Asp Ser Leu Lys Leu Ile Thr
        595                 600                 605

Arg Phe Val Ala Ser Arg Ser Ser Gln Leu Val Ile Ile Phe Phe Leu
    610                 615                 620

Pro Ile Arg Leu Leu Ile Met Ser Val Tyr Ser Val Val Phe His His
625                 630                 635                 640

Ser Gln Ala His Phe Ser Phe Phe Lys
                645
```

<210> SEQ ID NO 22
<211> LENGTH: 1950
<212> TYPE: DNA
<213> ORGANISM: Arabidopsis thaliana

<400> SEQUENCE: 22

```
atggaggtg ttttcttaaa aatgtcggtg gttggagtat ctccgatgat accggtggga    60
ccttcttctt tcatatgcgc catcggaggc tctgttgagg agaaatcaac ggctgcttct   120
ctgccgcgtt gggtttccct tcgtcgtctt cgtccgcttg agtttcttcg atcggtggt   180
aagagagagg aaaagggaac ggtaagagac gacgacgccg ttttgttgga gagaagggac   240
cggaaccgca acgaaaacga taacggaaac tgggttttga aattttggag gttggatca   300
atctggaaag ggaagagaca cgatcaggt ggcggtggcg gtggagaaga ggacgaggaa   360
gaggaagttg ctgagcctaa gaagaaggaa gatttatgtg aggaatgcga tttctgcagg   420
atcgatgatg atgatgaaga cgaagaaaag gagaagacag tgtttgagtt ctcggagatg   480
ttaagcaaaa ttcctgttga agatgctcag atgtttgcca aattgtcgtt tctggggaat   540
ttggcttatt caatccctaa aatcaagcct gagaatctgt tgaaatatca gaaactgaga   600
ttcgttacat cctcaattga agaggatg agtcttaagg ttgaagagaa caacaatggc   660
gaggaagatg aggagaagaa gaagctaatc aaccctgctg ttgcttacag aatcgctgct   720
tctgcagcct ctcgtctctt ttcccattct aagtctgtgc ttcctttgg atcatctaaa   780
cgtcaagaca cgaagaagc ttctctactg gctactgctg attcggttac tgcagtcgtg   840
gcagccaaag aggaagttaa gcaggccgtc gcagatgatc tcaaatcaaa ccgttcaccg   900
ccttgtgagt ggtttgtatg tgatgatgat aaaagcggca ccaggttctt ctttattcag   960
ggatcagatt cactggcctc atggcaagct aaccttctgt tcgagcctgt tccatttgag  1020
gaccttgatg tgcttgttca cagaggcata tacgaagctg caaaaggaat atacgaacag  1080
atgttaccag aagttcatgc ccacctcaat tcccgtggca agaaccgtgc ttttctcagg  1140
tttagtggac attctctagg cggaagcttg tcattgttag tgaacctcat gcttctgata  1200
agaggtcaag tccctgcttc ttctctgctt ccagtgatca cttttggttc gccttgcatc  1260
atgtgcggag gcgataggct tcttcagaaa cttggtttgc ctaagagtca tcttctcgga  1320
atctcaatgc atagagatat tgttcctcga gcattctcct gcaattaccc taaccgagcc  1380
gcaaagcttc tcaaggcatt gaatggaaac ttccggaacc atccttgtct gaataaccag  1440
```

```
aatgtattgt attctccaat ggggaagctt ctaattctgc aaccatccga gagattctct    1500
cccccacacc ccctgcttcc tcccggaagt ggtctctatc tcttagcatc taagaatacc    1560
gatgaaacag agaaaagtct aagggctgca aagattctct tctttaactc accacacccc    1620
ctagagattc tcagtgatcg tcgttcttac gggtcggaag gaaaaatcaa agaaaccat     1680 gacatgagct cttacctgaa ggccttgagg catgtgatcc ggaaggagct gaagcagatg    1740
aaagctgagc gggatcaatg gctgcgcaag ttctttatta taaacatttt atttagtggg    1800
agagattctt tgaaactcat aacaagattc gtggcatcaa ggagtagtca actagtgatc    1860
atcttctttc tcccaattag attgttaata atgagtgtct acagtgtggt ctttcaccat    1920
tcacaagcac attttagttt cttcaagtga                                     1950
```

<210> SEQ ID NO 23
<211> LENGTH: 643
<212> TYPE: PRT
<213> ORGANISM: Arabidopsis lyrata

<400> SEQUENCE: 23

```
Met Ser Val Gln Gly Val Val Ser Pro Met Ile Pro Val Gly Pro Ser
1               5                   10                  15

Ser Phe Ile Arg Ala Ile Gly Gly Ser Val Glu Glu Lys Ser Thr Ala
                20                  25                  30

Gly Ser Leu Pro Arg Trp Val Ser Arg Arg Pro Arg Pro Leu Glu
            35                  40                  45

Phe Leu Arg Ile Gly Gly Lys Arg Asp Glu Lys Gly Pro Val Arg Asp
        50                  55                  60

Asp Ala Ala Val Leu Leu Glu Arg Glu Arg Val Gly Asn Asp Asn
65                  70                  75                  80

Gly Asn Trp Val Leu Lys Ile Leu Glu Val Gly Ser Ile Trp Lys Gly
                85                  90                  95

Lys Arg Gln Arg Ser Gly Gly Gly Glu Glu Asp Asp Glu Glu Gln
            100                 105                 110

Val Thr Glu Ser Lys Asn Asp Lys Glu Asp Leu Cys Glu Glu Cys Asp
        115                 120                 125

Phe Cys Arg Val Asp Asp Asp Asp Glu Glu Glu Lys Glu Glu Thr
    130                 135                 140

Val Phe Gly Arg Glu Glu Phe Ser Glu Met Leu Ser Lys Val Pro Val
145                 150                 155                 160

Glu Asp Ala Gln Ile Phe Ala Lys Leu Ser Phe Leu Gly Asn Leu Ala
                165                 170                 175

Tyr Ser Ile Pro Lys Ile Lys Pro Asp Asn Leu Leu Lys Tyr Gln Lys
            180                 185                 190

Leu Arg Phe Val Thr Ser Ser Ile Glu Lys Arg Thr Ser Leu Lys Val
        195                 200                 205

Glu Glu Asn Asn Asn Gly Glu Glu Glu Glu Lys Lys Lys Leu Ile
    210                 215                 220

Asn Pro Ala Val Ala Tyr Arg Ile Ala Ala Ser Ala Ala Ser Arg Leu
225                 230                 235                 240

Phe Ser His Ser Lys Ser Val Leu Pro Phe Gly Ser Lys Arg Gln
                245                 250                 255

Asp Asn Glu Glu Ala Ser Leu Leu Ala Thr Ala Asp Ser Val Thr Ala
            260                 265                 270

Val Val Ala Ala Lys Glu Glu Val Lys Gln Ala Val Ala Asp Asp Leu
```

```
            275                 280                 285
Lys Ser Asn Arg Ser Pro Pro Cys Glu Trp Phe Val Cys Asp Asp Asp
290                 295                 300
Lys Ser Gly Thr Arg Phe Phe Phe Ile Gln Gly Ser Asp Ser Leu Ala
305                 310                 315                 320
Ser Trp Gln Ala Asn Leu Leu Phe Glu Pro Val Pro Phe Glu Asp Leu
                    325                 330                 335
Asp Val Leu Val His Arg Gly Ile Tyr Glu Ala Ala Lys Gly Leu Tyr
                340                 345                 350
Glu Gln Met Leu Pro Glu Val His Ala His Leu Asn Ser Arg Gly Arg
                    355                 360                 365
His Arg Ala Phe Leu Arg Phe Ser Gly His Ser Leu Gly Gly Ser Leu
                370                 375                 380
Ser Leu Leu Val Asn Leu Met Leu Leu Ile Arg Gly Gln Val Pro Ala
385                 390                 395                 400
Ser Ser Leu Leu Pro Val Ile Thr Phe Gly Ser Pro Cys Ile Met Cys
                    405                 410                 415
Gly Gly Asp Arg Leu Leu Gln Lys Leu Gly Leu Pro Lys Ser His Leu
                420                 425                 430
Leu Gly Ile Ser Met His Arg Asp Ile Val Pro Arg Ala Phe Ser Cys
                435                 440                 445
Asn Tyr Pro Asn Arg Ala Ala Asn Ile Leu Lys Ala Leu Asn Gly Asn
450                 455                 460
Phe Arg Asn His Pro Cys Leu Asn Asn Gln Asn Val Leu Tyr Ser Pro
465                 470                 475                 480
Met Gly Lys Leu Leu Ile Leu Gln Pro Ser Glu Arg Phe Ser Pro Pro
                    485                 490                 495
His Pro Leu Leu Pro Pro Gly Ser Gly Ile Tyr Leu Leu Thr Ser Lys
                500                 505                 510
Asn Thr Asp Glu Thr Glu Lys Ser Leu Arg Ala Ala Lys Ser Val Phe
                515                 520                 525
Phe Asn Ser Pro His Pro Leu Glu Ile Leu Ser Asp Arg Arg Ser Tyr
530                 535                 540
Gly Ser Glu Gly Lys Ile Lys Arg Asn His Asp Met Ser Ser Tyr Leu
545                 550                 555                 560
Lys Ala Leu Arg His Val Ile Arg Lys Glu Leu Lys Gln Ile Lys Ala
                    565                 570                 575
Glu Arg Asp Gln Trp Arg Arg Lys Phe Phe Ile Ile Asn Ile Leu Phe
                580                 585                 590
Thr Gly Arg Asp Ser Leu Lys Leu Ile Thr Arg Phe Val Ala Ser Arg
                595                 600                 605
Ser Ser Gln Leu Val Ile Ile Phe Phe Leu Pro Ile Arg Leu Leu Ile
                610                 615                 620
Met Asn Val Tyr Gly Val Val Phe His His Ser Gln Ala His Phe Ser
625                 630                 635                 640
Phe Phe Lys
```

<210> SEQ ID NO 24
<211> LENGTH: 628
<212> TYPE: PRT
<213> ORGANISM: Brassica napus

<400> SEQUENCE: 24

Met Asp Ser Gly Val Phe Leu Lys Met Ser Val Gln Cys Val Ser Pro

-continued

```
1               5                   10                  15
Lys Ile Pro Val Gly Pro Ser Met Ile Arg Ala Ile Gly Gly Ser Val
                20                  25                  30

Glu Glu Arg Arg Thr Ser Gly Ser Leu Pro Arg Arg Val Ser Arg Arg
                35                  40                  45

Pro Leu Glu Phe Leu Arg Ile Gly Gly Lys Gly Arg Lys Glu Ser Ala
            50                  55                  60

Arg Asp Asp Asn Asp Ala Val Leu Leu Glu Arg Glu Arg Asn Gly
65                  70                  75                  80

Asn Trp Val Leu Lys Ile Leu Glu Val Gly Ser Ile Trp Lys Gly Lys
                85                  90                  95

Arg Gln Arg Ser Gly Gly Asp Gly Glu Asp Glu Glu Gly Ser
                100                 105                 110

Lys Lys Asp Glu Ser Cys Asp Phe Cys Arg Ile Asp Glu Glu Glu
                115                 120                 125

Glu Glu Met Val Phe Asp Arg Glu Asn Phe Ser Lys Met Leu Met Lys
                130                 135                 140

Ile Pro Leu Asp Asp Ala Gln Met Phe Ala Lys Leu Ser Tyr Leu Gly
145                 150                 155                 160

Asn Leu Ala Tyr Ser Ile Pro Asn Ile Lys Pro Glu Asn Leu Leu Lys
                165                 170                 175

Tyr Gln Lys Leu Arg Phe Val Thr Ser Ser Ile Glu Lys Arg Ser Ser
                180                 185                 190

Leu Asp Gln Gln Asp Glu Ile Ser Asn Glu Glu Glu Glu Glu Glu
                195                 200                 205

Lys Lys Leu Ile Asn Pro Ala Ala Tyr Arg Ile Ala Ala Ser Ala
210                 215                 220

Ala Ser Arg Leu Phe Ser His Ser Lys Ser Val Leu Pro Phe Gly Arg
225                 230                 235                 240

Arg Glu Asn Glu Ala Ser Leu Met Ala Thr Ala Asp Ser Val Thr Ala
                245                 250                 255

Val Val Ala Ala Glu Glu Val Lys Gln Ala Val Ala Asp Asp Leu
                260                 265                 270

Lys Ser Asn His Ser Pro Pro Cys Glu Trp Phe Val Cys Asp Asp Asp
                275                 280                 285

Lys Thr Ser Thr Arg Phe Phe Phe Ile Gln Gly Ser Asp Ser Leu Ala
                290                 295                 300

Ser Trp Gln Ala Asn Leu Leu Phe Glu Pro Val Pro Phe Glu Asp Phe
305                 310                 315                 320

Asp Val Pro Val His Arg Gly Ile Tyr Glu Ala Ala Lys Gly Ile Tyr
                325                 330                 335

Glu Gln Met Leu Pro Glu Val His Ala His Leu Asn Ser Arg Gly Lys
                340                 345                 350

Asn Arg Ala Phe Leu Arg Phe Ser Gly His Ser Leu Gly Gly Ser Leu
                355                 360                 365

Ser Leu Leu Val Asn Leu Met Leu Leu Ile Arg Gly Gln Val Pro Ala
                370                 375                 380

Ser Ser Leu Leu Pro Val Ile Thr Phe Gly Ser Pro Cys Ile Met Cys
385                 390                 395                 400

Gly Gly Asp Arg Leu Leu Glu Lys Leu Gly Leu Pro Lys Ser His Leu
                405                 410                 415

Leu Gly Ile Ser Met His Arg Asp Ile Val Pro Arg Ala Phe Ser Cys
                420                 425                 430
```

Ser Tyr Pro Asn Arg Ala Ala Lys Leu Leu Lys Ala Leu Asn Arg Asn
        435                 440                 445

Phe Arg Asn His Pro Cys Leu Asn Asn Gln Asn Leu Leu Tyr Ser Pro
    450                 455                 460

Met Gly Lys Leu Leu Ile Leu Gln Pro Ser Glu Arg Phe Ser Pro Pro
465                 470                 475                 480

His Pro Leu Leu Pro Pro Gly Ser Gly Leu Tyr Val Leu Thr Ser Lys
                485                 490                 495

Asn Thr Asp Glu Thr Glu Lys Gly Leu Arg Ala Ala Lys Thr Val Phe
            500                 505                 510

Phe Asn Ser Pro His Pro Leu Glu Ile Leu Ser Asp Arg Arg Ser Tyr
        515                 520                 525

Gly Ser Glu Gly Lys Ile Lys Arg Asn His Asp Met Ser Ser Tyr Leu
    530                 535                 540

Lys Ala Leu Arg His Val Ile Arg Lys Glu Leu Lys Gln Ile Lys Ala
545                 550                 555                 560

Glu Arg Asp Gln Trp Arg Ala Lys Phe Leu Ile Val Asn Ile Ile Cys
                565                 570                 575

Thr Gly Arg Asp Ser Leu Lys Leu Ile Ala Arg Phe Val Ala Ser Arg
            580                 585                 590

Ser Ser Gln Leu Val Ile Ile Phe Phe Leu Pro Ile Arg Leu Leu Thr
        595                 600                 605

Thr Ser Val Tyr Gly Val Leu Leu His His Ser His Glu His Phe Phe
    610                 615                 620

Ser Phe Phe Lys
625

<210> SEQ ID NO 25
<211> LENGTH: 691
<212> TYPE: PRT
<213> ORGANISM: Zea mays

<400> SEQUENCE: 25

Met Asp Val Leu Arg Phe Val Pro Gly Val Arg Pro Pro Leu Pro Thr
1               5                   10                  15

Phe Ala Thr Pro Val Ser Pro Ala Thr Ala Pro Ser Pro His Ala Ala
            20                  25                  30

Ala Ala Ala Ala Ala Pro Gly Pro Gly Phe His Ser Gly Met Leu Gly
        35                  40                  45

Leu Trp Pro Arg Arg Ala Gly Glu Asn Ala Leu Gly Ala Ala Ala Glu
    50                  55                  60

Ala Ala Gly Val Glu Glu Ala Arg Glu Arg Arg Arg Arg Arg Ala Val
65                  70                  75                  80

Glu Ala Glu Asp Gly Arg Gly Asn Trp Val Leu Gln Ile Leu Arg
            85                  90                  95

Val Gln Ser Ser Pro Pro Ser Pro Ser Arg Asp Asp Gly Arg Cys
        100                 105                 110

Gly Val Asp Asp Gly Gly Ser Val Pro Gly Ser Gly Glu Asp Gly
            115                 120                 125

Ser Ser Gln Arg Cys Val Glu Arg Gly Val Gly Pro Asp Ser Glu
        130                 135                 140

Glu Gly Cys Ser Val Ala Asp Gly Glu Glu Leu Asp Arg Ala Ala Phe
145                 150                 155                 160

Ser Arg Leu Leu Arg Lys Val Ser Leu Ala Glu Ala Lys Leu Phe Ser

-continued

```
                165                 170                 175
Glu Met Ser Gly Leu Cys Asn Leu Ala Tyr Met Val Pro Arg Ile Lys
            180                 185                 190

Pro Arg Tyr Leu His Lys Tyr Asn Met Thr Phe Val Thr Ser Ser Val
        195                 200                 205

Glu Glu Arg Ala Lys Leu Pro Asn Pro Cys Asn Gln Glu Asp Gln Asn
    210                 215                 220

Leu Asn Gly Arg Lys Asn Ala Asn Ile Ser Thr Ser Ser Arg His Ser
225                 230                 235                 240

Asp Glu Gln Glu Ser Thr Tyr Gly Ala Thr Ser Glu His Glu Arg Met
                245                 250                 255

Gln Glu Asn Gln Ser Gly Gln Gly Ile Asn Pro Leu Ala Ala Tyr Arg
            260                 265                 270

Ile Ala Ala Ser Ala Ala Ser Tyr Met Gln Ser Arg Ala Met Glu Val
        275                 280                 285

Leu Pro Phe Gly Ser Gln Asn Glu Ala Arg Arg Asp Val Arg Thr Ile
    290                 295                 300

Gln Ala Ile Val Asn Ala Gln Thr Glu Gly Leu Thr Met Asp Glu Ala
305                 310                 315                 320

Ser Phe Val Ala Thr Thr Asn Ser Met Thr Ser Met Val Ala Ala Lys
                325                 330                 335

Glu Glu Thr Lys Gln Ala Val Ala Asp Asp Leu Asn Ser Ser Arg Ser
            340                 345                 350

Cys Pro Cys Glu Trp Phe Ile Cys Asp Gly Asn Arg Asn Ser Thr Arg
        355                 360                 365

Tyr Phe Val Ile Gln Gly Ser Glu Thr Ile Ala Ser Trp Gln Ala Asn
    370                 375                 380

Leu Leu Phe Glu Pro Ile Lys Phe Glu Gly Leu Asp Val Leu Val His
385                 390                 395                 400

Arg Gly Ile Tyr Glu Ala Ala Lys Gly Ile Tyr Gln Gln Met Leu Pro
                405                 410                 415

Tyr Val Lys Ser His Phe Ile Val His Gly Glu Ser Ala Arg Leu Arg
            420                 425                 430

Phe Thr Gly His Ser Leu Gly Gly Ser Leu Ala Leu Leu Val Asn Leu
        435                 440                 445

Met Phe Leu Ile Arg Gly Val Ala Pro Ala Ala Ser Leu Leu Pro Val
    450                 455                 460

Ile Thr Phe Gly Ser Pro Ser Val Met Cys Gly Gly Asp Tyr Leu Leu
465                 470                 475                 480

Gln Lys Leu Gly Leu Pro Lys Ser His Val Gln Ser Val Thr Leu His
                485                 490                 495

Arg Asp Ile Val Pro Arg Ala Phe Ser Cys His Tyr Pro Asp His Ile
            500                 505                 510

Ala Ser Ile Leu Lys Leu Val Asn Gly Asn Phe Arg Ser His Pro Cys
        515                 520                 525

Leu Thr Asn Gln Lys Leu Leu Tyr Ala Pro Met Gly Glu Val Phe Ile
    530                 535                 540

Leu Gln Pro Asp Glu Lys Leu Ser Pro His His Leu Leu Pro Ala
545                 550                 555                 560

Gly Ser Gly Leu Tyr Leu Ile Gly Gly Gln Thr Val Asp Ser Gly Thr
                565                 570                 575

Ser Ser Thr Ala Leu Arg Ser Ala Leu Ser Ala Phe Phe Asn Ser Pro
            580                 585                 590
```

```
His Pro Leu Glu Ile Leu Arg Asp Ala Gly Ala Tyr Gly Pro Lys Gly
            595                 600                 605

Thr Val Tyr Arg Asp His Asp Val His Ser Tyr Leu Arg Ser Ile Arg
    610                 615                 620

Ala Val Val Arg Lys Glu Met Arg Ala Glu Lys Glu Arg Arg Arg Leu
625                 630                 635                 640

Leu Arg Trp Pro Ile Glu Val Tyr Gly Ala Leu Ala Thr Ile Asp Arg
                645                 650                 655

Arg Gln Val Leu Arg Gln Leu Arg Arg His Ala His Leu Leu Val Val
                660                 665                 670

Phe Leu Leu Pro Ala Lys Leu Leu Phe Leu Gly Val Leu Ser Leu Ile
            675                 680                 685

Arg Pro Thr
        690

<210> SEQ ID NO 26
<211> LENGTH: 688
<212> TYPE: PRT
<213> ORGANISM: Zea mays

<400> SEQUENCE: 26

Met Asp Val Leu Arg Phe Val Arg Ala Ala Ala Pro Gln Pro Ala
1               5                   10                  15

Val Ala Pro Pro Ala Ser Ala Ala Thr Val Pro Ala Gln Arg Gln Arg
            20                  25                  30

Leu Arg Met Trp Pro Arg Gly Gly Asp Gln Pro Pro Val Gly
            35                  40                  45

Ala Ala Ser Thr Arg Gly Ala Glu Pro Arg Ser Pro Pro Asp Glu Glu
        50                  55                  60

Arg Lys Ala Glu Gly Ala Gln Arg Gly Gln Gly Asn Trp Val Leu Gln
65                  70                  75                  80

Met Leu Arg Val Gln Pro Arg Trp Val Asp Ala Asp Ala Glu Ala
                85                  90                  95

Thr Gly Gly Gly Gln Glu Pro Asp Glu Glu Thr Ala Ala Ala Ala
            100                 105                 110

Ala Gly Ala Gly Gly Val Glu Glu Cys Ala Ser Cys Gly Cys Gly Glu
        115                 120                 125

Asp Asp Glu Gly Cys Ala Val Gly Tyr Gly Asp Gly Asp Gly Glu Val
    130                 135                 140

Phe Asp Arg Ala Ser Phe Ser Arg Leu Leu Arg Lys Ala Ser Leu Gly
145                 150                 155                 160

Glu Ala Lys Glu Tyr Ser Met Met Ser Tyr Leu Cys Asn Ile Ala Tyr
                165                 170                 175

Met Ile Pro Arg Ile Gln Pro Lys Cys Leu Arg Arg Tyr Asn Leu Arg
                180                 185                 190

Phe Val Thr Ser Ser Val Gln Asp Lys Ala Gly Val Ser Asn Pro Asp
            195                 200                 205

Gln Lys Gln Glu Arg Ser Thr Lys Lys Asp Glu Ser Gly Asp Gln Ala
    210                 215                 220

Ser Glu Ala Val Asp Asp Ala Val Pro Arg Arg Gly Leu Gly Thr Ile
225                 230                 235                 240

Lys Pro Phe Gly Ala Tyr His Val Val Ser Ser Ala Ala Ser Tyr Leu
                245                 250                 255

His Ser Arg Ala Met Gly Val Met Pro Phe Gly Pro Gly Asn Gly Val
```

```
            260                 265                 270
Lys Asp Asp His Pro Ala Ala Val Thr Ser Leu Val Ser Gly Ala Ser
            275                 280                 285

Gly Asp Gly Leu Ser Val Asp Glu Ala Ser Phe Val Ala Thr Thr Ser
            290                 295                 300

Ser Val Thr Ser Met Val Ala Ala Lys Glu Glu Thr Arg Gln Ala Val
305                 310                 315                 320

Ala Asp Asp Leu Asn Ser Ser Arg Ser Cys Pro Cys Glu Trp Phe Val
                325                 330                 335

Cys Glu Asp Asp Gln Asn Ser Thr Ile Tyr Phe Val Gln Gly Ser
            340                 345                 350

Glu Ser Ile Ala Ser Trp Gln Ala Asn Leu Leu Phe Glu Pro Val Lys
            355                 360                 365

Phe Glu Glu Val Asp Val Leu Val His Arg Gly Ile Tyr Glu Ala Ala
            370                 375                 380

Lys Gly Met Tyr His Gln Met Leu Pro Tyr Val Lys Ala His Leu Lys
385                 390                 395                 400

Ser Trp Gly Lys Ser Ala Arg Leu Arg Phe Thr Gly His Ser Leu Gly
                405                 410                 415

Gly Ser Leu Ala Leu Leu Val Asn Leu Met Leu Leu Val Arg Gly Glu
            420                 425                 430

Ala Pro Ala Ser Ser Leu Leu Pro Val Ile Thr Phe Gly Ala Pro Cys
            435                 440                 445

Ile Met Cys Gly Gly Asp His Leu Leu Arg Arg Leu Gly Leu Pro Arg
450                 455                 460

Ser His Val Gln Ser Val Thr Met His Arg Asp Ile Val Pro Arg Val
465                 470                 475                 480

Phe Ser Cys His Tyr Pro Asp His Val Ala Asn Ile Leu Lys Leu Ala
                485                 490                 495

Asn Gly Asn Phe Arg Ser His Pro Cys Leu Ala Asn Gln Lys Leu Leu
                500                 505                 510

Tyr Ala Pro Met Gly Glu Val Leu Ile Leu Gln Pro Asp Glu Arg Leu
            515                 520                 525

Ser Pro His His His Leu Leu Pro Pro Asp Ser Gly Ile Tyr His Leu
            530                 535                 540

Gly Gly Gly Gly Gly Gly Gly Ala Gly Thr Ala Ala Asn Ala Gly
545                 550                 555                 560

Glu Gly Ser Leu Pro Gln Leu Arg Ser Ala Leu Ser Ala Phe Phe Asn
                565                 570                 575

Ser Pro His Pro Leu Glu Ile Leu Lys Asp Gly Ala Ala Tyr Gly Pro
            580                 585                 590

Arg Gly Ser Val Tyr Arg Asp His Asp Val Asn Ser Tyr Leu Arg Ser
            595                 600                 605

Val Arg Ala Val Arg Lys Glu Ala Arg Ala Arg Glu Ala Glu
            610                 615                 620

Arg Glu Arg Trp Arg Leu Leu Trp Trp Pro Phe Gly Val His Gly
625                 630                 635                 640

Val Ser Ser Ala Ser Ala Gly Arg Gly Gly Leu Val Asp Ala Val
                645                 650                 655

Ser Glu Ala Ala Arg Arg Ala His Leu Leu Leu Val Val Leu Leu Pro
            660                 665                 670

Ala Glu Leu Leu Ala Leu Gly Ala Leu Leu Ala Val Ile Arg Phe Arg
            675                 680                 685
```

```
<210> SEQ ID NO 27
<211> LENGTH: 704
<212> TYPE: PRT
<213> ORGANISM: Glycine max

<400> SEQUENCE: 27

Met Glu Thr Met Cys Leu Lys Ser Gly Ile Val Pro Thr Ile Ser Ile
1               5                   10                  15

Ser Gly Ser Leu Asp Ala Arg Ala Asn Pro Ser Gln Val Ser Thr Val
            20                  25                  30

Gly Arg Ser Ala Ser Asp Lys Pro Pro Gln Arg Ser Val Phe Ser Arg
        35                  40                  45

Phe Ser Phe Trp Tyr Pro Leu Glu Ser Leu Trp Pro Arg Gly Asn Asn
    50                  55                  60

Ser Arg Tyr Lys Gly Leu Ala Leu Asp Asp Ala Val Leu Ser Asp Asn
65                  70                  75                  80

Asn Ala Glu Ala Lys Ala Val Gly Asp Asp Gly Thr Glu Arg Gln Thr
                85                  90                  95

Gly Asn Trp Val Leu Lys Ile Leu His Val Lys Ser Leu Trp Glu Gly
            100                 105                 110

Lys Gln Arg Asp Glu Glu Gly Ser Val Arg Asp Gln Thr Gln Thr
        115                 120                 125

Asn Tyr Glu Glu Glu Glu Val Cys Glu Cys Asp Ala Cys Asp Glu
    130                 135                 140

Val Glu Glu Ala Gln Phe Asp Arg Gly Ser Phe Ser Arg Met Leu Arg
145                 150                 155                 160

Arg Val Ser Leu Ala Glu Ser Arg Leu Tyr Ala Gln Met Ser His Leu
                165                 170                 175

Gly Asn Leu Ala Tyr Asp Ile Pro Arg Ile Lys Pro Gly Lys Leu Leu
            180                 185                 190

Lys His Tyr Gly Leu Arg Phe Val Thr Ser Ser Ile Glu Lys Lys Glu
        195                 200                 205

Leu Ala Val Ala Ala Thr Ala Glu Lys Asp Pro Gln Lys Val Gln Thr
    210                 215                 220

Asp Glu Lys Val Asp Glu Lys Glu Arg Lys Asp Pro Lys Asn Gly
225                 230                 235                 240

Glu Tyr Lys Ile Ser Ala Thr Ala Ala Tyr Asn Ile Ala Ala Ser Ala
                245                 250                 255

Ala Thr Tyr Leu His Ser Gln Thr Arg Ser Ile Phe Pro Leu Lys Ser
            260                 265                 270

Ser Asn Ala Val Ala Gly Glu Gly Ser Leu Ala Gly Asn Asn Glu Ser
        275                 280                 285

Leu Asp Ser Val Asn Met Leu Asn Thr Glu Val Ala Ser Leu Met Ala
    290                 295                 300

Thr Thr Asp Ser Val Thr Ala Val Val Ala Ala Lys Glu Glu Val Lys
305                 310                 315                 320

Gln Ala Val Ala Asp Asp Leu Asn Ser Ser His Ser Thr Pro Cys Glu
                325                 330                 335

Trp Phe Val Cys Asp Asn Asp Gln Ser Gly Thr Arg Phe Phe Val Ile
            340                 345                 350

Gln Gly Ser Glu Thr Leu Ala Ser Trp Gln Ala Asn Leu Leu Phe Glu
        355                 360                 365

Pro Ile Lys Phe Glu Gly Leu Asp Val Leu Val His Arg Gly Ile Tyr
```

```
                    370                 375                 380
        Glu Ala Ala Lys Gly Ile Tyr Gln Gln Met Leu Pro Glu Val His Ala
        385                 390                 395                 400

His Leu Lys Ser Arg Gly Ser Arg Ala Thr Phe Arg Phe Thr Gly His
                        405                 410                 415

Ser Leu Gly Gly Ser Leu Ala Leu Leu Val Asn Leu Met Leu Leu Ile
                    420                 425                 430

Arg His Glu Val Pro Ile Ser Ser Leu Leu Pro Val Ile Thr Phe Gly
                    435                 440                 445

Ser Pro Ser Ile Met Cys Gly Gly Asp Ser Leu Leu Glu Lys Leu Gly
        450                 455                 460

Leu Pro Lys Ser His Val Gln Ala Ile Thr Met His Arg Asp Ile Val
        465                 470                 475                 480

Pro Arg Ala Phe Ser Cys Asn Tyr Pro Asn His Val Ala Glu Leu Leu
                        485                 490                 495

Lys Ala Val Asn Gly Asn Phe Arg Ser His Pro Cys Leu Asn Lys Gln
                    500                 505                 510

Lys Leu Leu Tyr Ala Pro Met Gly Asn Leu Leu Ile Leu Gln Pro Asp
                    515                 520                 525

Glu Lys Phe Ser Pro Ser His His Leu Leu Pro Ser Gly Ser Gly Leu
        530                 535                 540

Tyr Leu Leu Cys Cys Pro Leu Ser Glu Ser Asn Asp Thr Glu Lys Gln
        545                 550                 555                 560

Leu Arg Ala Ala Gln Met Val Phe Leu Asn Ser Pro His Pro Leu Glu
                        565                 570                 575

Ile Leu Ser Asp Arg Ser Ala Tyr Gly Ser Gly Ser Val Gln Arg
                    580                 585                 590

Asp His Asp Met Asn Ser Tyr Leu Lys Ser Val Arg Thr Val Ile Arg
                    595                 600                 605

Gln Glu Leu Asn Gln Ile Arg Lys Ala Lys Arg Glu Gln Arg Lys
        610                 615                 620

Val Trp Trp Pro Leu Leu Leu Pro Arg Gly Val Asp Thr Ser Ile Val
        625                 630                 635                 640

Ala Gly Arg Ser Met Ile Ser Ile Asn Val Gly Gln Arg Gln Ser Pro
                        645                 650                 655

Phe Ser Gly Val Ile Gln Thr Gly Arg Glu Ser Leu Lys Arg Phe Ser
                    660                 665                 670

Arg Val Val Thr Ser Gln His Met His Leu Phe Val Leu Leu Leu Phe
                    675                 680                 685

Pro Ala Arg Leu Leu Leu Leu Gly Thr Tyr Ser Val Ile Asn Leu Lys
        690                 695                 700

<210> SEQ ID NO 28
<211> LENGTH: 323
<212> TYPE: PRT
<213> ORGANISM: Arabidopsis thaliana

<400> SEQUENCE: 28

Met Ala Val Ser Leu Pro Thr Lys Tyr Pro Leu Arg Pro Ile Thr Asn
        1               5                   10                  15

Ile Pro Lys Ser His Arg Pro Ser Leu Leu Arg Val Arg Val Thr Cys
                    20                  25                  30

Ser Val Thr Thr Thr Lys Pro Gln Pro Asn Arg Glu Lys Leu Leu Val
                    35                  40                  45
```

```
Glu Gln Arg Thr Val Asn Leu Pro Leu Ser Asn Asp Gln Ser Leu Gln
 50                  55                  60
Ser Thr Lys Pro Arg Pro Asn Arg Glu Lys Leu Val Val Glu Gln Arg
 65                  70                  75                  80
Leu Ala Ser Pro Pro Leu Ser Asn Asp Pro Thr Leu Lys Ser Thr Trp
                 85                  90                  95
Thr His Arg Leu Trp Val Ala Ala Gly Cys Thr Thr Leu Phe Val Ser
            100                 105                 110
Leu Ala Lys Ser Val Ile Gly Gly Phe Asp Ser His Leu Cys Leu Glu
        115                 120                 125
Pro Ala Leu Ala Gly Tyr Ala Gly Tyr Ile Leu Ala Asp Leu Gly Ser
130                 135                 140
Gly Val Tyr His Trp Ala Ile Asp Asn Tyr Gly Asp Glu Ser Thr Pro
145                 150                 155                 160
Val Val Gly Thr Gln Ile Glu Ala Phe Gln Gly His His Lys Trp Pro
                165                 170                 175
Trp Thr Ile Thr Arg Arg Gln Phe Ala Asn Asn Leu His Ala Leu Ala
            180                 185                 190
Gln Val Ile Thr Phe Thr Val Leu Pro Leu Asp Leu Ala Phe Asn Asp
        195                 200                 205
Pro Val Phe His Gly Phe Val Cys Thr Phe Ala Phe Cys Ile Leu Phe
210                 215                 220
Ser Gln Gln Phe His Ala Trp Ala His Gly Thr Lys Ser Lys Leu Pro
225                 230                 235                 240
Pro Leu Val Val Ala Leu Gln Asp Met Gly Leu Leu Val Ser Arg Arg
                245                 250                 255
Gln His Ala Glu His His Arg Ala Pro Tyr Asn Asn Asn Tyr Cys Ile
            260                 265                 270
Val Ser Gly Ala Trp Asn Asn Val Leu Asp Glu Ser Lys Val Phe Glu
        275                 280                 285
Ala Leu Glu Met Val Phe Tyr Phe Gln Leu Gly Val Arg Pro Arg Ser
290                 295                 300
Trp Ser Glu Pro Asn Ser Asp Trp Ile Glu Glu Thr Glu Ile Ser Asn
305                 310                 315                 320

Asn Gln Ala

<210> SEQ ID NO 29
<211> LENGTH: 1150
<212> TYPE: DNA
<213> ORGANISM: Arabidopsis thaliana

<400> SEQUENCE: 29
tttgacaact tcacctgca  atcactctca atggctgtat cacttccaac caagtaccct      60
ctacgaccta tcaccaacat cccaaaaagc accgtccct  cgcttctccg tgtacgtgtc     120
acctgctctg ttactaccac caagcctcag cctaatcgtg agaagcttct ggtagagcaa     180
cgcactgtga atcttcctct gtccaacgac caatctctgc aatcgaccaa gcctcgccct     240
aaccgtgaga agcttgtggt tgagcaacgc cttgccagcc ctcctctgtc caatgaccca     300
actttgaaat cgacatggac tcaccggtta tgggttgcag cgggctgcac cactttgttt     360
gtctctttag ctaaatctgt cattggaggg tttgattctc atctctgcct cgaaccagct     420
ttagccggtt atgcagggta catcttagct gatctaggtt ccggtgtcta ccactgggcc     480
attgataact acggtgatga gtcaacacct gtagtaggaa cccaaatcga agcatttcag     540
```

```
ggtcaccaca agtggccttg acaatcacc agacggcaat tgccaacaa tctacacgct    600 ctggctcaag tcataacctt cacagttctt ccactagacc ttgcatttaa cgaccctgtg    660
tttcacggct ttgtgtgcac atttgcattt tgcatattgt ttagccagca attccatgct    720
tgggcacatg gaaccaagag caagcttcca cctctcgtgg tcgcgttgca ggacatgggg    780
ttacttgttt cacggagaca gcatgcggaa catcatcgag caccgtataa caacaattac    840
tgcatcgtga gtggagcatg gaacaatgtt ctggatgaga gtaaggtctt tgaggcattg    900
gagatggtgt tttatttcca gcttggggtg agacctaggt catggagtga gccaaactct    960
gactggatag aagaaaccga aatctccaac aaccaagcat aaatattttt tttacagagt   1020
gatacatgta caagaaaatt tcagtaatat actgaaaaga tttcttcgta atttatatgt   1080
aacgagtgtg actgtattta atactgtata aacaagcaa acaactgag catgtaccat   1140 ttaagtatca                                                           1150
```

<210> SEQ ID NO 30
<211> LENGTH: 295
<212> TYPE: PRT
<213> ORGANISM: Brassica napus

<400> SEQUENCE: 30

```
Met Ala Val Ser Leu Gln Thr Lys Tyr Pro Leu Arg Pro Ile Thr Asn
1               5                   10                  15

Asn Ile Pro Ser Thr His Arg Tyr Ser Leu Leu His Val Arg Val Thr
            20                  25                  30

Cys Ser Ala Thr Thr Thr Thr Asn Lys Pro Gln Ala Lys Leu Val Val
        35                  40                  45

Glu Asn Arg Phe Met Ser Pro Pro Leu Ser Asn Asp Pro Ser Leu Gln
    50                  55                  60

Ser Thr Trp Thr His Arg Leu Trp Val Ala Ala Gly Cys Thr Thr Leu
65                  70                  75                  80

Phe Ala Ser Leu Ser Lys Ser Ile Ile Gly Gly Val Gly Ser His Leu
                85                  90                  95

Trp Leu Glu Pro Ala Leu Ala Gly Tyr Ala Gly Tyr Ile Leu Ala Asp
            100                 105                 110

Leu Gly Ser Gly Val Tyr His Trp Ala Ile Asp Asn Tyr Gly Asp Glu
        115                 120                 125

Ser Thr Pro Ile Val Gly Thr Gln Ile Glu Ala Phe Gln Gly His His
    130                 135                 140

Lys Trp Pro Trp Thr Ile Thr Arg Arg Gln Phe Ala Asn Asn Leu His
145                 150                 155                 160

Ala Leu Ala Arg Val Ile Thr Phe Thr Val Leu Pro Leu Asp Leu Ala
                165                 170                 175

Phe Asn Asp Pro Val Val His Gly Phe Val Ser Thr Phe Ala Phe Cys
            180                 185                 190

Ile Met Phe Ser Gln Gln Phe His Ala Trp Ala His Gly Thr Lys Ser
        195                 200                 205

Lys Leu Pro Pro Leu Val Val Ala Leu Gln Asp Met Gly Val Leu Val
    210                 215                 220

Ser Arg Arg Glu His Ala Glu His His Arg Ala Pro Tyr Asn Asn Asn
225                 230                 235                 240

Tyr Cys Ile Val Ser Gly Ala Trp Asn Lys Val Leu Asp Glu Ser Lys
                245                 250                 255

Val Phe Glu Ala Leu Glu Met Val Leu Tyr Phe Lys Leu Gly Val Arg
```

```
                260                 265                 270
Pro Arg Ser Trp Ser Glu Pro Asn Ser Glu Trp Thr Glu Glu Lys Asp
            275                 280                 285

Ile Ser Asn Asn His Lys Val
            290                 295

<210> SEQ ID NO 31
<211> LENGTH: 302
<212> TYPE: PRT
<213> ORGANISM: Zea mays

<400> SEQUENCE: 31

Met Tyr Thr Leu Ile Pro Arg Cys His Leu Gln Pro Val His Arg Ser
1               5                  10                  15

Pro Pro Pro Cys Gln Ala Ala Thr Thr Thr Ser Ser Ala Pro Pro Ser
            20                  25                  30

Pro Ser Pro Ser Leu Ser Ile Arg Phe Arg Pro Asp Gln Asp Glu Leu
        35                  40                  45

Arg Ser Thr Trp Pro Gln Arg Ala Trp Thr Leu Ala Gly Thr Ala Ala
    50                  55                  60

Ile Leu Ser Ser Leu Ser Thr Ser Ala Ser Leu Ala Ala Ser Gly Ser
65                  70                  75                  80

Gly Ser Pro Ala Glu Pro Ile Ala Ala Leu Ala Ala Tyr Ser Leu
                85                  90                  95

Ala Asp Leu Ala Thr Gly Val Tyr His Trp Phe Val Asp Asn Tyr Gly
            100                 105                 110

Asp Ala Ala Thr Pro Val Phe Gly Ser Gln Ile Ala Ala Phe Gln Gly
        115                 120                 125

His His Arg Tyr Pro Ser Thr Ile Thr Leu Arg Glu Thr Cys Asn Asn
    130                 135                 140

Leu His Ala Leu Ala Arg Gly Ala Ala Leu Ala Leu Ala Pro Val Asp
145                 150                 155                 160

Ala Ala Leu Ser Ala Thr Gly Ala Pro Ala Ala His Ala Phe Val
                165                 170                 175

Gly Ala Phe Thr Ala Cys Val Val Leu Ser Gln Gln Phe His Ala Trp
            180                 185                 190

Ala His Glu Lys Arg Arg Arg Leu Pro Pro Gly Val Glu Ala Leu Gln
        195                 200                 205

Asp Ala Gly Val Leu Val Ser Arg Ala Gln His Ala His His Arg
    210                 215                 220

Gln Pro Tyr Asn Thr Asn Tyr Cys Ile Val Ser Gly Met Trp Asn Gly
225                 230                 235                 240

Leu Leu Asp Arg Tyr Lys Val Phe Glu Ala Leu Glu Met Val Val Tyr
                245                 250                 255

Phe Arg Thr Gly Ile Arg Pro Arg Ser Trp Gly Glu Thr Asp Ala Ser
            260                 265                 270

Trp Lys Glu Asp Thr Gly Ala Glu Ala Ala Ala Ala Ser Asn
        275                 280                 285

Ala Gly Leu Leu Gln Thr Ala Gly Ile Ser Ser Asp Ser Asp
    290                 295                 300

<210> SEQ ID NO 32
<211> LENGTH: 248
<212> TYPE: PRT
<213> ORGANISM: Zea mays
```

<400> SEQUENCE: 32

```
Met Ser Ala Thr Pro Ser Gly Asp Val Pro Asp Glu Leu Arg Val Arg
1               5                   10                  15

Ser Thr Trp Leu Gln Arg Ala Trp Thr Leu Ala Gly Thr Ala Ala Ile
            20                  25                  30

Leu Met Ser Phe Phe Thr Thr Ala Arg Leu Val Ala Ala Ser Ser Thr
        35                  40                  45

Val Val Thr Asp Ser Leu Ala Val Ala Leu Ala Val Trp Ala Ala Tyr
    50                  55                  60

Ser Val Ala Asp Leu Thr Thr Gly Val Tyr His Trp Phe Ile Asp Asn
65                  70                  75                  80

Tyr Gly Asp Ala Gly Thr Pro Val Phe Gly Ala Gln Ile Val Ala Phe
                85                  90                  95

His Asp His His Val His Pro Thr Ala Ile Thr Arg Leu Glu Pro Cys
            100                 105                 110

Asn Ser Leu His Val Ile Ala Gly Thr Val Ala Val Ala Leu Pro Ala
        115                 120                 125

Val Asp Ala Ala Leu Leu Tyr Phe Ala Gly Ser Ser Pro Ala Ala
    130                 135                 140

Ala His Ala Phe Ala Cys Thr Phe Ala Val Cys Val Met Leu Ser Val
145                 150                 155                 160

Gln Phe His Ala Trp Ala His Glu Arg Pro Ser Arg Leu Pro Pro Gly
                165                 170                 175

Val Glu Ala Leu Gln Ala Ala Gly Val Leu Val Ser Arg Ser Gln His
            180                 185                 190

Ala Gly His His Arg Pro Pro Tyr Asn Ser Asn Tyr Cys Thr Val Ser
        195                 200                 205

Gly Met Trp Asn Trp Ala Leu Asp Gly Tyr Lys Val Phe Leu Ala Val
    210                 215                 220

Glu Lys Val Ile Tyr Leu Ala Thr Gly Ala Pro Pro Arg Ser Trp Arg
225                 230                 235                 240

Met Lys Met Thr Glu His Gly Val
                245
```

<210> SEQ ID NO 33
<211> LENGTH: 309
<212> TYPE: PRT
<213> ORGANISM: Glycine max

<400> SEQUENCE: 33

```
Met Tyr Ser Leu Ala Gln His Lys Tyr Ile Pro Arg Phe His Leu Gln
1               5                   10                  15

Ala Cys Lys Asn His Pro Pro His Pro Ser Ser Val Phe Cys
            20                  25                  30

Ser Thr Thr Thr Thr Thr Ser Arg Asp Lys Pro Asn Pro Lys Pro Leu
        35                  40                  45

Val Ile Glu Pro Trp Leu Val Pro Val Pro Thr Val Val Thr Ala
    50                  55                  60

Asp Asn Pro Arg Pro Met Asn Asn Asp Pro Ser Leu Gln Ser Thr Trp
65                  70                  75                  80

Ser His Arg Ala Trp Val Ala Ala Gly Cys Thr Thr Leu Leu Ile Ser
                85                  90                  95

Leu Gly Glu Ser Ile Lys Gly Ala Met Asp Leu Asn Met Trp Ala Glu
            100                 105                 110
```

```
Pro Ile Leu Ala Gly Trp Val Gly Tyr Ile Leu Ala Asp Leu Gly Ser
            115                 120                 125

Gly Val Tyr His Trp Ala Ile Asp Asn Tyr Gly Asp Ala Ser Ile Pro
        130                 135                 140

Ile Val Gly Thr Gln Ile Glu Ala Phe Gln Gly His His Lys Trp Pro
145                 150                 155                 160

Trp Thr Ile Thr Lys Arg Gln Phe Ala Asn Asn Leu His Ala Leu Ala
                165                 170                 175

Arg Ala Val Thr Phe Thr Val Leu Pro Ile Val Leu Leu Cys His Asp
            180                 185                 190

Pro Ile Val Glu Gly Phe Val Gly Met Cys Ser Gly Cys Ile Met Phe
        195                 200                 205

Ser Gln Gln Phe His Ala Trp Ser His Gly Thr Lys Ser Arg Leu Pro
    210                 215                 220

Pro Leu Val Val Ala Leu Gln Glu Ala Gly Val Leu Val Ser Arg Ser
225                 230                 235                 240

Gln His Ala Ala His His Arg Pro Pro Tyr Asn Asn Asn Tyr Cys Ile
                245                 250                 255

Val Ser Gly Val Trp Asn Glu Phe Leu Asp Lys His Lys Val Phe Glu
            260                 265                 270

Ala Leu Glu Met Val Leu Tyr Phe Lys Thr Gly Val Arg Pro Arg Ser
        275                 280                 285

Trp Ser Glu Thr Ala Ser Glu Trp Ile Glu Glu Ile Glu Thr Pro Ser
    290                 295                 300

Gln Ile Gln Ala Gln
305

<210> SEQ ID NO 34
<211> LENGTH: 315
<212> TYPE: PRT
<213> ORGANISM: Glycine max

<400> SEQUENCE: 34

Met Tyr Ser Leu Ala Gln His Lys Tyr Thr Pro Asn Phe His His Gln
1               5                   10                  15

Val Cys Lys Asn His Pro Pro Arg His Pro Ser Arg Val His Cys Ser
            20                  25                  30

Thr Thr Thr Thr Thr Thr Thr Ser Arg Ser Lys Ser Asn Ala Lys
        35                  40                  45

Ser Leu Val Ile Glu Thr Arg Leu Val Pro Val Pro Pro Met Pro Thr
    50                  55                  60

Val Val Thr Thr Glu Ile His Arg Pro Met Asn Asn Asp Pro Ser Leu
65                  70                  75                  80

Gln Ser Thr Trp Ser His Arg Ala Trp Val Ala Ala Gly Cys Ser Thr
                85                  90                  95

Leu Val Ile Ser Leu Gly Glu Ser Ile Lys Gly Ala Ile Asp Leu Asn
            100                 105                 110

Met Trp Val Glu Pro Ile Val Ala Gly Trp Val Gly Tyr Ile Leu Ala
        115                 120                 125

Asp Leu Gly Ser Gly Val Tyr His Trp Ala Ile Asp Asn Tyr Gly Asp
    130                 135                 140

Gly Ser Thr Pro Ile Val Gly Ala Gln Ile Glu Ala Phe Gln Gly His
145                 150                 155                 160

His Lys Trp Pro Trp Thr Ile Thr Arg Arg Gln Phe Ala Asn Asn Leu
                165                 170                 175
```

```
His Ala Leu Ala Arg Ala Val Thr Leu Ala Val Leu Pro Val Val Leu
            180                 185                 190

Leu Cys His Asp Pro Ile Val Glu Gly Phe Val Val Cys Ser Gly
        195                 200                 205

Cys Ile Met Phe Ser Gln Gln Phe His Ala Trp Ser His Gly Thr Lys
210                 215                 220

Ser Arg Leu Pro Pro Leu Val Val Ala Leu Gln Glu Ala Gly Val Leu
225                 230                 235                 240

Val Ser Arg Trp Gln His Ala Ala His His Arg Ala Pro Tyr Asn Asn
                245                 250                 255

Asn Tyr Cys Ile Val Ser Gly Val Trp Asn Glu Phe Leu Asp Lys His
            260                 265                 270

Lys Val Phe Glu Ala Met Glu Met Val Leu Tyr Phe Lys Thr Gly Val
        275                 280                 285

Arg Pro Arg Ser Trp Ser Glu Pro Ala Pro Glu Trp Val Glu Glu Ile
    290                 295                 300

Glu Thr Pro Ser Gln Ile Gln Ile Gln Thr Gln
305                 310                 315

<210> SEQ ID NO 35
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 35
caccatggcg tttaatacgg ctatg                                  25

<210> SEQ ID NO 36
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 36
gacacgtgtc atgatctcct cgg                                    23

<210> SEQ ID NO 37
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 37
ttagacacgt gtcatgatct cctcg                                  25

<210> SEQ ID NO 38
<211> LENGTH: 29
<212> TYPE: DNA
<213> ORGANISM: Artificial Sequence
<220> FEATURE:
<223> OTHER INFORMATION: A synthetic oligonucleotide primer

<400> SEQUENCE: 38
tcggatccat ggcgtttaat acggctatg                              29

<210> SEQ ID NO 39
<211> LENGTH: 30
```

```
<212> TYPE: DNA
<213> ORGANISM: Artificial Sequence
<220> FEATURE:
<223> OTHER INFORMATION: A synthetic oligonucleotide primer

<400> SEQUENCE: 39
gactcgagtt agacacgtgt catgatctcc                                    30

<210> SEQ ID NO 40
<211> LENGTH: 28
<212> TYPE: DNA
<213> ORGANISM: Artificial Sequence
<220> FEATURE:
<223> OTHER INFORMATION: A synthetic oligonucleotide primer

<400> SEQUENCE: 40
atgtatatct ccttctaaag taaacaaa                                      28

<210> SEQ ID NO 41
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 41
atggcgttta atacggctat g                                             21

<210> SEQ ID NO 42
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 42
gccgaggaga tcatgacacg tgtc                                          24

<210> SEQ ID NO 43
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 43
acgaacagac acagcaagaa tgcg                                          24

<210> SEQ ID NO 44
<211> LENGTH: 33
<212> TYPE: DNA
<213> ORGANISM: Artificial Sequence
<220> FEATURE:
<223> OTHER INFORMATION: A synthetic oligonucleotide primer

<400> SEQUENCE: 44
agtctctcat taatagtgaa tttgatgctt atc                                33

<210> SEQ ID NO 45
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 45
```
gcctccaaga gcatgacccg tg                                              22

<210> SEQ ID NO 46
<211> LENGTH: 28
<212> TYPE: DNA
<213> ORGANISM: Artificial Sequence
<220> FEATURE:
<223> OTHER INFORMATION: A synthetic oligonucleotide primer

<400> SEQUENCE: 46
gagccttttc gtgtaattat cctgacca                                        28

<210> SEQ ID NO 47
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 47
gtgggacgat agctctatgc atca                                            24

<210> SEQ ID NO 48
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 48
agttctataa tcccaagtcc ga                                              22

<210> SEQ ID NO 49
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 49
ctccttatct caagcagcct                                                 20

<210> SEQ ID NO 50
<211> LENGTH: 24
<212> TYPE: DNA
<213> ORGANISM: Artificial Sequence
<220> FEATURE:
<223> OTHER INFORMATION: A synthetic oligonucleotide primer

<400> SEQUENCE: 50
gtgaaaactg ttggagagaa gcaa                                            24

<210> SEQ ID NO 51
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 51
tcaactggat accctttcgc a                                               21

<210> SEQ ID NO 52
<211> LENGTH: 20
<212> TYPE: DNA
<213> ORGANISM: Artificial Sequence

```
<220> FEATURE:
<223> OTHER INFORMATION: A synthetic oligonucleotide primer

<400> SEQUENCE: 52
taacgtggcc aaaatgatgc                                           20

<210> SEQ ID NO 53
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 53
gttctccaca accgcttggt                                           20

<210> SEQ ID NO 54
<211> LENGTH: 19
<212> TYPE: DNA
<213> ORGANISM: Artificial Sequence
<220> FEATURE:
<223> OTHER INFORMATION: A synthetic oligonucleotide primer

<400> SEQUENCE: 54
attttgccga tttcggaac                                            19

<210> SEQ ID NO 55
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 55
agattctagc ggagcttggt c                                         21

<210> SEQ ID NO 56
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 56
gcctcttcaa accaaatctc c                                         21

<210> SEQ ID NO 57
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 57
ttattaccgg agcgacaaca c                                         21

<210> SEQ ID NO 58
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 58
tccaataacg gttaagcaac g                                         21
```

<210> SEQ ID NO 59
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 59
gtcacgatga gaagttgcct tgg                                    23

<210> SEQ ID NO 60
<211> LENGTH: 29
<212> TYPE: DNA
<213> ORGANISM: Artificial Sequence
<220> FEATURE:
<223> OTHER INFORMATION: A synthetic oligonucleotide primer

<400> SEQUENCE: 60
caatgtcgtg atgaatgttg ttaaagaat                              29

<210> SEQ ID NO 61
<211> LENGTH: 386
<212> TYPE: PRT
<213> ORGANISM: Arabidopsis thaliana

<400> SEQUENCE: 61

```
Met Val Val Ala Met Asp Gln Arg Thr Asn Val Asn Gly Asp Pro Gly
1               5                   10                  15

Ala Gly Asp Arg Lys Lys Glu Glu Arg Phe Asp Pro Ser Ala Gln Pro
                20                  25                  30

Pro Phe Lys Ile Gly Asp Ile Arg Ala Ala Ile Pro Lys His Cys Trp
            35                  40                  45

Val Lys Ser Pro Leu Arg Ser Met Ser Tyr Val Val Arg Asp Ile Ile
        50                  55                  60

Ala Val Ala Ala Leu Ala Ile Ala Ala Val Tyr Val Asp Ser Trp Phe
65                  70                  75                  80

Leu Trp Pro Leu Tyr Trp Ala Ala Gln Gly Thr Leu Phe Trp Ala Ile
                85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
        115                 120                 125

Pro Tyr His Gly Trp Arg Ile Ser His Arg Thr His His Gln Asn His
    130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
        195                 200                 205

Glu Arg Lys Leu Ile Ala Thr Ser Thr Thr Cys Trp Ser Ile Met Phe
    210                 215                 220

Val Ser Leu Ile Ala Leu Ser Phe Val Phe Gly Pro Leu Ala Val Leu
225                 230                 235                 240

Lys Val Tyr Gly Val Pro Tyr Ile Ile Phe Val Met Trp Leu Asp Ala
                245                 250                 255
```

```
Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
            275                 280                 285

Arg Asp Tyr Gly Ile Phe Asn Asn Ile His His Asp Ile Gly Thr His
            290                 295                 300

Val Ile His His Leu Phe Pro Gln Ile Pro His Tyr His Leu Val Asp
305                 310                 315                 320

Ala Thr Lys Ala Ala Lys His Val Leu Gly Arg Tyr Tyr Arg Glu Pro
                325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
            355                 360                 365

Tyr Glu Thr Asp Pro Asp Leu Tyr Val Tyr Ala Ser Asp Lys Ser Lys
            370                 375                 380

Ile Asn
385

<210> SEQ ID NO 62
<211> LENGTH: 668
<212> TYPE: PRT
<213> ORGANISM: Arabidopsis thaliana

<400> SEQUENCE: 62

Met Ala Arg Ser Phe Gly Ala Asn Ser Thr Val Val Leu Ala Ile Ile
1               5                   10                  15

Phe Phe Gly Cys Leu Phe Ala Phe Ser Thr Ala Lys Glu Glu Ala Thr
            20                  25                  30

Lys Leu Gly Ser Val Ile Gly Ile Asp Leu Gly Thr Thr Tyr Ser Cys
        35                  40                  45

Val Gly Val Tyr Lys Asn Gly His Val Glu Ile Ile Ala Asn Asp Gln
    50                  55                  60

Gly Asn Arg Ile Thr Pro Ser Trp Val Gly Phe Thr Asp Ser Glu Arg
65                  70                  75                  80

Leu Ile Gly Glu Ala Ala Lys Asn Gln Ala Ala Val Asn Pro Glu Arg
                85                  90                  95

Thr Val Phe Asp Val Lys Arg Leu Ile Gly Arg Lys Phe Glu Asp Lys
            100                 105                 110

Glu Val Gln Lys Asp Arg Lys Leu Val Pro Tyr Gln Ile Val Asn Lys
        115                 120                 125

Asp Gly Lys Pro Tyr Ile Gln Val Lys Ile Lys Asp Gly Glu Thr Lys
    130                 135                 140

Val Phe Ser Pro Glu Glu Ile Ser Ala Met Ile Leu Thr Lys Met Lys
145                 150                 155                 160

Glu Thr Ala Glu Ala Tyr Leu Gly Lys Lys Ile Lys Asp Ala Val Val
                165                 170                 175

Thr Val Pro Ala Tyr Phe Asn Asp Ala Gln Arg Gln Ala Thr Lys Asp
            180                 185                 190

Ala Gly Val Ile Ala Gly Leu Asn Val Ala Arg Ile Ile Asn Glu Pro
        195                 200                 205

Thr Ala Ala Ala Ile Ala Tyr Gly Leu Asp Lys Lys Gly Gly Glu Lys
    210                 215                 220

Asn Ile Leu Val Phe Asp Leu Gly Gly Gly Thr Phe Asp Val Ser Val
```

```
                225                 230                 235                 240
        Leu Thr Ile Asp Asn Gly Val Phe Glu Val Leu Ser Thr Asn Gly Asp
                        245                 250                 255

Thr His Leu Gly Gly Glu Asp Phe Asp His Arg Ile Met Glu Tyr Phe
                        260                 265                 270

Ile Lys Leu Ile Lys Lys His Gln Lys Asp Ile Ser Lys Asp Asn
                    275                 280             285

Lys Ala Leu Gly Lys Leu Arg Arg Glu Cys Glu Arg Ala Lys Arg Ala
                    290                 295             300

Leu Ser Ser Gln His Gln Val Arg Val Glu Ile Glu Ser Leu Phe Asp
        305                 310                 315                 320

Gly Val Asp Leu Ser Glu Pro Leu Thr Arg Ala Arg Phe Glu Glu Leu
                            325                 330                 335

Asn Asn Asp Leu Phe Arg Lys Thr Met Gly Pro Val Lys Lys Ala Met
                        340                 345                 350

Asp Asp Ala Gly Leu Gln Lys Ser Gln Ile Asp Glu Ile Val Leu Val
                        355                 360                 365

Gly Gly Ser Thr Arg Ile Pro Lys Val Gln Gln Leu Leu Lys Asp Phe
                    370                 375                 380

Phe Glu Gly Lys Glu Pro Asn Lys Gly Val Asn Pro Asp Glu Ala Val
        385                 390                 395                 400

Ala Tyr Gly Ala Ala Val Gln Gly Gly Ile Leu Ser Gly Glu Gly Gly
                            405                 410                 415

Asp Glu Thr Lys Asp Ile Leu Leu Leu Asp Val Ala Pro Leu Thr Leu
                        420                 425                 430

Gly Ile Glu Thr Val Gly Gly Val Met Thr Lys Leu Ile Pro Arg Asn
                        435                 440                 445

Thr Val Ile Pro Thr Lys Lys Ser Gln Val Phe Thr Thr Tyr Gln Asp
                    450                 455                 460

Gln Gln Thr Thr Val Ser Ile Gln Val Phe Glu Gly Glu Arg Ser Leu
        465                 470                 475                 480

Thr Lys Asp Cys Arg Leu Leu Gly Lys Phe Asp Leu Thr Gly Val Pro
                            485                 490                 495

Pro Ala Pro Arg Gly Thr Pro Gln Ile Glu Val Thr Phe Glu Val Asp
                        500                 505                 510

Ala Asn Gly Ile Leu Asn Val Lys Ala Glu Asp Lys Ala Ser Gly Lys
                        515                 520                 525

Ser Glu Lys Ile Thr Ile Thr Asn Glu Lys Gly Arg Leu Ser Gln Glu
                    530                 535                 540

Glu Ile Asp Arg Met Val Lys Glu Ala Glu Phe Ala Glu Glu Asp
        545                 550                 555                 560

Lys Lys Val Lys Glu Lys Ile Asp Ala Arg Asn Ala Leu Glu Thr Tyr
                            565                 570                 575

Val Tyr Asn Met Lys Asn Gln Val Ser Asp Lys Asp Lys Leu Ala Asp
                        580                 585                 590

Lys Leu Glu Gly Asp Glu Lys Glu Lys Ile Glu Ala Ala Thr Lys Glu
                        595                 600                 605

Ala Leu Glu Trp Leu Asp Glu Asn Gln Asn Ser Glu Lys Glu Glu Tyr
                    610                 615                 620

Asp Glu Lys Leu Lys Glu Val Glu Ala Val Cys Asn Pro Ile Ile Thr
        625                 630                 635                 640

Ala Val Tyr Gln Arg Ser Gly Gly Ala Pro Gly Ala Gly Gly Glu Ser
                            645                 650                 655
```

Ser Thr Glu Glu Glu Asp Glu Ser His Asp Glu Leu
            660                 665

<210> SEQ ID NO 63
<211> LENGTH: 685
<212> TYPE: PRT
<213> ORGANISM: Arabidopsis thaliana

<400> SEQUENCE: 63

Met Ala Ala Ser Ser Ala Cys Leu Leu Gly Asn Gly Leu Ser Val Tyr
1               5                   10                  15

Thr Thr Lys Gln Arg Phe Gln Lys Leu Gly Leu Asp Arg Thr Ser Lys
            20                  25                  30

Val Thr Val Lys Ala Ser Leu Asp Glu Lys Lys His Glu Gly Arg
        35                  40                  45

Arg Gly Phe Phe Lys Leu Leu Leu Gly Asn Ala Ala Ala Gly Val Gly
    50                  55                  60

Leu Leu Ala Ser Gly Asn Ala Asn Ala Asp Glu Gln Gly Gln Gly Val
65                  70                  75                  80

Ser Ser Ser Arg Met Ser Tyr Ser Arg Phe Leu Glu Tyr Leu Asp Lys
                85                  90                  95

Gly Arg Val Glu Lys Val Asp Leu Tyr Glu Asn Gly Thr Ile Ala Ile
            100                 105                 110

Val Glu Ala Val Ser Pro Glu Leu Gly Asn Arg Ile Gln Arg Val Arg
        115                 120                 125

Val Gln Leu Pro Gly Leu Ser Gln Glu Leu Leu Gln Lys Leu Arg Ala
130                 135                 140

Lys Asn Ile Asp Phe Ala Ala His Asn Ala Gln Glu Asp Gln Gly Ser
145                 150                 155                 160

Pro Ile Leu Asn Leu Ile Gly Asn Leu Ala Phe Pro Val Ile Leu Ile
                165                 170                 175

Gly Gly Leu Phe Leu Leu Ser Arg Arg Ser Ser Gly Gly Met Gly Gly
            180                 185                 190

Pro Gly Gly Pro Gly Phe Pro Leu Gln Ile Gly Gln Ser Lys Ala Lys
        195                 200                 205

Phe Gln Met Glu Pro Asn Thr Gly Val Thr Phe Asp Asp Val Ala Gly
    210                 215                 220

Val Asp Glu Ala Lys Gln Asp Phe Met Glu Val Val Glu Phe Leu Lys
225                 230                 235                 240

Lys Pro Glu Arg Phe Thr Ala Val Gly Ala Arg Ile Pro Lys Gly Val
                245                 250                 255

Leu Leu Val Gly Pro Pro Gly Thr Gly Lys Thr Leu Leu Ala Lys Ala
            260                 265                 270

Ile Ala Gly Glu Ala Gly Val Pro Phe Phe Ser Ile Ser Gly Ser Glu
        275                 280                 285

Phe Val Glu Met Phe Val Gly Val Gly Ala Ser Arg Val Arg Asp Leu
    290                 295                 300

Phe Lys Lys Ala Lys Glu Asn Ala Pro Cys Ile Val Phe Val Asp Glu
305                 310                 315                 320

Ile Asp Ala Val Gly Arg Gln Arg Gly Thr Gly Ile Gly Gly Gly Asn
                325                 330                 335

Asp Glu Arg Glu Gln Thr Leu Asn Gln Leu Leu Thr Glu Met Asp Gly
            340                 345                 350

Phe Glu Gly Asn Thr Gly Val Ile Val Val Ala Ala Thr Asn Arg Ala

```
                355                 360                 365
Asp Ile Leu Asp Ser Ala Leu Leu Arg Pro Gly Arg Phe Asp Arg Gln
    370                 375                 380

Val Ser Val Asp Val Pro Asp Val Lys Gly Arg Thr Asp Ile Leu Lys
385                 390                 395                 400

Val His Ser Gly Asn Lys Lys Phe Glu Ser Gly Val Ser Leu Glu Val
                405                 410                 415

Ile Ala Met Arg Thr Pro Gly Phe Ser Gly Ala Asp Leu Ala Asn Leu
            420                 425                 430

Leu Asn Glu Ala Ala Ile Leu Ala Gly Arg Arg Gly Lys Thr Ala Ile
        435                 440                 445

Ser Ser Lys Glu Ile Asp Asp Ser Ile Asp Arg Ile Val Ala Gly Met
    450                 455                 460

Glu Gly Thr Val Met Thr Asp Gly Lys Ser Lys Ser Leu Val Ala Tyr
465                 470                 475                 480

His Glu Val Gly His Ala Ile Cys Gly Thr Leu Thr Pro Gly His Asp
                485                 490                 495

Ala Val Gln Lys Val Thr Leu Ile Pro Arg Gly Gln Ala Arg Gly Leu
            500                 505                 510

Thr Trp Phe Ile Pro Ser Asp Asp Pro Thr Leu Ile Ser Lys Gln Gln
        515                 520                 525

Leu Phe Ala Arg Ile Val Gly Gly Leu Gly Gly Arg Ala Ala Glu Glu
    530                 535                 540

Val Ile Phe Gly Glu Ser Glu Val Thr Thr Gly Ala Val Ser Asp Leu
545                 550                 555                 560

Gln Gln Ile Thr Gly Leu Ala Lys Gln Met Val Thr Phe Gly Met
                565                 570                 575

Ser Glu Ile Gly Pro Trp Ser Leu Met Asp Ser Ser Glu Gln Ser Asp
            580                 585                 590

Val Ile Met Arg Met Met Ala Arg Asn Ser Met Ser Glu Lys Leu Ala
        595                 600                 605

Asn Asp Ile Asp Thr Ala Val Lys Thr Leu Ser Asp Lys Ala Tyr Glu
    610                 615                 620

Ile Ala Leu Ser Gln Ile Arg Asn Asn Arg Glu Ala Met Asp Lys Ile
625                 630                 635                 640

Val Glu Ile Leu Leu Glu Lys Glu Thr Met Ser Gly Asp Glu Phe Arg
                645                 650                 655

Ala Ile Leu Ser Glu Phe Thr Glu Ile Pro Pro Glu Asn Arg Val Ala
            660                 665                 670

Ser Ser Thr Ser Thr Ser Thr Pro Thr Pro Ala Ser Val
        675                 680                 685

<210> SEQ ID NO 64
<211> LENGTH: 696
<212> TYPE: PRT
<213> ORGANISM: Gossypium hirsutum

<400> SEQUENCE: 64

Met Ala Cys Thr Ser Met Val Val Pro Thr Ser His Val Thr Ala Val
1               5                   10                  15

Ala Lys Lys Asp Gly Cys Lys Glu Glu Ile Gly Gly Leu Arg Arg Ser
            20                  25                  30

Asn Ser Gly Val Asn Leu His Lys Arg Val Gly Ile Gln Arg Ser Tyr
        35                  40                  45
```

```
Ser Asp Asn His Leu Cys Tyr Tyr Thr Asn Arg Ile Val Ala Ala Ser
 50                  55                  60

Thr Lys Ser Thr Leu Lys Thr Ser Arg Ser Phe Gly Ile Leu Pro Pro
 65                  70                  75                  80

Leu Pro Phe Arg Ile Ser Gly Ser Met Ile Pro Asn Ser Val Arg Ser
                 85                  90                  95

Phe Leu Phe Asp Pro Glu Thr Ser Lys Asp Leu Ser Gly Val Gly Lys
                100                 105                 110

Asp Val Asn Val Ile Asp Gly Asn Ser Arg Gly Asn Asp Asp Glu Glu
                115                 120                 125

Lys Glu Ile Lys Arg Ala Asn Trp Leu Asn Arg Leu Leu Glu Ile Gln
130                 135                 140

Ser Ser Phe Lys His Lys Gln Val Glu Glu Val Glu Gly Ala Gly
145                 150                 155                 160

Ile Tyr Asp Glu Asn Glu Asn Gly Asp Asp Gly Gly Cys Glu Val Asn
                165                 170                 175

Tyr Asp Ser Glu Asp Glu Gly Gly Glu Val Lys Tyr Asp Arg Asp Ser
                180                 185                 190

Phe Ser Lys Leu Leu Val Gln Val Pro Trp Ser Asp Thr Lys Val Ile
                195                 200                 205

Ser Gln Leu Ala Phe Leu Cys Asn Met Ala Tyr Val Ile Pro Ser Ile
210                 215                 220

Lys Glu Lys Asp Leu Arg Lys Tyr Tyr Gly Leu Arg Phe Val Thr Ser
225                 230                 235                 240

Ser Leu Glu Lys Lys Ala Lys Ala Ala Lys Ile Lys Ala Lys Leu Asp
                245                 250                 255

Gln Asp Ser Thr Arg Val Pro Ile Ala Glu Thr Ser Glu Ser Glu Ser
                260                 265                 270

Lys Lys Val Glu Ser Lys Glu Trp Lys His Pro Ile Arg Ile Ser Val
                275                 280                 285

Val Tyr Glu Ile Ala Ala Ser Ala Ala Cys Tyr Val Gln Ser Gln Ala
                290                 295                 300

Lys Gly Leu Leu Ser Pro Gly Ser Lys Ser Gln Glu Glu Glu Asp Asp
305                 310                 315                 320

Met Asn Ser Cys Arg Ile Ser Glu Gln Pro Glu Met Glu Gly Glu Asn
                325                 330                 335

Ser Pro Pro Arg Val Tyr Asn Ser Glu Val Ala Ala Leu Met Ala Ala
                340                 345                 350

Glu Ala Met Thr Ala Val Val Arg Ala Gly Lys Glu Lys Gln Glu
                355                 360                 365

Thr Ala Lys Asp Leu Gln Ser Leu His Ser Ser Pro Cys Glu Trp Phe
                370                 375                 380

Val Cys Asp Asp Leu Asn Thr Tyr Thr Arg Cys Phe Val Ile Gln Gly
385                 390                 395                 400

Ser Asp Ser Leu Ala Ser Trp Gln Ala Asn Leu Leu Phe Glu Pro Thr
                405                 410                 415

Glu Phe Glu Gly Thr Gly Val Leu Val His Arg Gly Ile Tyr Glu Ala
                420                 425                 430

Ala Lys Gly Ile Tyr Glu Gln Phe Ile Pro Glu Ile Met Asp His Leu
                435                 440                 445

Lys Arg His Gly His Arg Ala Lys Leu Gln Phe Thr Gly His Ser Leu
450                 455                 460

Gly Gly Ser Leu Ser Leu Leu Val Asn Leu Met Leu Leu Ala Arg Lys
```

```
            465                 470                 475                 480
Val Val Lys Pro Ser Ala Leu Arg Pro Val Val Thr Phe Gly Ser Pro
                    485                 490                 495

Phe Val Phe Cys Gly Gly Gln Arg Ile Leu Asp Glu Leu Gly Leu Asp
                500                 505                 510

Asp Asn His Val His Cys Val Met Met His Arg Asp Ile Val Pro Arg
                515                 520                 525

Ala Phe Ser Cys Lys Tyr Pro Asn His Val Ala Val Leu Lys Arg
                530                 535                 540

Leu Pro Gly Ser Leu Arg Ser His Pro Cys Leu Leu Lys Asn Lys Leu
545                 550                 555                 560

Leu Tyr Thr Pro Leu Gly Lys Gln Phe Ile Leu Gln Pro Ser Glu Lys
                565                 570                 575

Ser Ser Pro Pro His Pro Leu Ile Pro Pro Gly Asn Ala Leu Tyr Ala
                580                 585                 590

Leu Asp Lys Thr His Ser Glu Tyr Ser Met Gln Ala Leu Met Ala Phe
                595                 600                 605

Leu Asn Cys Pro His Pro Leu Asp Thr Leu Gly Asp Leu Thr Ala Tyr
                610                 615                 620

Gly Leu Asp Gly Thr Ile Leu Arg Asp His Asp Ser Ser Asn Tyr Leu
625                 630                 635                 640

Lys Ala Val Asn Gly Val Leu Arg Leu Gln Lys Met Ala Asn Arg Cys
                645                 650                 655

Ser Arg Met Asp Thr Ser Leu Leu Trp Pro Leu Leu Asn Ser Pro Ser
                660                 665                 670

Pro His Ser Trp Ser His Asp Arg Ser Leu Glu Asn Ile Leu Leu Ser
                675                 680                 685

Asn Lys Glu Ile Met Ser Gly Val
                690                 695

<210> SEQ ID NO 65
<211> LENGTH: 644
<212> TYPE: PRT
<213> ORGANISM: Gossypium hirsutum

<400> SEQUENCE: 65

Met Ala Val Pro Thr Ser Arg Val Ala Ser Lys Ala Lys Glu Glu Glu
1               5                   10                  15

Ile Asn Gly Leu Arg Arg Leu Asp Ser Ser Met Asn Lys Ala Gly Ile
                20                  25                  30

Arg Arg Ser Tyr Ser Asp Asn His Leu Cys Cys Ser Ile Asn Arg Ile
            35                  40                  45

Arg Ala Ala Ala Ser Thr Lys Pro Thr Met Thr Lys Ser Ser Ser Val
50                  55                  60

Gly Ile Leu Pro Ser Leu Leu Pro Val Gln Ile Ser Ser Ser Thr Ile
65                  70                  75                  80

Pro Asn Ser Val Arg Ser Phe Trp Phe Asp Asp Asn Asp Asp Glu Glu
                85                  90                  95

Glu Glu Ile Lys Arg Ala Asn Trp Val Asn Arg Leu Leu Glu Val His
                100                 105                 110

Ser Arg Trp Lys His Arg Gln Ile Glu Asp Gly Val Glu Gly Gly Glu
            115                 120                 125

Ile Tyr Asp Glu Asn Glu Asn Asp Gly Asn Glu Asp Glu His Glu Gly
        130                 135                 140
```

```
Gly Cys Glu Val Asn Tyr Asn Ser Asp Glu Gly Asp Glu Val Val
145                 150                 155                 160

Tyr Asp Arg Glu Ser Phe Ser Lys Leu Leu Val Arg Val Pro Leu Ser
            165                 170                 175

Asp Thr Lys Leu Phe Ser Glu Leu Ala Phe Leu Cys Asn Ile Ala Tyr
                180                 185                 190

Val Ile Pro Lys Ile Glu Gly Met Glu Leu Arg Lys Tyr Tyr Gly Leu
            195                 200                 205

Lys Phe Val Thr Ser Ser Ile Glu Lys Lys Ala Glu Val Ala Thr Ile
        210                 215                 220

Lys Ala Lys Met Asp Gln Asp Ser Ile Arg Val Pro Val Ala Thr Pro
225                 230                 235                 240

Lys Ser Thr Glu Leu Glu Lys Val Glu Gly Thr Glu Thr Lys Arg Leu
                245                 250                 255

Ile Ser Leu Ser Ala Val Tyr Glu Ile Ala Ala Ser Ala Ala Tyr Tyr
                260                 265                 270

Val Gln Ser Arg Ala Lys Gly Leu Leu Ser Pro Gly Phe Lys Ser Pro
            275                 280                 285

Val Glu Asp Glu Arg Asp Ser Arg Arg Ser Gly Asp Glu His Glu Met
290                 295                 300

Glu Gly Glu Asn Ser Pro Arg Val Tyr Asn Ser Glu Val Ala Ala Tyr
305                 310                 315                 320

Met Ala Ala Ser Ala Met Thr Ala Val Val Arg Ser Gly Glu Lys Ala
                325                 330                 335

Lys Gln Ala Thr Ala Lys Asp Leu Gln Ser Leu Gln Ser Ser Pro Ser
            340                 345                 350

Glu Trp Ser Val Cys Asp Glu Leu Ser Thr Tyr Thr Arg Cys Phe Val
            355                 360                 365

Ile Gln Gly Ser Asp Ser Leu Ala Ser Trp Gln Ala Asn Leu Leu Phe
            370                 375                 380

Glu Pro Thr Thr Phe Glu Tyr Thr Asp Val Leu Val His Arg Gly Ile
385                 390                 395                 400

Tyr Glu Ala Ala Lys Gly Ile Tyr Glu Gln Phe Leu Pro Glu Ile Met
                405                 410                 415

Asp His Leu Asn Arg His Gly Asp Arg Ala Lys Leu Gln Phe Thr Gly
                420                 425                 430

His Ser Leu Gly Gly Ser Leu Ser Leu Leu Val Ser Leu Met Leu Leu
            435                 440                 445

Ala Lys Lys Val Lys Pro Ser Ala Leu Arg Pro Val Ile Thr Phe
450                 455                 460

Gly Ser Pro Phe Val Phe Cys Gly Gly Gln Lys Ile Leu Glu Glu Phe
465                 470                 475                 480

Gly Leu Asp Asp Asn His Val His Cys Val Met Met His Arg Asp Ile
                485                 490                 495

Val Pro Arg Ala Phe Ser Cys Lys Tyr Pro Asn His Val Ala Ile Val
            500                 505                 510

Leu Lys Arg Leu Pro Gly Ser Leu Arg Ser His Arg Cys Leu Leu Lys
            515                 520                 525

Asn Lys Leu Leu Tyr Thr Pro Leu Gly Lys Leu Phe Ile Val Gln Pro
            530                 535                 540

Ser Glu Lys Ser Pro Pro His Pro Leu Leu Pro Leu Gly Thr Ala
545                 550                 555                 560

Pro Leu Asp Thr Leu Ser Asp Leu Thr Ala Tyr Gly Ser Glu Gly Thr
```

```
            565                 570                 575
Ile Leu Arg Asp His Asp Ser Ser Asn Tyr Leu Lys Ala Ile Asn Gly
            580                 585                 590

Val Leu Arg Gln His Lys Lys Thr Val Pro Ser Leu Thr Thr Arg Thr
            595                 600                 605

Val Ser Asp Thr Ser Leu Leu Trp Pro Leu Leu Val Ser Pro Ser Pro
            610                 615                 620

Arg Thr Trp Asn His His Arg Gln Met Met Phe Ser Asn Lys Glu Ile
625                 630                 635                 640

Met Thr Gly Val

<210> SEQ ID NO 66
<211> LENGTH: 694
<212> TYPE: PRT
<213> ORGANISM: Arachis hypogaea

<400> SEQUENCE: 66

Met Ala Phe Ser Ala Val Gly Met Ala Thr Ser Pro Ala Ser Ser Ala
1               5                   10                  15

Thr Met Asp Ile Arg Thr Thr Lys His Asn Gly Leu Arg Arg Ser Ser
            20                  25                  30

Ser Gly Ile Glu Leu Ser Thr Arg Ser Ile Met Gln Arg Ser Tyr Ser
        35                  40                  45

Asp Thr His Leu Cys Cys Ala Val Asn Pro Ile Gln Ala Thr Ser Leu
    50                  55                  60

Gln Pro Lys Gln Lys Ser Asn Lys Ser Met Gly Ile Ser Pro Phe Gln
65                  70                  75                  80

Phe Ser Gly Ser Ile Leu Pro Asn Ser Leu Arg Ser Phe Leu Phe Asp
                85                  90                  95

Pro Glu Thr Ser Lys Glu Met Asn Met Gly Glu Lys Asp His Ser Ser
            100                 105                 110

His Phe Glu Glu Ser Ala Val Glu Cys Asn Glu Asp Glu Lys Ile Asn
        115                 120                 125

Arg Thr Asn Trp Ile Glu Arg Leu Met Glu Ile Lys Lys Asn Trp Arg
    130                 135                 140

Asn Arg Ile Pro Lys Glu Glu Met Asp Pro Asp Met Ile Cys Asp Asn
145                 150                 155                 160

Asn Ser Asn Asp Glu Cys Asp Cys Asp Glu Gly Cys Val Val Asp Tyr
                165                 170                 175

Val Glu Asp Gly Gln Glu Gly Thr Tyr Asp His Asp Ser Phe Thr Lys
            180                 185                 190

Phe Leu Ser Gln Val Ser Trp Ser Asp Thr Lys Leu Tyr Ser Lys Leu
        195                 200                 205

Ala Phe Leu Cys Asn Met Ala Tyr Val Ile Pro Glu Ile Lys Ala Lys
    210                 215                 220

Asp Leu Arg Arg Tyr Tyr Ser Leu Gln Phe Ile Thr Ser Ser Leu Glu
225                 230                 235                 240

Lys Lys Ala Glu Val Glu Lys Leu Lys Glu Arg Leu Asp Lys Asp Ser
                245                 250                 255

Thr Arg Ile Pro Ile Asn Gly Ser Val Ala Ser Gln Asp Gly Ser Glu
            260                 265                 270

Lys Gly Lys Asp Asn Lys Glu Arg His Gln Ile Arg Leu Ala Tyr Asp
        275                 280                 285

Ile Ala Thr Ser Ala Ala Ser Tyr Val Gln Leu Arg Ala Lys Asp Leu
```

```
              290                 295                 300
Leu Ser Leu Thr Ala Lys Arg Gln Gln Pro Gln Ser Asp Ile Leu Asp
305                 310                 315                 320

Ser Asn Gly Arg Glu Asn Ser Glu Gly Phe Glu Ala Glu Ala Leu Pro
                325                 330                 335

Gly Leu Ile His Gln Ser Cys Ser Leu Cys Cys Ser Ile Asn Asn Asp
                340                 345                 350

Ala Val Val Ala Ala Cys Glu Lys Glu Lys Gln Glu Ala Ala Lys Asp
                355                 360                 365

Leu Gln Ser Leu His Ser Ser Leu Cys Glu Trp Phe Ile Cys Asp Asp
370                 375                 380

Ser Asn Thr Tyr Thr Arg Tyr Phe Val Ile Gln Gly Ser Asp Ser Leu
385                 390                 395                 400

Ala Ser Trp Gln Ala Asn Leu Phe Phe Glu Pro Thr Lys Phe Glu Asp
                405                 410                 415

Thr Asp Val Leu Val His Arg Gly Ile Tyr Glu Ala Ala Lys Gly Ile
                420                 425                 430

Tyr Glu Gln Phe Leu Pro Glu Ile Lys Ala His Leu Lys Arg His Gly
                435                 440                 445

Asp Arg Ala Lys Leu Gln Phe Thr Gly His Ser Leu Gly Gly Ser Leu
                450                 455                 460

Ser Leu Leu Val His Leu Met Leu Leu Ser Arg Lys Val Val Ser Pro
465                 470                 475                 480

Ser Thr Leu Arg Pro Val Val Thr Phe Gly Ser Pro Phe Val Phe Cys
                485                 490                 495

Gly Gly His Lys Leu Leu Asp His Leu Gly Leu Asp Glu Ser His Ile
                500                 505                 510

His Cys Val Met Met His Arg Asp Ile Val Pro Arg Ala Phe Ser Cys
                515                 520                 525

Asn Tyr Pro Asn His Val Ala Leu Val Leu Lys Arg Leu Asn Ser Thr
                530                 535                 540

Phe Arg Ser His Pro Cys Leu Ile Lys Asn Lys Leu Leu Tyr Ser Pro
545                 550                 555                 560

Leu Gly Lys Ile Phe Ile Leu Gln Pro Asp Glu Arg Thr Ser Pro Pro
                565                 570                 575

His Pro Leu Leu Pro Ser Gly Ser Ala Phe Tyr Ala Leu Asp Ser Ala
                580                 585                 590

Arg Cys Gly Tyr Thr Pro Ser Val Leu Arg Thr Phe Leu Asn Gln Pro
                595                 600                 605

His Pro Ile Glu Thr Leu Ser Asp Pro Thr Ala Tyr Gly Ser Glu Gly
                610                 615                 620

Thr Ile Leu Arg Asp His Asp Ser Ser Asn Tyr Leu Lys Val Val Asn
625                 630                 635                 640

Gly Val Leu Arg Gln His Ser Lys Asn Ile Val Arg Gln Met Arg Lys
                645                 650                 655

Gln Arg Ile Asn Glu Leu Trp Pro Leu Leu Thr Thr Pro Ser Pro His
                660                 665                 670

Ser Trp Asn His Glu Gln Asn Leu Glu Arg Cys Asn Leu Met Thr Lys
                675                 680                 685

Glu Ile Val Thr Gly Val
                690

<210> SEQ ID NO 67
```

<211> LENGTH: 666
<212> TYPE: PRT
<213> ORGANISM: Helianthus annuus

<400> SEQUENCE: 67

```
Met Met Val Cys Ser Ser Ile Ser Val Ser Ser Gln Pro Thr Thr Pro
1               5                   10                  15

Asn Ile Leu Asn Arg Ser Ile Ser Ser Gln Asn Leu Arg Gln His Ala
            20                  25                  30

Arg Ile Arg Arg Ala His Ser Asp Asn Asn Leu Cys Tyr Ser Ala Asn
        35                  40                  45

His Val Gln Ala Ser Met Asn Gln Pro Lys Leu Lys Asn Ser Arg Ser
    50                  55                  60

Val Gly Ile Phe Asn Leu Asn Leu Ser Ser Phe Ile Pro Asn Ser
65                  70                  75                  80

Leu Lys Thr Leu Leu Phe Asp Pro Asp Thr Ser Thr Gly Met Asp Thr
                85                  90                  95

Asp Thr Asp Thr Glu Arg Gly Asp Glu Val Ala Asp Val Ser Asp Val
            100                 105                 110

Glu Met Thr Lys Glu Glu Lys Asn Arg Ala Asn Trp Ile Glu Arg Leu
        115                 120                 125

Val Glu Ile Arg Ser Arg Trp Val Gln Lys Gln Asn Asn Glu Leu Asp
130                 135                 140

Gly Glu Asn Gly Glu Glu Lys Gly Cys Asp Glu Asp Gly Asn Gly Glu
145                 150                 155                 160

Gly Cys Glu Val Asp Tyr Ser Asp Asp Glu Asp Asn Val Ile Val Asn
                165                 170                 175

Gln Glu Thr Phe Ser Gly Met Leu Lys Gln Val Ser Trp Ser Asp Thr
            180                 185                 190

Lys Gln Phe Ser Gln Leu Ala Phe Leu Cys Asn Met Ala Tyr Val Ile
        195                 200                 205

Pro Glu Ile Glu Glu Asp Asp Leu Arg Arg Tyr Tyr Asp Leu Thr Phe
    210                 215                 220

Val Thr Ser Ser Leu Glu Lys Lys Val Ser Ala Gln Glu Ile Pro Arg
225                 230                 235                 240

Glu Leu Asn Ser Val Pro Val Thr Ala Ser Thr Asn Asn Gln Arg Pro
                245                 250                 255

Glu Lys His Thr Thr Arg Thr Ser Ala Tyr Glu Ile Ala Ala Ser Ala
            260                 265                 270

Ala Thr Tyr Val Gln Ser Gln Ala Gly Gly Leu Ile Asn Leu Glu Ser
        275                 280                 285

Asp Pro Leu Ala Glu Glu Asp Asp Ile Thr Asp Pro Ser Ser Arg
    290                 295                 300

Val Tyr Asn Ser Glu Met Ala Ala Tyr Met Ala Ser Thr Met Thr
305                 310                 315                 320

Ala Val Val Ala Ala Pro Glu Lys Glu Lys Gln Glu Ala Ala Arg Asp
                325                 330                 335

Leu Gln Ser Leu His Ser Ser Pro Cys Glu Trp Phe Ile Cys Asp Asp
            340                 345                 350

Ser Ser Ile Tyr Thr Arg Cys Phe Val Ile Gln Gly Ser Asp Ser Val
        355                 360                 365

Ala Ser Trp Gln Ala Asn Leu Phe Phe Glu Pro Thr Lys Phe Glu Glu
    370                 375                 380

Thr Gly Val Pro Val His Arg Gly Ile Tyr Glu Ala Ala Lys Gly Ile
```

```
385                 390                 395                 400
Tyr Glu Gln Phe Met Pro His Ile Gln Glu His Leu Asn Arg Tyr Gly
                405                 410                 415

Glu Arg Ala Lys Leu Gln Phe Thr Gly His Ser Leu Gly Gly Ser Leu
            420                 425                 430

Ser Leu Leu Val Asn Leu Met Leu Leu Thr Arg Lys Val Val Lys Pro
                435                 440                 445

Ser Ala Leu Arg Pro Val Val Thr Phe Gly Ser Pro Phe Val Phe Cys
            450                 455                 460

Asn Gly Gln Lys Ile Leu Asp Gln Leu Gly Leu Asp Glu Asn His Val
465                 470                 475                 480

His Cys Val Met Met His Arg Asp Ile Val Pro Arg Ala Phe Ser Cys
                485                 490                 495

Asn Tyr Pro Lys His Val Ala Gln Leu Leu Lys Arg Leu Cys Gly Thr
            500                 505                 510

Phe Arg Ser His Pro Cys Leu Asn Arg Asn Ser Ile Leu Tyr Thr Pro
            515                 520                 525

Leu Gly Lys Met Phe Ile Leu Gln Pro Asp Glu Lys Ser Ser Pro His
    530                 535                 540

His Pro Leu Leu Pro Ala Gly Ser Ala Leu Tyr Val Met Glu Asn Thr
545                 550                 555                 560

Asn Arg Gly Leu Thr Lys Thr Ala Ile Arg Ala Phe Leu Asn Ser Pro
                565                 570                 575

His Pro Ile Glu Thr Leu Gln His Pro Thr Ala Tyr Gly Ser Asp Gly
            580                 585                 590

Thr Ile Leu Arg Asp His Asp Ser Ser Asn Tyr Leu Lys Ala Val Asn
                595                 600                 605

Gly Ile Ile Arg Gln His Thr Lys Thr Phe Ile Arg Lys Pro Lys Gln
            610                 615                 620

Gln Arg Asn Leu Leu Trp Pro Leu Leu Thr Ser Gln Ser Pro His Tyr
625                 630                 635                 640

Trp Ser Gln Glu Thr Lys Val Lys Glu Lys Gln Leu Thr Val Ser Asp
                645                 650                 655

Gln Arg Arg Leu Val Thr Thr Glu Val Ala
            660                 665

<210> SEQ ID NO 68
<211> LENGTH: 700
<212> TYPE: PRT
<213> ORGANISM: Helianthus annuus

<400> SEQUENCE: 68

Met Tyr Ile Ile Cys Ser Met Arg Ser Pro Ile Ser Tyr Gly Thr Glu
1               5                   10                  15

Thr Ala Gly Val Asp Ser Arg Ser Val Phe Phe Ser Ala Leu Leu Leu
            20                  25                  30

Leu Val Met Met Val Cys Ser Ser Ile Ser Val Ser Ser Gln Pro Thr
        35                  40                  45

Thr Pro Asn Ile Leu Asn Arg Ser Ile Ser Ser Gln Asn Leu Arg Gln
    50                  55                  60

His Ala Arg Ile Arg Arg Ala His Ser Asp Asn Asn Leu Cys Tyr Ser
65                  70                  75                  80

Ala Asn His Val Gln Ala Ser Met Asn Gln Pro Lys Leu Lys Asn Ser
                85                  90                  95
```

```
Arg Ser Val Gly Ile Phe Asn Leu Asn Leu Ser Ser Phe Ile Pro
             100                 105                 110

Asn Ser Leu Lys Thr Leu Leu Phe Asp Pro Asp Thr Ser Thr Gly Met
             115                 120                 125

Asp Thr Asp Thr Asp Thr Glu Arg Gly Asp Glu Val Ala Asp Val Ser
130                 135                 140

Asp Val Glu Met Thr Lys Glu Lys Asn Arg Ala Asn Trp Ile Glu
145                 150                 155                 160

Arg Leu Val Glu Ile Arg Ser Arg Trp Val Gln Lys Gln Asn Asn Glu
                 165                 170                 175

Leu Asp Gly Glu Asn Gly Glu Glu Lys Gly Cys Asp Glu Asp Gly Asn
             180                 185                 190

Gly Glu Gly Cys Glu Val Asp Tyr Ser Asp Asp Glu Asp Asn Val Ile
             195                 200                 205

Val Asn Gln Glu Thr Phe Ser Gly Met Leu Lys Gln Val Ser Trp Ser
210                 215                 220

Asp Thr Lys Gln Phe Ser Gln Leu Ala Phe Leu Cys Asn Met Ala Tyr
225                 230                 235                 240

Val Ile Pro Glu Ile Glu Glu Asp Asp Leu Arg Arg Tyr Tyr Asp Leu
                 245                 250                 255

Thr Phe Val Thr Ser Ser Leu Glu Lys Lys Val Ser Ala Gln Glu Ile
             260                 265                 270

Pro Arg Glu Leu Asn Ser Val Pro Val Thr Ala Ser Thr Asn Asn Gln
             275                 280                 285

Arg Pro Glu Lys His Thr Thr Arg Thr Ser Ala Tyr Glu Ile Ala Ala
290                 295                 300

Ser Ala Ala Thr Tyr Val Gln Ser Gln Ala Gly Gly Leu Ile Asn Leu
305                 310                 315                 320

Glu Ser Asp Pro Leu Ala Glu Asp Asp Ile Thr Asp Pro Ser
                 325                 330                 335

Ser Arg Val Tyr Asn Ser Glu Met Ala Ala Tyr Met Ala Ala Ser Thr
             340                 345                 350

Met Thr Ala Val Val Ala Ala Pro Glu Lys Glu Lys Gln Glu Ala Ala
             355                 360                 365

Arg Asp Leu Gln Ser Leu His Ser Ser Pro Cys Glu Trp Phe Ile Cys
370                 375                 380

Asp Asp Ser Ser Ile Tyr Thr Arg Cys Phe Val Ile Gln Gly Ser Asp
385                 390                 395                 400

Ser Val Ala Ser Trp Gln Ala Asn Leu Phe Phe Glu Pro Thr Lys Phe
                 405                 410                 415

Glu Glu Thr Gly Val Pro Val His Arg Gly Ile Tyr Glu Ala Ala Lys
             420                 425                 430

Gly Ile Tyr Glu Gln Phe Met Pro His Ile Gln Glu His Leu Asn Arg
             435                 440                 445

Tyr Gly Glu Arg Ala Lys Leu Gln Phe Thr Gly His Ser Leu Gly Gly
             450                 455                 460

Ser Leu Ser Leu Leu Val Asn Leu Met Leu Leu Thr Arg Lys Val Val
465                 470                 475                 480

Lys Pro Ser Ala Leu Arg Pro Val Val Thr Phe Gly Ser Pro Phe Val
                 485                 490                 495

Phe Cys Asn Gly Gln Lys Ile Leu Asp Gln Leu Gly Leu Asp Glu Asn
             500                 505                 510

His Val His Cys Val Met Met His Arg Asp Ile Val Pro Arg Ala Phe
```

```
            515                 520                 525
Ser Cys Asn Tyr Pro Lys His Val Ala Gln Leu Leu Lys Arg Leu Cys
    530                 535                 540

Gly Thr Phe Arg Ser His Pro Cys Leu Asn Arg Asn Ser Ile Leu Tyr
545                 550                 555                 560

Thr Pro Leu Gly Lys Met Phe Ile Leu Gln Pro Asp Glu Lys Ser Ser
                565                 570                 575

Pro His His Pro Leu Leu Pro Ala Gly Ser Ala Leu Tyr Val Met Glu
            580                 585                 590

Asn Thr Asn Arg Gly Leu Thr Lys Thr Ala Ile Arg Ala Phe Leu Asn
        595                 600                 605

Ser Pro His Pro Ile Glu Thr Leu Gln His Pro Thr Ala Tyr Gly Ser
    610                 615                 620

Asp Gly Thr Ile Leu Arg Asp His Asp Ser Ser Asn Tyr Leu Lys Ala
625                 630                 635                 640

Val Asn Gly Ile Ile Arg Gln His Thr Lys Thr Phe Ile Arg Lys Pro
                645                 650                 655

Lys Gln Gln Arg Asn Leu Leu Trp Pro Leu Leu Thr Ser Gln Ser Pro
            660                 665                 670

His Tyr Trp Ser Gln Glu Thr Lys Val Lys Glu Lys Gln Leu Thr Val
        675                 680                 685

Ser Asp Gln Arg Arg Leu Val Thr Thr Glu Val Ala
    690                 695                 700

<210> SEQ ID NO 69
<211> LENGTH: 668
<212> TYPE: PRT
<213> ORGANISM: Olea europaea

<400> SEQUENCE: 69

Met Ala Cys Ser Leu Pro Ser Ile Thr Ser Ser Ser Phe Thr Ile
1               5                   10                  15

Glu Asn Ser Gln Lys Asn Glu Gly Arg Leu Arg Lys Ser Trp Ser Ser
                20                  25                  30

Lys Asn Leu Thr Arg Arg Ala Gly Ile Arg Arg Ala Phe Ser Asp Asn
            35                  40                  45

Asn Leu Phe Cys Arg Val Ser Arg Ile Gln Ala Ser Thr Val Glu Pro
        50                  55                  60

Lys Leu Lys Ser Ser Ser Ser Ala Gly Phe Phe Asn Ile Gln Leu
65                  70                  75                  80

Ser Ser Thr Met Ile Pro Asp Thr Leu Lys Pro Phe Leu Phe Asp Leu
                85                  90                  95

Glu Leu Ser Lys Glu Ile Thr Ile Glu Asp Lys Leu Val Glu Ser Glu
            100                 105                 110

Arg Glu Asp Glu Ile Asp Val Glu Lys Val Lys Lys Arg Ala Asn Trp
        115                 120                 125

Ile Glu Arg Leu Met Glu Ile Arg Asp Ser Trp Lys Glu Lys Gln Gln
    130                 135                 140

Arg Glu Asp Val Asn Asp Val Gly Glu Asn Asn Glu Ala Cys Asp Glu
145                 150                 155                 160

Asp Gly Gly Cys Glu Val Asp Tyr Asp Asp Ala Glu Gly Lys Glu
                165                 170                 175

Met Asn Ile Asp Gly Lys Ile Phe Ser Ser Leu Leu Gly Lys Val Ser
            180                 185                 190
```

```
Trp Ser Asp Thr Lys Tyr Phe Ser Lys Leu Ala Phe Leu Cys Asn Met
            195                 200                 205
Ala Tyr Val Ile Pro Asp Ile Lys Thr Arg Asp Leu Ser Arg Tyr Tyr
    210                 215                 220
Gly Leu Glu Leu Val Thr Ser Ser Leu Glu Lys Lys Ala Glu Ala Glu
225                 230                 235                 240
Val Thr Lys Asp Lys Pro Glu Gln Asp Ser Thr Val His Val Ala
                245                 250                 255
Thr Ser Ala Ser Val Asp Ser Ile Ser Thr Lys Thr Met Asp Arg Glu
            260                 265                 270
Gln Lys Cys Arg Leu Arg Pro Ser Asp Ala Tyr Glu Ile Ala Ala Ser
        275                 280                 285
Ala Ala Val Tyr Val Gln Ser Arg Thr Lys Asp Asp Leu Gln Glu Glu
        290                 295                 300
Glu Lys Lys Ser Ser Ser His Arg Val Ser Lys Ser Glu Met Ala Ala
305                 310                 315                 320
Ser Val Ala Ala Ser Thr Val Thr Ala Val Ile Ala Ala Asp Glu Lys
                325                 330                 335
Glu Lys Gln Glu Ala Ala Lys Asp Leu Gln Ser Leu His Ser Ser Pro
            340                 345                 350
Cys Glu Trp Phe Val Cys Asp Asp Ser Ser Ile Tyr Thr Arg Cys Phe
        355                 360                 365
Val Ile Gln Gly Ser Asp Ser Val Glu Ser Trp Gln Ala Asn Leu Phe
        370                 375                 380
Phe Glu Pro Thr Glu Phe Glu Gly Thr Asp Val Leu Val His Arg Gly
385                 390                 395                 400
Ile Tyr Glu Ala Ala Lys Gly Ile Tyr Glu Gln Phe Met Pro Glu Ile
                405                 410                 415
Met Gln His Leu Asn Arg Phe Gly Asp Arg Ala Lys Leu Gln Phe Thr
            420                 425                 430
Gly His Ser Leu Gly Gly Ser Leu Ala Leu Leu Val Asn Met Met Leu
        435                 440                 445
Leu Thr Arg Lys Val Ile Lys Pro Ser Ala Leu Leu Pro Val Val Thr
        450                 455                 460
Phe Gly Ser Pro Phe Val Phe Cys Gly Gly His Arg Ile Leu Asn Glu
465                 470                 475                 480
Leu Gly Leu Asp Glu Asn His Val His Cys Val Met Met His Arg Asp
                485                 490                 495
Ile Val Pro Arg Ala Phe Ser Cys Asn Tyr Pro Asn Tyr Val Ala Gln
            500                 505                 510
Val Leu Lys Arg Leu Ser Arg Thr Phe Arg Ser His Pro Cys Leu Asn
        515                 520                 525
Lys Ser Lys Leu Leu Tyr Ser Pro Met Gly Lys Ile Phe Ile Leu Gln
        530                 535                 540
Pro Asp Glu Lys Ser Ser Pro His Pro Leu Leu Pro Ser Gly Ser
545                 550                 555                 560
Ala Leu Tyr Ala Leu Asp Ser Thr Asn Phe Ser Leu Thr Lys Thr Ala
                565                 570                 575
Phe Arg Ala Phe Leu Asn Ser Pro His Pro Leu Glu Thr Leu Ser Tyr
            580                 585                 590
Pro Thr Ala Tyr Gly Ser Glu Gly Thr Ile Ile Arg Asp His Asp Ser
        595                 600                 605
Ser Asn Tyr Leu Lys Ala Met Asn Glu Val Ile Arg Gln His Thr Arg
```

```
                    610                615                620
Gln Val Asn Lys Lys Val Ser Lys Gln Thr Lys Gln Leu Trp Pro Leu
625                 630                635                640

Leu Thr Ser Gln Ser Pro His Met Trp Ser Asn Lys Arg Asn Ile Gly
                    645                650                655

Asp Thr Met Val Thr Lys Glu Ile Leu Thr Gly Val
                    660                665

<210> SEQ ID NO 70
<211> LENGTH: 668
<212> TYPE: PRT
<213> ORGANISM: Olea europaea

<400> SEQUENCE: 70

Met Ala Ser Ser Leu Pro Ser Ile Thr Ser Ser Pro Val Thr Thr Glu
1               5                   10                  15

Glu Gly Arg Leu Arg Lys Ser Trp Ser Ser Lys Gly Leu Thr Glu Arg
                20                  25                  30

Ala Arg Leu Arg Arg Thr Tyr Ser Asp Asn Asn Leu Ser Cys Arg Val
            35                  40                  45

Ser Arg Ile Gln Ala Ser Lys Val Glu Pro Lys Leu Lys Ser Ser Ser
50                  55                  60

Ser Ser Ala Ser Phe Phe Asn Ile Gln Leu Pro Ser Thr Met Phe Pro
65                  70                  75                  80

Asp Ser Leu Lys Ser Phe Phe Ser Asp Leu Glu Ser Ser Lys Glu Ile
                85                  90                  95

Asn Ile Glu Glu Ile Leu Val Glu Ser Glu Gln Glu Asp Glu Ile Asp
            100                 105                 110

Val Glu Lys Val Lys Lys Arg Ala Asn Trp Ile Glu Arg Leu Met Glu
        115                 120                 125

Ile Arg Asn Asn Trp Lys Glu Lys Gln Arg Lys Glu Asp Val Asn Val
130                 135                 140

Ala Gly Glu Asn Asp Glu His Cys Asp Glu Asp Gly Gly Cys Glu Val
145                 150                 155                 160

Asp Tyr Asp Asp Asp Asp Ala Lys Gly Lys Glu Met Asn Ile Asp
                165                 170                 175

Ser Lys Arg Phe Thr Pro Phe Leu Gly Gln Val Ser Trp Ser Asp Thr
            180                 185                 190

Lys His Phe Ser Lys Leu Ala Phe Leu Cys Asn Met Ala Tyr Ile Ile
        195                 200                 205

Pro Asn Ile Lys Thr Arg Asp Leu Arg Arg Tyr Gly Leu Glu Leu
210                 215                 220

Val Thr Ser Ser Leu Gln Lys Lys Val Glu Ala Lys Val Met Lys Val
225                 230                 235                 240

Lys Pro Glu Gln Asn Ser Thr Ser Val Tyr Val Ala Thr Pro Ala Val
                245                 250                 255

Leu Asp Ser Ile Ser Ala Lys Thr Glu Asp Phe Glu Gln Lys Cys Leu
            260                 265                 270

Leu Arg Ser Ser Ala Ala Tyr Glu Ile Ala Ala Ser Ala Ala Phe Tyr
        275                 280                 285

Val Gln Ser Gln Thr Lys Asp Val Lys Asp Asp His Gln Glu Glu Glu
290                 295                 300

Glu Glu Glu Ser Ser Ser Pro Arg Val Tyr Lys Ser Glu Met Ala Ala
305                 310                 315                 320
```

```
Ser Val Ala Ala Ser Thr Met Thr Ala Val Ile Ala Ala Asp Glu Asn
                325                 330                 335

Gln Lys Gln Glu Ala Ala Arg Asp Leu Gln Ser Ile His Ser Ser Pro
            340                 345                 350

Cys Glu Trp Phe Val Cys Asp Asp Ser Ser Ile Tyr Thr Arg Cys Phe
        355                 360                 365

Val Ile Gln Gly Ser Asp Ser Val Glu Ser Trp Gln Ala Asn Leu Phe
370                 375                 380

Phe Glu Pro Thr Lys Phe Glu Gly Thr Asp Val Leu Val His Arg Gly
385                 390                 395                 400

Ile Tyr Glu Ala Ala Lys Gly Ile Tyr Glu Gln Phe Met Pro Glu Ile
                405                 410                 415

Met Gln His Leu Asn Arg Phe Gly Asn Arg Ala Lys Leu Gln Phe Thr
            420                 425                 430

Gly His Ser Leu Gly Gly Ser Leu Ala Leu Leu Val Asn Leu Met Leu
        435                 440                 445

Leu Thr Arg Lys Val Val Lys Pro Ser Ala Leu Leu Pro Val Val Thr
    450                 455                 460

Phe Gly Ser Pro Phe Val Phe Cys Gly Gly His Lys Ile Leu Asp Glu
465                 470                 475                 480

Leu Gly Leu Asp Glu Asn His Val His Cys Val Met Met His Arg Asp
                485                 490                 495

Ile Val Pro Arg Ala Phe Ser Cys Asn Tyr Pro Asn Tyr Val Ala Gln
            500                 505                 510

Val Leu Lys Arg Leu Ser Arg Thr Phe Arg Ala His Pro Cys Leu Asn
        515                 520                 525

Lys Asn Lys Leu Leu Tyr Ser Pro Met Gly Arg Ile Phe Ile Leu Gln
530                 535                 540

Pro Asp Glu Lys Leu Ser Pro Pro His Pro Leu Leu Pro Ser Gly Ser
545                 550                 555                 560

Ala Leu Tyr Ser Leu Asp Ser Ile Lys Cys Ser Leu Ala Lys Ser Ala
                565                 570                 575

Phe Arg Ala Phe Leu Asn Ser Pro His Pro Leu Glu Thr Leu Ser Asn
            580                 585                 590

Pro Thr Ala Tyr Gly Ser Glu Gly Thr Ile Ile Arg Asp His Asp Ser
        595                 600                 605

Ser Asn Tyr Leu Lys Val Met Asn Glu Val Ile Arg Gln His Thr Trp
610                 615                 620

Gln Val Asp Arg Lys Ala Gly Lys Gln Thr Asn Gln Leu Trp Pro Leu
625                 630                 635                 640

Leu Thr Ser Gln Ser Pro His Met Trp Ser Ala Lys Ser Asn Ile Gly
                645                 650                 655

Gly Met Thr Ala Thr Glu Glu Ile Leu Thr Gly Val
            660                 665

<210> SEQ ID NO 71
<211> LENGTH: 714
<212> TYPE: PRT
<213> ORGANISM: Elaeis guineensis

<400> SEQUENCE: 71

Met Pro Cys Ala Ala Ala Ile Ile His Gly Gly Ser Ser Ala Ala
1               5                   10                  15

Ser Ala Val Ala Lys Asp His Leu His Gly Arg Gln Asp Gly Ile Arg
                20                  25                  30
```

```
Arg Ser Leu Ser Gly Thr Asp Leu Val Gly Arg Ser Arg Ser
        35                  40                  45

Glu Pro Leu Leu Arg Cys Ser Leu Ser Ile Pro Arg Pro Ala Thr Ala
 50                      55                  60

Ala Ser Ala Pro Ala Lys Leu Lys Thr Ser Arg Ser Val Gly Leu Phe
 65                  70                  75                  80

Ser Phe Ile Pro Asn Ser Ile Arg Ser Phe Leu Phe Asn Ser Glu Glu
                 85                  90                  95

Ala His Gly Gly Met Arg Phe Val Asp Pro Glu Ser Ser Glu Glu
            100                 105                 110

Glu Val Gly Ser Glu Thr Glu Lys Arg Ser Asn Trp Val Glu Arg Ile
            115                 120                 125

Trp Glu Leu Arg Ser Arg Trp Arg Asp Arg Lys Pro Lys Ala Asp Glu
        130                 135                 140

Glu Asp Ala Ser Asp Gly Gly Gly Glu Glu Ser Asp Glu Phe Cys Arg
145                 150                 155                 160

Val Ser Tyr Asp Ser Gly Glu Glu Ala Glu Arg Glu Glu Glu Arg Ser
                165                 170                 175

Glu Trp Asp Arg Glu Ser Phe Glu Arg Leu Leu Ala Pro Val Ser Trp
            180                 185                 190

Thr Asp Ala Lys Leu Phe Ser Gln Leu Ala Phe Leu Cys Asn Met Ala
        195                 200                 205

Tyr Val Ile Pro Glu Ile Lys Ala Glu Asp Leu Arg Lys Tyr Tyr Asp
        210                 215                 220

Leu Arg Tyr Val Thr Ser Ser Leu Glu Lys Lys Ser Glu Ala Ala Ile
225                 230                 235                 240

Lys Ala Arg Leu Glu Ser Asp Ser Thr Arg Pro Pro Gly Pro Thr
                245                 250                 255

Gly Pro Cys Pro Arg Ser Asp Ser Glu Thr Gln Arg Arg Pro Leu Ile
                260                 265                 270

Arg Pro Ser Val Ala Tyr Glu Ile Ala Ala Ser Ala Ala Ser Tyr Ile
        275                 280                 285

His Ser Arg Ala Arg Gly Leu Leu Ser Leu Gly Gly Glu Pro Gly Ser
        290                 295                 300

Thr Asn Gly Met Glu Arg Leu Gly Glu Arg Pro Glu Glu Ala Val Ser
305                 310                 315                 320

Pro Gln Glu Thr Leu Gly Gln Glu Thr Thr Gly Glu Gly Leu Glu Glu
                325                 330                 335

Ala Gln Ser Leu Lys Gly Ser Pro Gly Arg Met Tyr Lys Ser Asn Val
                340                 345                 350

Ala Ala Phe Val Ala Arg Ser Thr Met Thr Ala Val Val Ala Ala Glu
            355                 360                 365

Asp Glu Ala Arg Gln Glu Ala Ala Lys Asp Leu Arg Ser Leu His Ser
        370                 375                 380

Ser Pro Cys Glu Trp Phe Val Cys Asp Asp Pro Ser Thr Gly Thr Arg
385                 390                 395                 400

Cys Phe Val Ile Gln Gly Ser Asp Ser Leu Ala Ser Trp Gln Ala Asn
                405                 410                 415

Leu Phe Phe Glu Pro Thr Lys Phe Glu Glu Thr Glu Val Leu Val His
                420                 425                 430

Arg Gly Ile Tyr Glu Ala Ala Lys Gly Ile Tyr Glu Gln Phe Met Pro
            435                 440                 445
```

-continued

```
Glu Ile Glu Val His Leu Gln Arg Trp Gly Asp Met Ala Lys Leu Arg
    450                 455                 460
Phe Thr Gly His Ser Leu Gly Gly Ser Leu Ser Leu Leu Val His Leu
465                 470                 475                 480
Met Leu Leu Ser Arg Gly Ala Val Lys Pro Ser Thr Leu Leu Pro Val
                485                 490                 495
Val Thr Phe Gly Ser Pro Ser Val Phe Cys Arg Gly Lys Arg Val Leu
                500                 505                 510
Glu Gly Leu Gly Leu Asp Glu Gly Gln Val His Ser Val Met Met His
            515                 520                 525
Arg Asp Ile Val Pro Arg Ala Phe Ser Cys Gly Tyr Pro Asn His Val
    530                 535                 540
Ala Gln Val Leu Lys Arg Leu Asn Lys Ala Phe Arg Ser His Pro Cys
545                 550                 555                 560
Leu Asn Asn Glu Lys Val Leu Tyr Ser Pro Leu Gly Gln Thr Tyr Ile
                565                 570                 575
Leu Gln Pro Asp Asp Lys Ser Ser Pro Pro His Pro Leu Leu Pro Pro
                580                 585                 590
Gly Ala Ala Leu Tyr Ile Leu Asp Gly Lys Lys Ala Ala Glu Arg Gly
            595                 600                 605
Glu Thr Lys Lys Ala Thr Val Ala Gly Ala Leu Arg Ala Phe Leu Asn
    610                 615                 620
Ser Pro His Pro Leu Glu Thr Leu Ser Asp Pro Ala Ala Tyr Gly Ser
625                 630                 635                 640
Asp Gly Thr Ile Leu Arg Asp His Asp Ser Ser Asn Tyr Leu Lys Ala
                645                 650                 655
Met Asn Gly Leu Val Arg Glu His Thr Lys Ser Val Val Arg Arg Thr
                660                 665                 670
Arg Arg Gln Arg Phe Tyr Gln Leu Trp Pro Leu Leu Ala Thr Pro Thr
            675                 680                 685
Asn Arg Leu Thr Gly Gly His His Ser Arg Met Glu Lys Ser Glu Pro
    690                 695                 700
Val Asn Gln Glu Val Leu Thr Thr Ser Val
705                 710
```

ENHANCED LIPID BIOSYNTHESIS VIA ENGINEERED PLASTID LIPASES

This application is a U.S. national stage filing under 35 U.S.C. 371 from International Application No. PCT/US2018/025234, filed on 29 Mar. 2018, and published as WO 2018/183734 on 4 Oct. 2018, which claims benefit of priority to the filing date of U.S. Provisional Application Ser. No. 62/479,599, filed Mar. 31, 2017, the contents of which are specifically incorporated herein by reference in their entity.

FEDERAL FUNDING

This invention was made with government support under DE-FG02-98ER20305, DE-FG02-91ER20021, and DE-FC02-07ER64494, awarded by the U.S. Department of Energy. The government has certain rights in the invention.

BACKGROUND OF THE INVENTION

Plant oils such as triacylglycerols (TAGs) are useful for food, industrial feedstock and biofuel production. TAG is generally harvested from the seeds of oil crop species, such as canola.

Most fuels are currently produced from petroleum products, but such production involves considerable cost, both financially and environmentally. Sources of petroleum must be discovered, but petroleum exploration is an expensive and risky venture. The cost of exploring deep water wells can exceed $100 million. In addition to the economic cost, petroleum exploration carries a high environmental cost. For example, offshore exploration frequently disturbs the surrounding marine environments.

After a productive well is discovered, the petroleum must be extracted from the Earth, but such extraction is expensive and, even under the best circumstances, only 50% of the petroleum in a well can be extracted. Petroleum extraction also carries an environmental cost. For example, petroleum extraction can result in large seepages of petroleum rising to the surface. Offshore drilling involves dredging the seabed which disrupts or destroys the surrounding marine environment.

After extraction, petroleum must be transported over great distances from petroleum producing regions to petroleum consuming regions. In addition to the shipping costs, there is also the environmental risk of oil spills.

In its natural form, crude petroleum extracted from the Earth has few commercial uses. It is a mixture of hydrocarbons (e.g., paraffins (or alkanes), olefins (or alkenes), alkynes, napthenes (or cycloalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.). Hence, crude petroleum must be refined and purified before it can be used commercially.

Production of petroleum-based fuels typically involves extensive exploration, significant extraction, transportation over long distances, substantial refining, and/or significant distribution costs. There is a need for a renewable oil source that can be produced economically without environmental damage.

SUMMARY

Described herein are transgenic plants with increased oil content. Also described are methods for producing oils from plants that exhibit enhanced expression of plastid-specific lipases. The plants can also express enzymes that increase the substrates for such lipases to facilitate increasing oil accumulation in oil seed crops. The lipase can be a plastid lipase (PLIP). For example, the lipase can be a PLASTID LIPASE 1 (PLIP1), for example a PLIP1 of Arabidopsis. The lipase can also be a PLIP2 or PLIP3 lipase. In some cases, the lipase is not a PLIP2 or PLIP3 lipase. The substrate can be a mixture of lipids, including for example a $16:1^{\Delta 3trans}$-containing phosphatidylglycerol or a monogalactosyldiacylglycerol (MGDG). In some cases, the manufacture of such substrates can be enhanced by expression of FAD4.

Described herein are also, plants, seeds, and plant cells that have at least about 1.2-fold, or at least about 15-fold more oil in its plant tissues, seeds or plant cells, as measured by percent oil per dry weight, than a plant or seed or plant cell, respectively, of the same species that has not been modified to contain nucleic acid, expression cassette, or expression vector that expresses a lipase described herein. For example, the lipases described herein are particularly useful for increasing oil content of plant seeds. The plant, plant seed, or plant cell can be, for example, an alfalfa, algae, avocado, barley, broccoli, Brussels sprout, cabbage, camelina, canola, cassava, cauliflower, coconut, cole vegetable, collard, crucifer, flax, grain, legume, forage grass, jatropa, kale, kohlrabi, maize, miscanthus, mustard, nut sedge, oat, oil firewood tree, oilseeds, olive, palm, peanut, potato, radish, rice, rutabaga, safflower, sorghum, soybean, sugar beet, sugarcane, sunflower, switchgrass, tobacco, tomato, turnip, or wheat seed plant, plant seed, or seed. In some cases, the plant, plant seed, or plant cell is not an *Arabidopsis thaliana* plant, plant seed, or plant cell.

DESCRIPTION OF THE FIGURES

FIG. 1A-1F illustrates subcellular localization of PLIP1 in *Arabidopsis*. FIG. 1A illustrates subcellular localization of PLIP1-YFP in leaf mesophyll cells of 3-week-old *Arabidopsis* Col-0 transformed with PLIP1-YFP driven by 35S promoter or empty vector (EV) control using confocal laser scanning microscopy. Chlorophyll autofluorescence is shown in red, and YFP fluorescence is shown in green. Overlay of chlorophyll and YFP are shown as well (Merge). Representative images from one experiment are presented. Scale bars: 30 µm. FIG. 1B illustrates PLIP1 enrichment in chloroplast fractions analyzed by immunoblotting. Intact and subfractionated chloroplasts were prepared using 4-week-old *Arabidopsis* (Col-0) plants grown on MS medium. Equal amounts of protein of leaf tissues from the whole plant (wp), intact chloroplasts (chl), thylakoid (thy) and stroma (str) were separated by SDS-PAGE or further subjected to immunoblotting analysis using an antibody against PLIP1$^{S422A}$, a non-functional mutant of PLIP1. Immunoblotting was used to detect marker proteins BiP2 (endoplasmic reticulum) and LHCb1 (thylakoid). For protein loading, 12 µg per fraction were loaded for PLIP1; 2 µg per fraction for BiP2 and LHCb1. FIG. 1C illustrates SDS-PAGE Coomassie Brilliant Blue staining to detect rubisco large subunit (stroma) and light-harvesting chlorophyll a/b-binding protein (LHCP) (thylakoid), which were used as makers. Numbers indicate protein molecular mass in kDa. For protein loading, 12 µg per fraction were loaded. FIG. 1D illustrates chloroplast import experiments with labeled PLIP1 and control protein FtsH8. Chloroplasts were treated with (+) or without (−) trypsin. Total chloroplast membranes (P) or soluble (S) fractions were analyzed by SDS-PAGE followed by fluorography. TP, translation products; p, precursor; i, intermediate; m, mature form; MW, molecular weight markers. FIG. 1E shows a thin layer chromatography plates illustrating separation of polar (left) and neutral (right) lipids in *E. coli* containing a 6×His-PLIP1 expression cassette or an empty vector control (EV) at 6 hours following induction of PLIP1 expression. FFA, free fatty acid; O, origin of sample loading; PE, phosphatidylethanolamine; PG, phosphatidylglycerol. TLC plates were stained by iodine vapor. FIG. 1F illustrates expression of PLIP1 active site mutants compared to wild type PLIP1. Lipid extracts of *E. coli* cultures 6 h after induction expressing 6×His-PLIP1 (PLIP1) or two-point mutation alleles, 6×His-PLIP1-S422A or 6×His-PLIP1-D483A, or *E. coli* cultures containing an empty vector control (EV) were analyzed by thin layer chromatography to detect free fatty acid (FFA) products (top panel). Protein extracts were analyzed for protein production using an antibody against the 6×His tag present on the expressed mutant and wild type PLIP1 proteins.

FIG. 2A-2H illustrates in vitro PLIP1 activity. FIG. 2A illustrates SDS-PAGE separation and analysis of purified PLIP1 and PLIP1$_{S422A}$ proteins. Loading was 5 μg per lane for both samples. SDS-PAGE separated proteins were stained by Coomassie Brilliant Blue (left) or detected by immunoblotting with an antibody raised against PLIP1$^{S422A}$. Numbers indicate protein molecular mass in kDa. 6×His-PLIP1 and 6×His-PLIP1$^{S422A}$ are indicated by the arrow. FIG. 2B shows a thin-layer chromatogram of products of a representative in vitro lipase reaction using phosphatidylcholine (PC) with wild-type (PLIP1+PC) and the mutant enzyme (PLIP1$^{S422A}$+PC). Substrate without enzyme (Buffer+PC), or enzyme without substrate (PLIP1) were included as controls. PC, phosphatidylcholine. O, origin of sample loading. FIG. 2C shows illustrative gas-liquid chromatograms of methyl esters derived from commercial PC substrates or lyso-PC fractions from PLIP1 lipase reactions with different PC substrates. 15:0 was used as an internal standard. FIG. 2D illustrates PLIP1 lipase activity on commercial PC substrates (carbon number:double bond number; sn-1/sn-2) with different degree of saturation of the sn-1 acyl groups. PC containing 18.0/18:1 and 18:1/18:1 and PC containing 18:0/18:2 and 18:2/18:2 were compared, respectively. n=4, ±SD. Student's t-test was applied (indicates p<0.01). FIG. 2E illustrates the activity of purified recombinant PLIP1 on PC with different sn-2 acyl groups. PC containing 16.0/18:0, 16:0/18:1, and 16:0/18:2 were used as substrates. n=4, ±SD. Student's t-test was applied ( indicates p<0.01). FIG. 2F graphically illustrates PLIP1 enzyme activity preferences for molecular species of phosphatidylglycerol isolated from tobacco leaves. Acyl groups of lyso-phosphatidylglycerol are shown as molar percentages of total acyl groups at any given time point. Experiments were repeated three times with similar results and data from one representative experiment are shown. FIG. 2G illustrates the activity of purified recombinant PLIP1 on PC. Fatty acid methyl esters of acyl groups of both PC and Lyso-PC at each time point were analyzed by liquid gas chromatography. The fraction of PC degradation was calculated as 2 (molarity of lyso-PC acyl groups)/(2 (molarity of lyso-PC acyl groups)+ (molarity of PC acyl groups))*100. FIG. 2H illustrates PLIP1 enzyme activity on different molecular species of phosphatidylglycerol. Acyl groups of lyso-phosphatidylglycerol are shown as molar percentages of total acyl groups at any given time point. Experiments were repeated three times with similar results and data from one representative experiment are shown. For each PLIP1 lipase reaction, 60 μg lipids and 0.5 μg protein were used. The reactions were incubated at ambient temperature (~22° C.) for 1.5 h still during the linear portion of the reaction time course for PC in FIG. 2G. Reactions were stopped by lipid extraction, followed by lipid analysis with TLC and gas chromatography. PLIP1$_{S422A}$ was included as a negative control and is shown in the top panel. All lipids contained two oleic acids (18:1), except MGDG, DGDG, and SQDG, which were isolated from plants, and PI, which was isolated from bovine liver. n=3-4 for each substrate, ±SD. DGDG, digalactosyldiacylglycerol; MGDG, monogalactosyldiacylglycerol; PA, phosphatidic acid; PC, phosphatidylcholine; PE, phosphatidylethanolamine; PG, phosphatidylglycerol; PI, phosphatidylinositol; PS, phosphatidylserine; SQDG, sulfoquinovosyldiacylglycerol; TAG, triacylglycerol.

FIG. 3A illustrates growth of 4-week-old soil-grown *Arabidopsis* plants. *Arabidopsis* wild-type plant (WT), one empty vector control line, two PLIP1$^{S422A}$-OX and three PLIP1-OX overexpression lines are shown. Scale bar: 5 cm. FIG. 3B graphically illustrates the relative acyl composition of phosphatidylglycerol (PG) in PLIP1-OX and empty vector (EV) control lines. FIG. 3C graphically illustrates relative acyl composition of phosphatidylcholine (PC) in PLIP1-OX and empty vector (EV) control lines. FIGS. 3D and 3E illustrate the radioactivity in polar lipids after in vivo pulse-chase acetate labeling of lipids in wild-type and PLIP1-OX1 plants. FIG. 3D illustrates the radioactivity in polar lipids after a [$^{14}$C]-acetate labeling pulse of 60 min. FIG. 3E illustrates the radioactivity in polar lipids after a [$^{14}$C]-acetate labeling pulse of 60 min followed by replacement of the medium with non-labeled free acetate to initiate the chase with a duration of three days. The fractions of label in all polar lipids are given as percentages of total incorporation of label in polar lipids. Experiments were repeated three times with similar results and one representative result is shown. MGDG, monogalactosyldiacylglycerol; PC, phosphatidylcholine; PE, phosphatidylethanolamine; PG, phosphatidylglycerol. FIG. 3F illustrates the relative acyl composition of PC in wild-type (WT), fad3-2 and fad3-2, PLIP1-OX plants. n=4, ±SD. FIG. 3G illustrates triacylglycerol (TAG) content in leaves of 4-week-old wild type (WT), plip1-1, plip1-2 and three PLIP1-OX lines. n=4-5, ±SD. FIG. 3H illustrates the radioactivity in polar lipids after a [$^{14}$C]-acetate labeling analysis of vegetative TAG in plants with the empty vector (EV) control and the PLIP1-OX transgene. Excised leaves were floated on medium with [$^{14}$C]-acetate for 60 min, followed by changing to non-labeled acetate to initiate the chase continued for two days. Experiments were repeated three times and one representative result is shown. Where appropriate, Student's t-test was applied (* indicates p<0.05; ** indicates p<0.01). FIG. 3I graphically illustrates the relative acyl group composition of TAG found in PLIP1-OX lines as described for FIG. 3G. Acyl groups with a molar percentage less than 0.5% were omitted. n=4-5, ±SD. Student's t-test was applied (* indicates p<0.05; ** p<0.01). FIG. 3J graphically illustrates the ratio of 18:3/18:2 lipids in PLIP1-OX lines.

FIG. 4A PLIP1 transcript levels in different tissues or developmental stages determined by quantitative PCR. Expression levels were normalized to those lowest in 4-week-old leaf tissues and shown as relative fold changes. n=3 for each tissue, ±SD. FIG. 4B illustrates the total acyl group content in dry seeds of wild type (WT), plip1-1, plip1-2, PLIP1-OX1 and PLIP1-OX2. 30 seeds were analyzed in bulk for each repeat; n=5, ±SD. FIG. 4C illustrates the weight of the seeds used for the analysis and results shown in FIG. 4B. 200 seeds were used for each repeat; n=4-7, ±SD. FIG. 4D illustrates percent germination of WT, plip1-1, and plip1-2 seeds. The fraction of seeds showing radical emergence was determined 40 h after stratified seeds were sowed on the MS medium. 100 seeds were used for each repeat, n=3, ±SD. FIG. 4E illustrates the relative acyl group composition of dry seeds used in FIG. 4B. Acyl groups with a molar percentage less than 0.5% were omitted. Where appropriate, Student's t-test was applied (* indicates p<0.05; ** indicates p<0.01).

FIG. 5A illustrates the morphology of wild-type (WT) and PLIP1-OX1 siliques nine days after flowering. Scale bar: 0.5 cm. The numbers indicate the length of siliques. n=9-12, ±SD. Student's t-test was applied (** indicates p<0.01). FIG. 5B shows differential interference contrast images of embryos isolated from siliques of WT and PLIP1-OX1 plants. Scale bars: 50 μm. Representative images are shown. FIG. 5C graphically illustrates radioactivity incorporated in pulse-chase labeled developing embryos isolated from siliques of wild-type (WT) and a PLIP1-OX1 plants. The first two-time points represent the labeling pulse. Embryos were transferred to unlabeled medium after one hour. Values represent the fraction of label in select individual lipids compared to label in total lipids. The top panels show four lipids as indicated. The lower panels show PG and MGDG again, but on an expanded scale. MGDG, monogalactosyldiacylglycerol; PC, phosphatidylcholine; PG, phosphatidylglycerol; TAG, triacylglycerol.

FIG. 7A shows an example of an expression vector for expressing PLIP1, where the PLIP1 gene is under control of seed specific promoter, and a red fluorescence marker DsRED was used for selection of transformants. FIG. 7B shows an example of an expression vector for expressing FAD4 from the seed specific, Oleosin, promoter. FIG. 7C shows an example of an expression vector for expressing PLIP1 and FAD4. FIG. 7D shows another example of an expression vector for expressing PLIP1 and FAD4.

DETAILED DESCRIPTION

Figure 1A:
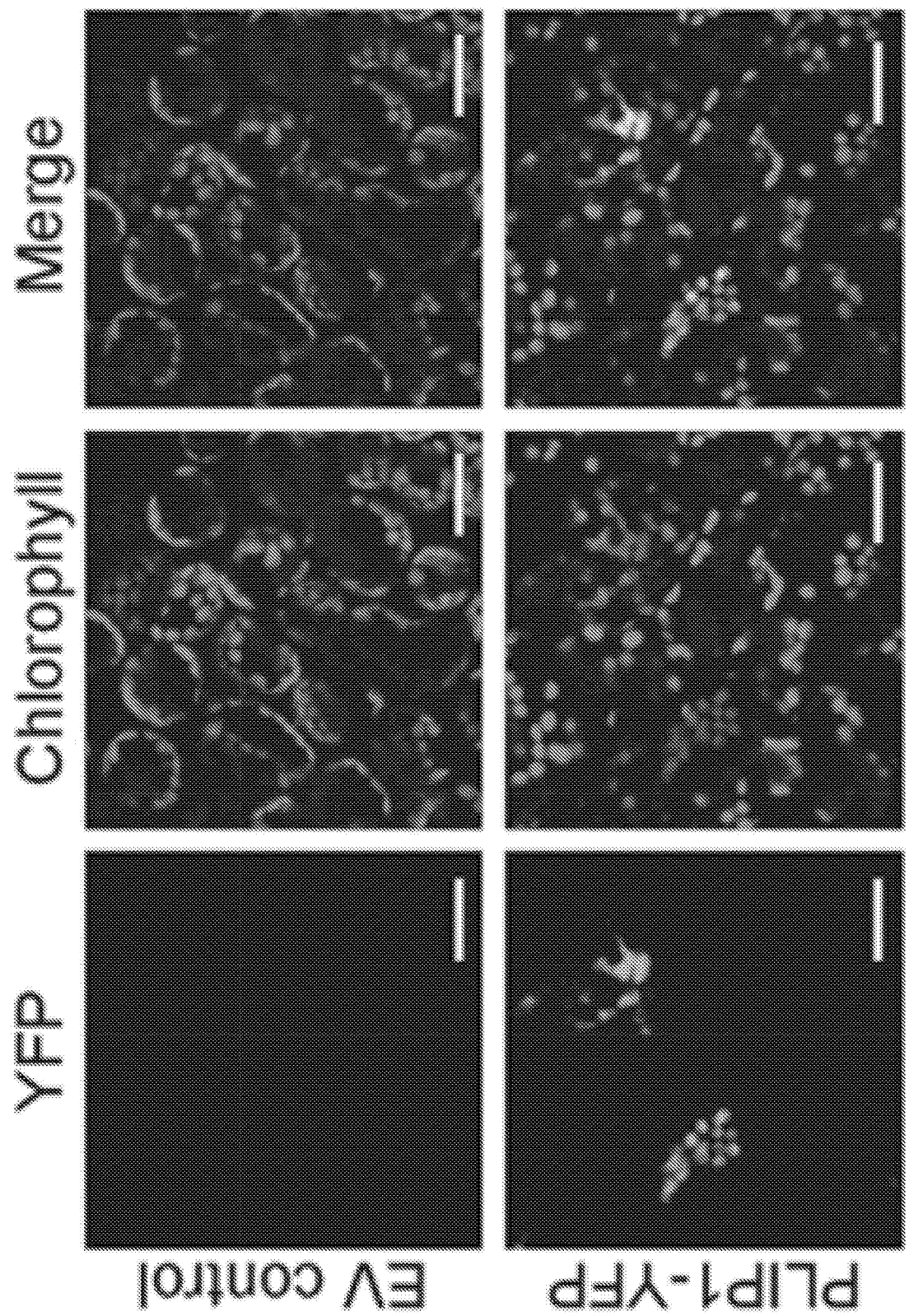

Described herein are transgenic plants, plant cells, and seeds that have one or more expression cassettes, each with a nucleic acid segment encoding a lipase operably linked to a heterologous promoter that can express the encoded lipase enzyme. The lipase can be a plastid lipase (PLIP). In some cases, the transgenic plants, plant cells, and seeds can have one or more additional expression cassettes that encode an enzyme capable of generating a substrate for a lipase. For example, the transgenic plants, plant cells, and seeds can express FAD4 in addition to one or more types of lipases. The lipases can be plastid-specific lipases, for example, PLIP1, PLIP2, PLIP3, or a combination thereof.

Such transgenic plants, plant cells, and seeds can accumulate enhanced amounts of lipids in their tissues, for example, in their seeds and/or in their vegetative tissues. The seeds and/or vegetative tissues of transgenic plants can, for example, have at least about 1.2-fold, at least about 1.5-fold, least about 2-fold, at least about 3-fold, at least about 4-fold, at least about 5-fold, at least about 7-fold, at least about 10-fold, at least about 12-fold, at least about 15-fold more lipid than a seed or vegetative tissue of the same species that has not been modified to contain a nucleic acid, expression cassette, or expression vector encoding the lipase and/or FAD4.

Overview of Lipid Biosynthesis

In plants, the lipid composition of thylakoid membranes inside chloroplasts is conserved from leaves to developing embryos. A finely tuned lipid assembly machinery builds these membranes during embryo and leaf development. Unlike thylakoid lipid biosynthetic enzymes, the function of most chloroplast lipid-degrading enzymes remains to be elucidated.

Lipid turnover requires lipases, which are enzymes that hydrolyze ester bonds of glycerolipids (Troncoso-Ponce et al., 2013; Kelly and Feussner, 2016). They are involved in a large number of cell biological processes from maintaining lipid homeostasis to lipid signaling (Wang, 2004; Scherer et al., 2010; Richmond and Smith, 2011). Phospholipases can be classified into four major types based on their lipid substrate cleavage sites: phospholipase D (PLD), phospholipase C (PLC). phospholipase $A_1$ ($PLA_1$), and phospholipase $A_2$ ($PLA_2$). PLD releases the polar head group and produces phosphatidic acid while PLC cleaves the phosphodiester bond at the glyceryl sn-3 position and produces the phosphorylated head group and diacylglycerol. $PLA_1$ and $PLA_2$ release acyl groups from the glyceryl moiety at the sn-1 and sn-2 positions, respectively (Wang et al., 2012).

The *Arabidopsis* genome encodes approximately 300 proteins that are annotated as lipases, but most of them have not been biochemically verified or have unknown physiological functions (Li-Beisson et al., 2013; Troncoso-Ponce et al., 2013; Kelly and Feussner, 2016).

Some chloroplast-located lipases have intriguing physiological functions. For example, DEFECTIVE IN ANTHER DEHISCENT1 (DAD1) (Ishiguro et al., 2001) is a chloroplast located $PLA_1$ that catalyzes the initial step of jasmonic acid production, which is involved in proper pollen development and biotic resistance. Despite the potential important functions in membrane maintenance and signaling, the bulk of chloroplast-localized lipases remains uncharacterized.

In land plants, fatty acid (FA) biosynthesis begins in plastids. In *Arabidopsis*, two pathways are responsible for glycerolipid biosynthesis (Benning, 2009; Hurlock et al., 2014). De novo synthesized fatty acids either directly enter the prokaryotic pathway in plastids or they are exported to the endoplasmic reticulum (ER) to be assembled into glycerolipids by the eukaryotic pathway. In developing embryos, the bulk of synthesized fatty acids, especially polyunsaturated fatty acids, is incorporated into triacylglycerol (TAG), which serves as the primary energy repository to fuel seed germination. Oleic acid (18:1; carbon:double bonds) is the fatty acid predominantly exported from chloroplasts.

Exported fatty acids are activated to acyl-CoAs and initially incorporated into phosphatidylcholine (PC), which is present in the outer envelope membrane of chloroplasts and in the endoplasmic reticulum, before reentering the cytosolic acyl-CoA pool by a process referred to as acyl-editing (Bates et al., 2007). Acyl-editing allows 18:1 to be further desaturated into polyunsaturated acyl groups attached to phosphatidylcholine (PC) before reentering the acyl-CoA pool for incorporation of FAs into other lipids, including triacylglycerols. In fact, acyl-editing is one of the two mechanisms reported for directing polyunsaturated fatty acids into triacylglycerols during embryogenesis, in parallel to direct head group exchange between PC and diacylglycerol (DAG) (Bates et al., 2012). Whether lipids other than phosphatidylcholine are subject to acyl exchange remains to be determined, as well as the nature of most of the enzymes involved in the process.

Lipases

Lipases are enzymes that can catalyze the hydrolysis of fats (lipids). Most lipases are a subclass of the esterases. For example, an *Arabidopsis* thylakoid membrane-associated lipase, PLASTID LIPASE 1 (PLIP1) is a phospholipase A1 type enzyme that specifically hydrolyzes 18:3 (carbon: double bonds) acyl groups from a unique chloroplast-specific phosphatidylglycerol that contains $16:1^{\Delta 3 trans}$ as its second acyl group. Thus far, a specific function of this $16:1^{\Delta 3 t}$-containing phosphatidylglycerol in chloroplasts has remained elusive. The PLIP1 gene is highly expressed during seed development, and plip1 mutant seeds contain less oil and exhibit delayed germination. Acyl groups released by PLIP1 are exported from the chloroplast and reincorporated into phosphatidylcholine, and, ultimately, enter seed triacylglycerol. Thus, $16:1^{\Delta 3 t}$ uniquely labels a plastid phosphatidylglycerol pool that in developing embryos serves to channel polyunsaturated fatty acids into seed oil mediated by the action of PLIP1. Acyl exchange on thylakoid lipids can have a role in acyl export and seed oil biosynthesis.

One example of PLIP1 amino acid sequence from *Arabidopsis thaliana* is the At3g61680 sequence, which is shown below as SEQ ID NO:1.

```
  1 MAFNTAMAST SPAAANDVLR EHIGLRRSLS GQDLVLKGGG IRRSSSDNHL

51 CCRSGNNNNR ILAVSVRPGM KTSRSVGVFS FQISSSIIPS PIKTLLFETD

101 TSQDEQESDE IEIETEPNLD GAKKANWVER LLEIRRQWKR EQKTESGNSD

151 VAEESVDVTC GCEEEEGCIA NYGSVNGDWG RESFSRLLVK VSWSEAKKLS

201 QLAYLCNLAY TIPEIKGEDL RRNYGLKFVT SSLEKKAKAA ILREKLEQDP

251 THVPVITSPD LESEKQSQRS ASSSASAYKI AASAASYIHS CKEYDLSEPI

301 YKSAAAAQAA ASTMTAVVAA GEEEKLEAAR ELQSLQSSPC EWFVCDDPNT

351 YTRCFVIQGS DSLASWKANL FFEPTKFEDT DVLVHRGIYE AAKGIYEQFL

401 PEITEHLSRH GDRAKFQFTG HSLGGSLSLI VNLMLISRGL VSSEAMKSVV

451 TFGSPFVFCG GEKILAELGL DESHVHCVMM HRDIVPRAFS CNYPDHVALV

501 LKRLNGSFRT HPCLNKNKLL YSPMGKVYIL QPSESVSPTH PWLPPGNALY

551 ILENSNEGYS PTALRAFLNR PHPLETLSQR AAYGSEGSVL RDHDSKNYVK

601 AVNGVLRQHT KLIVRKARIQ RRSVWPVLTS AGRGLNESLT TAEEIMTRV
```

A nucleotide sequence encoding the SEQ ID NO:1 *Arabidopsis thaliana* PLIP1 amino acid sequence is shown below as SEQ ID NO:2.

```
   1 CGTATATATT AATCTGGCTC CATCTACATC TGTGAAAGAG AGAGAGAGAT
  51 TCATGAATCT TTTTACAGAA ACACGAACAA GTTTCAGAAT CTGGTCTGAC
 101 TCTTTGTAAC CTTCTCGTTT AAGATTCATT GTACGTATTC AAATCTACAT
 151 TTCTTTGCCA TTGTTGGAAT CTCCGCCTCG ATCGTTTCTT ATCAAAGGAT
 201 CTGGTATTCG ATTTTTGCTA TCGTTTCAAA GCATGGTCTA ATGATGATCC
 251 TGATCTCCGA CTGATCCAAT AACGGTTAAG CAACGCTGTT TTTGATCCTC
 301 CATTGTTGTT TGCCATCGAT CAACACTCAG AAATAAGTTG GAGTTTTGTT
 351 CATAAAGAAT GGCGTTTAAT ACGGCTATGG CGTCTACATC TCCAGCGGCG
 401 GCAAATGACG TTTTAAGAGA ACATATTGGC CTCCGTAGAT CGTTGTCCGG
 451 TCAAGATCTC GTCTTAAAAG GCGGTGGTAT ACGGAGATCG AGTTCCGACA
 501 ATCACTTGTG TTGTCGCTCC GGTAATAATA ATAATCGCAT TCTTGCTGTG
 551 TCTGTTCGTC CGGGGATGAA AACGAGTCGA TCTGTGGGAG TGTTCTCGTT
 601 TCAGATATCG AGTTCTATAA TCCCAAGTCC GATAAAAACG TTGCTATTTG
 651 AAACGGACAC GTCTCAAGAC GAGCAAGAGA GCGATGAGAT TGAGATTGAG
 701 ACAGAGCCAA ATCTAGATGG AGCCAAGAAG GCAAATTGGG TCGAGAGGCT
 751 GCTTGAGATA AGGAGACAGT GGAAGAGAGA GCAAAAAACA GAGAGTGGAA
 801 ACAGTGACGT TGCAGAGGAA AGTGTTGACG TTACGTGTGG TTGTGAAGAA
 851 GAAGAAGGTT GCATTGCGAA TTACGGATCT GTAAATGGTG ATTGGGGACG
 901 AGAATCGTTC TCTAGATTGC TTGTGAAGGT TTCTTGGTCT GAGGCTAAAA
 951 AGCTTTCTCA GTTAGCTTAT TTGTGTAACT TGGCTTACAC GATACCTGAG
1001 ATCAAGGGTG AGGATTTGAG AAGAAACTAT GGGTTAAAGT TTGTGACATC
1051 TTCATTGGAA AAGAAAGCTA AAGCAGCGAT ACTTAGAGAG AAACTAGAGC
1101 AAGATCCAAC ACATGTCCCT GTTATTACAT CCCCGGATTT AGAATCCGAG
1151 AAGCAGTCTC AACGATCAGC TTCATCTTCT GCTTCTGCTT ACAAGATTGC
1201 TGCTTCAGCT GCGTCTTACA TTCACTCTTG CAAAGAGTAT GATCTTTCAG
1251 AACCAATTTA TAAATCAGCT GCTGCTGCTC AGGCTGCAGC GTCTACCATG
1301 ACCGCGGTGG TTGCTGCGGG TGAGGAGGAG AAGCTAGAAG CGGCAAGGGA
1351 GTTACAGTCG CTACAATCAT CTCCTTGTGA GTGGTTTGTT TGTGATGATC
1401 CAAACACATA CACTAGGTGC TTTGTGATTC AGGGATCTGA TTCTTTAGCT
1451 TCTTGGAAAG CAAACCTTTT CTTCGAGCCA ACTAAGTTTG AGGACACAGA
1501 TGTATTAGTC CACAGAGGAA TCTACGAGGC AGCAAAGGA ATATACGAAC
1551 AGTTCTTACC AGAAATAACA GAGCATTTGT CTAGACATGG AGATAGAGCT
1601 AAGTTTCAGT TCACGGGTCA TTCTCTTGGA GGCAGTCTCT CATTAATAGT
1651 GAATTTGATG CTTATCTCTA GAGGACTCGT TAGCTCTGAA GCTATGAAAT
1701 CCGTTGTCAC GTTCGGTTCA CCGTTTGTGT TTGTGGTGG TGAGAAGATT
1751 CTAGCGGAGC TTGGTCTTGA CGAGAGTCAT GTTCACTGTG TGATGATGCA
1801 TAGAGATATC GTCCCACGAG CCTTTTCGTG TAATTATCCT GACCATGTTG
1851 CTCTCGTTCT CAAGCGTTTG AATGGCTCCT TCCGTACACA TCCTTGTCTC
```

```
-continued
1901 AACAAAAATA AACTGTTGTA TTCACCGATG GGGAAAGTAT ATATTCTACA

1951 GCCGAGTGAG AGCGTCTCGC CGACGCACCC ATGGCTTCCA CCGGGAAACG

2001 CTCTGTACAT TTTAGAAAAT AGCAACGAAG GTTACTCTCC TACGGCGTTA

2051 CGAGCATTTT TAAACCGCCC TCACCCGCTC GAAACGCTGA GTCAACGCGC

2101 AGCTTATGGC TCGGAAGGTT CAGTCTTGAG GGACCACGAC TCCAAGAACT

2151 ACGTTAAGGC CGTGAACGGA GTTCTCAGGC AGCACACGAA GCTCATAGTT

2201 AGGAAAGCCA GGATACAAAG GAGGAGTGT TGGCCCGTGC TGACATCAGC

2251 AGGACGTGGA TTAAACGAGA GCCTGACGAC GGCCGAGGAG ATCATGACAC

2301 GTGTCTAATG AAGGAAAATG TACGGTTGTA TATAAGTGGA ATCACTTCTG

2351 ATTATGCGTT TATTTACATT TCTT
```

Sequence comparisons with related proteins illuminate which of the amino acids are conserved amino acids, for example, showing which amino acids may be important for activity and function of the protein. Such related protein can also be employed in the expression cassettes, plants, seeds, and plant cells, as well as the methods described herein.

For example, a PLIP1-related lipase protein from *Arabidopsis thaliana* with SEQ ID NO:3 shares about 98.6% sequence identity with the SEQ ID NO:1 sequence as illustrated below, where the asterisks identify amino acids that are identical in the two sequences.

```
Seq1    1 MAFNTAMASTSPAAANDVLREHIGLRRSLSGQDLVLKGGGIRRSSSDNHLCCRSGNNNNR
Seq3    1 MAFNTAMASTSPAAANDVLREHIGLRRSLSGQDLVLKGGGIRRSSSDNHLCCRSGNNNNR
          ************************************************************

Seq1   61 ILAVSVRPGMKTSRSVGVFSFQISSSIIPSPIKTLLFETDTSQDEQESDEIEIETEPNLD
Seq3   61 ILAVSVRPGMKTSRSVGVFSFQISSSIIPSPIKTLLFETDTSQDEQESDEIEIETEPNLD
          ************************************************************

Seq1  121 GAKKANWVERLLEIRRQWKREQKTESGNSDVAEESVDVTCGCEEEEGCIANYGSVNGDWG
Seq3  121 GAKKANWVERLLEIRRQWKREQKTESGNSDVAEESVDVTCGCEEEEGCIANYGSVNGDWG
          ************************************************************

Seq1  181 RESFSRLLVKVSWSEAKKLSQLAYLCNLAYTIPEIKGEDLRRNYGLKFVTSSLEKKAKAA
Seq3  181 RESFSRLLVKVSWSEAKKLSQLAYLCNLAYTIPEIKGEDLRRNYGLKFVTSSLEKKAKAA
          ************************************************************

Seq1  241 ILREKLEQDPTHVPVITSPDLESEKQSQRSASSSASAYKIAASAASYIHSCKEYDLSEPI
Seq3  241 ILREKLEQDPTHVPVITSPDLESEKQSQRSASSSASAYKIAASAASYIHSCKEYDLSEPI
          ************************************************************

Seq1  301 YKSAAAAQAAASTMTAVVAAGEEEKLEAARELQSLQSSPCEWFVCDDPNTYTRCFVIQGS
Seq3  301 YKSAAAAQAAASTMTAVVAAGEEEKLEAARELQSLQSSPCEWFVCDDPNTYTRCFVIQGS
          ************************************************************

Seq1  361 DSLASWKANLFFEPTKFE---------DTDVLVHRGIYEAAKGIYEQFLPEITEHLSRHG
Seq3  361 DSLASWKANLFFEPTKFEVKILILARDDTDVLVHRGIYEAAKGIYEQFLPEITEHLSRHG
          ******************         *********************************

Seq1  412 DRAKFQFTGHSLGGSLSLIVNLMLISRGLVSSEAMKSVVTFGSPFVFCGGEKILAELGLD
Seq3  421 DRAKFQFTGHSLGGSLSLIVNLMLISRGLVSSEAMKSVVTFGSPFVFCGGEKILAELGLD
          ************************************************************

Seq1  472 ESHVHCVMMHRDIVPRAFSCNYPDHVALVLKRLNGSFRTHPCLNKNKLLYSPMGKVYILQ
Seq3  481 ESHVHCVMMHRDIVPRAFSCNYPDHVALVLKRLNGSFRTHPCLNKNKLLYSPMGKVYILQ
          ************************************************************

Seq1  532 PSESVSPTHPWLPPGNALYILENSNEGYSPTALRAFLNRPHPLETLSQRAAYGSEGSVLR
Seq3  541 PSESVSPTHPWLPPGNALYILENSNEGYSPTALRAFLNRPHPLETLSQRAAYGSEGSVLR
          ************************************************************

Seq1  592 DHDSKNYVKAVNGVLRQHTKLIVRKARIQRRSVWPVLTSAGRGLNESLTTAEEIMTRV
Seq3  601 DHDSKNYVKAVNGVLRQHTKLIVRKARIQRRSVWPVLTSAGRGLNESLTTAEEIMTRV
          **********************************************************
```

This related protein from *Arabidopsis thaliana* with SEQ ID NO:3 has accession number CAB71098 and the following sequence.

```
  1 MAFNTAMAST SPAAANDVLR EHIGLRRSLS GQDLVLKGGG
 41 IRRSSSDNHL CCRSGNNNNR ILAVSVRPGM KTSRSVGVFS
 81 FQISSSIIPS PIKTLLFETD TSQDEQESDE IEIETEPNLD
121 GAKKANWVER LLEIRRQWKR EQKTESGNSD VAEESVDVTC
161 GCEEEEGCIA NYGSVNGDWG RESFSRLLVK VSWSEAKKLS
201 QLAYLCNLAY TIPEIKGEDL RRNYGLKFVT SSLEKKAKAA
241 ILREKLEQDP THVPVITSPD LESEKQSQRS ASSSASAYKI
281 AASAASYIHS CKEYDLSEPI YKSAAAAQAA ASTMTAVVAA
321 GEEEKLEAAR ELQSLQSSPC EWFVCDDPNT YTRCFVIQGS
361 DSLASWKANL FFEPTKFEVK ILILARDDTD VLVHRGIYEA
401 AKGIYEQFLP EITEHLSRHG DRAKFQFTGH SLGGSLSLIV
441 NLMLISRGLV SSEAMKSVVT FGSPFVFCGG EKILAELGLD
481 ESHVHCVMMH RDIVPRAFSC NYPDHVALVL KRLNGSFRTH
521 PCLNKNKLLY SPMGKVYILQ PSESVSPTHP WLPPGNALYI
561 LENSNEGYSP TALRAFLNRP HPLETLSQRA AYGSEGSVLR
601 DHDSKNYVKA VNGVLRQHTK LIVRKARIQR RSVWPVLTSA
641 GRGLNESLTT AEEIMTRV
```

Another PLIP1-related lipase protein from *Zea mays* with SEQ ID NO:5 shares about 49% sequence identity as illustrated below.

```
Seq1  70 MKTSRSVGVFSFQISSSIIPSPIKTLLFETDISQDEQESDEIEIETEPNLDGAKK--ANW
Seq5  55 LTTSRSIGVFPFQFGAAPLRPPPLPDGGGDGSRLLTVADDADPPEPCPEMPPARRPEAHW
         ****  ***  **              *          *    *    *     *   *

Seq1 128 VERLLEIRRQWKR---EQKTESGNSDVAEESVDVTCGCEEEEGCIANYGSVNGD----WG
Seq5 115 LDRLLEVRSRFHDPTWRDVLDHDDDDDDEDLYRLDADHHHDGGCGVSYEDDGEEEDARWD
            ****  *           *  *             **   *              *

Seq1 181 RESFSRLLVKVSWSEAKKLSQLAYLCNLAYTIPEIKGEDLRRNYGLKFVTSSLEKKAKAA
Seq5 175 RDSFAKLLARAPLGEARLFAQLAFLCNMAYVIPEIKVEELKRHYGLRFVTSSLEKKAEAG
         * **  **           **   *** ***  ** ***** *  * *** ********** *

Seq1 241 ILREKLEQDPTHVPVITSPDLESEKQSQRSASSSASAYKIAASAASYIHSCKEYDLS---
Seq5 235 IISAKLDADSTRPRTAPAYEVASGPQPRRPIRSSHLAYEVAASAASYVHARARGLLSFGA
         *  ** *  *        *     * *    **  **  *******  *       **

Seq1 298 -----------EPIYKSAAAAQAAASTMTAVVAAGEEEKLEAARELQSLQSSPCEWFVCD
Seq5 295 PIRQQQQAAGQGRLYNSGVAAYMAASTVTAVVAAEDEARQEAARDLRSPLSSPCEWFVCD
                    *   *  **  **** ******   *  **** *    **********

Seq1 347 DPNTYIRCFVIQGSDSLASWKANLFFEPTKFEDTDVLVHRGIYEAAKGIYEQFLPEITEH
Seq5 355 EADARTRCLVIQGSDSLASWQANLLFEPTEFEGTGVLVHRGIYEAAKGIYEQVMPEIEAH
           *    ** ********** *** ****  **  * ***************   ***  *

Seq1 407 LSRHGDRA--KFQFTGHSLGGSLSLIVNLMLISRGLVSSEAMKSVVTFGSPFVFCGGEKI
Seq5 415 LRAHAGRAPPRLRLTGHSLGGSLAVLVSLMLLARGVVTPDALHPVVTFGAPSVFCGGNRV
         *  *  **       *********   *  ***  **       ****** *******

Seq1 465 LAELGLDESHVHCVMMHRDIVPRAFSCNYPDHVALVLKRLNGSFRTHPCLNKNKLLYSPM
Seq5 475 LEALGVGEAHVRSVAMHRDIVPRAFSCRYPGHAIALLKRLNGVLRTHPCLNTHKALYTPM
         *  **  *  **   * **************  ** *  ****** *  *******  ** **

Seq1 525 GKVYILQPSESVSPTHPWLPPGNALYILENSNEGYS-----------PTALRAFLNRPHP
Seq5 535 GSTYILQPDSSVSPRHPFLPEGAALFRLDSDDAGLRGGAERPPRALVASALRAFLNSPHP
         *  ***** * ****  ** **  **   *    *              ******* ***

Seq1 574 LETLSQRAAYGSEGSVLRDHDSKNYVKAVNGVLR
Seq5 595 LETLSDLSAYGAGGAILRDHESSNYFRALSALAR
         *****    *** *** **** * ***   *   *
```

This related protein from *Zea mays* with SEQ ID NO:5 has accession number NP_001183891 and the SEQ ID NO:5 sequence shown below.

```
  1 MVATVAAAGA AAAAASGRRR GARREPATMH AGIRRSRSEP
 41 HLRCPRRGGA AGAALTTSRS IGVFPFQFGA APLRPPPLPD
 81 GGGDGSRLLT VADDADPPEP CPEMPPARRP EAHWLDRLLE
121 VRSRFHDPTW RDVLDHDDDD DDEDLYRLDA DHHHDGGCGV
161 SYEDDGEEED ARWDRDSFAK LLARAPLGEA RLFAQLAFLC
201 NMAYVIPEIK VEELKRHYGL RFVTSSLEKK AEAGIISAKL
241 DADSTRPRTA PAYEVASGPQ PRRPIRSSHL AYEVAASAAS
281 YVHARARGLL SFGAPTRQQQ QAAGQGRLYN SGVAAYMAAS
321 TVTAVVAAED EARQEAARDL RSPLSSPCEW FVCDEADART
361 RCLVIQGSDS LASWQANLLF EPTEFEGTGV LVHRGIYEAA
401 KGIYEQVMPE IEAHLRAHAG RAPPRLRLTG HSLGGSLAVL
441 VSLMLLARGV VTPDALHPVV TFGAPSVFCG GNRVLEALGV
481 GEAHVRSVAM HRDIVPRAFS CRYPGHAIAL LKRLNGVLRT
521 HPCLNTHKAL YTPMGSTYIL QPDSSVSPRH PFLPEGAALF
561 RLDSDDAGLR GGAERPPRAL VASALRAFLN SPHPLETLSD
601 LSAYGAGGAI LRDHESSNYF RALSALARAP PRRRKQPEVV
641 WQLPGVERLQ QYWWPGIAST VIPAPLAVSK KELVSEA
```

Another PLIP1-related lipase protein from *Zea mays* with SEQ ID NO:6 shares about 46% sequence identity with the SEQ ID NO:1 protein as illustrated below.

This protein from *Zea mays* with SEQ ID NO:6 has NP_001148192 and the SEQ ID NO:6 amino acid sequence is shown below.

```
  1 MDVLRFVPGV RPPLPTFATP VSPATAPSPH AAAAAAAPGP
 41 GFHSGMLGLW PRRAGENALG AAAEAAGVEE ARERRRRRAV
 81 EAEDGRGGNW VLQILRVQSS PPPSPSRDDG RCGVDDGGSV
121 PGSGEGDGSS QRCVERGGVG PDSEEGCSVA DGEELDRAAF
161 SRLLRKVSLA EAKLFSEMSG LCNLAYMVPR IKPRYLHKYN
201 MTFVTSSVEE RAKLPNPCNQ EDQNLNGRKN ANISTSSRHS
241 DEQESTYGAT SEHERMQENQ SGQGINPLAA YRIAASAASY
281 MQSRAMEVLP FGSQNEARRD RTIQAIVNAQ TEGLTMDEAS
321 FVATTNSMTS MVAAKEETKQ AVADDLNSSR SCPCEWFICD
361 GNRNSTRYFV IQGSETIASW QANLLFEPIK FEGLDVLVHR
401 GIYEAAKGIY QQMLPYVKSH FIVHGESARL RFTGHSLGGS
441 LALLVNLMFL IRGVAPAASL LPVITFGSPS VMCGGDYLLQ
481 KLGLPKSHVQ SVTLHRDIVP RAFSCHYPDH IASILKLVNG
521 NFRSHPCLTN QKLLYAPMGE VFILQPDEKL SPHHHLLPAG
561 SGLYLIGGQT VDSGTSSTAL RSALSAFFNS PHPLEILRDA
601 GAYGPKGTVY RDHDVHSYLR SIRAVVRKEM RAEKERRRLL
641 RWPIEVYGAL ATIDRRQVLR QLRRHAHLLV VFLLPAKLLF
681 LGVLSLIRPT
```

```
Seq1 161 GCEEEEGCIANYGSVNGDWGRESFSRLLVKVSWSEAKKLSQLAYLCNLAYTIPEIKGEDL
Seq6 140 GPDSEEGCSVADGE---ELDRAAFSRLLRKVSLAEAKLFSEMSGLCNLAYMVPRIKPRYL
          *  ****     *       *  ***** ***  ***  *     ******  **    *

Seq1 221 RRNYGLKFVTSSLEKKAKAAILREKLEQDPT---HVPVITSPDLESEKQSQRSASSS---
Seq6 197 HK-YNMTFVTSSVEERAKLPNPCNQEDQNLNGRKNANISTSSRHSDEQESTYGATSEHER
            * *****  **    *        *           **      *    *    *

Seq1 275            ASAYKIAASAASYIHSCKEYDL            SEPIY
Seq6 256 MQENQSGQGINPLAAYRIAASAASYMQSRAMEVLPFGSQNEARRDRTIQAIVNAQTEGLT
                       ** ********   *     *                  *

Seq1 302 KSAAAAQAAASTMTAVVAAGEEEKLEAARELQSLQSSPCEWFVCDDPNTYTRCFVIQGSD
Seq6 316 MDEASFVATTNSMTSMVAAKEETKQAVADDLNSSRSCPCEWFICDGNRNSTRYFVIQGSE
           *    *  ** ***  ****  *       *    *  ***** **   **  ******

Seq1 362 SLASWKANLFFEPTKFEDTDVLVHRGIYEAAKGIYEQFLPEITEHLSRHGDRAKFQFTGH
Seq6 376 TIASWQANLLFEPIKFEGLDVLVHRGIYEAAKGIYQQMLPYVKSHFIVHGESARLRFTGH
          *** *** *** ** ** ****************  ** *    *   **   * ****

Seq1 422 SLGGSLSLIVNLMLISRGLVSSEAMKSVVTFGSPFVFCGGEKILAELGLDESHVHCVMMH
Seq6 436 SLGGSLALLVNLMFLIRGVAPAASLLPVITFGSPSVMCGGDYLLQKLGLPKSHVQSVTLH
         ****** * **** *  ** *      *  *****  * ****     *****  **   *

Seq1 482 RDIVPRAFSCNYPDHVALVLKRLNGSFRTHPCLNKNKLLYSPMGKVYILQPSESVSPTHP
Seq6 496 RDIVPRAFSCHYPDHIASILKLVNGNFRSHPCLTNQKLLYAPMGEVFILQPDEKLSPHHH
         **********  **** *  **  ** **  ****  **  **** *** ****    ***  *

Seq1 542 WLPPGNALYIL--ENSNEGYSPTALR AFLNRPHPLETLSQRAAYGSEGSVLRDHDS
Seq6 556 LLPAGSGLYLIGGQTVDSGTSSTALRSALSAFFNSPHPLEILRDAGAYGPKGTVYRDHDV
          ** *   ** *           *  ****           *  ***   **     *   ***  * * ****

Seq1 596 KNYVKAVNGVLRQHTKLIVRKARIQR
Seq6 616 HSYLRSIRAVVRKEMRAEKERRRLLR
            *      *        *   *
```

Another PLIP1-related lipase protein from *Glycine max* with SEQ ID NO:7 shares about 55-56% sequence identity with the SEQ ID NO:1 protein as illustrated below.

```
Seq1    1 MAFNTAMASTSPAAAN---DVLREHIGLRRSLSGQDLVLKGGGIRRSSSDNHLCCRSGNN
Seq7   11 MAYTAVAMPTSPAATSATMDIAKEHNGLRRSQSSKELCTRSI-MRRSYSDNHLCC----S
          **    *****   * ** ***** *    *     *** *******

Seq1   58 NNRILAVSVRPGMKTSRSVGVFSFQISSSIIPSPIKTLLFETDTSQDEQESDEIEIETEP
Seq7   66 INRIQATSVPPKLKSNRSMGISPFQFSGSMLPNSLRSFLFDPETSKDVSVEEKVVSIEEN
          *** ** **  ** *  *  ***  *       ** ** *                 *

Seq1  118 NLDGAK-----KANWVERLLEIRRQWKREQKTESGNSD-VAEESVDVTCGCE---EEEGC
Seq7  126 MVESSKEEIANRANWVERLMEIKKHWRNRLPKESMDPDAICNENTYDECECDGDGDDNVC
              *      ******* ** *  ** *    *   *  *    *  *        *

Seq1  169 IANYGSVNGD--WGRESFSRLLVKVSWSEAKKLSQLAYLCNLAYTIPEIKGEDLRRNYGL
Seq7  186 VVGEDEDEQEVTYDCDSFSNFLVQVPWSDTKLYSQLAFLCNMAYVIPQIKAKDLRRYYSL
                        *** **  ** * ** ***** *** ** **  ** **** * *

Seq1  227 KFVISSLEKKAKAAILREKLEQDPTHVPVITSPDLESEKQSQRSASSSASAYKIAASAAS
Seq7  246 QFITSSLEKKVEVAKLKVKLDQDSTRVPIDDSDVSEKGKDSIKKPQIKL-AYDIAASAAS
           * *******   **  * * ***   **  *  ***   *    *   ** *******

Seq1  287 YIH---------------------------SCKEYDLSEPIYKSAAAAQAAASTMTA
Seq7  305 YVQLRAKDLLHRAAKSRDTQQTENEDSNGRGDSPREELESTSRGYKSEVAAYVAASTMTA
           *                           *          *** **  *******

Seq1  317 VVAAGEEEKLEAARELQSLQSSPCEWFVCDDPNTYTRCFVIQGSDSLASWKANLFFEPTK
Seq7  365 VVAAGEKEKQEAANDLQSLHSSPCEWFVCDDPGNYTRCFVIQGSDSLASWQANLFFEPTK
          ****** ** *** **** ************  ***************** ********

Seq1  377 FEDTDVLVHRGIYEAAKGIYEQFLPEITEHLSRHGDRAKFQFTGHSLGGSLSLIVNLMLI
Seq7  425 FEDTDVLVHRGIYEAAKGIYKQFMPEIMEHLKRHGDRAKLQFTGHSLGGSLSLLVHLMLL
          ********************  ** *** *** ******* ************ * **

Seq1  437 SRGLVSSEAMKSVVTFGSPFVFCGGEKILAELGLDESHVHCVMMHRDIVPRAFSCNYPDH
Seq7  485 TNKVVSPSTLRPVVTFGSPFVFCGGQQIINELGLDESQIHCVMMHRDIVPRAFSCNYPNH
           *  **     ************* *  ******* * ******************* *

Seq1  497 VALVLKRLNGSFRTHPCLNKNKLLYSPMGKVYILQPSESVSPTHPWLPPGNALYILENSN
Seq7  545 VAVVLKRLNSSFRSHPCLLKNKLLYSPLGKIFILQPDEKTSPPHPLLPRGSAFYALDNTK
          ** ****** *** **** ********  **  ****     ** ** *  * * * *

Seq1  557 EGYSPTALRAFLNRPHPLETLSQRAAYGSEGSVLRDHDSKNYVKAVNGVLRQHTKLIVRK
Seq7  605 GGYSPSVLRTFLNQPHPIDTLSDPTAYGSEGTILRDHDSSNYLKAINGVLRKHSKITVGR
           ****   ** *** ***   **     ****** *  ***  ** ***** *  *

Seq1  617 ARIQR-RSVWPVLTS
Seq7  665 MRKQRINQLWPLLTS
           * **    ** ***
```

This protein from *Glycine max* with SEQ ID NO:7 has XP_014627545 and the SEQ ID NO:7 amino acid sequence is shown below.

```
  1 MQQVSNTGIS MAYTAVAMPT SPAATSATMD IAKEHNGLRR
 41 SQSSKELCTR SIMRRSYSDN HLCCSINRIQ ATSVPPKLKS
 81 NRSMGISPFQ FSGSMLPNSL RSFLFDPETS KDVSVEEKVV
121 SIEENMVESS KEEIANRANW VERLMEIKKH WRNRLPKESM
161 DPDAICNENT YDECECDGDG DDNVCVVGED EDEQEVTYDC
201 DSFSNFLVQV PWSDTKLYSQ LAFLCNMAYV IPQIKAKDLR
241 RYYSLQFITS SLEKKVEVAK LKVKLDQDST RVPIDDSDVS
281 EKGKDSIKKP QIKLAYDIAA SAASYVQLRA KDLLHRAAKS
321 RDTQQTENED SNGRGDSPRE ELESTSRGYK SEVAAYVAAS
361 TMTAVVAAGE KEKQEAANDL QSLHSSPCEW FVCDDPGNYT
401 RCFVIQGSDS LASWQANLFF EPTKFEDTDV LVHRGIYEAA
441 KGIYKQFMPE IMEHLKRHGD RAKLQFTGHS LGGSLSLLVH
481 LMLLTNKVVS PSTLRPVVTF GSPFVFCGGQ QIINELGLDE
521 SQIHCVMMHR DIVPRAFSCN YPNHVAVVLK RLNSSFRSHP
561 CLLKNKLLYS PLGKIFILQP DEKTSPPHPL LPRGSAFYAL
601 DNTKGGYSPS VLRTFLNQPH PIDTLSDPTA YGSEGTILRD
641 HDSSNYLKAI NGVLRKHSKI TVGRMRKQRI NQLWPLLTSP
681 SPHSWSHEQN LERCSLRTKE IVTGV
```

Another PLIP1-related lipase protein from *Glycine max* with SEQ ID NO:8 shares about 55-56% sequence identity with the SEQ ID NO:1 protein as illustrated below.

```
Seq1   13 AAANDVLREHIGLRRSLSGQDLVLKGGGIRRSSSDNHLCCRSGNNNNRILAVSVRPGMKT
Seq8    9 SATMDIAKEHNGLRRSQSSKELCTRSI-MRRSYSDNHLCC----SINRIQATSVPPKLKS
           *    *  **  ***** *     *       *** *******    *** * **   *

Seq1   73 SRSVGVFSFQISSSIIPSPIKILLFETDTSQDEQESDEIEIETEPNLDGAK-----KANW
Seq8   64 NRSMGISPFQFSGSMLPNSLRSFLFDPETSKDVSVEEKVVSIEENMVESSKEEIANRANW
           **  ** ** ** *       **  ** **      *         *        ***

Seq1  128 VERLLEIRRQWKREQKTESGNSD-VAEESVDVTCGCE---EEEGCIANYGSVNGD--WGR
Seq8  124 VERLMEIKKHWRNRLPKESMDPDAICNENTYDECECDGDGDDNVCVVGEDEDEQEVTYDC
          **** **   *    **  *   *   *   *    *      *

Seq1  182 ESFSRLLVKVSWSEAKKLSQLAYLCNLAYTIPEIKGEDLRRNYGLKFVISSLEKKAKAAI
Seq8  184 DSFSNFLVQVPWSDTKLYSQLAFLCNMAYVIPQIKAKDLRRYYSLQFITSSLEKKVEVAK
           ***  ** ** **  * **** *** ** ** **  **** *  ** ******* * *

Seq1  242 LREKLEQDPTHVPVITSPDLESEKQSRSASSSASAYKIAASAASYIH------------
Seq8  244 LKVKLDQDSTRVPIDDSDVSEKGKDSIKKPQIKL-AYDIAASAASYVQLRAKDLLHRAAK
          *  ** ** * ***  * ****  *   *    *    *  ** ********

Seq1  290 -----------------SCKEYDLSEPIYKSAAAAQAAASTMTAVVAAGEEEKLEAARE
Seq8  303 SRDTQQTENEDSNGRGDSPREELESTSRGYKSEVAAYVAASTMTAVVAAGEKEKQEEAAND
                             *     ***  **   ** *************** ** ***

Seq1  332 LQSLQSSPCEWFVCDDPNTYTRCFVIQGSDSLASWKANLFFEPTKFEDTDVLVHRGIYEA
Seq8  363 LQSLHSSPCEWFVCDDPGNYTRCFVIQGSDSLASWQANLFFEPTKFEDTDVLVHRGIYEA
          **** ************ ***************** ***********************

Seq1  392 AKGIYEQFLPEITEHLSRHGDRAKFQFIGHSLGGSLSLIVNLMLISRGLVSSEAMKSVVT
Seq8  423 AKGIYKQFMPEIMEHLKRHGDRAKLQFTGHSLGGSLSLLVHLMLLINKVVSPSTLRPVVT
          ***** ** *** *** ******* ** ********* * *** *  **   *   ***

Seq1  452 FGSPFVFCGGEKILAELGLDESHVHCVMMHRDIVPRAFSCNYPDHVALVLKRLNGSFRTH
Seq8  483 FGSPFVFCGGQQIINELGLDESQIHCVMMHRDIVPRAFSCNYPNHVAVVLKRLNSSFRSH
          **********  * * ******  ******************* *** ****** *** *

Seq1  512 PCLNKNKLLYSPMGKVYILQPSESVSPTHPWLPPGNALYILENSNEGYSPTALRAFLNRP
Seq8  543 PCLLKNKLLYSPLGKIFILQPDEKTSPPHPLLPRGSAFYALDNTKGGYSPSVLRTFLNQP
          *** ********  **  ****** *  ***  ** *  * **  * ****  ** *** *

Seq1  572 HPLETLSQRAAYGSEGSVLRDHDSKNYVKAVNGVLRQHTKLIVRKARIQR-RSVWPVLTS
Seq8  603 HPIDTLSDPTAYGSEGTILRDHDSSNYLKAINGVLRKHSKITVGRMRKQRINQLWPLLTS
          **  ***      ******  ****** ** ***** * **  *  * *   ** ***
```

This protein from *Glycine max* with SEQ ID NO:8 has XP_014627549.1 and the SEQ ID NO:8 amino acid sequence is shown below.

```
  1 MPTSPAATSA TMDIAKEHNG LRRSQSSKEL CTRSIMRRSY
 41 SDNHLCCSIN RIQATSVPPK LKSNRSMGIS PFQFSGSMLP
 81 NSLRSFLFDP ETSKDVSVEE KVVSIEENMV ESSKEEIANR
121 ANWVERLMEI KKHWRNRLPK ESMDPDAICN ENTYDECECD
161 GDGDDNVCVV GEDEDEQEVT YDCDSFSNFL VQVPWSDTKL
201 YSQLAFLCNM AYVIPQIKAK DLRRYYSLQF ITSSLEKKVE
241 VAKLKVKLDQ DSTRVPIDDS DVSEKGKDSI KKPQIKLAYD
281 IAASAASYVQ LRAKDLLHRA AKSRDTQQTE NEDSNGRGDS
321 PREELESTSR GYKSEVAAYV AASTMTAVVA AGEKEKQEAA
361 NDLQSLHSSP CEWFVCDDPG NYTRCFVIQG SDSLASWQAN
401 LFFEPTKFED TDVLVHRGIY EAAKGIYKQF MPEIMEHLKR
441 HGDRAKLQFT GHSLGGSLSL VHLMLLTNK VVSPSTLRPV
481 VTFGSPFVFC GGQQIINELG LDESQIHCVM MHRDIVPRAF
521 SCNYPNHVAV VLKRLNSSFR SHPCLLKNKL LYSPLGKIFI
561 LQPDEKTSPP HPLLPRGSAF YALDNTKGGY SPSVLRTFLN
601 QPHPIDTLSD PTAYGSEGTI LRDHDSSNYL KAINGVLRKH
641 SKITVGRMRK QRINQLWPLL TSPSPHSWSH EQNLERCSLR
681 TKEIVTGV
```

Another PLIP1-related lipase protein from *Glycine max* with SEQ ID NO:9 shares about 54% sequence identity with the SEQ ID NO:1 protein as illustrated below.

```
Seq1  1 MAFNTAMASTSPAAAN---DVLREHIGLRRSLSGQDLVLKGGGIRRSSSDNHLCCRSGNN
Seq9  1 MAYTAVAMPTSPAATSATVDIAKEHNGLRRSQSSKELHTRAV-MRRSYSDNHLCC----S
          **     *****       *  ** ****** **  *  *      *** *******

Seq1 58 NNRILAVSVRPGMKTSRSVGVFSFQISSSIIPSPIKTLLFETDTSQDEQESDEIEIETEP
Seq9 56 INRVQATSVPPKLKSNQPMGISPFQFSGSILPNSLRSFLFDPETSNDLVVEEKVVSIEEN
         **  * *   * *     ** *** ** ** **         **  * *          *
```

```
-continued
Seq1  118 NLDGAK-----KANWVERLLEIRRQWKREQKTESGNSD-VAEESVDVTCGCE---EEEGC
Seq9  116 MVESSKEEIVNRANWVERLMEIKKHWRNRLPKESMNTDAICNDNTYDECECDGDGDDNVC
              *      *******  **  *    ** * *            * *       *

Seq1  169 IANYGSVNGD--WGRESFSRLLVKVSWSEAKKLSQLAYLCNLAYTIPEIKGEDLRRNYGL
Seq9  176 VVGEDEDEQEVTYDRDSFSSFLVQVPWSDTKLYSQLAFLCNMAYVIPQIKAKDLRRYYSL
              *  ***    ** ** **  *  **** *** ** ** **  **** * *

Seq1  227 KFVTSSLEKKAKAAILREKLEQDPTHVPV---ITSPDLESEKQSRSASSSASAYKIAAS
Seq9  236 QFITSSLEKKAEVAKLKVQLNQDSTCVPVDDSVASQDVSKKDKDNTKKPQIKLAYDIAAS
           * ********  *   * *  ***   ** *                   **  ****

Seq1  284 AASYIH---------SCKEYDLSEPI---------------------YKSAAAAQAAAS
Seq9  296 AASYVQLRAKDLLHRAAKSQDTQQTENEDSNEREDLPGREELEGTSRGYKSEVAAYVAAS
          ****             *   *                          ***  **  ***

Seq1  313 TMTAVVAAGEEEKLEAARELQSLQSSPCEWFVCDDPNTYTRCFVIQGSDSLASWKANLFF
Seq9  356 TMTAVVAAGEKEKQETANDLQSLHSSPCEWFVCDDPGNYTRCFVIQGSDSLASWQANLFF
          **********  **  *    **** ************ ****************** ****

Seq1  373 EPTKFEDTDVLVHRGIYEAAKGIYEQFLPEITEHLSRHGDRAKFQFIGHSLGGSLSLIVN
Seq9  416 EPTKFEGTDVLVHRGIYEAAKGIYKQFMPEIMEHLKRHGDRAKLQFIGHSLGGSLSLLVH
          ****** ***************** ** *** *** ******* ************** *

Seq1  433 LMLISRGLVSSEAMKSVVTFGSPFVFCGGEKILAELGLDESHVHCVMMHRDIVPRAFSCN
Seq9  476 LMLLTNKVVSPSTLGPIVTFGSPFVFCGGQQIIDELGLDESQIHCVMMHRDIVPRAFSCN
          ***   **   **   ************ * * ********  *****************

Seq1  493 YPDHVALVLKRLNGSFRTHPCLNKNKLLYSPMGKVYILQPSESVSPTHPWLPPGNALYIL
Seq9  536 YPNHVALVLKRLHTSFRSHPCLLKNKLLYSPLGKIFILQPDEKTSPPHPLLPRGSAFYAL
          ** *********  *** **** ********  ** **** *  ** **  * *  * *

Seq1  553 ENSNEGYSPTALRAFLNRPHPLETLSQRAAYGSEGSVLRDHDSKNYVKAVNGVLRQHTKL
Seq9  596 DNTK---CPSVLRTFLNQPHPIDTLSDPTAYGSEGTILRDHDSSNYLKAINGVLRKHSKI
           *       *   ** ** ***  *** **  ****** ****** ** * ***** * *

Seq1  613 IVRKARIQR-RSVWPVLTS
Seq9  653 IVGRVRKQRINQLWPLLTS
          **  *  **   ** ***
```

This protein from *Glycine max* with SEQ ID NO:9 has K7KH33 and the SEQ ID NO:9 amino acid sequence is shown below.

```
              10         20         30         40
         MAYTAVAMPT SPAATSATVD IAKEHNGLRR SQSSKELHTR 50         60         70         80
         AVMRRSYSDN HLCCSINRVQ ATSVPPKLKS NQPMGISPFQ 90        100        110        120
         FSGSILPNSL RSFLFDPETS NDLVVEEKVV SIEENMVESS 130        140        150        160
         KEEIVNRANW VERLMEIKKH WRNRLPKESM NTDAICNDNT 170        180        190        200
         YDECECDGDG DDNVCVVGED EDEQEVTYDR DSFSSFLVQV 210        220        230        240
         PWSDTKLYSQ LAFLCNMAYV IPQIKAKDLR RYYSLQFITS 250        260        270        280
         SLEKKAEVAK LKVQLNQDST CVPVDDSVAS QDVSKKDKDN 290        300        310        320
         TKKPQIKLAY DIAASAASYV QLRAKDLLHR AAKSQDTQQT 330        340        350        360
         ENEDSNERED LPGREELEGT SRGYKSEVAA YVAASTMTAV 370        380        390        400
         VAAGEKEKQE TANDLQSLHS SPCEWFVCDD PGNYTRCFVI 410        420        430        440
         QGSDSLASWQ ANLFFEPTKF EGTDVLVHRG IYEAAKGIYK 450        460        470        480
         QFMPEIMEHL KRHGDRAKLQ FTGHSLGGSL SLLVHLMLLT 490        500        510        520
         NKVVSPSTLG PIVTFGSPFV FCGGQQIIDE LGLDESQIHC 530        540        550        560
         VMMHRDIVPR AFSCNYPNHV ALVLKRLHTS FRSHPCLLKN 570        580        590        600
         KLLYSPLGKI FILQPDEKTS PPHPLLPRGS AFYALDNTKC 610        620        630        640
         PSVLRTFLNQ PHPIDTLSDP TAYGSEGTIL RDHDSSNYLK 650        660        670        680
         AINGVLRKHS KIIVGRVRKQ RINQLWPLLT SPSPHSRSHE

690
         QNSERCSLRT KEIVTGV
```

Another PLIP1-related lipase protein from *Brassica napus* with SEQ ID NO:10 shares about 84% sequence identity with the SEQ ID NO:1 protein as illustrated below.

```
Seq1    1 MAFNTAMASTSPAAA-NDVLREHIGLRRSLSGQDLVLKGGGIRRSSSDNHLCCRSGNNNN
Seq10   1 MAFNAAMASPPPAAAANDVFKEHFGLRRSLSGQDLVVKAGGIRRSSSDNHLCC-----N
          ****.****.****.***.**.**********.**.**************.    **

Seq1   60 RILAVSVRPG--MKTSRSVGVFSFQISSSIIPSPIKTLLFETDTSQDEQESDEIEIETEP
Seq10  56 RIRAVSVRPGQGMKSSRSVGVFSFQISSSIIPSPIKTLLFETE---DDKDSDD-EPEVQP
          **.*******  **:************************** .  *  *. . *.

Seq1  118 NLDGAKKANWVERLLEIRRQWKREQKTESGNSDVAEESVDVTCGCEEEEGCIANYGSVNG
Seq10 112 NLDGVKKANWVQRLLEIRRQWKKETKTENVNGDVVSEHENVTCGCEDGEGCVADY--ENG
          ****.******.**********:*.****.   *..**..*****:.***.* :  ..

Seq1  178 DWGRESFSRLLVKVSWSEAKKLSQLAYLCNLAYTIPEIKGEDLRRNYGLKFVTSSLEKKA
Seq10 170 DWERESFSKLLVRVSWSDAKQLSQLAYLCNVAYTIPEIKGEDLRRNYGLKFVTSSLEKKA
          **.*****:***:****.**:*********.*****************************

Seq1  238 KAAILREKLEQDPTHVPVITSPDLESEKQSQRSASSSASAYKIAASAASYIHSCKEYDLS
Seq10 230 KAALLREKLEQDSTRVPVVISPESESEKPQQRSSSSSA--YNIAASAASYIHSCKEVDSS
          ***:********. .***:**.:****.*:***:***:  * :***************.*.

Seq1  298 EPI--YKSAAAAQAAASTMTAVVAAGEEEKLEAARELQSLQSSPCEWFVCDDPNTYTRCF
Seq10 288 DLSNPYKSAAAAQAAASTMTAVVAAGEDEKLEAARELQSLQSSPCEWFVCDDLSSYTRCF
          :   .**********************:************************* ::****

Seq1  356 VIQGSDSLASWKANLFFEPTKFEDTDVLVHRGIYEAAKGIYEQFLPEITEHLSRHGDRAK
Seq10 348 VIQGSDSLASWKANLFFEPTKFEDTDVLVHRGIYEAAKGIYEQFLPEITEHLSLHGDRAR
          ****************************************************.*****:

Seq1  416 FQFTGHSLGGSLSLIVNLMLISRGLVSSEAMKSVVTFGSPFVFCGGEKILAELGLDESHV
Seq10 408 FQFTGHSLGGSLSLIVNLMLLSRGLVSSEAMKPVVTFGSPFVFCGGEKILEELGLDESHV
          ********************.**********.****************.*********

Seq1  476 HCVMMHRDIVPRAFSCNYPDHVALVLKRLNGSFRTHPCLNKNKLLYSPMGKVYILQPSES
Seq10 468 HCVMMHRDIVPRAFSCNYPDHVALVLKRLNGTFRTHPCLNKNKLLYSPMGKVFILQPSES
          *******************************:*******************:*******

Seq1  536 VSPTHPWLPPGNALYILENSNEGYSPTALRAFLNRPHPLETLSQRAAYGSEGSVLRDHDS
Seq10 528 VSPTHPWLPPGNALYVLDKNNEDYSPTALRGFLNRPHPLETLSQRAAYGSEGSVLRDHDS
          ***************:*::.**.*******.*****************************

Seq1  596 KNYVKAVNGVLRQHTKLIVRKARIQRRSVWPVLTSA--GRGLNE-SLTTAEEIMIR
Seq10 588 KNYVKAVNGVIRQHTKLIVRKVRRQRSTIWPVLTSAEPNSSVNDWSLTATEEIMIR
          **********:**********.*:***::*******  .. .:. ***:*****
```

This lipase protein from *Brassica napus* with SEQ ID NO:10 has CDY43945.1 and the SEQ ID NO: 10 amino acid sequence is shown below.

```
  1 MAFNAAMASP PPAAAANDVF KEHFGLRRSL SGQDLVVKAG
 41 GIRRSSSDNH LCCNNRIRAV SVRPGQGMKS SRSVGVFSFQ
 81 ISSSIIPSPI KTLLFETEDD KDSDDEPEVQ PNLDGVKKAN
121 WVQRLLEIRR QWKKETKTEN VNGDVVSEHE NVTCGCEDGE
161 GCVADYENGD WERESFSKLL VRVSWSDAKQ LSQLAYLCNV
201 AYTIPEIKGE DLRRNYGLKF VTSSLEKKAK AALLREKLEQ
241 DSTRVPVVTS PESESEKPQQ RSSSSSAYNI AASAASYIHS
281 CKEVDSSDLS NPYKSAAAAQ AAASTMTAVV AAGEDEKLEA
301 ARELQSLQSS PCEWFVCDDL SSYTRCFVIQ GSDSLASWKA
361 NLFFEPTKFE DTDVLVHRGI YEAAKGIYEQ FLPEITEHLS
401 LHGDRARFQF TGHSLGGSLS LIVNLMLLSR GLVSSEAMKP
441 VVTFGSPFVF CGGEKILEEL GLDESHVHCV MMHRDIVPRA
481 FSCNYPDHVA LVLKRLNGTF RTHPCLNKNK LLYSPMGKVF
521 ILQPSESVSP THPWLPPGNA LYVLDKNNED YSPTALRGFL
561 NRPHPLETLS QRAAYGSEGS VLRDHDSKNY VKAVNGVIRQ
601 HTKLIVRKVR RQRSTIWPVL TSAEPNSSVN DWSLTATEEI
641 MTRA
```

Another PLIP1-related lipase protein from *Brassica napus* with SEQ ID NO:11 shares about 83-84% sequence identity with the SEQ ID NO: 1 protein as illustrated below.

```
Seq1    1 MAFNTAMASTSPAAANDVLREHIGLRRSLSGQDLVLKGGGIRRSSSDNHLCCRSGNNNNR
Seq 11  1 MSFNAAMASPSPPAANDVFKEHFGLRRSLSGQDLVVKAGGIRRSSSDNHLCCK-----NR
          *:**.**** .* ****. ***.************.*.************     **

Seq1   61 ILAVSVRPG--MKTSRSVGVFSFQISSSIIPSPIKTLLFETDTSQDEQESDEIEIETEPN
Seq 11 56 IRAVSVRPGQGMKSSRSVGVFSFQISSSIIPSPIKTLLFETE---DDIDSDD-EPEVEPN
          * *******  **:***************************    *  *.* ** . **
```

```
Seq1   119 LDGAKKANWVERLLEIRRQWKREQKTESGNSDVAEESVDVTCGCEEEEGCIANYGSVNGD
Seq 11 112 LDGAKKANWVQRLLEIRRQWKKETRTENSNGDVVSEHENVTCGCEDGEGCVADY--ENGD
           **********  *********** **   *  *  ****** *** * *   ***

Seq1   179 WGRESFSRLLVKVSWSEAKKLSQLAYLCNLAYTIPEIKGEDLRRNYGLKFVTSSLEKKAK
Seq 11 170 WERESFSKLLVRVSWSDAKQLSQLAYLCNVAYTIPEIKGEDLRRNYGLKFVTSSLEKKAK
           * ***** *** ** ********** ** ********************* *******

Seq1   239 AAILREKLEQDPTHVPVITSPDLESEKQSQRSASSSASAYKIAASAASYIHSCKEYDLSE
Seq 11 230 AALLREKLEQDSTRVPVVTSPESESDKFQQRS-SSSSSAYKIAASAASYTHSCKEYESSD
           ** ********  * ** ****  ** * ***  ***  ******** ******** *

Seq1   299 --PIYKSAAAAQAAASTMTAVVAAGEEEKLEAARELQSLQSSPCEWFVCDDPNTYTRCFV
Seq 11 289 LNNPYKSAAAAQAAASTMTAVVAAGEDEKLEAARELQSLQSSPCEWFVCDEPNSYTRCFV
             ************************ ******************** ** ******

Seq1   357 IQGSDSLASWKANLFFEPTKFEDTDVLVHRGIYEAAKGIYEQFLPEITEHLSRHGDRAKF
Seq 11 349 IQGSDSLASWKANLFFEPTRFEDTDVLVHRGIYEAAKGIYEQFLPEITEHLSLHGDRAKF
           ******************* ******************************* *******

Seq1   417 QFTGHSLGGSLSLIVNLMLISRGLVSSEAMKSVVTFGSPFVFCGGEKILAELGLDESHVH
Seq 11 409 QFTGHSLGGSLSLIVNLMLLSRGLVSSEAMKPVVTFGSPFVFCGGEKILEELGLEESHVH
           ******************* *********** ****************  **** ****

Seq1   477 CVMMHRDIVPRAFSCNYPDHVALVLKRLNGSFRTHPCLNKNKLLYSPMGKVYILQPSESV
Seq 11 469 CVMMHRDIVPRAFSCNYPDHVALVLKRLNGTFRTHPCLNKNKLLYSPMGKVFILQPSESV
           ****************************** ******************* ********

Seq1   537 SPTHPWLPPGNALYILENSNEGYSPTALRAFLNRPHPLETLSQRAAYGSEGSVLRDHDSK
Seq 11 529 SPTHPWLPPGNALYVLDKNNEGYSPTALRGFLNRPHPLETLSQRAAYGSEGSVLRDHDSK
           ************** *   ********* ********************************

Seq1   597 NYVKAVNGVLRQHTKLIVRKARIQRRS-VWPVLISA--GRGLNE-SLITAEEIMTR
Seq 11 589 NYVKAVNGVIRQHTKLIVRKVRRQRRSTVWPVLIPAEPNSSVNDWSLTATEEIMTR
           ********* ********** * ****  *****  *      *  ** *******
```

This lipase protein from *Brassica napus* with SEQ ID NO:11 has accession number XP_013741914.1 and the SEQ ID NO:11 amino acid sequence is shown below.

```
  1 MSFNAAMASP SPPAANDVFK EHFGLRRSLS GQDLVVKAGG
 41 IRRSSSDNHL CCKNRIRAVS VRPGQGMKSS RSVGVFSFQI
 81 SSSIIPSPIK TLLFETEDDT DSDDEPEVEP NLDGAKKANW
121 VQRLLEIRRQ WKKETRTENS NGDVVSEHEN VTCGCEDGEG
161 CVADYENGDW ERESFSKLLV RVSWSDAKQL SQLAYLCNVA
181 YTIPEIKGED LRRNYGLKFV TSSLEKKAKA ALLREKLEQD
241 STRVPVVTSP ESESDKFQQR SSSSSSAYKI AASAASYIHS
281 CKEYESSDLN NPYKSAAAAQ AAASTMTAVV AAGEDEKLEA
321 ARELQSLQSS PCEWFVCDEP NSYTRCFVIQ GSDSLASWKA
361 NLFFEPTRFE DTDVLVHRGI YEAAKGIYEQ FLPEITEHLS
401 LHGDRAKFQF TGHSLGGSLS LIVNLMLLSR GLVSSEAMKP
421 VVTFGSPFVF CGGEKILEEL GLEESHVHCV MMHRDIVPRA
481 FSCNYPDHVA LVLKRLNGTF RTHPCLNKNK LLYSPMGKVF
521 ILQPSESVSP THPWLPPGNA LYVLDKNNEG YSPTALRGFL
561 NRPHPLETLS QRAAYGSEGS VLRDHDSKNY VKAVNGVIRQ
601 HTKLIVRKVR RQRRSTVWPV LTPAEPNSSV NDWSLTATEE
641 IMTRA
```

Another PLIP1-related lipase protein from *Gossypium hirsutum* (cotton) with SEQ ID NO:64 shares about 53-56% sequence identity with the SEQ ID NO:1 protein as illustrated below.

```
Seq1    10 TSPAAANDVLREHIGLRRSLSGQDLVLKGGGIRRSSSDNHLCCRSGNNNNRILAVSVRPG
Seq64   14 TAVAKKDGCKEEIGGLRRSNSGVNLH-KRVGIQRSYSDNHLCYYT----NRIVAASTKST
           *  *          * ***** **  **   * ** ** ****  *       *** * *

Seq1    70 MKTSRSVGVFS---FQISSSIIPSPIKILLFETDTSQD----EQESDEIEIETEPNLDGA
Seq64   69 LKTSRSFGILPPLPFRISGSMIPNSVRSFLFDPETSKDLSGVGKDVNVIDGNSRGNDDEE
           ***** *      * **  *** *   * **  ** *         *        *  *

Seq1   123 K---KANWVERLLEIRRQWKREQKTES--GNSDVAEESVDVTCGCEEEEGCIANYGSVNG
Seq64  129 KEIKRANWLNRLLEIQSSFKHKQVEEGVEGAGIYDENENGDDGGCEVNYDSEDEGGEVKY
           *    *** *****     *  * *      *  *        **   *   *  *

Seq1   178 DWGRESFSRLLVKVSWSEAKKLSQLAYLCNLAYTIPEIKGEDLRRNYGLKFVTSSLEKKA
Seq64  189 D--RDSFSKLLVQVPWSDTKVISQLAFLCNMAYVIPSIKEKDLRKYYGLRFVTSSLEKKA
           *    ***  ***  ** *   ****  ***  ** *** ***  **** *********
```

```
Seq1   238 KAAILREKLEQDPTHVPVITSPDLESEKQSQRSASSS---ASAYKIAASAASYI------
Seq64  247 KAAKIKAKLDQDSTRVPIAETSESESKKVESKEWKHPIRISVVYEIAASAACYVQSQAKG
           ***  ** ** * **           ** *            * ******  *

Seq1   289 ---------------HSCK-------EYDLSEP-IYKSAAAAQAAASTMTAVVAAGEEEK
Seq64  307 LLSPGSKSQEEEDDMNSCRISEQPEMEGENSPPRVYNSEVAALMAAEAMTAVVRAGEKEK
                          **      *  * *  *  ** **  ***** *** **

Seq1   326 LEAARELQSLQSSPCEWFVCDDPNTYTRCFVIQGSDSLASWKANLFFEPTKFEDTDVLVH
Seq64  367 QETAKDLQSLHSSPCEWFVCDDLNTYTRCFVIQGSDSLASWQANLLFEPTEFEGTGVLVH
            *  * **** ************ ******************* *** **** **  * ****

Seq1   386 RGIYEAAKGIYEQFLPEITEHLSRHGDRAKFQFIGHSLGGSLSLIVNLMLISRGLVSSEA
Seq64  427 RGIYEAAKGIYEQFIPEIMDHLKRHGHRAKLQFIGHSLGGSLSLLVNLMLLARKVVKPSA
           ************** ***  ** *** *** ************ ***** *   *   *

Seq1   446 MKSVVTFGSPFVFCGGEKILAELGLDESHVHCVMMHRDIVPRAFSCNYPDHVALVLKRLN
Seq64  487 LRPVVTFGSPFVFCGGQRILDELGLDDNHVHCVMMHRDIVPRAFSCKYPNHVAVVLKRLP
             *************  ** *****  ****************** ** *** *****

Seq1   506 GSFRTHPCLNKNKLLYSPMGKVYILQPSESVSPTHPWLPPGNALYILENSNEGYSPTALR
Seq64  547 GSLRSHPCLLKNKLLYTPLGKQFILQPSEKSSPPHPLIPPGNALYALDKTHSEYSMQALM
           ** * **** ****** * **  ****** *  ***  ******  *    ** * **

Seq1   566 AFLNRPHPLETLSQRAAYGSEGSVLRDHDSKNYVKAVNGVLRQHTKLIVRKARIQRRSVW
Seq64  607 AFLNCPHPLDTLGDLTAYGLDGTILRDHDSSNYLKAVNGVLRLQ-KMANRCSRMDTSLLW
           **** **** **    ***  *  ****** ** *******    *    *      *

Seq1   626 PVLTS
Seq64  666 PLLNS
           * * *
```

This lipase protein from *Gossypium hirsutum* (cotton) with SEQ ID NO:64 has accession number XP_016692941.1 and the SEQ ID NO:64 amino acid sequence is shown below.

```
  1 MACTSMVVPT SHVTAVAKKD GCKEEIGGLR RSNSGVNLHK
 41 RVGIQRSYSD NHLCYYTNRI VAASTKSTLK TSRSFGILPP
 81 LPFRISGSMI PNSVRSFLFD PETSKDLSGV GKDVNVIDGN
121 SRGNDDEEKE IKRANWLNRL LEIQSSFKHK QVEEGVEGAG
161 IYDENENGDD GGCEVNYDSE DEGGEVKYDR DSFSKLLVQV
201 PWSDTKVISQ LAFLCNMAYV IPSIKEKDLR KYYGLRFVTS
241 SLEKKAKAAK IKAKLDQDST RVPIAETSES ESKKVESKEW
281 KHPIRISVVY EIAASAACYV QSQAKGLLSP GSKSQEEEDD
321 MNSCRISEQP EMEGENSPPR VYNSEVAALM AAEAMTAVVR
361 AGEKEKQETA KDLQSLHSSP CEWFVCDDLN TYTRCFVIQG
401 SDSLASWQAN LLFEPTEFEG TGVLVHRGIY EAAKGIYEQF
441 IPEIMDHLKR HGHRAKLQFT GHSLGGSLSL VNLMLLARK
481 VVKPSALRPV VTFGSPFVFC GGQRILDELG LDDNHVHCVM
521 MHRDIVPRAF SCKYPNHVAV VLKRLPGSLR SHPCLLKNKL
561 LYTPLGKQFI LQPSEKSSPP HPLIPPGNAL YALDKTHSEY
601 SMQALMAFLN CPHPLDTLGD LTAYGLDGTI LRDHDSSNYL
641 KAVNGVLRLQ KMANRCSRMD TSLLWPLLNS PSPHSWSHDR
681 SLENILLSNK EIMSGV
```

Another PLIP1-related lipase protein from *Gossypium hirsutum* (cotton) with SEQ ID NO:65 shares about 53-54% sequence identity with the SEQ ID NO: 1 protein as illustrated below.

```
Seq1   33 DLVLKGGGIRRSSSDNHLCCRSGNNNNRILAVSVRPGMKTSRSVGVFSFQISSSIIPSPI
Seq65  24 DSSMNKAGIRRSYSDNHLCC---SINRIRAAASTKPTMTKSSSVGILPSLLPVQISSSTI
              *  ***** *******      *   *   *  * *  ***  *   *    * * *

Seq1   93 KTLLFETDTSQDEQESDEIEIETEPNLDGAKKANWVERLLEIRRQWKREQKTES-GNSDV
Seq65  81 PNSVRSFWFDDNDDEEEEI----------KRANWVNRLLEVHSRWKHRQIEDGVEGGEI
              *  **                    *****  ***    ***  **   *

Seq1  152 AEESVDVTCGCEEEEGCIANYGS-VNGD---WGRESFSRLLVKVSWSEAKKLSQLAYLCN
Seq65  130 YDENENDGNEDEHEGGCEVNYNSDEEGDEVVYDRESFSKLLVRVPLSDTKLFSELAFLCN
            *          *  ****  *   *   *   ***** ***  *     * * * ***

Seq1  208 LAYTIPEIKGEDLRRNYGLKFVTSSLEKKAKAAILREKLEQDPTHVPVITSPDLESEK--
Seq65  190 IAYVIPKIEGMELRKYYGLKFVTSSIEKKAEVATIKAKMDQDSIRVPVATPKSTELEKVE
            ** **  *  **  ********* **** *  *     ***   *** *   **  *

Seq1  266 -QSQRSASSSASAYKIAASAASYIHSCK-------------------------EYDLS
Seq65  250 GTETKRLISLSAVYEIAASAAYYVQSRAKGLLSPGFKSPVEDERDSRRSGDEHEMEGENS
                       *  ******  *  *                            *  *
```

```
Seq1   298 EPIYKSAAAAQAAASTMTAVVAAGEEEKLEAARELQSLQSSPCEWFVCDDPNTYTRCFVI
Seq65  310 PRVYNSEVAAYMAASAMTAVVRSGEKAKQATAKDLQSLQSSPSEWSVCDELSTYTRCFVI
           *  *   **   *** ***** **  *   * ******** **  ***   ********

Seq1   358 QGSDSLASWKANLFFEPTKFEDTDVLVHRGIYEAAKGIYEQFLPEITEHLSRHGDRAKFQ
Seq65  370 QGSDSLASWQANLLFEPTIFEYTDVLVHRGIYEAAKGIYEQFLPEIMDHLNRHGDRAKLQ
           ********* *** **** ** ************************  **  ****** *

Seq1   418 FTGHSLGGSLSLIVNLMLISRGLVSSEAMKSVVTFGSPFVFCGGEKILAELGLDESHVHC
Seq65  430 FTGHSLGGSLSLLVSLMLLAKKVVKPSALRPVITFGSPFVFCGGQKILEEFGLDDNHVHC
           ************ *  ***    *   *   * *********** ***  *   * ****

Seq1   478 VMMHRDIVPRAFSCNYPDHVALVLKRLNGSFRTHPCLNKNLLYSPMGKVYILQPSESVS
Seq65  490 VMMHRDIVPRAFSCKYPNHVAIVLKRLPGSLRSHRCLLKNKLLYTPLGKLFIVQPSEKSS
           **************  **  ***  *** ****     **  ** ****  *  **** *

Seq1   538 PTHPWLPPGNALYILENSNEGYSPTALRAFLNRPHPLETLSQRAAYGSEGSVLRDHDSKN
Seq65  550 PPHPLLPLGTA----------------------PLDTLSDLTAYGSEGTILRDHDSSN
           * ** **  *                       *  ***    ****** ****** *

Seq1   598 YVKAVNGVLRQHTKLI
Seq65  586 YLKAINGVLRQHKKTV
           * ** ********  *
```

This lipase protein from *Gossypium hirsutum* (cotton) with SEQ ID NO:65 has accession number XP_016738139.1 and the SEQ ID NO:65 amino acid sequence is shown below.

```
  1 MAVPTSRVAS KAKEEEINGL RRLDSSMNKA GIRRSYSDNH

41 LCCSINRIRA AASTKPTMTK SSSVGILPSL LPVQISSSTI

81 PNSVRSFWFD DNDDEEEEIK RANWVNRLLE VHSRWKHRQI

121 EDGVEGGEIY DENENDGNED EHEGGCEVNY NSDEEGDEVV

161 YDRESFSKLL VRVPLSDTKL FSELAFLCNI AYVIPKIEGM

201 ELRKYYGLKF VTSSIEKKAE VATIKAKMDQ DSIRVPVATP

241 KSTELEKVEG TETKRLISLS AVYEIAASAA YYVQSRAKGL

281 LSPGFKSPVE DERDSRRSGD EHEMEGENSP RVYNSEVAAY

321 MAASAMTAVV RSGEKAKQAT AKDLQSLQSS PSEWSVCDEL

361 STYTRCFVIQ GSDSLASWQA NLLFEPTTFE YTDVLVHRGI

401 YEAAKGIYEQ FLPEIMDHLN RHGDRAKLQF TGHSLGGSLS

441 LLVSLMLLAK KVVKPSALRP VITFGSPFVF CGGQKILEEF

481 GLDDNHVHCV MMHRDIVPRA FSCKYPNHVA IVLKRLPGSL

521 RSHRCLLKNK LLYTPLGKLF IVQPSEKSSP PHPLLPLGTA

561 PLDTLSDLTA YGSEGTILRD HDSSNYLKAI NGVLRQHKKT

601 VPSLTTRTVS DTSLLWPLLV SPSPRTWNHH RQMMFSNKEI

641 MTGV
```

Another PLIP1-related lipase protein from *Arachis hypogaea* (peanut) with SEQ ID NO:66 shares about 53-54% sequence identity with the SEQ ID NO:1 protein as illustrated below.

```
Seq1    1 MAFNTAMASTSPAAANDV---LREHIGLRRSLSGQDLVLKGGGIRRSSSDNHLCCRSGNN
Seq66   1 MAFSAVGMATSPASSATMDIRTIKHNGLRRSSSGIELSTRSI-MQRSYSDTHLCCAV---
          ***    ****    *       * ****** **     *** * ** ****

Seq1   58 NNRILAVSVRPGMKTSRSVGVFSFQISSSIIPSPIKTLLFETDTSQD------EQESDEI
Seq66  57 -NPIQATSLQPKQKSNKSMGISPFQFSGSILPNSLRSFLFDPETSKEMNMGEKDHSSHFE
           *  *   *  *  * **  *** * *  **    * **   **                *

Seq1  112 EIETEPNLDGA-KKANWVERLLEIRRQWKREQKTESGNSDVAEESVDVTCGCEEEEGCIA
Seq66 116 ESAVECNEDEKINRTNWIERLMEIKKNWRNRIPKEEMDPDMICDN-NSNDECDCDEGCVV
          *   *   *     * **  *** ***  ** * *   *  *  *   *  *  ***

Seq1  171 NY--GSVNGDWGRESFSRLLVKVSWSEAKKLSQLAYLCNLAYTIPEIKGEDLRRNYGLKF
Seq66 175 DYVEDGQEGTYDHDSFIKFLSQVSWSDTKLYSKLAFLCNMAYVIPEIKAKDLRRYYSLQF
           *          *   * *  * **** *    ** *** ** ****  ****   * *

Seq1  229 VTSSLEKKAKAAILREKLEQDPTHVPV---ITSPDLESEKQSQRSASSSASAYKIAASAA
Seq66 235 ITSSLEKKAEVEKLKERLDKDSTRIPINGSVASQDGSEKGKDNKERHQIRLAYDIATSAA
           ********     *  * * *   *     *  * ***                ** ** ***

Seq1  286 SYIH---------SCKEYDLSEPIYKS-------------------AAAQAAASTMTAV
Seq66 295 SYVQLRAKDLLSLTAKRQQPQSDILDSNGRENSEGFEAEALPGLIHQSCSLCCSINNDAV
          **                  *      *                                    **

Seq1  318 VAAGEEEKLEAARELQSLQSSPCEWFVCDDPNTYTRCFVIQGSDSLASWKANLFFEPTKF
Seq66 355 VAACEKEKQEAAKDLQSLHSSLCEWFICDDSNTYTRYFVIQGSDSLASWQANLFFEPTKF
          *** * ** ****  ***** ***** ***** ***** ****** ***** *********** **********
```

```
Seq1   378 EDTDVLVHRGIYEAAKGIYEQFLPEITEHLSRHGDRAKFQFTGHSLGGSLSLIVNLMLIS
Seq66  415 EDTDVLVHRGIYEAAKGIYEQFLPEIKAHLKRHGDRAKLQFTGHSLGGSLSLLVHLMLLS
           *************************  ** ******* ************* *** *

Seq1   438 RGLVSSEAMKSVVTFGSPFVFCGGEKILAELGLDESHVHCVMMHRDIVPRAFSCNYPDHV
Seq66  475 RKVVSPSTLRPVVTFGSPFVFCGGHKLLDHLGLDESHIHCVMMHRDIVPRAFSCNYPNHV
           * **         ************ *  ******* ******************* **

Seq1   498 ALVLKRLNGSFRTHPCLNKNKLLYSPMGKVYILQPSESVSPTHPWLPPGNALYILENSNE
Seq66  535 ALVLKRLNSTFRSHPCLIKNKLLYSPLGKIFILQPDERTSPPHPLLPSGSAFYALDSARC
           ********  ** **** ******** **  **** *  **  ***  *  ** *

Seq1   558 GYSPTALRAFLNRPHPLETLSQRAAYGSEGSVLRDHDSKNYVKAVNGVLRQHTKLIVRKA
Seq66  595 GYTPSVLRTFLNQPHPIETLSDPTAYGSEGTILRDHDSSNYLKVVNGVLRQHSKNIVRQM
           ** *  ** *** *** ****   ****** ****** ** * ******** *  **

Seq1   618 RIQR-RSVWPVLTS
Seq66  655 RKQRINELWPLLTT
           * **     ** **
```

This lipase protein from *Arachis hypogaea* (peanut) with SEQ ID NO:66 has accession number ADY38373.1 and the SEQ ID NO:66 amino acid sequence is shown below.

```
  1 MAFSAVGMAT SPASSATMDI RTTKHNGLRR SSSGIELSTR

41 SIMQRSYSDT HLCCAVNPIQ ATSLQPKQKS NKSMGISPFQ

81 FSGSILPNSL RSFLFDPETS KEMNMGEKDH SSHFEESAVE

121 CNEDEKINRT NWIERLMEIK KNWRNRIPKE EMDPDMICDN

161 NSNDECDCDE GCVVDYVEDG QEGTYDHDSF TKFLSQVSWS

201 DTKLYSKLAF LCNMAYVIPE IKAKDLRRYY SLQFITSSLE

241 KKAEVEKLKE RLDKDSTRIP INGSVASQDG SEKGKDNKER

281 HQIRLAYDIA TSAASYVQLR AKDLLSLTAK RQQPQSDILD

321 SNGRENSEGF EAEALPGLIH QSCSLCCSIN NDAVVAACEK

361 EKQEAAKDLQ SLHSSLCEWF ICDDSNTYTR YFVIQGSDSL

401 ASWQANLFFE PTKFEDTDVL VHRGIYEAAK GIYEQFLPEI

441 KAHLKRHGDR AKLQFTGHSL GGSLSLLVHL MLLSRKVVSP

481 STLRPVVTFG SPFVFCGGHK LLDHLGLDES HIHCVMMHRD

521 IVPRAFSCNY PNHVALVLKR LNSTFRSHPC LIKNKLLYSP

561 LGKIFILQPD ERTSPPHPLL PSGSAFYALD SARCGYTPSV

601 LRTFLNQPHP IETLSDPTAY GSEGTILRDH DSSNYLKVVN

641 GVLRQHSKNI VRQMRKQRIN ELWPLLTTPS PHSWNHEQNL

681 ERCNLMTKEI VTGV
```

Another PLIP1-related lipase protein from *Helianthus annuus* (sunflower) with 50 SEQ ID NO:67 shares about 55-56% sequence identity with the SEQ ID NO: 1 protein as illustrated below.

```
Seq1    25 LRRSLSGQDLVLKGGGIRRSSSDNHLCCRSGNNNNRILAVSVRPGMKTSRSVGVFSFQIS
Seq67   19 LNRSISSQNL-RQHARIRRAHSDNNLCYSA----NHVQASMNQPKLKNSRSVGIFNLNLS
           * **  *   *   *** *** **  *        *     * * ****** *    *

Seq1    85 SSIIPSPIKTLLFETDTSQ------DEQESDEIE--IETEPNLDGAKKANWVERLLEIRR
Seq67   74 SSFIPNSLKTLLFDPDTSTGMDTDTDTERGDEVADVSDVEMTKEEKNRANWIERLVEIRS
           ** **  ***** * ***         *  **    *        *  *** *** ***

Seq1   137 QWKREQKTESGNSDVAEESVDVTCGCEEEEGCIANYGSVNGDW--GRESFSRLLVKVSWS
Seq67  134 RWVQKQNNELDGENGEEKGCDED---GNGEGCEVDYSDDEDNVIVNQETFSGMLKQVSWS
            *  *  *  *  *   *  *       * ** *        *   ** * * * ****

Seq1   195 EAKKLSQLAYLCNLAYTIPEIKGEDLRRNYGLKFVTSSLEKKAKAAILREKLEQDPTHVP
Seq67  191 DTKQFSQLAFLCNMAYVIPEIEEDDLRRYYDLTFVTSSLEKKVSAQEIPRELNSVPVTAS
             *  **** *** ** ****   **** * * ********  *  *  *     *

Seq1   255 VITS-PDLESEKQSQRSASSSASAYKIAASAASYIH------SCKEYDLSEP---IYKSA
Seq67  251 TNNQRPEKHTTRTSAYEIAASAATY-VQSQAGGLINLESDPLAEEDDDITDPSSRVYNSE
                *  *         ***   *    *    *             *        *

Seq1   305 AAAQAAASTMTAVVAAGEEEKLEAARELQSLQSSPCEWFVCDDPNTYTRCFVIQGSDSLA
Seq67  310 MAAYMAASTMTAVVAAPEKEKQEAARDLQSLHSSPCEWFICDDSSIYTRCFVIQGSDSVA
            **  *********** *  *  **** **** ****** ***   *********** *

Seq1   365 SWKANLFFEPTKFEDTDVLVHRGIYEAAKGIYEQFLPEITEHLSRHGDRAKFQFTGHSLG
Seq67  370 SWQANLFFEPTKFEETGVPVHRGIYEAAKGIYEQFMPHIQEHLNRYGERAKLQFTGHSLG
           ** ***********  *  *************** *  ***  * *  *** *******

Seq1   425 GSLSLIVNLMLISRGLVSSEAMKSVVTFGSPFVFCGGEKILAELGLDESHVHCVMMHRDI
Seq67  430 GSLSLLVNLMLLTRKVVKPSALRPVVTFGSPFVFCNGQKILDQLGLDENHVHCVMMHRDI
           ***** *****  *   *  *  ***********  *** **** ** ***********
```

```
Seq1   485 VPRAFSCNYPDHVALVLKRLNGSFRTHPCLNKNLLYSPMGKVYILQPSESVSPTHPWLP
Seq67  490 VPRAFSCNYPKHVAQLLKRLCGTFRSHPCLNRNSILYTPLGKMFILQPDEKSSPHHPLLP
           **********  ***  ****  *  ** *****  *   ** * **  ****  *  ** ** **

Seq1   545 PGNALYILENSNEGYSPTALRAFLNRPHPLETLSQRAAYGSEGSVLRDHDSKNYVKAVNG
Seq67  550 AGSALYVMENTNRGLTKTAIRAFLNSPHPIETLQHPTAYGSDGTILRDHDSSNYLKAVNG
             ***  ** *   *      ** ***** *** ***       ****  *  ****** **  *****

Seq1   605 VLRQHTKLIVRKARIQRRSVWPVLTS
Seq67  610 IIRQHTKTFIRKPKQQRNLLWPLLTS
             *****  **   **   ** ***
```

This lipase protein from *Helianthus annuus* (sunflower) with SEQ ID NO:67 has accession number XP_022035660.1 and the SEQ ID NO:67 amino acid sequence is shown below.

```
  1 MMVCSSISVS SQPTTPNILN RSISSQNLRQ HARIRRAHSD
 41 NNLCYSANHV QASMNQPKLK NSRSVGIFNL NLSSSFIPNS
 81 LKTLLFDPDT STGMDTDTDT ERGDEVADVS DVEMTKEEKN
121 RANWIERLVE IRSRWVQKQN NELDGENGEE KGCDEDGNGE
161 GCEVDYSDDE DNVIVNQETF SGMLKQVSWS DTKQFSQLAF
201 LCNMAYVIPE IEEDDLRRYY DLTFVTSSLE KKVSAQEIPR
241 ELNSVPVTAS TNNQRPEKHT TRTSAYEIAA SAATYVQSQA
281 GGLINLESDP LAEEDDDITD PSSRVYNSEM AAYMAASTMT
321 AVVAAPEKEK QEAARDLQSL HSSPCEWFIC DDSSIYTRCF
361 VIQGSDSVAS WQANLFFEPT KFEETGVPVH RGIYEAAKGI
401 YEQFMPHIQE HLNRYGERAK LQFTGHSLGG SLSLLVNLML
441 LTRKVVKPSA LRPVVTFGSP FVFCNGQKIL DQLGLDENHV
481 HCVMMHRDIV PRAFSCNYPK HVAQLLKRLC GTFRSHPCLN
521 RNSILYTPLG KMFILQPDEK SSPHHPLLPA GSALYVMENT
561 NRGLTKTAIR AFLNSPHPIE TLQHPTAYGS DGTILRDHDS
601 SNYLKAVNGI IRQHTKTFIR KPKQQRNLLW PLLTSQSPHY
641 WSQETKVKEK QLTVSDQRRL VTTEVA
```

Another PLIP1-related lipase protein from *Helianthus annuus* (sunflower) with SEQ ID NO:68 shares about 55-56% sequence identity with the SEQ ID NO: 1 protein as illustrated below.

```
Seq1    25 LRRSLSGQDLVLKGGGIRRSSSDNHLCCRSGNNNNRILAVSVRPGMKTSRSVGVFSFQIS
Seq68   53 LNRSISSQNL-RQHARIRRAHSDNNLCYSA----NHVQASMNQPKLKNSRSVGIFNLNLS
            *  **  * *     ***  *** **    *   *     * *****   *

Seq1    85 SSIIPSPIKTLLFETDTSQ------DEQESDEIE--IETEPNLDGAKKANWVERLLEIRR
Seq68  108 SSFIPNSLKTLLFDPDTSTGMDTDTDTERGDEVADVSDVEMTKEEKNRANWIERLVEIRS
           ** **  ***** ***    *    **         *** *** ***

Seq1   137 QWKREQKTESGNSDVAEESVDVTCGCEEEEGCIANYGSVNGDW--GRESFSRLLVKVSWS
Seq68  168 RWVQKQNNELDGENGEEKGCDED---GNGEGCEVDYSDDEDNVIVNQETFSGMLKQVSWS
            *  *     *      *  *       ***   *       * **   * ****

Seq1   195 EAKKLSQLAYLCNLAYTIPEIKGEDLRRNYGLKFVTSSLEKKAKAAILREKLEQDPTHVP
Seq68  225 DTKQFSQLAFLCNMAYVIPEIEEDDLRRYYDLTFVTSSLEKKVSAQEIPRELNSVPVTAS
             ** ****  *** **  ***    ****  **  *********  *     *       *  *

Seq1   255 VITS-PDLESEKQSQRSASSSASAYKIAASAASYIH------SCKEYDLSEP---IYKSA
Seq68  285 TNNQRPEKHTTRTSAYEIAASAATY-VQSQAGGLINLESDPLAEEDDDITDPSSRVYNSE
                    *          ** *     *   *         *        *    * *

Seq1   305 AAAQAAASTMTAVVAAGEEEKLEAARELQSLQSSPCEWFVCDDPNTYTRCFVIQGSDSLA
Seq68  344 MAAYMAASTMTAVVAAPEKEKQEAARDLQSLHSSPCEWFICDDSSIYTRCFVIQGSDSVA
            **  *********** * ** ****  ***** ******  ****  ** ************  *

Seq1   365 SWKANLFFEPTKFEDTDVLVHRGIYEAAKGIYEQFLPEITEHLSRHGDRAKFQFTGHSLG
Seq68  404 SWQANLFFEPTKFEETGVPVHRGIYEAAKGIYEQFMPHIQEHLNRYGERAKLQFTGHSLG
           ** ***********  *  * **************** *  *** *  * *** ********

Seq1   425 GSLSLIVNLMLISRGLVSSEAMKSVVTFGSPFVFCGGEKILAELGLDESHVHCVMMHRDI
Seq68  464 GSLSLLVNLMLLTRKVVKPSALRPVVTFGSPFVFCNGQKILDQLGLDENHVHCVMMHRDI
           *****  ****** *  *    *    *********** * ****   ******* ***********

Seq1   485 VPRAFSCNYPDHVALVLKRLNGSFRTHPCLNKNLLYSPMGKVYILQPSESVSPTHPWLP
Seq68  524 VPRAFSCNYPKHVAQLLKRLCGTFRSHPCLNRNSILYTPLGKMFILQPDEKSSPHHPLLP
           **********  ***  ****  *  ** *****  *    ** * **  ****  *  ** ** **
```

```
Seq1   545 PGNALYILENSNEGYSPTALRAFLNRPHPLETLSQRAAYGSEGSVLRDHDSKNYVKAVNG
Seq68  584 AGSALYVMENTNRGLTKTAIRAFLNSPHPIETLQHPTAYGSDGTILRDHDSSNYLKAVNG
           * ***  ** *   *   ** ***** *** ***    ****  * ****** ** *****

Seq1   605 VLRQHTKLIVRKARIQRRSVWPVLTS
Seq68  644 IIRQHTKTFIRKPKQQRNLLWPLLTS
           *****  **  **   ** ** ***
```

This lipase protein from *Helianthus annuus* (sunflower) with SEQ ID NO:68 has accession number OTG29254.1 and the SEQ ID NO:68 amino acid sequence is shown below.

```
  1 MYIICSMRSP ISYGTETAGV DSRSVFFSAL LLLVMMVCSS
 41 ISVSSQPTTP NILNRSISSQ NLRQHARIRR AHSDNNLCYS
 81 ANHVQASMNQ PKLKNSRSVG IFNLNLSSSF IPNSLKTLLF
121 DPDTSTGMDT DTDTERGDEV ADVSDVEMTK EEKNRANWIE
161 RLVEIRSRWV QKQNNELDGE NGEEKGCDED GNGEGCEVDY
201 SDDEDNVIVN QETFSGMLKQ VSWSDTKQFS QLAFLCNMAY
241 VIPEIEEDDL RRYYDLTFVT SSLEKKVSAQ EIPRELNSVP
281 VTASTNNQRP EKHTTRTSAY EIAASAATYV QSQAGGLINL
321 ESDPLAEEDD DITDPSSRVY NSEMAAYMAA STMTAVVAAP
361 EKEKQEAARD LQSLHSSPCE WFICDDSSIY TRCFVIQGSD
401 SVASWQANLF FEPTKFEETG VPVHRGIYEA AKGIYEQFMP
441 HIQEHLNRYG ERAKLQFTGH SLGGSLSLLV NLMLLTRKVV
481 KPSALRPVVT FGSPFVFCNG QKILDQLGLD ENHVHCVMMH
521 RDIVPRAFSC NYPKHVAQLL KRLCGTFRSH PCLNRNSILY
561 TPLGKMFILQ PDEKSSPHHP LLPAGSALYV MENTNRGLTK
601 TAIRAFLNSP HPIETLQHPT AYGSDGTILR DHDSSNYLKA
641 VNGIIRQHTK TFIRKPKQQR NLLWPLLTSQ SPHYWSQETK
681 VKEKQLTVSD QRRLVTTEVA
```

Another PLIP1-related lipase protein from *Olea europaea* (olive) with SEQ ID NO:69 shares about 57-58% sequence identity with the SEQ ID NO:1 protein as illustrated below.

```
Seq1   25 LRRSLSGQDLVLKGGGIRRSSSDNHLCCRSGNNNNRILAVSVRPGMKTSRS-VGVFSFQI
Seq69  26 LRKSWSSKNLTRRAG-IRRAFSDNNLFCRV----SRIQASTVEPKLKSSSSSAGFFNIQL
          ** **    *      ***  ****  ***        *  *  * *      * * * *

Seq1   84 SSSIIPSPIKTLLFETDTSQDEQESDE-IEIETEPNLDGAK---KANWVERLLEIRRQWK
Seq69  81 SSIMIPDTLKPFLFDLELSKEITIEDKLVESEREDEIDVEKVKKRANWIERLMEIRDSWK
          ** **   * * ** *   *    *    *    *        ***  *** **** **

Seq1  140 REQKTESGNSDVAE--ESVDVTCGCEEEEGCIANYGSVNGDWGRESFSRLLVKVSWSEAK
Seq69  141 EKQQREDVN-DVGENNEACDEDGGCEVDYDDDAEGKEMNIDG--KIFSSLLGKVSWSDIK
          * *   *   **     * *  ***         *     *    * * **  ***** *

Seq1  198 KLSQLAYLCNLAYTIPEIKGEDLRRNYGLKFVTSSLEKKAKAAILREKLEQDPTHVPVIT
Seq69  198 YFSKLAFLCNMAYVIPDIKTRDLSRYYGLELVTSSLEKKAEAEVTKDKPEQDSTTVHVAT
           *  ** *** **  ** **  **  ****  ********** *   ** *** * * *

Seq1  258 SPDLESEK-----QSQRSASSSASAYKIAASAASYIHSCKEYDLSEP--------IYKSA
Seq69  258 SASVDSISTKTMDREQKCRLRPSDAYEIAASAAVYVQSRIKDDLQEEEKKSSSHRVSKSE
          *    *         *        ** ****** *     **   **              **

Seq1  305 AAAQAAASTMTAVVAAGEEEKLEAARELQSLQSSPCEWFVCDDPNTYTRCFVIQGSDSLA
Seq69  318 MAASVAASTVTAVIAADEKEKQEAAKDLQSLHSSPCEWFVCDDSSIYTRCFVIQGSDSVE
           **  **** ***  ** * **  ****  ***** ***** *  * ********** *

Seq1  365 SWKANLFFEPTKFEDTDVLVHRGIYEAAKGIYEQFLPEITEHLSRHGDRAKFQFTGHSLG
Seq69  378 SWQANLFFEPTEFEGTDVLVHRGIYEAAKGIYEQFMPEIMQHLNRFGDRAKLQFTGHSLG
          ** ******** ** *******************  ***   ** * *****  *******

Seq1  425 GSLSLIVNLMLISRGLVSSEAMKSVVTFGSPFVFCGGEKILAELGLDESHVHCVMMHRDI
Seq69  438 GSLALLVNMMLLTRKVIKPSALLPVVTFGSPFVFCGGHRILNELGLDENHVHCVMMHRDI
          *** * ** **  *  *   *   ************ **** ****** ************

Seq1  485 VPRAFSCNYPDHVALVLKRLNGSFRTHPCLNKNLLYSPMGKVYILQPSESVSPTHPWLP
Seq69  498 VPRAFSCNYPNYVAQVLKRLSRTFRSHPCLNKSKLLYSPMGKIFILQPDEKSSPPHPLLP
          **********  **  ****   ***  ******    ********  ****  * **  **

Seq1  545 PGNALYILENSNEGYSPTALRAFLNRPHPLETLSQRAAYGSEGSVLRDHDSKNYVKAVNG
Seq69  558 SGSALYALDSTNFSLTKTAFRAFLNSPHPLETLSYPTAYGSEGTIIRDHDSSNYLKAMNE
            * ***  *     *   ** *****  ****** ******    ****** *** * **

Seq1  605 VLRQHTKLIVRKARIQRRSVWPVLTS
Seq69  618 VIRQHTRQVNKKVSKQTKQLWPLLTS
          * ****       *      ** ***
```

This lipase protein from *Olea europaea* (olive) with SEQ ID NO:69 has accession number XP_022857295.1 and the SEQ ID NO:69 amino acid sequence is shown below.

```
  1 MACSLPSITS SSSFTIENSQ KNEGRLRKSW SSKNLTRRAG
 41 IRRAFSDNNL FCRVSRIQAS TVEPKLKSSS SSAGFFNIQL
 81 SSTMIPDTLK PFLFDLELSK EITIEDKLVE SEREDEIDVE
121 KVKKRANWIE RLMEIRDSWK EKQQREDVND VGENNEACDE
161 DGGCEVDYDD DAEGKEMNID GKIFSSLLGK VSWSDTKYFS
201 KLAFLCNMAY VIPDIKTRDL SRYYGLELVT SSLEKKAEAE
241 VTKDKPEQDS TTVHVATSAS VDSISTKTMD REQKCRLRPS
281 DAYEIAASAA VYVQSRTKDD LQEEEKKSSS HRVSKSEMAA
321 SVAASTVTAV IAADEKEKQE AAKDLQSLHS SPCEWFVCDD
361 SSIYTRCFVI QGSDSVESWQ ANLFFEPTEF EGTDVLVHRG
401 IYEAAKGIYE QFMPEIMQHL NRFGDRAKLQ FTGHSLGGSL
441 ALLVNMMLLT RKVIKPSALL PVVTFGSPFV FCGGHRILNE
481 LGLDENHVHC VMMHRDIVPR AFSCNYPNYV AQVLKRLSRT
521 FRSHPCLNKS KLLYSPMGKI FILQPDEKSS PPHPLLPSGS
561 ALYALDSTNF SLTKTAFRAF LNSPHPLETL SYPTAYGSEG
601 TIIRDHDSSN YLKAMNEVIR QHTRQVNKKV SKQTKQLWPL
641 LTSQSPHMWS NKRNIGDTMV TKEILTGV
```

Another PLIP1-related lipase protein from *Olea europaea* (olive) with SEQ ID NO:70 shares about 53-54% sequence identity with the SEQ ID NO:1 protein as illustrated below.

```
Seq1    7 MASTSPAAANDVLREHIGLRRSLSGQDLVLKGGGIRRSSSDNHLCCRSGNNNNRILAVSV
Seq70   1 MASSLPSITSSPVITEEGRLRKSWSSKGLTERARLRRTYSDNNLSCRV----SRIQASKV
          ***    *             *  *        **  ***  **       **  *  *

Seq1   67 RPGMKTSRS-VGVFSFQISSSIIPSPIKTLLFETDTSQD---EQESDEIEIETEPNLDGA
Seq70  57 EPKLKSSSSSASFFNIQLPSTMFPDSLKSFFSDLESSKEINIEEILVESEQEDEIDVEKV
            *   **       *          *       *         *   *      * ***

Seq1  123 KK-ANWVERLLEIRRQWKREQKTESGN-SDVAEESVDVTCGCEEEEGCIANYGSVNGDWG
Seq70 117 KKRANWIERLMEIRNNWKEKQRKEDVNVAGENDEHCDEDGGCEVDYDDDDDAKGKEMNID
          ** *** *** ***  **  *  *         *  *   **   *     ***

Seq1  181 RESFSRLLVKVSWSEAKKLSQLAYLCNLAYTIPEIKGEDLRRNYGLKFVTSSLEKKAKAA
Seq70 177 SKRFTPFLGQVSWSDTKHFSKLAFLCNMAYIIPNIKTRDLRRYYGLELVTSSLQKKVEAK
            *   *  **** *   *  ** ***  *** ** **** *   *   **** **  *

Seq1  241 ILREKLEQDPTHVPVITSPDLES-----EKQSQRSASSSASAYKIAASAASYIHSC----
Seq70 237 VMKVKPEQNSTSVYVATPAVLDSISAKTEDFEQKCLLRSSAAYEIAASAAFYVQSQTKDV
           * * *** *    *  *   *       * *    **    ** ****** * *

Seq1  292 -------KEYDLSEP-IYKSAAAAQAAASTMTAVVAAGEEEKLEAARELQSLQSSPCEWF
Seq70 297 KDDHQEEEEEESSPRVYKSEMAASVAASTMTAVIAADENQKQEAARDLQSIHSSPCEWF
                 *   *** **  ******** ** *  **  ***  ** *******

Seq1  344 VCDDPNTYTRCFVIQGSDSLASWKANLFFEPTKFEDTDVLVHRGIYEAAKGIYEQFLPEI
Seq70 357 VCDDSSIYTRCFVIQGSDSVESWQANLFFEPTKFEGTDVLVHRGIYEAAKGIYEQFMPEI
          ****   ************ *** *********** ******************** ***

Seq1  404 TEHLSRHGDRAKFQFTGHSLGGSLSLIVNLMLISRGLVSSEAMKSVVTFGSPFVFCGGEK
Seq70 417 MQHLNRFGNRAKLQFTGHSLGGSLALLVNLMLLTRKVVKPSALLPVVTFGSPFVFCGGHK
           ** * *  ***  *********   ****** *   *   *   ************ *

Seq1  464 ILAELGLDESHVHCVMMHRDIVPRAFSCNYPDHVALVLKRLNGSFRTHPCLNKNKLLYSP
Seq70 477 ILDELGLDENHVHCVMMHRDIVPRAFSCNYPNYVAQVLKRLSRTFRAHPCLNKNKLLYSP
          ** ****** ********************* **  *****   ** *************

Seq1  524 MGKVYILQPSESVSPTHPWLPPGNALYILENSNEGYSPTALRAFLNRPHPLETLSQRAAY
Seq70 537 MGRIFILQPDEKLSPPHPLLPSGSALYSLDSIKCSLAKSAFRAFLNSPHPLETLSNPTAY
          **    **** *  ** ** * * ***  *         * ***** ********    **

Seq1  584 GSEGSVLRDHDSKNYVKAVNGVLRQHTKLIVRKARIQRRSVWPVLTS
Seq70 597 GSEGTIIRDHDSSNYLKVMNEVIRQHTWQVDRKAGKQINQLWPLLTS
          ****  ***** ** *  *  * ****       *     **  ***
```

This lipase protein from *Olea europaea* (olive) with SEQ ID NO:70 has accession number XP_022897656.1 and the SEQ ID NO:70 amino acid sequence is shown below.

```
  1 MASSLPSITS SPVTTEEGRL RKSWSSKGLT ERARLRRTYS
 41 DNNLSCRVSR IQASKVEPKL KSSSSSASFF NIQLPSTMFP
 81 DSLKSFFSDL ESSKEINIEE ILVESEQEDE IDVEKVKKRA
121 NWIERLMEIR NNWKEKQRKE DVNVAGENDE HCDEDGGCEV
161 DYDDDDDAKG KEMNIDSKRF TPFLGQVSWS DTKHFSKLAF
201 LCNMAYIIPN IKTRDLRRYY GLELVTSSLQ KKVEAKVMKV
241 KPEQNSTSVY VATPAVLDSI SAKTEDFEQK CLLRSSAAYE
281 IAASAAFYVQ SQTKDVKDDH QEEEEEESSS PRVYKSEMAA
321 SVAASTMTAV IAADENQKQE AARDLQSIHS SPCEWFVCDD
361 SSIYTRCFVI QGSDSVESWQ ANLFFEPTKF EGTDVLVHRG
401 IYEAAKGIYE QFMPEIMQHL NRFGNRAKLQ FTGHSLGGSL
441 ALLVNLMLLT RKVVKPSALL PVVTFGSPFV FCGGHKILDE
481 LGLDENHVHC VMMHRDIVPR AFSCNYPNYV AQVLKRLSRT
521 FRAHPCLNKN KLLYSPMGRI FILQPDEKLS PPHPLLPSGS
561 ALYSLDSIKC SLAKSAFRAF LNSPHPLETL SNPTAYGSEG
601 TIIRDHDSSN YLKVMNEVIR QHTWQVDRKA GKQTNQLWPL
641 LTSQSPHMWS AKSNIGGMTA TEEILTGV
```

Another PLIP1-related lipase protein from *Elaeis guineensis* (oil palm) with SEQ ID NO:71 shares about 52-54% sequence identity with the SEQ ID NO:1 protein as illustrated below.

```
Seq1     8 ASTSPAAANDVLREHIGLRRSLSGQDLVLKGGGIRRSSSDNHLCCRSGNNNNRILAVSVR
Seq71   14 SAASAVAKDHLHGRQDGIRRSLSGTDLV----GVRRSRSEPLLRC-SLSIPRPATAASAP
            * *         * ****** ***    * *** *   * **           * *

Seq1    68 PGMKTSRSVGVFSFQISSSIIPSPIKTLLFETDTSQDEQE--SDEIEIETEPNLDGAKKA
Seq71   69 AKLKTSRSVGLFSF------IPNSIRSFLFNSEEAHGGMRFVDPEESSEEEVGSETEKRS
              ******* ***       **  *    **         *     * *        *

Seq1   126 NWVERLLEIRRQWK--REQKTESGNSDVAEESVDVTCGCEEEEGCIANYGSVNGDWGRES
Seq71  123 NWVERIWELRSRWRDRKPKADEEDASDGGGEESDEFCRVSYDSGEEAEREEERSEWDRES
           ***** *  *  *         *   *   ** *  *  * ** *      *  * ***

Seq1   184 FSRLLVKVSWSEAKKLSQLAYLCNLAYTIPEIKGEDLRRNYGLKFVTSSLEKKAKAAILR
Seq71  183 FERLLAPVSWIDAKLFSQLAFLCNMAYVIPEIKAEDLRKYYDLRYVTSSLEKKSEAAI-K
           * ***   *** *** **** *** ** ***** **** *  * * ******** *** *

Seq1   244 EKLEQDPTHVPV-ITSPDLESEKQSQRSASSSAS-AYKIAASAASYIHSCKEYDLS---E
Seq71  242 ARLESDSTRPPPGPTGPCPRSDSETQRRPLIRPSVAYEIAASAASYIHSRARGLLSLGGE
            * * *  *   * *  * *  **  **   *   ** *********** *  **  *

Seq1   299 P---------------------------------------------IYKSAAAAQAAASTM
Seq71  302 PGSINGMERLGERPEEAVSPQETLGQETTGEGLEEAQSLKGSPGRMYKSNVAAFVARSTM
           *                                             *** **  * ***

Seq1   315 TAVVAAGEEEKLEAARELQSLQSSPCEWFVCDDPNTYTRCFVIQGSDSLASWKANLFFEP
Seq71  362 TAVVAAEDEARQEAAKDLRSLHSSPCEWFVCDDPSTGIRCFVIQGSDSLASWQANLFFEP
           ******    *  *** * ** ************ *  ************* *******

Seq1   375 TKFEDTDVLVHRGIYEAAKGIYEQFLPEITEHLSRHGDRAKFQFTGHSLGGSLSLIVNLM
Seq71  422 TKFEETEVLVHRGIYEAAKGIYEQFMPEIEVHLQRWGDMAKLRFTGHSLGGSLSLLVHLM
           **** * ****************** ***  ** * ** **  ************ * **

Seq1   435 LISRGLVSSEAMKSVVTFGSPFVFCGGEKILAELGLDESHVHCVMMHRDIVPRAFSCNYP
Seq71  482 LLSRGAVKPSILLPVVTFGSPSVFCRGKRVLEGLGLDEGQVHSVMMHRDIVPRAFSCGYP
           * ***   *    ******** *** *  *  ****** ** ************** **

Seq1   495 DHVALVLKRLNGSFRTHPCLNKNKLLYSPMGKVYILQPSESVSPTHPWLPPGNALYILEN
Seq71  542 NHVAQVLKRLNKAFRSHPCLNNEKVLYSPLGQTYILQPDDKSSPPHPLLPPGAALYILDG
           ***  ****** ** ******  * **** *  ******   * * ** **** ****

Seq1   555 --------SNEGYSPTALRAFLNRPHPLETLSQRAAYGSEGSVLRDHDSKNYVKAVNGVL
Seq71  602 KKAAERGETKKATVAGALRAFLNSPHPLETLSDPAAYGSDGTILRDHDSSNYLKAMNGLV
                          ******* ********  ****** *  ******* ** ** **

Seq1   607 RQHTKLIVRKARIQR-RSVWPVLTS
Seq71  662 REHTKSVVRRTRRQRFYQLWPLLAT
           * *** * *  *  *     **  *
```

This lipase protein from *Elaeis guineensis* (oil palm) with SEQ ID NO:71 has accession number XP_010913778.1 and the SEQ ID NO:71 amino acid sequence is shown below.

```
  1 MPCAAAAIIH GGSSAASAVA KDHLHGRQDG IRRSLSGTDL
 41 VGVRRSRSEP LLRCSLSIPR PATAASAPAK LKTSRSVGLF
 81 SFIPNSIRSF LFNSEEAHGG MRFVDPEESS EEEVGSETEK
121 RSNWVERIWE LRSRWRDRKP KADEEDASDG GGEESDEFCR
161 VSYDSGEEAE REEERSEWDR ESFERLLAPV SWTDAKLFSQ
201 LAFLCNMAYV IPEIKAEDLR KYYDLRYVTS SLEKKSEAAI
241 KARLESDSTR PPPGPTGPCP RSDSETQRRP LIRPSVAYEI
281 AASAASYIHS RARGLLSLGG EPGSTNGMER LGERPEEAVS
321 PQETLGQETT GEGLEEAQSL KGSPGRMYKS NVAAFVARST
361 MTAVVAAEDE ARQEAAKDLR SLHSSPCEWF VCDDPSTGTR
401 CFVIQGSDSL ASWQANLFFE PTKFEETEVL VHRGIYEAAK
441 GIYEQFMPEI EVHLQRWGDM AKLRFTGHSL GGSLSLLVHL
481 MLLSRGAVKP STLLPVVTFG SPSVFCRGKR VLEGLGLDEG
521 QVHSVMMHRD IVPRAFSCGY PNHVAQVLKR LNKAFRSHPC
561 LNNEKVLYSP LGQTYILQPD DKSSPPHPLL PPGAALYILD
601 GKKAAERGET KKATVAGALR AFLNSPHPLE TLSDPAAYGS
641 DGTILRDHDS SNYLKAMNGL VREHTKSVVR RTRRQRFYQL
681 WPLLATPTNR LTGGHHSRME KSEPVNQEVL TTSV
```

Figure 8:
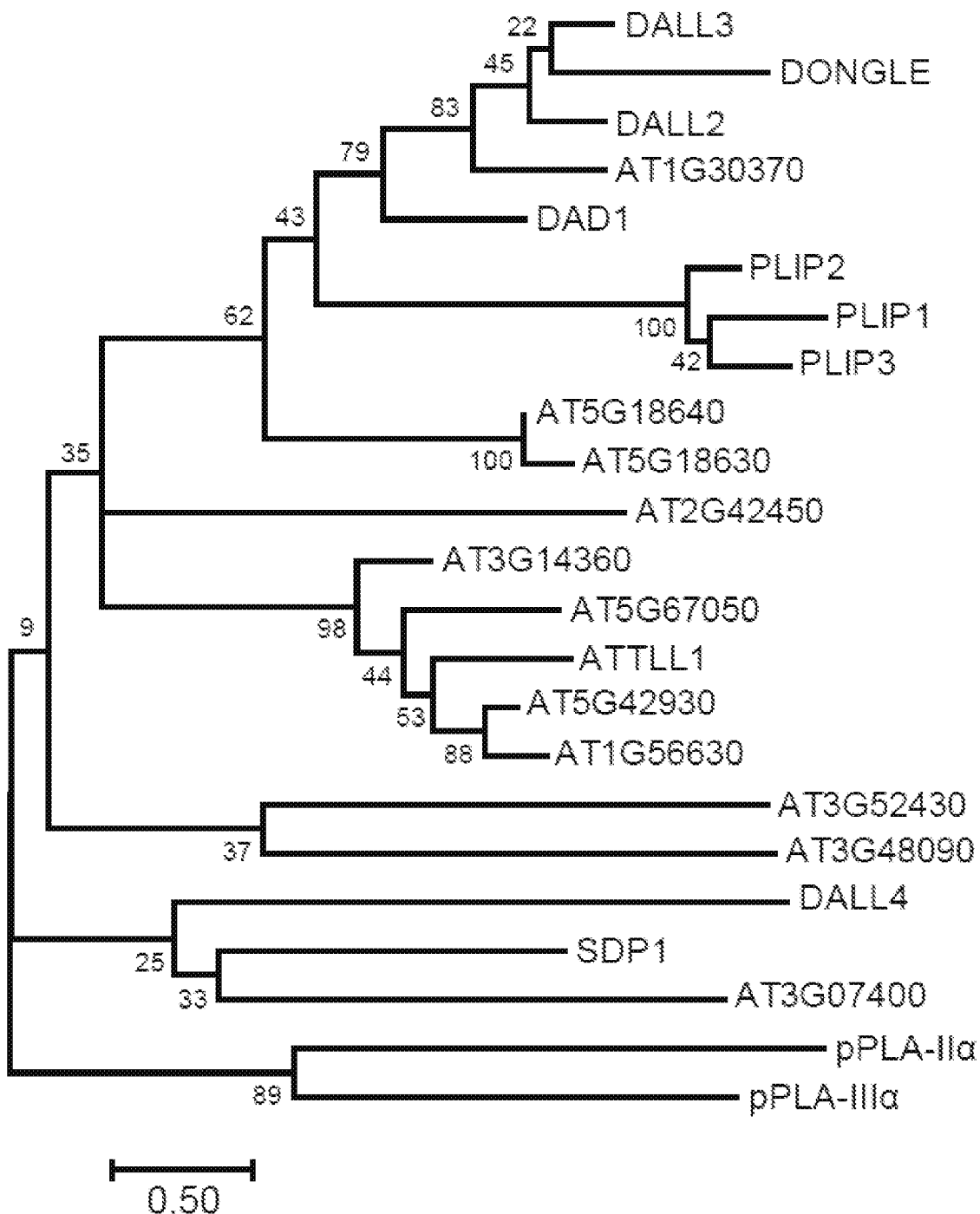
FIG. 8 illustrates phylogenetic relationships of PLIP1-similar protein sequences and other characterized lipase sequences in *Arabidopsis*. The illustrated phylogenetic tree was built using the Maximum Likelihood method with PLIP1 and the top 17 *Arabidopsis* similar protein sequences identified from the BLASTp search, as well as five other known *Arabidopsis* lipases. Previously studied lipases were presented with their gene names; others with their gene accession numbers. Bootstrap values (based on 500 repetitions) are indicated at the tree nodes. The scale measures evolutionary distances in substitution per amino acid. Any of the proteins identified in this figure can be used in the transgenic expression vectors, seeds and plants described herein.

As illustrated in FIG. 8, the PLIP1 enzyme is evolutionarily related to PLIP2 and PLIP3 lipases. In some cases, the lipase used in the expression cassettes and methods described herein can be a PLIP2 or PLIP3 lipase. However, some preliminary evidence indicates that the activities of the PLIP2 and PLIP3 lipases are different from the PLIP1 lipase. Hence, in some cases the lipase used in the expression cassettes and methods described herein is not a PLIP2 or PLIP3 lipase. However, in some cases, expression of a combination of PLIP1, PLIP2, and/or PLIP3 lipases may be useful and can be employed when making the expression cassettes and using the methods described herein.

A PLIP2 lipase can in some cases be encoded in expression cassettes and utilized in the methods described herein. However, in some cases the lipase is not a PLIP2 lipase. One example of an *Arabidopsis thaliana* PLIP2 protein sequence is shown below as SEQ ID NO:12.

```
  1 MDSLCLNSGL HGVIPAITAV GNGGCGGVVE VRATASAPSQ
 41 KRGPFGFSFK YPLTPFWSRG GGGGIASRRR SGLCLDDAVL
 81 VDSGDSRKPI AEETAVEMDT ERRNGSWVLK ILDVQSTWKH
121 EEEEDDDEVE DEDGDEDEEV ELDDAVVSED DGGCDVCSVL
161 EDDGNEANKF QLDRESFSKL LRRVTLPESK LYAQLSYLGN
201 LAYSISKIKP ANLSKYYGLR FVTSSAEKTE SALKAENGEV
241 SGETKPIVEA EEEVEEEEKN KSRKISASAA YEIVASAASY
281 LHSRTNNILP FNSSSKAENS DKHDVNLTNA ESSSDVAYSV
321 TSVVAAEEDV KQAVADDLKS TISSPCDWFI CDDDQSHTRF
361 VVIQGSESLA SWQANLLFEP IEFEGLGAIV HRGIYEAAKG
401 MYEQMLPEVK AHIKTHGTSA KFRFTGHSLG GSLSLLLNLM
441 LLVRGEVPAS SLLPVITYGA PFVLCGGDRL LKKLGLPKSH
481 VQAIVMHRDI VPRAFSCNYP YHVAELLKAV NGNFRSHPCL
521 NKQSMLYSPM GELLILQPDE TFSPGHELLP SGNGLYLLTS
561 DFESPDIEDS DEERLRAAQT VFLNTPHPLD ILSDRSAYGS
601 SGTIQRDHDM NSYLKAVRSV IRKEVNQIRR AKREHRRSLW
641 WPILVARESG SSGIAVSNGQ INGQDFSGMM QTGRKSLQRF
681 SRLVASQHMP LIVVMLFPVK LLFLGAFNVF SFR
```

A nucleic acid encoding the SEQ ID NO:12 *Arabidopsis thaliana* PLIP2 protein sequence is shown below as SEQ ID NO:13.

```
   1 ATGGACAGTT TGTGTTTGAA TAGCGGTTTA CACGGTGTAA
  41 TTCCAGCGAT CACTGCGGTT GGAAACGGCG GTTGCGGTGG
  81 AGTTGTTGAA GTCCGAGCAA CTGCGTCGGC ACCATCGCAA
 121 AAAAGAGGAC CTTTCGGGTT CTCATTTAAG TACCCACTGA
 161 CGCCGTTTTG GTCTCGCGGC GGTGGAGGAG GAATTGCGTC
 201 GAGGAGACGA AGTGGATTGT GTTTAGACGA CGCCGTTTTG
 241 GTTGATTCCG GCGATTCGAG AAAGCCGATC GCGGAGGAGA
 281 CGGCGGTGGA AATGGATACG GAGAGGCGAA ATGGGAGCTG
 321 GGTTTTGAAG ATCTTGGATG TACAATCTAC GTGGAAACAC
 361 GAAGAAGAAG AAGATGATGA TGAAGTAGAA GATGAAGACG
 401 GAGACGAAGA CGAGGAGGTT GAATTAGACG ACGCCGTAGT
 441 ATCTGAAGAT GATGGTGGAT GCGATGTATG TTCAGTTTTG
 481 GAAGATGATG GCAACGAAGC AAACAAATTT CAACTCGATA
 521 GAGAATCGTT CTCCAAATTG CTAAGGAGGG TTACGTTACC
 561 CGAATCAAAA CTCTATGCCC AACTATCGTA TTTGGGAAAC
 601 TTGGCTTATT CAATTTCAAA AATCAAGCCT GCGAATCTGT
 641 CGAAATATTA CGGCCTGAGA TTTGTAACTT CATCAGCTGA
 681 GAAAACAGAA TCGGCGTTAA AAGCTGAGAA TGGTGAAGTT
 721 TCAGGTGAGA CTAAGCCAAT TGTGGAAGCA GAAGAAGAAG
 761 TTGAAGAAGA AGAAGAAGAAC AAAAGTCGCA AGATTAGTGC
 801 TTCTGCTGCA TATGAGATTG TTGCATCAGC TGCTTCTTAC
 841 CTTCACTCTC GTACCAACAA CATACTTCCT TTCAACTCTT
 881 CATCGAAAGC CGAGAATTCG GACAAACATG ATGTAAATTT
 921 GACTAATGCG GAGTCATCAT CAGATGTTGC TTATTCTGTT
 961 ACTTCTGTTG TTGCTGCTGA GGAAGATGTG AAGCAAGCAG
1001 TTGCAGACGA TTTGAAATCC ACGATTTCGT CTCCCTGCGA
1041 TTGGTTTATA TGTGATGATG ATCAGAGTCA CACTAGATTC
1081 GTTGTGATTC AGGGATCTGA ATCTCTAGCT TCTTGGCAAG
```

```
1121 CAAATTTACT CTTTGAGCCT ATTGAATTTG AGGGCCTTGG
1161 TGCGATCGTA CACAGAGGAA TATACGAAGC TGCAAAAGGA
1201 ATGTATGAAC AAATGCTACC TGAAGTTAAA GCCCATATTA
1241 AAACCCATGG GACCAGCGCT AAATTCCGTT TCACCGGTCA
1281 TTCATTAGGT GGAAGCTTAT CGCTATTACT AAACCTCATG
1321 TTACTCGTTC GAGGCGAAGT ACCTGCGTCT TCTTTACTTC
1361 CGGTTATAAC ATATGGTGCA CCATTTGTGC TATGTGGAGG
1401 TGACCGTCTT CTTAAGAAAC TCGGATTGCC TAAAAGCCAT
1441 GTTCAAGCTA TTGTTATGCA CCGTGACATT GTTCCGAGAG
1481 CTTTTCTTG TAACTATCCG TACCATGTTG CTGAGCTTCT
1521 CAAAGCTGTT AATGGAAACT TCCGTAGCCA TCCTTGTCTT
1561 AACAAACAGA GTATGTTGTA TTCTCCGATG GGCGAGCTTC
1601 TGATTCTTCA ACCAGATGAG ACATTCTCCC CCGGGCATGA
1641 ACTTCTTCCT TCCGGAAACG GTTTATACCT TCTAACTAGT
```

```
1681 GATTTTGAAT CGCCGGATAT TGAAGATTCG GATGAGGAGC
1721 GGTTAAGAGC CGCGCAGACG GTTTTCTTGA ACACCCCGCA
1761 TCCTCTCGAC ATTCTCAGCG ACAGATCGGC TTATGGGTCC
1801 AGCGGAACAA TCCAAGAGA CCATGATATG AACTCGTATC
1841 TGAAAGCGGT TAGGAGTGTA ATAAGAAAGG AAGTGAATCA
1881 GATAAGGAGA GCAAAAGGG AGCATCGCCG GAGTCTTTGG
1921 TGGCCAATTC TGGTGGCTAG AGAAAGTGGA AGCTCAGGGA
1961 TTGCGGTCAG TAACGGCCAA ATCAACGGTC AGGATTTCTC
2001 CGGGATGATG CAGACAGGAA GAAAGTCGTT GCAGAGGTTT
2041 AGCCGCCTTG TGGCGTCTCA ACATATGCCG TTGATCGTTG
2081 TTATGTTGTT TCCGGTTAAG TTGTTGTTCC TTGGAGCTTT
2121 CAACGTCTTT AGTTTCCGTT GA
```

*Arabidopsis thaliana* has proteins related to the SEQ ID NO:12 PLIP2 protein, for example, the *Arabidopsis thaliana* PLIP2-related protein with SEQ ID NO:14 has 99% sequence identity to SEQ ID NO:12 as illustrated below.

```
Seq12    1 MDSLCLNSGLHGVIPAITAVGNGGCGGVVEVRATASAPSQKRGPFGFSFKYPLTPFWSRG
Seq14    1 MDSLCLNSGLHGVIPAITAVGNGGCGGVVEVRATASAPSQKRGPFGFSFKYPLTPFWSRG
           ************************************************************

Seq12   61 GGGGIASRRRSGLCLDDAVLVDSGDSRKPIAEETAVEMDTERRNGSWVLKILDVQSTWKH
Seq14   61 GGGGIASRRRSGLCLDDAVLVDSGDSRKPIAEETAVEMDTERRNGSWVLKILDVQSTWKH
           ************************************************************

Seq12  121 EEEEDDDEVEDEDGDEDEEVELDDAVVSEDDGGCDVCSVLEDDGNEANKFQLDRESFSKL
Seq14  121 EEEEDDDEVEDEDGDEDEEVELDDAVVSEDDGGCDVCSVLEDDGNEANKFQLDRESFSKL
           ************************************************************

Seq12  181 LRRVTLPESKLYAQLSYLGNLAYSISKIKPANLSKYYGLRFVTSSAEKTESALKAENGEV
Seq14  181 LRRVTLPESKLYAQLSYLGNLAYSISKIKPANLSKYYGLRFVISSAEKTESALKAENGEV
           ******************************************:*****************

Seq12  241 SGETKPIVEAEEEVEEEEKNKSRKISASAAYEIVASAASYLHSRTNNILPFNSSSKAENS
Seq14  241 SGETKPIVEAEEEVEEEEKNKSRKISASAAYEIVASAASYLHSRTNNILPFNSSSKAENS
           ************************************************************

Seq12  301 DKHDVNLTNAESSSDVAYSVTSVVAAEEDVKQAVADDLKSTISSPCDWFICDDDQSHTRF
Seq14  301 DKHDVNLTNAESSSDVAYSVTSVVAAEEDVKQAVADDLKSTISSPCDWFICDDDQSHTRF
           ************************************************************

Seq12  361 VVIQGSESLASWQANLLFEPIEFEGLGAIVHRGIYEAAKGMYEQMLPEVKAHIKTHGTSA
Seq14  361 VVIQGSESLASWQANLLFEPIEFEGLGAIVHRGIYEAAKGMYEQMLPEVKAHIKTHGTSA
           ************************************************************

Seq12  421 KFRFTGHSLGGSLSLLLNLMLLVRGEVPASSLLPVITYGAPFVLCGGDRLLKKLGLPKSH
Seq14  421 KFRFTGHSLGGSLSLLLNLMLLVRGEVPASSLLPVITYGAPFVLCGGDRLLKKLGLPKSH
           ************************************************************

Seq12  481 VQAIVMHRDIVPRAFSCNYPYHVAELLKAVNGNFRSHPCLNKQSMLYSPMGELLILQPDE
Seq14  481 VQAIVMHRDIVPRAFSCNYPYHVAELLKAVNGNFRSHPCLNKQSMLYSPMGELLILQPDE
           ************************************************************

Seq12  541 TFSPGHELLPSGNGLYLLTSDFESPDIEDSDEERLRAAQTVFLNTPHPLDILSDRSAYGS
Seq14  541 TFSPGHELLPSGNGLYLLTSDFESPDIEDSDEERLRAAQTVFLNTPHPLDILSDRSAYGS
           ************************************************************

Seq12  601 SGTIQRDHDMNSYLKAVRSVIRKEVNQIRRAKREHRRSLWWPILVARESGSSGIAVSNGQ
Seq14  601 SGTIQRDHDMNSYLKAVRSVIRKEVNQIRRAKREHRRSLWWPILVARESGSSVIAVSNGQ
           ***************************************************:********

Seq12  661 INGQDFSGMMQTGRKSLQRFSRLVASQHMPLIVVMLFPVKLLFLGAFNVFSFR
Seq14  661 INGQDFSGMMQTGRKSLQRFSRLVASQHMPLIVVMLFPVKLLFLGAFNVFSFR
           ****************************************************
```

This PLIP2-related lipase protein from *Arabidopsis thaliana* with SEQ ID NO:14 has accession number AAM98103.1 and the SEQ ID NO:14 amino acid sequence is shown below.

```
  1 MDSLCLNSGL HGVIPAITAV GNGGCGGVVE VRATASAPSQ
 41 KRGPFGFSFK YPLTPFWSRG GGGGIASRRR SGLCLDDAVL
 81 VDSGDSRKPI AEETAVEMDT ERRNGSWVLK ILDVQSTWKH
121 EEEEDDDEVE DEDGDEDEEV ELDDAVVSED DGGCDVCSVL
161 EDDGNEANKF QLDRESFSKL LRRVTLPESK LYAQLSYLGN
201 LAYSISKIKP ANLSKYYGLR FVTSSAEKTE SALKAENGEV
241 SGETKPIVEA EEEVEEEEKN KSRKISASAA YEIVASAASY
281 LHSRTNNILP FNSSSKAENS DKHDVNLTNA ESSSDVAYSV
321 TSVVAAEEDV KQAVADDLKS TISSPCDWFI CDDDQSHTRF
361 VVIQGSESLA SWQANLLFEP IEFEGLGAIV HRGIYEAAKG
401 MYEQMLPEVK AHIKTHGTSA KFRFTGHSLG GSLSLLLNLM
441 LLVRGEVPAS SLLPVITYGA PFVLCGGDRL LKKLGLPKSH
481 VQAIVMHRDI VPRAFSCNYP YHVAELLKAV NGNFRSHPCL
521 NKQSMLYSPM GELLILQPDE TFSPGHELLP SGNGLYLLTS
561 DFESPDIEDS DEERLRAAQT VFLNTPHPLD ILSDRSAYGS
601 SGTIQRDHDM NSYLKAVRSV IRKEVNQIRR AKREHRRSLW
641 WPILVARESG SSVIAVSNGQ INGQDFSGMM QTGRKSLQRF
681 SRLVASQHMP LIVVMLFPVK LLFLGAFNVF SFR
```

Another PLIP2-related lipase protein from *Arabidopsis thaliana* with SEQ ID NO:15 shares about 97% sequence identity with the SEQ ID NO:12 PLIP2 protein as illustrated below.

```
Seq12    1 MDSLCLNSGLHGVIPAITAVGNGGCGGVVEVRATASAPSQKRGPFGFSFKYPLTPFWSRG
Seq15    1 MDSLCLNSGLHGVIPAITAVGNGGCGGVVEVRATASAPSQKRGPFGFSFKYPLTPFWSRG
           ************************************************************

Seq12   61 GGGGIASRRRSGLCLDDAVLVDSGDSRKPIAEETAVEMDTERRNGSWVLKILDVQSTWKH
Seq15   61 GGGGIASRRRSGLCLDDAVLVDSGDSRKPIAEETAVEMDTERRNGSWVLKILDVQSTWKH
           ************************************************************

Seq12  121 EEEEDDDEVEDEDGDEDEEVELDDAVVSEDDGGCDVCSVLEDDGNEANKFQLDRESFSKL
Seq15  121 EEEEDDDEVEDEDGDEDEEVELDDAVVSEDDGGCDVCSVLEDDGNEANKFQLDRESFSKL
           ************************************************************

Seq12  181 LRRVTLPESKLYAQLSYLGNLAYSISKIKPANLSKYYGLRFVTSSAEKTESALKAENGEV
Seq15  181 LRRVTLPESKLYAQLSYLGNLAYSISKIKPANLSKYYGLRFVTSSAEKTESALKAENGEV
           ************************************************************

Seq12  241 SGETKPIVEAEEEVEEEEKNKSRKISASAAYEIVASAASYLHSRTNNILPFNSSSKAENS
Seq15  241 SGETKPIVEAEEEVEEEEKNKSRKISASAAYEIVASAASYLHSRTNNILPFNSSSKAENS
           ************************************************************

Seq12  301 DKHDVNLTNAESSSDVAYSVTSVVAAEEDVKQAVADDLKSTISSPCDWFICDDDQSHTRF
Seq15  301 DKHDVNLTNAESSSDVAYSVTSVVAAEEDVKQAVADDLKSTISSPCDWFICDDDQSHTRF
           ************************************************************

Seq12  361 VVIQGSESLASWQANLLFEPIEFEGLGAIVHRGIYEAAKGMYEQMLPEVKAHIKTHGTSA
Seq15  361 VVIQG------------------LGAIVHRGIYEAAKGMYEQMLPEVKAHIKTHGTSA
           *****             ******************************************

Seq12  421 KFRFTGHSLGGSLSLLLNLMLLVRGEVPASSLLPVITYGAPFVLCGGDRLLKKLGLPKSH
Seq15  401 KFRFTGHSLGGSLSLLLNLMLLVRGEVPASSLLPVITYGAPFVLCGGDRLLKKLGLPKSH
           ************************************************************

Seq12  481 VQAIVMHRDIVPRAFSCNYPYHVAELLKAVNGNFRSHPCLNKQSMLYSPMGELLILQPDE
Seq15  461 VQAIVMHRDIVPRAFSCNYPYHVAELLKAVNGNFRSHPCLNKQSMLYSPMGELLILQPDE
           ************************************************************

Seq12  541 TFSPGHELLPSGNGLYLLTSDFESPDIEDSDEERLRAAQTVFLNTPHPLDILSDRSAYGS
Seq15  521 TFSPGHELLPSGNGLYLLTSDFESPDIEDSDEERLRAAQTVFLNTPHPLDILSDRSAYGS
           ************************************************************

Seq12  601 SGTIQRDHDMNSYLKAVRSVIRKEVNQIRRAKREHRRSLWWPILVARESGSSGIAVSNGQ
Seq15  581 SGTIQRDHDMNSYLKAVRSVIRKEVNQIRRAKREHRRSLWWPILVARESGSSGIAVSNGQ
           ************************************************************

Seq12  661 INGQDFSGMMQTGRKSLQRFSRLVASQHMPLIVVMLFPVKLLFLGAFNVFSFR
Seq15  641 INGQDFSGMMQTGRKSLQRFSRLVASQHMPLIVVMLFPVKLLFLGAFNVFSFR
           ****************************************************
```

This PLIP2-related lipase protein from *Arabidopsis thaliana* with SEQ ID NO:15 has accession number AAG10634.1 and the SEQ ID NO:15 amino acid sequence is shown below.

```
  1  MDSLCLNSGL HGVIPAITAV GNGGCGGVVE VRATASAPSQ
 41  KRGPFGFSFK YPLTPFWSRG GGGGIASRRR SGLCLDDAVL
 81  VDSGDSRKPI AEETAVEMDT ERRNGSWVLK ILDVQSTWKH
121  EEEEDDDEVE DEDGDEDEEV ELDDAVVSED DGGCDVCSVL
161  EDDGNEANKF QLDRESFSKL LRRVTLPESK LYAQLSYLGN
201  LAYSISKIKP ANLSKYYGLR FVTSSAEKTE SALKAENGEV
241  SGETKPIVEA EEEVEEEEKN KSRKISASAA YEIVASAASY
281  LHSRTNNILP FNSSSKAENS DKHDVNLTNA ESSSDVAYSV
321  TSVVAAEEDV KQAVADDLKS TISSPCDWFI CDDDQSHTRF
361  VVIQGLGAIV HRGIYEAAKG MYEQMLPEVK AHIKTHGTSA
401  KFRFTGHSLG GSLSLLLNLM LLVRGEVPAS SLLPVITYGA
441  PFVLCGGDRL LKKLGLPKSH VQAIVMHRDI VPRAFSCNYP
481  YHVAELLKAV NGNFRSHPCL NKQSMLYSPM GELLILQPDE
521  TFSPGHELLP SGNGLYLLTS DFESPDIEDS DEERLRAAQT
561  VFLNTPHPLD ILSDRSAYGS SGTIQRDHDM NSYLKAVRSV
601  IRKEVNQIRR AKREHRRSLW WPILVARESG SSGIAVSNGQ
641  INGQDFSGMM QTGRKSLQRF SRLVASQHMP LIVVMLFPVK
681  LLFLGAFNVF SFR
```

Another PLIP2-related lipase protein from *Zea mays* with SEQ ID NO:16 shares about 48-50% sequence identity with the SEQ ID NO:12 PLIP2 protein as illustrated below.

```
Seq12  103  RNGSWVLKILDVQSTWKHEEEEDDDEVEDEDGDEDEEVELDDAVVSEDDGGCDVCSVLED
Seq16   86  RGGNWVLQILRVQSSPPPSPSRDDGRCGVDDGGSVPGSGEGDGSSQRCVERGGVGPDSEE
             *  *  *** **  ***            **        **         *    *       *

Seq12  163  DGNEANKFQLDRESFSKLLRRVTLPESKLYAQLSYLGNLAYSISKIKPANLSKYYGLRFV
Seq16  146  GCSVADGEELDRAAFSRLLRKVSLAEAKLFSEMSGLCNLAYMVPRIKPRYLHKY-NMTFV
                  ***  ** ***  *  *  **     * * ****    ***   *  **     **

Seq12  223  TSSAE---KTESALKAENGEVSG--------------ETKPIVEAEEEVEEEEKNKSRK-
Seq16  205  TSSVEERAKLPNPCNQEDQNLNGRKNANISTSSRHSDEQESTYGATSEHERMQENQSGQG
            *** *    *       *       *                   *      *   *   *   *  *

Seq12  265  ISASAAYEIVASAASYLHSRTNNILPFNSSSKAENS-------DKHDVNLTNAESSS-DV
Seq16  265  INPLAAYRIAASAASYMQSRAMEVLPFGSQNEARRDRTIQAIVNAQTEGLTMDEASFVAT
             *   *** *  ****** **    *** *  *              **   *  *

Seq12  317  AYSVTSVVAAEEDVKQAVADDLKSTISSPCDWFICDDDQSHTRFVVIQGSESLASWQANL
Seq16  325  TNSMTSMVAAKEETKQAVADDLNSSRSCPCEWFICDGNRNSTRYFVIQGSETIASWQANL
             * ** *** *  ********* *  *  ** *****    **  ****** *******

Seq12  377  LFEPIEFEGLGAIVHRGIYEAAKGMYEQMLPEVKAHIKTHGTSAKFRFTGHSLGGSLSLL
Seq16  385  LFEPIKFEGLDVLVHRGIYEAAKGIYQQMLPYVKSHFIVHGESARLRFTGHSLGGSLALL
            ***** ****     *********** ****  * *  ** **  *********** **

Seq12  437  LNLMLLVRGEVPASSLLPVITYGAPFVLCGGDRLLKKLGLPKSHVQAIVMHRDIVPRAFS
Seq16  445  VNLMFLIRGVAPAASLLPVITFGSPSVMCGGDYLLQKLGLPKSHVQSVTLHRDIVPRAFS
            *** **  **  **  ******* * * **** ** ***********    **********

Seq12  497  CNYPYHVAELLKAVNGNFRSHPCLNKQSMLYSPMGELLILQPDETFSPGHELLPSGNGLY
Seq16  505  CHYPDHIASILKLVNGNFRSHPCLTNQKLLYAPMGEVFILQPDEKLSPHHHLLPAGSGLY
            * **  **   ** **********  **   ** **** * *******  **  *  ***

Seq12  557  LLTSDFESPDIEDSDEERLRAAQTVFLNIPHPLDILSDRSAYGSSGTIQRDHDMNSYLKA
Seq16  565  LIGGQTVD---SGTSSTALRSALSAFFNSPHPLEILRDAGAYGPKGTVYRDHDVHSYLRS
            *           ** *    * **** ***** *   ***   *** ****  *****

Seq12  617  VRSVIRKEVNQIRRAKREHRRSLWWPILV
Seq16  622  IRAVVRKEM----RAEKERRRLLRWPIEV
             * ***      **    * ** *** *
```

This PLIP2-related lipase protein from *Zea mays* with SEQ ID NO: 16 has accession number NP_001148192.1 and the SEQ ID NO: 16 amino acid sequence is shown below.

```
  1 MDVLRFVPGV RPPLPTFATP VSPATAPSPH AAAAAAPGP
 41 GFHSGMLGLW PRRAGENALG AAAEAAGVEE ARERRRRAV
 81 EAEDGRGGNW VLQILRVQSS PPPSPSRDDG RCGVDDGGSV
121 PGSGEGDGSS QRCVERGGVG PDSEEGCSVA DGEELDRAAF
161 SRLLRKVSLA EAKLFSEMSG LCNLAYMVPR IKPRYLHKYN
201 MTFVTSSVEE RAKLPNPCNQ EDQNLNGRKN ANISTSSRHS
241 DEQESTYGAT SEHERMQENQ SGQGINPLAA YRIAASAASY
281 MQSRAMEVLP FGSQNEARRD RTIQAIVNAQ TEGLTMDEAS
321 FVATTNSMTS MVAAKEETKQ AVADDLNSSR SCPCEWFICD
361 GNRNSTRYFV IQGSETIASW QANLLFEPIK FEGLDVLVHR
401 GIYEAAKGIY QQMLPYVKSH FIVHGESARL RFTGHSLGGS
441 LALLVNLMFL IRGVAPAASL LPVITFGSPS VMCGGDYLLQ
481 KLGLPKSHVQ SVTLHRDIVP RAFSCHYPDH IASILKLVNG
521 NFRSHPCLTN QKLLYAPMGE VFILQPDEKL SPHHHLLPAG
561 SGLYLIGGQT VDSGTSSTAL RSALSAFFNS PHPLEILRDA
601 GAYGPKGTVY RDHDVHSYLR SIRAVVRKEM RAEKERRRLL
641 RWPIEVYGAL ATIDRRQVLR QLRRHAHLLV VFLLPAKLLF
681 LGVLSLIRPT
```

Another PLIP2-related lipase protein from *Zea mays* with SEQ ID NO:17 shares about 4749% sequence identity with the SEQ ID NO:12 PLIP2 protein as illustrated below.

```
Seq12  85 DSRKPIAEETAVEMDTERRNGSWVLKILDVQSTWKHEEEEDDDEVEDEDGDEDEEVELDD
Seq17  56 EPRSPPDEERKAE-GAQRGQGNWVLQMLRVQPRWV---DAADAEATGGGQEPDEETAAAA
           *  *  **    *     *  * ***  * **   *        * *          ***

Seq12 145 AVVSEDDGGCDVCSVLEDDGNEANKFQ------LDRESFSKLLRRVTLPESKLYAQLSYL
Seq17 112 AAGAGGVEECASCGCGEDDEGCAVGYGDGDGEVFDRASFSRLLRKASLGEAKEYSMMSYL
           *        *  *  ***    *         **  *** ***       *  *  * ***

Seq12 199 GNLAYSISKIKPANLSKYYGLRFVTSSAEKTESALKAENGEVSGETKPIV--EAEEEVEE
Seq17 172 CNIAYMIPRIQPKCLRRY-NLRFVTSSVQDKAGVSNPDQKQERSTKKDESGDQASEAVDD
           * **  *   *    *      *******                        *    * * *

Seq12 257 EEKNKSR-KISASAAYEIVASAASYLHSRTNNILPFNSSSKAENSDKHDVNLTNAESSSD
Seq17 231 AVPRRGLGTIKPFGAYHVVSSAASYLHSRAMGVMPFGPGNGVKDDHPAAVTSLVSGASGD
                 **  * ********        **        *              * *

Seq12 316 ----------VAYSVTSVVAAEEDVKQAVADDLKSTISSPCDWFICDDDQSHTRFVVIQ
Seq17 291 GLSVDEASFVATTSSVTSMVAAKEETRQAVADDLNSSRSCPCEWFVCEDDQNSTIYFVVQ
                    ****  ***  * ******* * * ** ** *** * *  * *  *

Seq12 365 GSESLASWQANLLFEPIEFEGLGAIVHRGIYEAAKGMYEQMLPEVKAHIKTHGTSAKFRF
Seq17 351 GSESIASWQANLLFEPVKFEEVDVLVHRGIYEAAKGMYHQMLPYVKAHLKSWGKSARLRF
          **** **********  ** *       ************* **** ****  * **  **

Seq12 425 TGHSLGGSLSLLLNLMLLVRGEVPASSLLPVITYGAPFVLCGGDRLLKKLGLPKSHVQAI
Seq17 411 TGHSLGGSLALLVNLMLLVRGEAPASSLLPVITFGAPCIMCGGDHLLRRLGLPRSHVQSV
          ********* ** ********** *********** ***  **** **  ****  ****

Seq12 485 VMHRDIVPRAFSCNYPYHVAELLKAVNGNFRSHPCLNKQSMLYSPMGELLILQPDETFSP
Seq17 471 TMHRDIVPRVFSCHYPDHVANILKLANGNFRSHPCLANQKLLYAPMGEVLILQPDERLSP
           ******* *** ** ***  ** ******** **     ** * **** ****** ** **

Seq12 545 GHELLPSGNGLYLLTSDF------ESPDIEDSDEERLRAAQTVFLNTPHPLDILSDRSAY
Seq17 531 HHHLLPPDSGIYHLGGGGGGGAGTAANAGEGSLPQLRSALSAFFNSPHPLEILKDGAAY
            *** *** *   *                         ** *   * * **** ** * **

Seq12 599 GSSGTIQRDHDMNSYLKAVRSVIRKEVNQIRRAKREH-RRSLWWPILVARESGSS
Seq17 591 GPRGSVYRDHDVNSYLRSVRAVVRKEARRAREAERERWRLLLWWPFGVHGVSSAS
           *  * **** **** *** ** ***           *    **** *     *  *
```

This PLIP2-related lipase protein from *Zea mays* with SEQ ID NO: 17 has accession number NP_001169446.1 and the SEQ ID NO: 17 amino acid sequence is shown below.

```
  1  MDVLRFVRAA AAPQPAVAPP ASAATVPAQR QRLRMWPRGG
 41  GDQPPPVGAA STRGAEPRSP PDEERKAEGA QRGQGNWVLQ
 81  MLRVQPRWVD AADAEATGGG QEPDEETAAA AAAGAGGVEE
121  CASCGCGEDD EGCAVGYGDG DGEVFDRASF SRLLRKASLG
161  EAKEYSMMSY LCNIAYMIPR IQPKCLRRYN LRFVTSSVQD
201  KAGVSNPDQK QERSTKKDES GDQASEAVDD AVPRRGLGTI
241  KPFGAYHVVS SAASYLHSRA MGVMPFGPGN GVKDDHPAAV
281  TSLVSGASGD GLSVDEASFV ATTSSVTSMV AAKEETRQAV
321  ADDLNSSRSC PCEWFVCEDD QNSTIYFVVQ GSESIASWQA
361  NLLFEPVKFE EVDVLVHRGI YEAAKGMYHQ MLPYVKAHLK
401  SWGKSARLRF TGHSLGGSLA LLVNLMLLVR GEAPASSLLP
441  VITFGAPCIM CGGDHLLRRL GLPRSHVQSV TMHRDIVPRV
481  FSCHYPDHVA NILKLANGNF RSHPCLANQK LLYAPMGEVL
521  ILQPDERLSP HHHLLPPDSG IYHLGGGGGG GGAGTAANAG
561  EGSLPQLRSA LSAFFNSPHP LEILKDGAAY GPRGSVYRDH
601  DVNSYLRSVR AVVRKEARRA REAERERWRL LLWWPFGVHG
641  VSSASAGRRG GLVDAVSEAA RRAHLLLVVL LPAELLALGA
681  LLAVIRFR
```

Another PLIP2-related lipase protein from *Glycine max* with SEQ ID NO: 18 shares at least 57% sequence identity with the SEQ ID NO: 12 PLIP2 protein as illustrated below.

```
Seq12    1 MDSLCLNSGLHGVIPAITAV-GNGGCGGVVEVRATASAPSQKRGPFG-FSFKYPLTPFWS
Seq18    1 METMCLKSGIVPTISISGSLDARANPSQVSTVGRSASDKPPQRSVFSRFSFWYPLESLWP
            *   ** **    *       *   *   **      *  *    *** ***    *

Seq12   59 RGGGGGIASRRRSGLCLDDAVLVDSGDSRKPIAEETAVEMDTERRNGSWVLKILDVQSTW
Seq18   61 RGN-----NSRYKGLALDDAVLSDNNAEAKAVGDD-----GTERQTGNWVLKILHVKSLW
           **         *  ** ******  *          ***  * ****** *  * *

Seq12  119 KHEEEEDDDEVEDEDGDEDEEVELDDAVVSEDDGGCDVCSVLEDDGNEANKFQLDRESFS
Seq18  111 ---EGKQRDEEEGSVRDQTQTNYEEEEEVCE----CDAC-------DEVEEAQFDRGSFS
              *  **  *        *      **    ** *       *    * ** ***

Seq12  179 KLLRRVTLPESKLYAQLSYLGNLAYSISKIKPANLSKYYGLRFVTSSAEKTESALKAENG
Seq18  157 RMLRRVSLAESRLYAQMSHLGNLAYDIPRIKPGKLLKHYGLRFVTSSIEKKELAVAATAE
            * **** *  ** *** * ******  * * ***  *  * ******** **    *

Seq12  239 EVSGETKPIVEAEEEVEEEE-KNKSRKISASAAYEIVASAASYLHSRTNNILPFNSS---
Seq18  217 KDPQKVQTDEKVDEKEERKDPKNGEYKISATAAYNIAASAATYLHSQTRSIFPLKSSNAV
              *  *   **    ****  ***  * ***** * **** ****  *   * **

Seq12  295 ----SKAENSDKHD-VNLTNAESSSDVAY--SVTSVVAAEEDVKQAVADDLKSTISSPCD
Seq18  277 AGEGSLAGNNESLDSVNMLNTEVASLMATTDSVTAVVAAKEEVKQAVADDLNSSHSTPCE
               *   *  **  ** * *     *    *** ***** ********** *   **

Seq12  348 WFICDDDQSHTRFVVIQGSESLASWQANLLFEPIEFEGLGAIVHRGIYEAAKGMYEQMLP
Seq18  337 WFVCDNDQSGTRFFVIQGSETLASWQANLLFEPIKFEGLDVLVHRGIYEAAKGIYQQMLP
           ** ** ***  *** ***** ************* **** * ********** * ****

Seq12  408 EVKAHIKTHGTSAKFRFTGHSLGGSLSLLLNLMLLVRGEVPASSLLPVITYGAPFVLCGG
Seq18  397 EVHAHLKSRGSRATFRFTGHSLGGSLALLVNLMLLIRHEVPISSLLPVITFGSPSIMCGG
           ** ** *  *  * *********** ** ***** * *** ******** *  * ***

Seq12  468 DRLLKKLGLPKSHVQAIVMHRDIVPRAFSCNYPYHVAELLKAVNGNFRSHPCLNKQSMLY
Seq18  457 DSLLEKLGLPKSHVQAITMHRDIVPRAFSCNYPNHVAELLKAVNGNFRSHPCLNKQKLLY
           *  * *********** *************** ***********************  **

Seq12  528 SPMGELLILQPDETFSPGHELLPSGNGLYLLTSDFESPDIEDSDEERLRAAQTVFLNTPH
Seq18  517 APMGNLLILQPDEKFSPSHHLLPSGSGLYLLCCPLSE---SNDTEKQLRAAQMVFLNSPH
           *** ********* *** ****** *****    *     *    ******  ****  **

Seq12  588 PLDILSDRSAYGSSGTIQRDHDMNSYLKAVRSVIRKEVNQIRRAKREHRRSLWWPILVAR
Seq18  574 PLEILSDRSAYGSGGSVQRDHDMNSYLKSVRTVIRQELNQIRKAKREQRRKVWWPLLLPR
           ** ********** *  *********** ** ***    ****  ****     * *

Seq12  648 E------SGSSGIAVSNGQINGQDFSGMMQTGRKSLQRFSRLVASQHMPLIVVMLFPVKL
Seq18  634 GVDTSIVAGRSMISINVGQ-RQSPFSGV-QTGRESLKRFSRVVTSQHMHLFVLLLFPARL
                   *      **           *   ****  **  ** ***  *  * *    *

Seq12  702 LFLGAFNVFSFR
Seq18  692 LLLGTYSVINLK
            * **    *
```

This PLIP2-related lipase protein from *Glycine max* with SEQ ID NO:18 has accession number XP_014619726.1 and the SEQ ID NO:18 amino acid sequence is shown below.

```
  1  METMCLKSGI VPTISISGSL DARANPSQVS TVGRSASDKP
 41  PQRSVFSRFS FWYPLESLWP RGNNSRYKGL ALDDAVLSDN
 81  NAEAKAVGDD GTERQTGNWV LKILHVKSLW EGKQRDEEEG
121  SVRDQTQTNY EEEEEVCECD ACDEVEEAQF DRGSFSRMLR
161  RVSLAESRLY AQMSHLGNLA YDIPRIKPGK LLKHYGLRFV
201  TSSIEKKELA VAATAEKDPQ KVQTDEKVDE KEERKDPKNG
241  EYKISATAAY NIAASAATYL HSQTRSIFPL KSSNAVAGEG
281  SLAGNNESLD SVNMLNTEVA SLMATTDSVT AVVAAKEEVK
321  QAVADDLNSS HSTPCEWFVC DNDQSGTRFF VIQGSETLAS
```
```
                    -continued
361  WQANLLFEPI KFEGLDVLVH RGIYEAAKGI YQQMLPEVHA
401  HLKSRGSRAT FRFTGHSLGG SLALLVNLML LIRHEVPISS
441  LLPVITFGSP SIMCGGDSLL EKLGLPKSHV QAITMHRDIV
481  PRAFSCNYPN HVAELLKAVN GNFRSHPCLN KQKLLYAPMG
521  NLLILQPDEK FSPSHHLLPS GSGLYLLCCP LSESNDTEKQ
561  LRAAQMVFLN SPHPLEILSD RSAYGSGGSV QRDHDMNSYL
601  KSVRTVIRQE LNQIRKAKRE QRRKVWWPLL LPRGVDTSIV
641  AGRSMISINV GQRQSPFSGV QTGRESLKR  FSRVVTSQHM
681  HLFVLLLFPA RLLLLGTYSV INLK
```

Another PLIP2-related lipase protein from *Glycine max* with SEQ ID NO:19 shares at least 54-55% sequence identity with the SEQ ID NO:12 PLIP2 protein as illustrated below.

```
Seq12    1 MDSLCLNSGLHGVIPAITAVGLIGGCGGVVEV--RATASAPSQKRGPFGFSFKYPLTPFWS
Seq19    1 METVCLKSGMVPTISISGSLDARANPSQVSTVGRAAGDKPPQRSVFSRFSFWYPLESLWP
              *   ** **   *       *     **    * *   *** ***       *

Seq12   59 RGGGGGIASRRRSGLCLDDAVLVDSGDSRKPIAEETAVEMDTERRNGSWVLKILDVQSTW
Seq19   61 RGN-----NSRYKGLALDDAVLADNNAEAKAVRDDGQGD-GTERQTGNWVLKILHVKSVW
           **      *  * ****** *   *     *         *** * ****** *  * *

Seq12  119 KHEEEEDDDEVEDEDGDEDEEVELDDAVVSEDDGGCDVCSVLEDDGN-EANKFQLDRESF
Seq19  115 EGKQRNE----EDGTVHDQTQTNFDEEEVCE----CDACGVDEDDGYCEEEEAEFDRGSF
            *  **         **        *  * **    ** *  **** *       ** **

Seq12  178 SKLLRRVILPESKLYAQLSYLGNLAYSISKIKPANLSKYYGLRFVTSSAEKTESAL----
Seq19  167 SRMLRRVSLGEARLYAQMSHLGNLAYDIPRIKPGKLLKHHGLRFVISSIEKKELAVAATA
           *  **** *   * ****  ****** *  * * **  *  *  *  * *

Seq12  234 -------------------------------KAENGEVSGETKPIVEAEEEVEEEE---
Seq19  227 EKDPQKVGSSIEKKEFAAIAEKDPQKVGSSTEKKEFAAIAEKDPQKVETDEKVEEKEETK
                                          *  *           **   *  ***  *

Seq12  259 --KNKSRKISASAAYEIVASAASYLHSRTNNILPFNSSS--------KAENSDKHDVNLT
Seq19  287 DPKNAGYKISATAAYNIAASAATYLHSQTSSIFPFKSSNAVTGEGSLEGSNESLDTVNML
             **    *****  *   ***  ****   *   **  *               **

Seq12  309 NAESSSDVAY--SVTSVVAAEEDVKQAVADDLKSTISSPCDWFICDDDQSHIRFVVIQGS
Seq19  347 NTEVASLMATTDSVTAVVAAKEEVKQAVADDLNSAHSTPCEWFVCDDDQSATRFFVIQGS
           *  *         *** **** *** *****  ****** ** ***** *   ***** *

Seq12  367 ESLASWQANLLFEPIEFEGLGAIVHRGIYEAAKGMYEQMLPEVKAHIKTHGTSAKFRFTG
Seq19  407 ETLASWQANLLFEPIKFEGLDVLVHRGIYEAAKGIYQQMLPEVRAHLKSRGSRATFRFTG
           * ************* ****   ********** * ******  *  *  *  *  *****

Seq12  427 HSLGGSLSLLLNLMLLVRGEVPASSLLPVITYGAPFVLCGGDRLLKKLGLPKSHVQAIVM
Seq19  467 HSLGGSLALLVNLMLLIRNEVPVSSLLPVITFGSPSIMCGGDSLLKKLGLPRSHVQAITM
           ******* ** *****  *  ** **  **** *  *  ****  *******  *******  *

Seq12  487 HRDIVPRAFSCNYPYHVAELLKAVNGNFRSHPCLNKQSMLYSPMGELLILQPDETFSPGH
Seq19  527 HRDIVPRAFSCNYPNHVAELLKAVNGNFRSHPCLNKQKLLYAPMGNLLILQPDEKFSPSH
           **************  ***************************  *** *** *****  *

Seq12  547 ELLPSGNGLYLLTSDFESPDIEDSDEERLRAAQTVFLNTPHPLDILSDRSAYGSSGTIQR
Seq19  587 HLLPSGSGLYLLCCPLSE---SDDTEKRLRAAQMVFLNSPHPLEILSDRSAYGSGGSIQR
            *****  *****      **    * *****  **** ****  ************** * ***

Seq12  607 DHDMNSYLKAVRSVIRKEVNQIRRAKREHRRSLWWPILVARES------GSSGIAVSNGQ
Seq19  644 DHDMNSYLKSLRTVIRKELNQIRKAKREQRRKVWWPLLLSRGADTSIVAGRSMISINVGQ
           ********* * *     * **** *     ****   *           *  *   *  **

Seq12  661 INGQDFSGMMQTGRKSLQRFSRLVASQHMPLIVVMLFPVKLLFLGAFNVFSFR
Seq19  704 -RQSPFSSVIQTGRESLKRFSRIVTSQHMHLFVLLLFPARLLLLGTYSVINLK
              **    ** **** * **** *  ****  *    ****  *** **   *  *
```

This PLIP2-related lipase protein from *Glycine max* with SEQ ID NO:19 has accession number XP_003535965.1 and the SEQ ID NO:19 amino acid sequence is shown 55 below.

```
  1 METVCLKSGM VPTISISGSL DARANPSQVS TVGRAAGDKP
 41 PQRSVFSRFS FWYPLESLWP RGNNSRYKGL ALDDAVLADN
 81 NAEAKAVRDD GQGDGTERQT GNWVLKILHV KSVWEGKQRN
121 EEDGTVHDQT QTNFDEEEVC ECDACGVDED DGYCEEEEAE
161 FDRGSFSRML RRVSLGEARL YAQMSHLGNL AYDIPRIKPG
201 KLLKHHGLRF VISSIEKKEL AVAATAEKDP QKVGSSIEKK
241 EFAAIAEKDP QKVGSSTEKK EFAAIAEKDP QKVETDEKVE
281 EKEETKDPKN AGYKISATAA YNIAASAATY LHSQTSSIFP
321 FKSSNAVTGE GSLEGSNESL DTVNMLNTEV ASLMATTDSV
361 TAVVAAKEEV KQAVADDLNS AHSTPCEWFV CDDDQSATRF
401 FVIQGSETLA SWQANLLFEP IKFEGLDVLV HRGIYEAAKG
441 IYQQMLPEVR AHLKSRGSRA TFRFTGHSLG GSLALLVNLM
481 LLIRNEVPVS SLLPVITFGS PSIMCGGDSL LKKLGLPRSH
521 VQAITMHRDI VPRAFSCNYP NHVAELLKAV NGNFRSHPCL
561 NKQKLLYAPM GNLLILQPDE KFSPSHHLLP SGSGLYLLCC
601 PLSESDDTEK RLRAAQMVFL NSPHPLEILS DRSAYGSGGS
641 IQRDHDMNSY LKSLRTVIRK ELNQIRKAKR EQRRKVWWPL
681 LLSRGADTSI VAGRSMISIN VGQRQSPFSS VIQTGRESLK
721 RFSRIVTSQH MHLFVLLLFP ARLLLLGTYS VINLK
```

Another PLIP2-related lipase protein from *Brassica napus* with SEQ ID NO:20 shares at least 80% sequence identity with the SEQ ID NO: 12 PLIP2 protein as illustrated below.

```
Seq12   1 MDSLCLNSGLHGVIPAITAVGNGGCGGVVEVRATASAPSQKRGPFGFSFKYPLTPFWSRG
Seq20   1 MDSLCLNP---GVIPAIKAVGSG-CGGVVEVRANA---SQKRRPSGSSFKHPLTPFWSRG
          *******    ***** ***  * ********* *     **** * *** *********

Seq12  61 GGGGIASRRRSGLCLDDAVLVDSGDSRKPIAEE--TAVEMDTERRNGSWVLKILDVQSTW
Seq20  54 G--GIASRRRSGLGLDDAVLVDSGDSRKPIAEEEPSAVEMETERRNGSWILKILDVHSMW
          *  ********** ******************  **** ********* ******* * *

Seq12 119 KHEEEEDDDEVEDEDGDEDEEVELDDAVVSEDDGGCDVCSVLEDDGNEANKFQLDRESFS
Seq20 112 R-----------DEEIEEEEEELNDAVLPEDDG---VCSVLED-GDEENKFQMHRESFS
                    **  * ** ** *** ****        *******  * **** *****

Seq12 179 KLLRRVTLPESKLYAQLSYLGNLAYSISKIKPANLSKYYGLRFVTSSAEKTESALKAENG
Seq20 157 KLLKRVSLSESKLYAQMSYLGNLAYSISKIKPANLSKYYGLRFVTSSAEKTELALKA---
          *** ** * ******* *********************************** ****

Seq12 239 EVSGETKPIVEAEEEVEEEEKNKSRKISASAAYEIVASAASYLHSRTNNILPFNSSSKAE
Seq20 214 QVSAETKP-KEEDEEVEDEENK-----GASAAYEVVASAASYLQSRTTNILPFPSSSKND
           ** **** * ****  *  **         ****** ******* *** ***** *****

Seq12 299 NSDKHDVNLTNAESSSDVAYSVTSVVAAEEDVKQAVADDLKSTISSPCDWFICDDDQSHT
Seq20 268 DEEE------SSSSSSSLTSSVTCVVAAEEDVKQAVADDLKFTISSPCDWFICDDDQTLT
           ***       ***    *** *** ***************** **************  *

Seq12 359 RFVVIQGSESLASWQANLLFEPIEFEGL--GAIVHRGIYEAAKGMYEQMLPEVKAHIKTH
Seq20 322 RFFVIQGSESLASWQANLLFEPIEFEELDDGAIVHRGIYEAAKGMYEQMLPEVKAHIKAH
          ** *********************** *  **************************** *

Seq12 417 GTSAKFRFTGHSLGGSLSLLLNLMLLVRGEVPASSLLPVITYGAPFVLCGGDRLLKKLGL
Seq20 382 GNRAKFRFTGHSLGGSLSLLLNLMLLVRGEVPASSLLPVITFGAPFVLCGGDSLLKMLGL
          *  ***************************************** ********** ** ***

Seq12 477 PKSHVQAIVMHRDIVPRAFSCNYPYHVAELLKAVNGNFRSHPCLNKQSMLYSPMGELLIL
Seq20 442 PKSHVQAIIMHRDIVPRAFSCNYPYHVAELLKAVNGHFRSHPCLNKQSMLYSPMGELLIL
          ******** ************************** ***********************

Seq12 537 QPDETFSPGHELLPSGNGLYLLTSD-FESPDIEDSDEERLRAAQTVFLNTPHPLDILSDR
Seq20 502 QPDESFSPGHDLLPIGNGLYLLTGGGFES--LDDEEEQRLRAAQTVFLNTPHPLDILSDR
          **** ***** *** *******    ***    *  * *********************

Seq12 596 SAYGSSGTIQRDHDMNSYLKAVRSVIRKEVNQIRRAKREHRRSLWWPILVARESG-SSGI
Seq20 560 SAYGSSGTIQRDHDMNSYLKAVRSVIRKEVSQIRRLKREHRRSLWWPILVARESGRSSGT
          ******************************  *** ******************** ***

Seq12 655 AVSNGQINGQDFSGMMQTGRKSLQRFSRLVASQHMPLIVVMLFPVKLLFLGAFNVFSFR
Seq20 620 AIGN---NGQDFSGMMKTGRKSLQRFSRLVASQHMPLIVVLFPVKLLFLEAFNVLSFR
          *  *    ********* ********************** ******** **** **** ***
```

This PLIP2-related lipase protein from *Brassica napus* with SEQ ID NO:20 has accession number CDY51303.1 and the SEQ ID NO:20 amino acid sequence is shown below.

```
  1 MDSLCLNPGV IPAIKAVGSG CGGVVEVRAN ASQKRRPSGS
 41 SFKHPLTPFW SRGGGIASRR RSGLGLDDAV LVDSGDSRKP
 81 IAEEEPSAVE METERRNGSW ILKILDVHSM WRDEEIEEEE
121 EEELNDAVLP EDDGVCSVLE DGDEENKFQM HRESFSKLLK
161 RVSLSESKLY AQMSYLGNLA YSISKIKPAN LSKYYGLRFV
201 TSSAEKTELA LKAQVSAETK PKEEDEEVED EENKGASAAY
241 EVVASAASYL QSRTTNILPF PSSSKNDDEE ESSSSSSSLT
281 SSVTCVVAAE EDVKQAVADD LKFTISSPCD WFICDDDQTL
321 TRFFVIQGSE SLASWQANLL FEPIEFEELD DGAIVHRGIY
361 EAAKGMYEQM LPEVKAHIKA HGNRAKFRFT GHSLGGSLSL
401 LLNLMLLVRG EVPASSLLPV ITFGAPFVLC GGDSLLKMLG
441 LPKSHVQAII MHRDIVPRAF SCNYPYHVAE LLKAVNGHFR
481 SHPCLNKQSM LYSPMGELLI LQPDESFSPG HDLLPIGNGL
521 YLLTGGGFES LDDEEEQRLR AAQTVFLNTP HPLDILSDRS
561 AYGSSGTIQR DHDMNSYLKA VRSVIRKEVS QIRRLKREHR
601 RSLWWPILVA RESGRSSGTA IGNNGQDFSG MMKTGRKSLQ
641 RFSRLVASQH MPLIVVLLFP VKLLFLEAFN VLSFR
```

In some cases, the lipase used in the expression cassettes and methods described herein can be a PLIP3 lipase. However, some preliminary evidence indicates that the activities of the PLIP3 lipases are different from the PLIP1 lipase. Hence, in some cases the lipase used in the expression cassettes and methods described herein is not a PLIP3 lipase. However, in some cases, expression of a combination of PLIP1, PLIP2, and/or PLIP3 lipases may be useful and can be employed when making the expression cassettes and using the methods described herein. One example of an *Arabidopsis thaliana* PLIP3 protein sequence is shown below as SEQ ID NO:21.

```
  1 MEGVFLKMSV VGVSPMIPVG PSSFICAIGG SVEEKSTAAS
 41 LPRWVSLRRL RPLEFLRIGG KREEKGTVRD DDAVLLERRD
 81 RNRNENDNGN WVLKILEVGS IWKGKRQRSG GGGGEEDEE
121 EEVAEPKKKE DLCEECDFCR IDDDDEDEEK EKTVFEFSEM
161 LSKIPVEDAQ MFAKLSFLGN LAYSIPKIKP ENLLKYQKLR
201 FVTSSIEKRM SLKVEENNNG EEDEEKKKLI NPAVAYRIAA
241 SAASRLFSHS KSVLPFGSSK RQDNEEASLL ATADSVTAVV
281 AAKEEVKQAV ADDLKSNRSP PCEWFVCDDD KSGTRFFFIQ
321 GSDSLASWQA NLLFEPVPFE DLDVLVHRGI YEAAKGIYEQ
361 MLPEVHAHLN SRGKNRAFLR FSGHSLGGSL SLLVNLMLLI
401 RGQVPASSLL PVITFGSPCI MCGGDRLLQK LGLPKSHLLG
441 ISMHRDIVPR AFSCNYPNRA AKLLKALNGN FRNHPCLNNQ
481 NVLYSPMGKL LILQPSERFS PPHPLLPPGS GLYLLASKNT
521 DETEKSLRAA KILFFNSPHP LEILSDRRSY GSEGKIKRNH
561 DMSSYLKALR HVIRKELKQM KAERDQWLRK FFIINILFSG
601 RDSLKLITRF VASRSSQLVI IFFLPIRLLI MSVYSVVFHH
641 SQAHFSFFK
```

A nucleic acid sequence encoding the *Arabidopsis thaliana* PLIP3 lipase with SEQ ID NO:21 is shown below as SEQ ID NO:22.

```
   1 ATGGAGGGTG TTTTCTTAAA AATGTCGGTG GTTGGAGTAT
  41 CTCCGATGAT ACCGGTGGGA CCTTCTTCTT TCATATGCGC
  81 CATCGGAGGC TCTGTTGAGG AGAAATCAAC GGCTGCTTCT
 121 CTGCCGCGTT GGGTTTCCCT TCGTCGTCTT CGTCCGCTTG
 161 AGTTTCTTCG GATCGGTGGT AAGAGAGAGG AAAAGGGAAC
 201 GGTAAGAGAC GACGACGCCG TTTTGTTGGA GAGAAGGGAC
 241 CGGAACCGCA ACGAAAACGA TAACGGAAAC TGGGTTTTGA
 281 AAATTTTGGA GGTTGGATCA ATCTGGAAAG GAAGAGACA
 321 ACGATCAGGT GGCGGTGGCG GTGGAGAAGA GGACGAGGAA
 361 GAGGAAGTTG CTGAGCCTAA GAAGAAGGAA GATTTATGTG
 401 AGGAATGCGA TTTCTGCAGG ATCGATGATG ATGATGAAGA
 441 CGAAGAAAAG GAGAAGACAG TGTTTGAGTT CTCGGAGATG
 481 TTAAGCAAAA TTCCTGTTGA AGATGCTCAG ATGTTTGCCA
 521 AATTGTCGTT TCTGGGGAAT TTGGCTTATT CAATCCCTAA
 561 AATCAAGCCT GAGAATCTGT TGAAATATCA GAAACTGAGA
 601 TTCGTTACAT CCTCAATTGA GAAGAGGATG AGTCTTAAGG
 641 TTGAAGAGAA CAACAATGGC GAGGAAGATG AGGAGAAGAA
 681 GAAGCTAATC AACCCTGCTG TTGCTTACAG AATCGCTGCT
 721 TCTGCAGCCT CTCGTCTCTT TTCCCATTCT AAGTCTGTGC
 761 TTCCTTTTGG ATCATCTAAA CGTCAAGACA ACGAAGAAGC
 801 TTCTCTACTG GCTACTGCTG ATTCGGTTAC TGCAGTCGTG
 841 GCAGCCAAAG AGGAAGTTAA GCAGGCCGTC GCAGATGATC
 881 TCAAATCAAA CCGTTCACCG CCTTGTGAGT GGTTTGTATG
 921 TGATGATGAT AAAAGCGGCA CCAGGTTCTT CTTTATTCAG
 961 GGATCAGATT CACTGGCCTC ATGGCAAGCT AACCTTCTGT
1001 TCGAGCCTGT TCCATTTGAG GACCTTGATG TGCTTGTTCA
1041 CAGAGGCATA TACGAAGCTG CAAAAGGAAT ATACGAACAG
1081 ATGTTACCAG AAGTTCATGC CCACCTCAAT TCCCGTGGCA
1121 AGAACCGTGC TTTTCTCAGG TTTAGTGGAC ATTCTCTAGG
1161 CGGAAGCTTG TCATTGTTAG TGAACCTCAT GCTTCTGATA
1201 AGAGGTCAAG TCCCTGCTTC TTCTCTGCTT CCAGTGATCA
1241 CTTTTGGTTC GCCTTGCATC ATGTGCGGAG GCGATAGGCT
```

```
1281 TCTTCAGAAA CTTGGTTTGC CTAAGAGTCA TCTTCTCGGA

1321 ATCTCAATGC ATAGAGATAT TGTTCCTCGA GCATTCTCCT

1361 GCAATTACCC TAACCGAGCC GCAAAGCTTC TCAAGGCATT

1401 GAATGGAAAC TTCCGGAACC ATCCTTGTCT GAATAACCAG

1441 AATGTATTGT ATTCTCCAAT GGGGAAGCTT CTAATTCTGC

1481 AACCATCCGA GAGATTCTCT CCCCCACACC CCCTGCTTCC

1521 TCCCGGAAGT GGTCTCTATC TCTTAGCATC TAAGAATACC

1561 GATGAAACAG AGAAAGTCT AAGGGCTGCA AGATTCTCT

1601 TCTTTAACTC ACCACACCCC CTAGAGATTC TCAGTGATCG

1641 TCGTTCTTAC GGGTCGGAAG GAAAAATCAA AAGAAACCAT

1681 GACATGAGCT CTTACCTGAA GGCCTTGAGG CATGTGATCC

1721 GGAAGGAGCT GAAGCAGATG AAAGCTGAGC GGGATCAATG

1761 GCTGCGCAAG TTCTTTATTA TAAACATTTT ATTTAGTGGG

1801 AGAGATTCTT TGAAACTCAT AACAAGATTC GTGGCATCAA

1841 GGAGTAGTCA ACTAGTGATC ATCTTCTTTC TCCCAATTAG

1881 ATTGTTAATA ATGAGTGTCT ACAGTGTGGT CTTTCACCAT

1921 TCACAAGCAC ATTTTAGTTT CTTCAAGTGA
```

Another PLIP3-related lipase protein from *Arabidopsis lyrata* with SEQ ID NO:23 shares at least 92% sequence identity with the SEQ ID NO:21 PLIP3 protein as illustrated below.

```
Seq21    8 MSVVGV-SPMIPVGPSSFICAIGGSVEEKSTAASLPRWVSLRRLRPLEFLRIGGKREEKG
Seq23    1 MSVQGVVSPMIPVGPSSFIRAIGGSVEEKSTAGSLPRWVSRRRPRPLEFLRIGGKRDEKG
           *** ** ************ ************ ****** ** ************ ***

Seq21   67 TVRDDDAVLLERRDRNRNENDNGNWVLKILEVGSIWKGKRQRSGGGGGGEEDEEEEVAEP
Seq23   61 PVRDDAAVLLEREERVGN--DNGNWVLKILEVGSIWKGKRQRSGGG--GEEDDEEQVTES
           **** ****** *  *  ************************** **** ** * *

Seq21  127 KK-KEDLCEECDFCRIDDDDEDEEKEKTVF---EFSEMLSKIPVEDAQMFAKLSFLGNLA
Seq23  117 KNDKEDLCEECDFCRVDDDDDEEEKEETVFGREEFSEMLSKVPVEDAQIFAKLSFLGNLA
           *  ************ ****  ****  ***      ******** ****** ***********

Seq21  183 YSIPKIKPENLLKYQKLRFVTSSIEKRMSLKVEENNNGEEDEEKKKLINPAVAYRIAASA
Seq23  177 YSIPKIKPDNLLKYQKLRFVTSSIEKRTSLKVEENNNGEEEEKKKLINPAVAYRIAASA
           ******** ****************** *************** ******************

Seq21  243 ASRLFSHSKSVLPFGSSKRQDNEEASLLATADSVTAVVAAKEEVKQAVADDLKSNRSPPC
Seq23  237 ASRLFSHSKSVLPFGSSKRQDNEEASLLATADSVTAVVAAKEEVKQAVADDLKSNRSPPC
           ************************************************************

Seq21  303 EWFVCDDDKSGTRFFFIQGSDSLASWQANLLFEPVPFEDLDVLVHRGIYEAAKGIYEQML
Seq23  297 EWFVCDDDKSGTRFFFIQGSDSLASWQANLLFEPVPFEDLDVLVHRGIYEAAKGLYEQML
           ****************************************************** *****

Seq21  363 PEVHAHLNSRGKNRAFLRFSGHSLGGSLSLLVNLMLLIRGQVPASSLLPVITFGSPCIMC
Seq23  357 PEVHAHLNSRGRHRAFLRFSGHSLGGSLSLLVNLMLLIRGQVPASSLLPVITFGSPCIMC
           ***********  ***********************************************

Seq21  423 GGDRLLQKLGLPKSHLLGISMHRDIVPRAFSCNYPNRAAKLLLKALNGNFRNHPCLNNQNV
Seq23  417 GGDRLLQKLGLPKSHLLGISMHRDIVPRAFSCNYPNRAANILKALNGNFRNHPCLNNQNV
           **************************************  ******************

Seq21  483 LYSPMGKLLILQPSERFSPPHPLLPPGSGLYLLASKNTDETEKSLRAAKILFFNSPHPLE
Seq23  477 LYSPMGKLLILQPSERFSPPHPLLPPGSGIYLLTSKNTDETEKSLRAAKSVFFNSPHPLE
           ***************************** *** ***************  *********

Seq21  543 ILSDRRSYGSEGKIKRNHDMSSYLKALRHVIRKELKQMKAERDQWLRKFFIINILFSGRD
Seq23  537 ILSDRRSYGSEGKIKRNHDMSSYLKALRHVIRKELKQIKAERDQWRRKFFIINILFTGRD
           ************************************* ****** ********** ***

Seq21  603 SLKLITRFVASRSSQLVIIFFLPIRLLIMSVYSVVFHHSQAHFSFFK
Seq23  597 SLKLITRFVASRSSQLVIIFFLPIRLLIMNVYGVVFHHSQAHFSFFK
           ***************************** ** **************
```

This PLIP3-related lipase protein from *Arabidopsis lyrata* with SEQ ID NO:23 has accession number XP_002878465.1 and the SEQ ID NO:23 amino acid sequence is shown below.

```
  1 MSVQGVVSPM IPVGPSSFIR AIGGSVEEKS TAGSLPRWVS
 41 RRRPRPLEFL RIGGKRDEKG PVRDDAAVLL EREERVGNDN
 81 GNWVLKILEV GSIWKGKRQR SGGGGEEDDE EQVTESKNDK
121 EDLCEECDFC RVDDDDDEEE KEETVFGREE FSEMLSKVPV
161 EDAQIFAKLS FLGNLAYSIP KIKPDNLLKY QKLRFVTSSI
201 EKRTSLKVEE NNNGEEEEEK KKLINPAVAY RIAASAASRL
241 FSHSKSVLPF GSSKRQDNEE ASLLATADSV TAVVAAKEEV
281 KQAVADDLKS NRSPPCEWFV CDDDKSGTRF FFIQGSDSLA
321 SWQANLLFEP VPFEDLDVLV HRGIYEAAKG LYEQMLPEVH
361 AHLNSRGRHR AFLRFSGHSL GGSLSLLVNL MLLIRGQVPA
401 SSLLPVITFG SPCIMCGGDR LLQKLGLPKS HLLGISMHRD
441 IVPRAFSCNY PNRAANILKA LNGNFRNHPC LNNQNVLYSP
481 MGKLLILQPS ERFSPPHPLL PPGSGIYLLT SKNTDETEKS
521 LRAAKSVFFN SPHPLEILSD RRSYGSEGKI KRNHDMSSYL
561 KALRHVIRKE LKQIKAERDQ WRRKFFIINI LFTGRDSLKL
601 ITRFVASRSS QLVIIFFLPI RLLIMNVYGV VFHHSQAHFS
641 FFK
```

Another PLIP3-related lipase protein from *Brassica napus* with SEQ ID NO:24 shares at least 82% sequence identity with the SEQ ID NO:21 PLIP3 protein as illustrated below.

```
Seq21   3 GVFLKMSVVGVSPMIPVGPSSFICAIGGSVEEKSTAASLPRWVSLRRLRPLEFLRIGGKR
Seq24   4 GVFLKMSVQCVSPKIPVGPS-MIRAIGGSVEERRTSGSLPRRVSRR---PLEFLRIGGKG
          *******  *** ****** * ******** *  *** ** *    **********

Seq21  63 EEKGIVRDDDAVLLERRDRNRNENDNGNWVLKILEVGSIWKGKRQRSGGGGGGEEDEEEE
Seq24  60 RKESARDDNDAVLLEREERN------GNWVLKILEVGSIWKGKRQRSGGGDG--EDEEEG
            * *******  **        ************************    *  *****

Seq21 123 VAEPKKKEDLCEECDFCRIDDDDEDEEKEKTVFEFSEMLSKIPVEDAQMFAKLSFLGNLA
Seq24 112 ----SKKD---ESCDFCRIDDE-EEEEMVFDRENFSKMLMKIPLDDAQMFAKLSYLGNLA
              *  *    * *******  *   ** ** *** ********  *****

Seq21 183 YSIPKIKPENLLKYQKLRFVTSSIEKRMSL-KVEENNNGEEDEEKKKLINPAVAYRIAAS
Seq24 164 YSIPNIKPENLLKYQKLRFVTSSIEKRSSLDQQDEISNEEEEEEKKLINPAAAYRIAAS
          **** **********************  **     *  * ** ******* *******

Seq21 242 AASRLFSHSKSVLPFGSSKRQDNEEASLLATADSVTAVVAAKEEVKQAVADDLKSNRSPP
Seq24 224 AASRLFSHSKSVLPFG---RRENE-ASLMATADSVTAVVAAEEEVKQAVADDLKSNHSPP
          ****************   *  ** *** ************ ***************  ***

Seq21 302 CEWFVCDDDKSGTRFFFIQGSDSLASWQANLLFEPVPFEDLDVLVHRGIYEAAKGIYEQM
Seq24 280 CEWFVCDDDKTSTRFFFIQGSDSLASWQANLLFEPVPFEDFDVPVHRGIYEAAKGIYEQM
          **********  *******************************  ** ***************

Seq21 362 LPEVHAHLNSRGKNRAFLRFSGHSLGGSLSLLVNLMLLIRGQVPASSLLPVITFGSPCIM
Seq24 340 LPEVHAHLNSRGKNRAFLRFSGHSLGGSLSLLVNLMLLIRGQVPASSLLPVITFGSPCIM
          ************************************************************

Seq21 422 CGGDRLLQKLGLPKSHLLGISMHRDIVPRAFSCNYPNRAAKLLKALNGNFRNHPCLNNQN
Seq24 400 CGGDRLLEKLGLPKSHLLGISMHRDIVPRAFSCSYPNRAAKLLKALNRNFRNHPCLNNQN
          ******* *************************  ***************  *********

Seq21 482 VLYSPMGKLLILQPSERFSPPHPLLPPGSGLYLLASKNTDETEKSLRAAKILFFNSPHPL
Seq24 460 LLYSPMGKLLILQPSERFSPPHPLLPPGSGLYVLTSKNTDETEKGLRAAKTVFFNSPHPL
           ******************************* * ********* *****  *******

Seq21 542 EILSDRRSYGSEGKIKRNHDMSSYLKALRHVIRKELKQMKAERDQWLRKFFIINILFSGR
Seq24 520 EILSDRRSYGSEGKIKRNHDMSSYLKALRHVIRKELKQIKAERDQWRAKFLIVNIICTGR
          *************************************  ******* *** **  * **

Seq21 602 DSLKLITRFVASRSSQLVIIFFLPIRLLIMSVYSVVFHHSQAHF-SFFK
Seq24 580 DSLKLIARFVASRSSQLVIIFFLPIRLLTTSVYGVLLHHSEHFFSFFK
          ****** *********************   *** *  ***   * ****
```

This PLIP3-related lipase protein from *Brassica napus* with SEQ ID NO:24 has accession number CDY11429.1 and the SEQ ID NO:24 amino acid sequence is shown below.

```
  1 MDSGVFLKMS VQCVSPKIPV GPSMIRAIGG SVEERRTSGS
 41 LPRRVSRRPL EFLRIGGKGR KESARDDNDA VLLEREERNG
 81 NWVLKILEVG SIWKGKRQRS GGGDGEDEEE GSKKDESCDF
121 CRIDDEEEEE MVFDRENFSK MLMKIPLDDA QMFAKLSYLG
161 NLAYSIPNIK PENLLKYQKL RFVTSSIEKR SSLDQQDEIS
201 NEEEEEEKK  LINPAAAYRI AASAASRLFS HSKSVLPFGR
241 RENEASLMAT ADSVTAVVAA EEEVKQAVAD DLKSNHSPPC
281 EWFVCDDDKT STRFFFIQGS DSLASWQANL LFEPVPFEDF
321 DVPVHRGIYE AAKGIYEQML PEVHAHLNSR GKNRAFLRFS
361 GHSLGGSLSL LVNLMLLIRG QVPASSLLPV ITFGSPCIMC
401 GGDRLLEKLG LPKSHLLGIS MHRDIVPRAF SCSYPNRAAK
441 LLKALNRNFR NHPCLNNQNL LYSPMGKLLI LQPSERFSPP
481 HPLLPPGSGL YVLTSKNTDE TEKGLRAAKT VFFNSPHPLE
521 ILSDRRSYGS EGKIKRNHDM SSYLKALRHV IRKELKQIKA
561 ERDQWRAKFL IVNIICTGRD SLKLIARFVA SRSSQLVIIF
601 FLPIRLLTTS VYGVLLHHSH EHFFSFFK
```

Another PLIP3-related lipase protein from *Zea mays* with SEQ ID NO:25 shares at least 48% sequence identity with the SEQ ID NO:21 PLIP3 protein as illustrated below.

```
Seq21 222 EDEEKKKLINPAVAYRIAASAASRLFSHSKSVLPFGSSK--RQD----------------
Seq25 257 QENQSGQGINPLAAYRIAASAASYMQSRAMEVLPFGSQNEARRDVRTIQAIVNAQTEGLT
          ***  ********** *    ******    *  *

Seq21 264 NEEASLLATADSVTAVVAAKEEVKQAVADDLKSNRSPPCEWFVCDDDKSGTRFFFIQGSD
Seq25 317 MDEASFVATINSMISMVAAKEETKQAVADDLNSSRSCPCEWFICDGNRNSTRYFVIQGSE
           *** **  *    * ****** ******** *  ** **** **  *  ** * ****

Seq21 324 SLASWQANLLFEPVPFEDLDVLVHRGIYEAAKGIYEQMLPEVHAHLNSRGKNRAFLRFSG
Seq25 377 TIASWQANLLFEPIKFEGLDVLVHRGIYEAAKGIYQQMLPYVKSHFIVHGES-ARLRFTG
           **********  ** ****************** ****  *  *  *   * *** *

Seq21 384 HSLGGSLSLLVNLMLLIRGQVPASSLLPVITFGSPCIMCGGDRLLQKLGLPKSHLLGISM
Seq25 436 HSLGGSLALLVNLMFLIRGVAPAASLLPVITFGSPSVMCGGDYLLQKLGLPKSHVQSVTL
          ******* ****** **** ** *********** *****  **************

Seq21 444 HRDIVPRAFSCNYPNRAAKLLKALNGNFRNHPCLNNQNVLYSPMGKLLILQPSERFSPPH
Seq25 496 HRDIVPRAFSCHYPDHIASILKLVNGNFRSHPCLTNQKLLYAPMGEVFILQPDEKLSPHH
          *********** **    *  **  **** ****  **  *** **  * *  **  *

Seq21 504 PLLPPGSGLYLLASKNIDETEKS--LRAAKILFFNSPHPLEILSDRRSYGSEGKIKRNHD
Seq25 556 HLLPAGSGLYLIGGQTVDSGTSSTALRSALSAFFNSPHPLEILRDAGAYGPKGTVYRDHD
           *** ******    *   *    **  *  *********** *   *   *   **

Seq21 562 MSSYLKALRHVIRKELKQMKAERDQWLRKFFIINILFSGRDSLKLITRFVASRSSQLVII
Seq25 616 VHSYLRSIRAVVRKEMRAEK-ERRLLRWPIEVYGALATIDRRQVLRQL--RRHAHLLVV
           *** *   * **** * *    ** *  *    *       * * *     *  *

Seq21 622 FFLPIRLLIMSVYSVV
Seq25 673 FLLPAKLLFLGVLSLI
          * ** **   *  *
```

This PLIP3-related lipase protein from *Zea mays* with SEQ ID NO:25 has accession number NP_001148192.1 and the SEQ ID NO:25 amino acid sequence is shown below.

```
  1 MDVLRFVPGV RPPLPTFATP VSPATAPSPH AAAAAAAPGP
 41 GFHSGMLGLW PRRAGENALG AAAEAAGVEE ARERRRRRAV
 81 EAEDGRGGNW VLQILRVQSS PPPSPSRDDG RCGVDDGGSV
121 PGSGEGDGSS QRCVERGGVG PDSEEGCSVA DGEELDRAAF
161 SRLLRKVSLA EAKLFSEMSG LCNLAYMVPR IKPRYLHKYN
201 MTFVTSSVEE RAKLPNPCNQ EDQNLNGRKN ANISTSSRHS
241 DEQESTYGAT SEHERMQENQ SGQGINPLAA YRIAASAASY
281 MQSRAMEVLP FGSQNEARRD VRTIQAIVNAQ TEGLTMDEAS
321 FVATTNSMTS MVAAKEETKQ AVADDLNSSR SCPCEWFICD
361 GNRNSTRYFV IQGSETIASW QANLLFEPIK FEGLDVLVHR
401 GIYEAAKGIY QQMLPYVKSH FIVHGESARL RFTGHSLGGS
441 LALLVNLMFL IRGVAPAASL LPVITFGSPS VMCGGDYLLQ
481 KLGLPKSHVQ SVTLHRDIVP RAFSCHYPDH IASILKLVNG
521 NFRSHPCLTN QKLLYAPMGE VFILQPDEKL SPHHHLLPAG
561 SGLYLIGGQT VDSGTSSTAL RSALSAFFNS PHPLEILRDA
601 GAYGPKGTVY RDHDVHSYLR SIRAVVRKEM RAEKERRRLL
641 RWPIEVYGAL ATIDRRQVLR QLRRHAHLLV VFLLPAKLLF
681 LGVLSLIRPT
```

Another PLIP3-related lipase protein from *Zea mays* with SEQ ID NO:26 shares at least 49% sequence identity with the SEQ ID NO:21 PLIP3 protein as illustrated below.

```
Seq21   77 ERRDRNRNENDNGNWVLKILEVGSIWKGKRQRSGGGGGGEEDEEEEVAEPKKKEDLCEEC
Seq26   63 EERKAEGAQRGQGNWVLQMLRVQPRWVDAADAEATGGGQEPDEETAAAAAAGAGGV-EEC
           *  *     ***** * *  *        *** * ***     *           ***

Seq21  137 DFCRIDDDDED-----EEKEKTVFE---FSEMLSKIPVEDAQMFAKLSFLGNLAYSIPKI
Seq26  122 ASCGCGEDDEGCAVGYGDGDGEVFDRASFSRLLRKASLGEAKEYSMMSYLCNIAYMIPRI
              *   ***        **   **  * *    *       *   *  * ** ** *

Seq21  189 KPENLLKYQKLRFVTSSIEKRMSL-----KVEENNNGEEDEEKKK-------------LI
Seq26  182 QPKCLRRYN-LRFVISSVQDKAGVSNPDQKQERSIKKDESGDQASEAVDDAVPRRGLGTI
            *   *  * ******  *   *      *     *                     *

Seq21  231 NPAVAYRIAASAASRLFSHSKSVLPFGSSK--RQDN-----------------EEASLL
Seq26  241 KPFGAYHVVSSAASYLHSRAMGVMPFGPGNGVKDDHPAAVTSLVSGASGDGLSVDEASFV
             **  **** *  * ***    * ***       *                   ***

Seq21  271 ATADSVTAVVAAKEEVKQAVADDLKSNRSPPCEWFVCDDDKSGTRFFFIQGSDSLASWQA
Seq26  301 ATTSSVTSMVAAKEETRQAVADDLNSSRSCPCEWFVCEDDQNSTIYFVVQGSESIASWQA
           **  *** ******* ******** ** ** ******  *    * * *** * *****

Seq21  331 NLLFEPVPFEDLDVLVHRGIYEAAKGIYEQMLPEVHAHLNSRGKNRAFLRFSGHSLGGSL
Seq26  361 NLLFEPVKFEEVDVLVHRGIYEAAKGMYHQMLPYVKAHLKSWGKS-ARLRFIGHSLGGSL
           ******* ** ************** * **** * *** *  *   * ** *******

Seq21  391 SLLVNLMLLIRGQVPASSLLPVITFGSPCIMCGGDRLLQKLGLPKSHLLGISMHRDIVPR
Seq26  420 ALLVNLMLLVRGEAPASSLLPVITFGAPCIMCGGDHLLRRLGLPRSHVQSVIMHRDIVPR
            ******** **  ************ ******** **  **** **       ********

Seq21  451 AFSCNYPNRAAKLLKALNGNFRNHPCLNNQNVLYSPMGKLLILQPSERFSPPHPLLPPGS
Seq26  480 VFSCHYPDHVANILKLANGNFRSHPCLANQKLLYAPMGEVLILQPDERLSPHHHLLPPDS
            *** **     *** ****** ****  ** ** ***  ******  ** ** ****  *

Seq21  511 GLYLL----------ASKNTDETEKSLRAAKILFFNSPHPLEILSDRRSYGSEGKIKRN
Seq26  540 GIYHLGGGGGGGAGTAANAGEGSLPQLRSALSAFFNSPHPLEILKDGAAYGPRGSVYRD
           * * *              *      * ** ************ *   **    * *

Seq21  560 HDMSSYLKALRHVIRKELKQMK-AERDQW
Seq26  600 HDVNSYLRSVRAVVRKEARRAREAERERW
           **  *** * *  ****          *  *
```

This PLIP3-related lipase protein from *Zea mays* with SEQ ID NO:26 ha accession number NP_001169446.1 and the SEQ ID NO:26 amino acid sequence is shown below.

```
  1 MDVLRFVRAA AAPQPAVAPP ASAATVPAQR QRLRMWPRGG
 41 GDQPPPVGAA STRGAEPRSP PDEERKAEGA QRGQGNWVLQ
 81 MLRVQPRWVD AADAEATGGG QEPDEETAAA AAAGAGGVEE
121 CASCGCGEDD EGCAVGYGDG DGEVFDRASF SRLLRKASLG
161 EAKEYSMMSY LCNIAYMIPR IQPKCLRRYN LRFVTSSVQD
201 KAGVSNPDQK QERSTKKDES GDQASEAVDD AVPRRGLGTI
241 KPFGAYHVVS SAASYLHSRA MGVMPFGPGN GVKDDHPAAV
281 TSLVSGASGD GLSVDEASFV ATTSSVTSMV AAKEETRQAV
301 ADDLNSSRSC PCEWFVCEDD QNSTIYFVVQ GSESIASWQA
```

```
                 -continued
361 NLLFEPVKFE EVDVLVHRGI YEAAKGMYHQ MLPYVKAHLK
401 SWGKSARLRF TGHSLGGSLA LLVNLMLLVR GEAPASSLLP
441 VITFGAPCIM CGGDHLLRRL GLPRSHVQSV TMHRDIVPRV
481 FSCHYPDHVA NILKLANGNF RSHPCLANQK LLYAPMGEVL
521 ILQPDERLSP HHHLLPPDSG IYHLGGGGGG GGAGTAANAG
561 EGSLPQLRSA LSAFFNSPHP LEILKDGAAY GPRGSVYRDH
601 DVNSYLRSVR AVVRKEARRA REAERERWRL LLWWPFGVHG
641 VSSASAGRRG GLVDAVSEAA RRAHLLLVVL LPAELLALGA
681 LLAVIRFR
```

Another PLIP3-related lipase protein from *Glycine max* with SEQ ID NO:27 shares at least 51-58% sequence identity with the SEQ ID NO:21 PLIP3 protein as illustrated below.

```
Seq21  85 ENDNGNWVLKILEVGSIWKGKRQRSGGGGGGEEDEEEEVAEPKKKEDLCEECDFCRIDDD
Seq27  93 ERQTGNWVLKILHVKSLWEGK---------QRDEEEGSVRDQTQTNYEEEEEVCECDAC
          * ******** * * * **          ****          **    *  *

Seq21 145 DEDEEKEKTVFEFSEMLSKIPVEDAQMFAKLSFLGNLAYSIPKIKPENLLKYQKLRFVTS
Seq27 143 DEVEEAQFDRGSFSRMLRRVSLAESRLYAQMSHLGNLAYDIPRIKPGKLLKHYGLRFVTS
          ** **     ** **      *   *     ****** ** ***  *** ******

Seq21 205 SIEKRMSL----------KVEENNNGEEDEEKKK------LINPAVAYRIAASAASRLFS
Seq27 203 SIEKKELAVAATAEKDPQKVQTDEKVDEKEERKDPKNGEYKISATAAYNIAASAATYLHS
          ****            **       * *** *        *  ** ****** * *

Seq21 249 HSKSVLPFGSSKRQ------------------DNEEASLLATADSVTAVVAAKEEVKQA
Seq27 263 QTRSIFPLKSSNAVAGEGSLAGNNESLDSVNMLNIEVASLMATTDSVTAVVAAKEEVKQA
           *  **  **                      * *** ** ***************

Seq21 290 VADDLKSNRSPPCEWFVCDDDKSGTRFFFIQGSDSLASWQANLLFEPVPFEDLDVLVHRG
Seq27 323 VADDLNSSHSTPCEWFVCDNDQSGTRFFVIQGSETLASWQANLLFEPIKFEGLDVLVHRG
          ***** * * ********* * ****** **** * ************  **  ********

Seq21 350 IYEAAKGIYEQMLPEVHAHLNSRGKNRAFLRFSGHSLGGSLSLLVNLMLLIRGQVPASSL
Seq27 383 IYEAAKGIYQQMLPEVHAHLKSRG-SRATFRFIGHSLGGSLALLVNLMLLIRHEVPISSL
          ********* ********** ***  **  ** ********* ********** ** ***

Seq21 410 LPVITFGSPCIMCGGDRLLQKLGLPKSHLLGISMHRDIVPRAFSCNYPNRAAKLLKALNG
Seq27 442 LPVITFGSPSIMCGGDSLLEKLGLPKSHVQAITMHRDIVPRAFSCNYPNHVAELLKAVNG
          ********* ****** ** ********   * *************** * **** ***

Seq21 470 NFRNHPCLNNQNVLYSPMGKLLILQPSERFSPPHPLLPPGSGLYLLAS--KNTDETEKSL
Seq27 502 NFRSHPCLNKQKLLYAPMGNLLILQPDEKFSPSHHLLPSGSGLYLLCCPLSESNDTEKQL
          *** ***** * *** *** ****** * *** * *** ******           *** *

Seq21 528 RAAKILFFNSPHPLEILSDRRSYGSEGKIKRNHDMSSYLKALRHVIRKELKQMKAERDQW
Seq27 562 RAAQMVFLNSPHPLEILSDRSAYGSGGSVQRDHDMNSYLKSVRTVIRQELNQIRKAKREQ
          ***   * ************  ***  *  * *** ****  * *** **  ***  *

Seq21 588 LRKFFIINILFSGRDS
Seq27 622 RRKVWWPLLLPRGVDT
           **       *   *
```

This PLIP3-related lipase protein from *Glycine max* with SEQ ID NO:27 has accession number XP_014619726.1 and the SEQ ID NO:27 amino acid sequence is shown below.

```
  1 METMCLKSGI VPTISISGSL DARANPSQVS TVGRSASDKP

41 PQRSVFSRFS FWYPLESLWP RGNNSRYKGL ALDDAVLSDN

81 NAEAKAVGDD GTERQTGNWV LKILHVKSLW EGKQRDEEEG

121 SVRDQTQTNY EEEEEVCECD ACDEVEEAQF DRGSFSRMLR

161 RVSLAESRLY AQMSHLGNLA YDIPRIKPGK LLKHYGLRFV

201 TSSIEKKELA VAATAEKDPQ KVQTDEKVDE KEERKDPKNG

241 EYKISATAAY NIAASAATYL HSQTRSIFPL KSSNAVAGEG

281 SLAGNNESLD SVNMLNTEVA SLMATTDSVT AVVAAKEEVK

321 QAVADDLNSS HSTPCEWFVC DNDQSGTRFF VIQGSETLAS

361 WQANLLFEPI KFEGLDVLVH RGIYEAAKGI YQQMLPEVHA

401 HLKSRGSRAT FRFTGHSLGG SLALLVNLML LIRHEVPISS

441 LLPVITFGSP SIMCGGDSLL EKLGLPKSHV QAITMHRDIV

481 PRAFSCNYPN HVAELLKAVN GNFRSHPCLN KQKLLYAPMG

521 NLLILQPDEK FSPSHHLLPS GSGLYLLCCP LSESNDTEKQ

561 LRAAQMVFLN SPHPLEILSD RSAYGSGGSV QRDHDMNSYL

601 KSVRTVIRQE LNQIRKAKRE QRRKVWWPLL LPRGVDTSIV

641 AGRSMISINV GQRQSPFSGV IQTGRESLKR FSRVVTSQHM

681 HLFVLLLFPA RLLLLGTYSV INLK
```

FAD4

Fatty acid desaturases are involved in the production of chloroplast-specific phosphatidylglycerol molecular species containing 16:1 (number of carbons:number of bond). These enzymes can catalyze the formation of a trans double bond introduced close to the carboxyl group of palmitic acid, which is specifically esterified to the sn-2 glyceryl carbon of phosphatidylglycerol. Expression of the FATTY ACID DESATURASE4 (FAD4) can facilitate lipid accumulation in plants.

Transgenic plants, plant cells, and/or seeds can include expression cassettes having a nucleic acid segment encoding a FAD4 protein in addition to one or more lipase expression cassettes. For example, an *Arabidopsis thaliana* FAD4 amino acid sequence with accession number At4g27030 is shown below as SEQ ID NO:28.

```
  1 MAVSLPTKYP LRPITNIPKS HRPSLLRVRV TCSVTTTKPQ PNREKLLVEQ

51 RTVNLPLSND QSLQSTKPRP NREKLVVEQR LASPPLSNDP TLKSTWTHRL

101 WVAAGCTTLF VSLAKSVIGG FDSHLCLEPA LAGYAGYILA DLGSGVYHWA

151 IDNYGDESTP VVGTQIEAFQ GHHKWPWTIT RRQFANNLHA LAQVITFTVL

201 PLDLAFNDPV FHGFVCTFAF CILFSQQFHA WAHGTKSKLP PLVVALQDMG

251 LLVSRRQHAE HHRAPYNNNY CIVSGAWNNV LDESKVFEAL EMVFYFQLGV

301 RPRSWSEPNS DWIEETEISN NQA
```

A nucleotide sequence encoding the SEQ ID NO:28 FAD4 protein is available as accession number NM 118837.2 and shown below as SEQ ID NO:29.

```
   1 TTTGACAACT TTCACCTGCA ATCACTCTCA ATGGCTGTAT
  41 CACTTCCAAC CAAGTACCCT CTACGACCTA TCACCAACAT
  81 CCCAAAAAGC CACCGTCCCT CGCTTCTCCG TGTACGTGTC
 121 ACCTGCTCTG TTACTACCAC CAAGCCTCAG CCTAATCGTG
 161 AGAAGCTTCT GGTAGAGCAA CGCACTGTGA ATCTTCCTCT
 201 GTCCAACGAC CAATCTCTGC AATCGACCAA GCCTCGCCCT
 241 AACCGTGAGA AGCTTGTGGT TGAGCAACGC CTTGCCAGCC
 281 CTCCTCTGTC CAATGACCCA ACTTTGAAAT CGACATGGAC
 321 TCACCGGTTA TGGGTTGCAG CGGGCTGCAC CACTTTGTTT
 361 GTCTCTTTAG CTAAATCTGT CATTGGAGGG TTTGATTCTC
 401 ATCTCTGCCT CGAACCAGCT TTAGCCGGTT ATGCAGGGTA
 441 CATCTTAGCT GATCTAGGTT CCGGTGTCTA CCACTGGGCC
 481 ATTGATAACT ACGGTGATGA GTCAACACCT GTAGTAGGAA
 521 CCCAAATCGA AGCATTTCAG GGTCACCACA AGTGGCCTTG
 561 GACAATCACC AGACGGCAAT TGCCAACAA TCTACACGCT
 601 CTGGCTCAAG TCATAACCTT CACAGTTCTT CCACTAGACC
 641 TTGCATTTAA CGACCCTGTG TTTCACGGCT TTGTGTGCAC
 681 ATTTGCATTT TGCATATTGT TTAGCCAGCA ATTCCATGCT
 721 TGGGCACATG GAACCAAGAG CAAGCTTCCA CCTCTCGTGG
 761 TCGCGTTGCA GGACATGGGG TTACTTGTTT CACGGAGACA
 801 GCATGCGGAA CATCATCGAG CACCGTATAA CAACAATTAC
 841 TGCATCGTGA GTGGAGCATG GAACAATGTT CTGGATGAGA
 881 GTAAGGTCTT TGAGGCATTG GAGATGGTGT TTTATTTCCA
 921 GCTTGGGGTG AGACCTAGGT CATGGAGTGA GCCAAACTCT
 961 GACTGGATAG AAGAAACCGA AATCTCCAAC AACCAAGCAT
1001 AAATATTTTT TTTACAGAGT GATACATGTA CAAGAAAATT
1041 TCAGTAATAT ACTGAAAAGA TTTCTTCGTA ATTTATATGT
1081 AACGAGTGTG ACTGTATTTA ATACTGTATA AAACAAGCAA
1121 AACAACTGAG CATGTACCAT TTAAGTATCA
```

A related FAD4 protein from *Brassica napus* with SEQ ID NO:30 shares at least about 79% sequence identity with the SEQ ID NO:28 protein as illustrated below.

```
Seq28     1 MAVSLPTKYPLRPITN-IPKSHRPSLLRVRVTCSVTTTKPQPNREKLLVEQRTVNLPLSN
Seq30     1 MAVSLQTKYPLRPITNNIPSTHRYSLLHVRVTCSATTTTNKP------------------
            ***** ********** **  ** *** ****** ***    *

Seq28    60 DQSLQSTKPRPNREKLVVEQRLASPPLSNDPTLKSTWTHRLWVAAGCTTLFVSLAKSVIG
Seq30    43 ------------QAKLVVENRFMSPPLSNDPSLQSTWTHRLWVAAGCTTLFASLSKSIIG
                        ***** *   ********* * *************** ** ** **

Seq28   120 GFDSHLCLEPALAGYAGYILADLGSGVYHWAIDNYGDESTPVVGTQIEAFQGHHKWPWTI
Seq30    91 GVGSHLWLEPALAGYAGYILADLGSGVYHWAIDNYGDESTPIVGTQIEAFQGHHKWPWTI
            *  *** **************************** ***** *****************

Seq28   180 TRRQFANNLHALAQVITFTVLPLDLAFNDPVFHGFVCTFAFCILFSQQFHAWAHGTKSKL
Seq30   151 TRRQFANNLHALARVITFTVLPLDLAFNDPVVHGFVSTFAFCIMFSQQFHAWAHGTKSKL
            ************* ***************** **** ****** ** ************

Seq28   240 PPLVVALQDMGLLVSRRQHAEHHRAPYNNNYCIVSGAWNNVLDESKVFEALEMVFYFQLG
Seq30   211 PPLVVALQDMGVLVSRREHAEHHRAPYNNNYCIVSGAWNKVLDESKVFEALEMVLYFKLG
            *********** ***** ********************** ***************** ** **

Seq28   300 VRPRSWSEPNSDWIEETEISNN
Seq30   271 VRPRSWSEPNSEWTEEKDISNN
            *********** * **  ****
```

This FAD4 protein from *Brassica napus* with SEQ ID NO:30 has XP_013709030.1 and the SEQ ID NO:30 amino acid sequence is shown below.

```
  1 MAVSLQTKYP LRPITNNIPS THRYSLLHVR VTCSATTTTN
 41 KPQAKLVVEN RFMSPPLSND PSLQSTWTHR LWVAAGCTTL
 81 FASLSKSIIG GVGSHLWLEP ALAGYAGYIL ADLGSGVYHW
121 AIDNYGDEST PIVGTQIEAF QGHHKWPWTI TRRQFANNLH
161 ALARVITFTV LPLDLAFNDP VVHGFVSTFA FCIMFSQQFH
201 AWAHGTKSKL PPLVVALQDM GVLVSRREHA EHHRAPYNNN
241 YCIVSGAWNK VLDESKVFEA LEMVLYFKLG VRPRSWSEPN
281 SEWTEEKDIS NNHKV
```

Another related FAD4 protein from *Zea mays* with SEQ ID NO:31 shares at least about 54% sequence identity with the SEQ ID NO:28 protein as illustrated below.

```
Seq28    92 LKSTWTHRLWVAAGCTTLFVSLAKSV-IGGFDSHLCLEPALAGYAGYILADLGSGVYHWA
Seq31    48 LRSTWPQRAWTLAGTAAILSSLSTSASLAASGSGSPAEPIAAALAAYSLADLATGVYHWF
            * ***    *  ** ** * **  *   *  *      **    * ** **** *****

Seq28   151 IDNYGDESTPVVGTQIEAFQGHHKWPWTITRRQFANNLHALAQVITFTVLPLDLAFN---
Seq31   108 VDNYGDAATPVFGSQIAAFQGHHRYPSTITLRETCNNLHALARGAALALAPVDAALSATG
             ***** *** * ** ******    *** *   ******  **  **     *  *

Seq28   208 -DPVFHGFVCTFAFCILFSQQFHAWAHGTKSKLPPLVVALQDMGLLVSRRQHAEHHRAPY
Seq31   168 APAAAHAFVGAFTACVVLSQQFHAWAHEKRRRLPPGVEALQDAGVLVSRAQHAAHHRQPY
              *  * **  *  *  *********   * *** * **** * ***** *** *** **

Seq28   267 NNNYCIVSGAWNNVLDESKVFEALEMVFYFQLGVRPRSWSEPNSDWIEET
Seq31   228 NTNYCIVSGMWNGLLDRYKVFEALEMVVYFRTGIRPRSWGETDASWKEDT
            * ******* **  **  ********* ** * ***** *  ** * *
```

This FAD4 protein from *Zea mays* with SEQ ID NO:31 has XP_008662704.1 and the SEQ ID NO:31 amino acid sequence is shown below.

```
  1 MYTLIPRCHL QPVHRSPPPC QAATTTSSAP PSPSPSLSIR
 41 FRPDQDELRS TWPQRAWTLA GTAAILSSLS TSASLAASGS
 81 GSPAEPIAAA LAAYSLADLA TGVYHWFVDN YGDAATPVFG
121 SQIAAFQGHH RYPSTITLRE TCNNLHALAR GAALALAPVD
161 AALSATGAPA AAHAFVGAFT ACVVLSQQFH AWAHEKRRRL
201 PPGVEALQDA GVLVSRAQHA AHHRQPYNTN YCIVSGMWNG
241 LLDRYKVFEA LEMVVYFRTG IRPRSWGETD ASWKEDTGAE
281 AAAAAASNAG LLQTAGISSD SD
```

Another related FAD4 protein from *Zea mays* with SEQ ID NO:32 shares about 47% sequence identity with the SEQ ID NO:28 protein as illustrated below.

```
Seq28  92 LKSTWTHRLWVAAGCTTLFVSLAKS--VIGGFDSHLC--LEPALAGYAGYILADLGSGVY
Seq32  15 VRSTWLQRAWTLAGTAAILMSFFTTARLVAASSTVVTDSLAVALAVWAAYSVADLTTGVY
          ***  * ** *         *           * *** * * *** ***

Seq28 148 HWAIDNYGDESTPVVGTQIEAFQGHHKWPWTITRRQFANNLHALAQVITFTVLPLDLAF-
Seq32  75 HWFIDNYGDAGTPVFGAQIVAFHDHHVHPTAITRLEPCNSLHVIAGTVAVALPAVDAALL
          ** ****** *** * ** **  **   * ***    * **  *           * *

Seq28 207 ------NDPVFHGFVCTFAFCILFSQQFHAWAHGTKSKLPPLVVALQDMGLLVSRRQHAE
Seq32 135 YFAGGSSPAAAHAFACTFAVCVMLSVQFHAWAHERPSRLPPGVEALQAAGVLVSRSQHAG
                * **** *   * ******   *** * ***  * **** ***

Seq28 261 HHRAPYNNNYCIVSGAWNNVLDESKVFEALEMVFYFQLGVRPRSW
Seq32 195 HHRPPYNSNYCTVSGMWNWALDGYKVFLAVEKVIYLATGAPPRSW
          *** *** *** ***  **  *** * * *   *   * ****
```

This FAD4 protein from *Zea mays* with SEQ ID NO:32 has XP_008663953.1 and the SEQ ID NO:32 amino acid sequence is shown below.

```
  1 MSATPSGDVP DELRVRSTWL QRAWTLAGTA AILMSFFTTA
 41 RLVAASSTVV TDSLAVALAV WAAYSVADLT TGVYHWFIDN
 81 YGDAGTPVFG AQIVAFHDHH VHPTAITRLE PCNSLHVIAG
121 TVAVALPAVD AALLYFAGGS SPAAAHAFAC TFAVCVMLSV
161 QFHAWAHERP SRLPPGVEAL QAAGVLVSRS QHAGHHRPPY
201 NSNYCTVSGM WNWALDGYKV FLAVEKVIYL ATGAPPRSWR
241 MKMTEHGV
```

Another related FAD4 protein from *Glycine max* with SEQ ID NO:33 shares at least about 62-72% sequence identity with the SEQ ID NO:28 protein as illustrated below.

```
Seq28  85 PLSNDPTLKSTWTHRLWVAAGCTTLFVSLAKSVIGGFDSHLCLEPALAGYAGYILADLGS
Seq33  69 PMNNDPSLQSTWSHRAWVAAGCTTLLISLGESIKGAMDLNMWAEPILAGWVGYILADLGS
          * *** * *** ** ********* * ** *  *   *    * * ****  *********

Seq28 145 GVYHWAIDNYGDESTPVVGTQIEAFQGHHKWPWTITRRQFANNLHALAQVITFTVLPLDL
Seq33 129 GVYHWAIDNYGDASIPIVGTQIEAFQGHHKWPWTITKRQFANNLHALARAVTFTVLPIVL
          ************ *  * ****************** **********   ******  *

Seq28 205 AFNDPVFHGFVCTFAFCILFSQQFHAWAHGTKSKLPPLVVALQDMGLLVSRRQHAEHHRA
Seq33 189 LCHDPIVEGFVGMCSGCIMFSQQFHAWSHGTKSRLPPLVVALQEAGVLVSRSQHAAHHRP
           * ***  * **    ** ******** **** ********   * ****  ***  ***

Seq28 265 PYNNNYCIVSGAWNNVLDESKVFEALEMVFYFQLGVRPRSWSEPNSDWIEETE
Seq33 249 PYNNNYCIVSGVWNEFLDKHKVFEALEMVLYFKTGVRPRSWSETASEWIEEIE
          *********** **  **  ********* ***  ********  * ***** *
```

This FAD4 protein from *Glycine max* with SEQ ID NO:33 has XP_003551889.1 and the SEQ ID NO:33 amino acid sequence is shown below.

```
  1 MYSLAQHKYI PRFHLQACKN HPPHHPSSPV FCSTTTTTSR

41 DKPNPKPLVI EPWLVPVPPT VVTADNPRPM NNDPSLQSTW

81 SHRAWVAAGC TTLLISLGES IKGAMDLNMW AEPILAGWVG

121 YILADLGSGV YHWAIDNYGD ASIPIVGTQI EAFQGHHKWP

161 WTITKRQFAN NLHALARAVT FTVLPIVLLC HDPIVEGFVG

201 MCSGCIMFSQ QFHAWSHGTK SRLPPLVVAL QEAGVLVSRS

241 QHAAHHRPPY NNNYCIVSGV WNEFLDKHKV FEALEMVLYF

281 KTGVRPRSWS ETASEWIEEI ETPSQIQAQ
```

Another related FAD4 protein from *Glycine max* with SEQ ID NO:34 shares about 65 71% sequence identity with the SEQ ID NO:28 protein as illustrated below.

```
Seq28  85 PLSNDPTLKSTWTHRLWVAAGCTTLFVSLAKSVIGGFDSHLCLEPALAGYAGYILADLGS
Seq34  73 PMNNDPSLQSTWSHRAWVAAGCSTLVISLGESIKGAIDLNMWVEPIVAGWVGYILADLGS
          * *** * *** ** ****** **  **  *  *  *     ** ** *********

Seq28 145 GVYHWAIDNYGDESTPVVGTQIEAFQGHHKWPWTITRRQFANNLHALAQVITFTVLPLDL
Seq34 133 GVYHWAIDNYGDGSTPIVGAQIEAFQGHHKWPWTITRRQFANNLHALARAVTLAVLPVVL
          ************ *** ** ****************************  *  ***  *

Seq28 205 AFNDPVFHGFVCTFAFCILFSQQFHAWAHGTKSKLPPLVVALQDMGLLVSRRQHAEHHRA
Seq34 193 LCHDPIVEGFVVVCSGCIMFSQQFHAWSHGTKSRLPPLVVALQEAGVLVSRWQHAAHHRA
           * ***   ** ** ******** ***** **** ***** *     ****  *** ****

Seq28 265 PYNNNYCIVSGAWNNVLDESKVFEALEMVFYFQLGVRPRSWSEPNSDWIEETE
Seq34 253 PYNNNYCIVSGVWNEFLDKHKVFEAMEMVLYFKTGVRPRSWSEPAPEWVEEIE
          ***********  ** **    ***** **** **   **********  *  ** *
```

This FAD4 protein from *Glycine max* with SEQ ID NO:34 has XP_003530742.1 and the SEQ ID NO:34 amino acid sequence is shown below.

```
  1 MYSLAQHKYT PNFHHQVCKN HPPRHPSRVH CSTTTTTTTT

41 SRSKSNAKSL VIETRLVPVP PMPTVVTTEI HRPMNNDPSL

81 QSTWSHRAWV AAGCSTLVIS LGESIKGAID LNMWVEPIVA

121 GWVGYILADL GSGVYHWAID NYGDGSTPIV GAQIEAFQGH

161 HKWPWTITRR QFANNLHALA RAVTLAVLPV VLLCHDPIVE

201 GFVVVCSGCI MFSQQFHAWS HGTKSRLPPL VVALQEAGVL

241 VSRWQHAAHH RAPYNNNYCI VSGVWNEFLD KHKVFEAMEM

281 VLYFKTGVRP RSWSEPAPEW VEEIETPSQI QIQTQ
```

Variants

Additional related lipase and/or FAD4 sequences can also be employed in expression cassettes and in the methods, seeds, plant cells, and plants described herein, including those with about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:1-34, 61-71.

In some cases, the lipase and/or FAD4 nucleic acid and amino acid sequences are not identical to a wild type sequence. Instead the lipase and/or FAD4 nucleic acid and amino acid sequences have at least one, or at least two, or at least three, or at least four nucleotide or amino acid substitutions, deletions, or insertions compared to the corresponding wild type lipase and/or FAD4 nucleic acid or amino acid sequence.

Related lipase and/or FAD4 sequences can be isolated from a variety of plant types such as alfalfa (e.g., forage legume alfalfa), algae, avocado, barley, broccoli, Brussels sprouts, cabbage, camelina, canola, cassava, cauliflower, coconut, cole vegetables, collards, crucifers, flax, grain legumes, grasses (e.g., forage grasses), jatropa, kale, kohlrabi, maize, miscanthus, mustards, nut sedge, oats, oil firewood trees, oilseeds, olive, palm, peanut, potato, rapeseed, radish, rice, rutabaga, safflower, sorghum, soybean, sugar beets, sugarcane, sunflower, switchgrass, tobacco, tomato, turnips, and wheat. In some embodiments, the plant is a corn, soybean, or rapeseed species. In some cases the plant is a *Brassicaceae* or other species. In some embodiments, the plant is not a species of *Arabidopsis*, for example, in some embodiments, the plant is not *Arabidopsis thaliana*.

As described herein, nucleic acids encoding a lipase and/or FAD4 is useful for expressing such proteins in plants. Such lipase and/or FAD4 proteins and nucleic acids can include any with at least at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity to any of SEQ ID NO:1-34, 61-70 and/or 71.

If desired, the proteins with any of SEQ ID NOs:1, 3-12, 14-21, 23-28, 30-34, 61-70 and/or 71 can have one or more amino acid substitution, deletion, or insertion compared to its corresponding wild type amino acid sequence.

Nucleic acids with at least 50% sequence identity to those described herein (e.g., with SEQ ID NO:2, 13, 22, and/or 29) can readily be identified, isolated and used to facilitate production of increased oil content in plants. Such nucleic acids can encode or hybridize to lipase and/or FAD4 nucleic acids, or fragments thereof. These related nucleic acids can be used to increase the expression of lipase and/or FAD4 in plants.

For example, related nucleic acids can be isolated and identified by mutation of the cDNA sequences encoding any of SEQ ID NOs: 1, 3-12, 14-21, 23-28, 30-34, 61-70 and/or 71 and/or by hybridization to DNA and/or RNA isolated from other plant species using nucleic acid encoding any of the SEQ ID NO: 1,3-12, 14-21, 23-28, 30-34, 61-70 and/or 71 as probes. Sequences of the lipase (e.g., SEQ ID NO: 1-27, 61-71) and sequences of FAD4 (e.g., SEQ ID NOs:

28-34) can also be examined and used a basis for designing alternative lipase and/or FAD4 proteins and nucleic acids.

In some embodiments, the lipase and/or FAD4 nucleic acids described herein include any nucleic acid that can selectively hybridize to a nucleic acid encoding any of the SEQ ID NO:1-34, 61-71 protein or cDNA sequences.

Alternatively, the lipase and/or FAD4 nucleic acids (e.g., SEQ ID NO:2, 13, 22, 29) can be examined and used a basis for designing additional nucleic acids (e.g., having optimized codons or selected mutant lipase and/or selected mutant FAD4 proteins) that function in selected plant species. As illustrated herein, two point mutation alleles, where the lipase has an alanine residue at position 422 (instead of a serine PLIP1-S422A) or at position 483 (instead of an aspartic acid PLIP1-D483A), express mutant lipase enzymes with reduced lipase activity. However, these mutant lipase proteins are useful as antigens for generating antibodies because these mutant proteins are expressed in greater amounts in some host cells than is the wild type lipase protein.

The term "selectively hybridize" includes hybridization, under stringent hybridization conditions, of a nucleic acid sequence to a specified nucleic acid target sequence (e.g., SEQ ID NO:2, 13, 22, and/or 29) to a detectably greater degree (e.g., at least 2-fold over background) than its hybridization to non-target nucleic acid sequences. Such selective hybridization substantially excludes non-target nucleic acids.

Related lipase and/or FAD4 nucleic acids sequences typically have about at least 40% sequence identity, or at least 50% sequence identity, or at least 60% sequence identity, or at least 70% sequence identity, or at least 80% sequence identity, or at least 85% sequence identity, or at least 90% sequence identity, or at least 95% sequence identity, or at least 97% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:2, 13, 22, and/or 29. In some embodiments, a selectively hybridizing sequence has about at least about 80% sequence identity or complementarity with any of SEQ ID NO: 2, 13, 22, and/or 29. The lipase and/or FAD4 nucleic acids employed in the expression vectors, transgenes, plants, plant cells, plant seeds and methods described herein can also have less than 100%, or less than 99.5%, or less than 99% sequence identity (or complementarity) with any of SEQ ID NO: 2, 13, 22, and/or 29. In other words, the lipase and/or FAD4 nucleic acids employed in the expression vectors, transgenes, plants, plant cells, plant seeds and methods described herein can also not include a wild type sequence. However, use of wild type lipase and/or FAD4 nucleic acids in the expression vectors, transgenes, plants, plant cells, plant seeds and methods described herein can also be useful.

In some embodiments, the nucleic acids used in the methods and plants provided herein can include fragments of lipase and/or FAD4 nucleic acids. For example, the nucleic acids of the invention include those with about 500 of the same nucleotides as any of the SEQ ID NO: 2, 13, 22, and/or 29 sequences, or about 700 of the same nucleotides as any of the SEQ ID NO: 2, 13, 22, and/or 29 sequences, or about 900 of the same nucleotides as any of the SEQ ID NO: 2, 13, 22, and/or 29 sequences, or about 1000 of the same nucleotides as any of the SEQ ID NO: 2, 13, 22, and/or 29 sequences, or about 1200 of the same nucleotides as any of the SEQ ID NO: 2, 13, 22, and/or 29 sequences, or about 1250 of the same nucleotides as any of the SEQ ID NO: 2, 13, 22, and/or 29 sequences, or about 1300 of the same nucleotides as any of the SEQ ID NO:2, 13, 22, and/or 29 sequences. The identical nucleotides can be distributed throughout the nucleic acid, and need not be contiguous but are present in homologous positions.

For example, the nucleic acid sequence of a lipase and/or FAD4 nucleic acids can be optimized for expression in a particular plant species by altering selected codons to encode the same amino acid but use nucleotide codons that are more easily 'read' by the transcription/translation machinery of a selected plant species.

Note that if a value of a variable that is necessarily an integer (e.g., the number of nucleotides or amino acids in a nucleic acid or protein), is described as a range, such as 80-99% sequence identity, what is meant is that the value can be any integer between 80 and 99 inclusive, i.e., 80, 81, 82, 83, 84, 85, 86, 87, 88, 89, 90, 91, 92, 93, 94, 95, 96, 97, 98 or 99, or any range between 80 and 99 inclusive, e.g., 81-99%, 81-98%, 82-99%, etc. Moreover, if a specifically recited percent sequence identity indicates that a partial nucleotide or amino acid is present (in a nucleic acid or polypeptide) the percent sequence identity is rounded up or down so that a complete nucleotide or amino acid is present.

In some embodiments, a related nucleic acid hybridizes to at least one of the nucleic acids described herein under "stringent conditions" or "stringent hybridization conditions." The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be hybridized that have up to 100% complementarity to the probe (homologous probing). Alternatively, stringency conditions can be adjusted to allow some mismatching in sequences so that lower degrees of sequence similarity are detected (heterologous probing).

A probe for identifying and/or isolating a related nucleic acid can be approximately 15-500 nucleotides in length, but can vary greatly in length from about 17 nucleotides to equal to the entire length of the target sequence. In some embodiments, the probe is about 10-50 nucleotides in length, or about 15-50 nucleotides in length, or about 16-45 nucleotides in length, or about 18-25 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution. Hence, high stringency conditions include can be achieved simply by employing a wash in 0.1×SSC at 60 to 65° C.

For DNA-DNA hybrids, the $T_m$ can be approximated from the equation of Meinkoth and Wahl (Anal. Biochem. 138: 267-84 (1984)):

$$T_m=81.5°\ C.+16.6(\log M)+0.41(\%\ GC)-0.61(\%\ \text{formamide})-500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point (T). Using the equation, hybridization and wash compositions, and a desired $T_m$, those of ordinary skill can identify and isolate nucleic acids with sequences related to any of the SEQ ID NO: 2, 13, 22, and/or 29 sequences.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application, high stringency is defined as a wash in 0.1×SSC, 0.1% SDS at 65° C. High stringency hybridization can include hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., followed by a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of the SEQ ID NO: 1-34 protein or cDNA sequences). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 16 contiguous nucleotides in length, and optionally can be 18, 20, 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric was maximized to facilitate alignment of the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul et al., (1997) Nucleic Acids Res. 25:3389402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that a related nucleic acid comprises a sequence with between 55-100% sequence identity to a reference sequence, with at least 55% sequence identity, or at least 60%, or at least 70%, or at least 80%, or at least 90% or at least 95% sequence identity or any percentage of range between 55-100% sequence identity relative to any of the reference sequence (e.g., any of SEQ ID NO: 1-34, 61-71) over a specified comparison window. Optimal alignment may be ascertained or conducted using the homology alignment algorithm of Needleman and Wunsch, supra.

An indication that two polypeptide sequences are substantially identical is that both polypeptides have similar activities. For example, when the polypeptide is related to lipase and/or FAD4, that polypeptide can act as a transcription factor by binding to the same or similar upstream regions of genes normally under the regulatory control of lipase and/or FAD4. For example, proteins related to the lipase and/or FAD4 can be identified and/or characterized in assays that involve binding of a test protein (i.e., a potential lipase or potential FAD4 related to a lipase and/or FAD4 described herein) to a promoter or regulatory sequence that is bound by a lipase and/or FAD4 with any of the sequences recited herein.

The related lipase and/or FAD4 polypeptide can be identified, evaluated or characterized in assays for observing increased (or decreased) expression. The related lipases can also be evaluated for in lipase activity assays including, for example, activity against substrates such as PG and MGDG. Kits are available for evaluation of FAD4 activity.

In some embodiments, a lipase and/or FAD4 protein with a sequence related to any of the SEQ ID NO: 1-34, 61-71 sequences may not have exactly the same level of activity as the lipase and/or FAD4 protein with a SEQ ID NO: 1-34, 61-71. Instead, the substantially identical polypeptide may exhibit greater or lesser levels of activity than the lipase and/or FAD4 protein with a SEQ ID NO: 1-34, 61-71 sequence, as measured by assays available in the art. For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the lipase and/or FAD4 protein with a SEQ ID NO: 1-34, 61-71 sequence, when measured by similar assay procedures.

Alternatively, substantial identity is present when second polypeptide is immunologically reactive with antibodies raised against the first polypeptide (e.g., a polypeptide with SEQ ID NO: 1, 3-12, 14-21, 23-28, 30-34, 61-70 and/or 71 sequence). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The lipase and/or FAD4 polypeptides can include at least the first 10, 12, 14, 15, 16, 17, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 112, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 N-terminal amino acid residues of a the SEQ ID NO: 1, 3-12, 14-21, 23-28, 30-34, 61-70 and/or 71 sequence.

The lipase and/or FAD4 polypeptides can include additional amino acids, for example, at the N-terminal or C-terminal end. For example, the lipase and/or FAD4 polypeptides can include a histidine tag.

Transgenic Plants

To engineer plants with increased vegetative tissue or seed oil content, one of skill in the art can introduce nucleic acids encoding the lipase and/or FAD4 proteins described herein into the plants to promote the production of oils.

For example, one of skill in the art can generate genetically-modified plants that contain nucleic acids encoding lipase and/or FAD4 proteins within their somatic and/or germ cells. Such genetic modification can be accomplished by procedures available in the art. For example, one of skill in the art can prepare an expression cassette or expression vector that can express one or more encoded lipase and/or FAD4 proteins. Plant cells can be transformed by the expression cassette or expression vector, and whole plants (and their seeds) can be generated from the plant cells that were successfully transformed with the lipase and/or FAD4 nucleic acids. Some procedures for making such genetically modified plants and their seeds are described below.

Promoters:

The lipase and/or FAD4 nucleic acids can be operably linked to a promoter, which provides for expression of an mRNA expressed from the lipase and/or FAD4 nucleic acids. The promoter can be a promoter functional in plants and/or seeds, and/or it can be a promoter functional during plant growth and development or in a mature plant. The promoter can be a heterologous promoter. As used herein, "heterologous" when used in reference to a gene or nucleic acid refers to a gene or nucleic acid that has been manipulated in some way. For example, a heterologous promoter is a promoter that contains sequences that are not naturally linked to an associated coding region.

A lipase and/or FAD4 nucleic acid is operably linked to the promoter when it is located downstream from the promoter, thereby forming a key portion of an expression cassette.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An isolated promoter sequence that is a strong promoter for heterologous DNAs can be advantageous because it provides for a sufficient level of gene expression for easy detection and selection of transformed cells and provides for a high level of gene expression when desired. However, as illustrated herein, expression of a lipase from a constitutive promoter can reduce seed production in transgenic plants. Hence, expression of lipase from an inducible or tissue-specific promoter can be used.

An inducible promoter is a promoter that can turn on and off gene expression of an operably linked coding region in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells.

The promoters can also be tissue specific or developmentally regulated promoters. In some embodiments, the promoter is an inducible promoter and/or a tissue-specific promoter. For example, the promoter can be a seed-specific promoter, such as those for seed storage proteins (for example, a phaseolin promoter, a napin promoter, an oleosin promoter, and a promoter for soybean beta conglycin (Beachy et al. (1985) EMBO J. 4: 3047-3053, herein incorporated by reference in its entirety).

Examples of promoters that can be used can also include, but are not limited to, the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)), the CCR (cinnamoyl CoA:NADP oxidoreductase, EC 1.2.1.44) promoter sequence isolated from *Lollium perenne*, (or a perennial ryegrass) and/or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci USA.* 83:3320-3324 (1985)). Other promoters useful in the practice of the invention are known to those of skill in the art.

Alternatively, novel tissue specific promoter sequences may be employed in the practice of the present invention. cDNA clones from particular tissues are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

For example, the promoter can be an inducible promoter. Such inducible promoters can be activated by agents such as chemicals, hormones, sugars, metabolites, or by the age or developmental stage of the plant. For example, the promoter can be an ethanol-inducible promoter, a sugar-inducible promoter, a senescence-induced promoter or any promoter activated in vegetative tissues of dicots and monocots.

A lipase and/or FAD4 nucleic acid can be combined with the promoter by standard methods to yield an expression cassette, for example, as described in Sambrook et al. (Molecular Cloning: A Laboratory Manual. Second Edition (Cold Spring Harbor, N.Y.: Cold Spring Harbor Press (1989); Molecular Cloning: A Laboratory Manual. Third Edition (Cold Spring Harbor, N.Y.: Cold Spring Harbor Press (2000)). Briefly, a plasmid containing a promoter such as the 35S CaMV promoter can be constructed as described in Jefferson (Plant Molecular Biology Reporter 5:387 405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The lipase and/or FAD4 nucleic acids can be subcloned downstream from the promoter using restriction enzymes and positioned to ensure that the DNA is inserted in proper orientation with respect to the promoter so that the DNA can be expressed as sense RNA. Once the lipase and/or FAD4 nucleic acid is operably linked to a promoter, the expression cassette so formed can be subcloned into a plasmid or other vector (e.g., an expression vector).

In some embodiments, a cDNA clone encoding a selected lipase and/or FAD4 protein is synthesized or isolated from vegetative tissue (e.g., stems, roots, and/or leaves). The cDNA clone encoding a selected lipase and/or FAD4 protein can be synthesized by available methods or isolated from mature plants. In other embodiments, cDNA clones from other species (that encode a lipase and/or FAD4 protein) are isolated from selected plant tissues, or a nucleic acid encoding a mutant or modified lipase and/or FAD4 protein is prepared by available methods or as described herein. For example, the nucleic acid encoding a mutant or modified lipase and/or FAD4 protein can be any nucleic acid with a coding region that hybridizes, for example, to SEQ ID NO:2, 13, 22, and/or 29, and that has lipase and/or FAD4 oil production activity.

Using restriction endonucleases, the coding sequence for the selected lipase and/or FAD4 is subcloned downstream of the promoter in a 5' to 3' sense orientation.

Targeting Sequences:

Additionally, expression cassettes can be constructed and employed to target the lipase and/or FAD4 expression cassettes/vectors to an intracellular compartment within plant cells (e.g., the nucleus, chloroplast, or plastid) or to direct the lipase and/or FAD4 to the extracellular environment (e.g., for collection and/or purification). This can generally be achieved by joining a DNA sequence encoding a transit or signal peptide sequence to the coding sequence of the lipase and/or FAD4 nucleic acid. The resultant transit, or signal, peptide transports the protein to a particular intracellular, or extracellular destination, respectively, and can then be posttranslational removed. Transit peptides act by facilitating the transport of proteins through intracellular membranes, e.g., vacuole, vesicle, plastid, chloroplast, and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences:

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., Nucleic Acid Research. 11:369 385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (Methods in Enzymology. 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the lipase and/or FAD4 nucleic acids by standard methods.

Selectable and Screenable Marker Sequences:

To improve identification of transformants, a selectable or screenable marker gene can be employed with the lipase and/or FAD4 nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., The Plant Cell. 2:785 793 (1990)) is well characterized in terms of molecular biology, expression, and protein structure and therefore can readily be employed. However, any one of a variety of extensins and/or glycine rich wall proteins (Keller et al., EMBO J. 8:1309 1314 (1989)) could be modified by the addition of an antigenic site to create a screenable marker.

Possible selectable markers for use in connection with the present invention include, but are not limited to, a neo gene (Potrykus et al., Mol. Gen. Genet. 199:183 188 (1985)) which codes for kanamycin resistance and can be selected for using kanamycin, G418, and the like; a bar gene which codes for bialaphos resistance; a gene which encodes an altered EPSP synthase protein (Hinchee et al., Bio/Technology. 6:915 922 (1988)) thus conferring glyphosate resistance; a nitrilase gene such as bxn from *Klebsiella ozaenae* which confers resistance to bromoxynil (Stalker et al., Science. 242:419 423 (1988)); a mutant acetolactate synthase gene (ALS) which confers resistance to imidazolinone, sulfonylurea or other ALS-inhibiting chemicals (European Patent Application 154, 204 (1985)); a methotrexate resistant DHFR gene (Thillet et al., J. Biol. Chem. 263:12500

12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., Mol. Gen. Genet. 205:42 50 (1986); Twell et al., Plant Physiol. 91:1270 1274 (1989)) causing rapid accumulation of ammonia and cell death. The success in using this selective system in conjunction with monocots was surprising because of the major difficulties that have been reported in transformation of cereals (Potrykus, Trends Biotech. 7:269 273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: Chromosome Structure and Function: Impact of New Concepts, 18th Stadler Genetics Symposium, J. P. Gustafson and R. Appels, eds. (New York: Plenum Press) pp. 263 282 (1988)); a β-lactamase gene (Sutcliffe, Proc. Natl. Acad. Sci. USA. 75:3737 3741 (1978)), which encodes an enzyme for which various chromogenic substrates are known (e.g., PADAC, a chromogenic cephalosporin; a xylE gene (Zukowsky et al., Proc. Natl. Acad. Sci. USA. 80:1101 (1983)) which encodes a catechol dioxygenase that can convert chromogenic catechols; an α-amylase gene (Ikuta et al., Bio/technology 8:241 242 (1990)); a tyrosinase gene (Katz et al., J. Gen. Microbiol. 129:2703 2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., Science. 234:856 859.1986), which allows for bioluminescence detection; or an aequorin gene (Prasher et al., Biochem. Biophys. Res. Comm. 126:1259 1268 (1985)), which may be employed in calcium sensitive bioluminescence detection, or a green or yellow fluorescent protein gene (Niedz et al., Plant Cell Reports. 14:403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TRI12, a K55 derivative that is r-g, b, Pl. Alternatively any genotype of maize can be utilized if the C1 and R alleles are introduced together.

The R gene regulatory regions may be employed in chimeric constructs to provide mechanisms for controlling the expression of chimeric genes. More diversity of phenotypic expression is known at the R locus than at any other locus (Coe et al., in Corn and Corn Improvement, eds. Sprague, G. F. & Dudley, J. W. (Am. Soc. Agron., Madison, Wis.), pp. 81 258 (1988)). It is contemplated that regulatory regions obtained from regions 5' to the structural R gene can be useful in directing the expression of genes, e.g., insect resistance, drought resistance, herbicide tolerance or other protein coding regions. In some embodiments, any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low light video cameras, photon counting cameras or multiwell luminometry. It is also envisioned that this system may be developed for population screening for bioluminescence, such as on tissue culture plates, or even for whole plant screening.

Some aspects of expression systems are exemplified using marker genes. However, numerous other possible selectable and/or screenable marker genes will be apparent to those of skill in the art in addition to the one set forth herein below. Therefore, it will be understood that the discussion provided herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC derived vectors such as pUC8, pUC9, pUC18, pUC19, pUC23, pUC119, and pUC120, pSK derived vectors, pGEM derived vectors, pSP derived vectors, or pBS derived vectors. The additional DNA sequences include origins of replication to provide for autonomous replication of the vector, additional selectable marker genes, such as antibiotic or herbicide resistance, unique multiple cloning sites providing for multiple sites to insert DNA sequences, and/or sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (Methods in Enzymology. 153:292 (1987)). This binary Ti vector can be replicated in prokaryotic bacteria such as *E. coli* and *Agrobacterium*. The *Agrobacterium* plasmid vectors can be used to transfer the expression cassette to dicot plant cells and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to express the encoded lipase and/or FAD4 proteins by available methods. For example, the lipase protein can hydrolyze a lipid substrate such as a phospholipid, a $16:1^{\Delta 3 trans}$-containing phosphatidylglycerol, or a monogalactosyldiacylglycerol (MGDG). The cleavage products of the lipase can be quantified by a variety of methods (e.g., thin layer chromatography, gas chromatography, or other methods available in the art). Expression of lipase or FAD4 can also be detected by observing mRNA expression, protein expression, and/or whether an expression cassette or vector encoding a lipase and/or FAD4 protein can facilitate synthesis of plant carbons into oils.

DNA Delivery of the DNA Molecules into Host Cells:

The lipase and/or FAD4 nucleic acid can be introduced into a recipient cell to create a transformed cell by available methods. The frequency of occurrence of cells taking up exogenous (foreign) DNA can be low, and it is likely that not all recipient cells receiving DNA segments or sequences will result in a transformed cell wherein the DNA is stably integrated into the plant genome and/or expressed. Some may show only initial and transient gene expression. However, cells from virtually any dicot or monocot species can be stably transformed, and those cells can be regenerated into transgenic plants, for example, through the application of the techniques disclosed herein.

Another aspect of the invention is a plant species with increased vegetative tissue oil content, wherein the plant has an introduced lipase and/or FAD4 nucleic acid. The plant can be a monocotyledon or a dicotyledon. Another aspect of the invention includes plant cells (e.g., embryonic cells or other cell lines) that can regenerate fertile transgenic plants. Another aspect of the invention includes transgenic seeds from which transgenic plants can be grown. The plants, cells and seeds can be either monocotyledons or dicotyledons. The cell(s) may be in a suspension cell culture or may be in an intact plant part, such as an immature embryo, or in a specialized plant tissue, such as callus, such as Type I or Type II callus.

Examples of plants, seeds, and/or plant cells that can be modified as described herein to express the lipase and/or FAD4 proteins include alfalfa (e.g., forage legume alfalfa), algae, avocado, barley, broccoli, Brussels sprouts, cabbage, camelina, canola, cassava, cauliflower, coconut, cole vegetables, collards, corn, crucifers, flax, grain legumes, grasses (e.g., forage grasses), jatropa, kale, kohlrabi, maize, miscanthus, mustards, nut sedge, oats, oil firewood trees, oilseeds, olive, palm, peanut, potato, radish, rape, rapeseed, rice, rutabaga, safflower, sorghum, soybean, sugar beets, sugarcane, sunflower, switchgrass, tobacco, tomato, turnips, and wheat. In some embodiments, the plant is a *Brassicaceae* or other species. In some embodiments, the plant or cell can be a maize plant or cell. In some embodiments, the plant is not a species of *Arabidopsis*, for example, in some embodiments the plant is not *Arabidopsis thaliana*.

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, Dekeyser et al., The Plant Cell. 2:591 602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/Technology. 6:923 926 (1988); Gordon Kamm et al., The Plant Cell. 2:603 618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli* derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf disk protocol (Horsch et al., Science 227:1229 1231 (1985). Monocots such as *Zea mays* can be transformed via microprojectile bombardment of embryogenic callus tissue or immature embryos, or by electroporation following partial enzymatic degradation of the cell wall with a pectinase containing enzyme (U.S. Pat. Nos. 5,384,253; and 5,472,869). For example, embryogenic cell lines derived from immature *Zea mays* embryos can be transformed by accelerated particle treatment as described by Gordon Kamm et al. (The Plant Cell. 2:603 618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli* derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA encoding the lipase and/or FAD4 protein for an effective period of time. This may range from a less than one second pulse of electricity for electroporation to a 2-3 day co-cultivation in the presence of plasmid bearing *Agrobacterium* cells. Buffers and media used will also vary with the plant tissue source and transformation protocol. Many transformation protocols employ a feeder layer of suspended culture cells (e.g., tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic Black Mexican Sweet (BMS) cells are bombarded with intact cells of the bacteria *E. coli* or *Agrobacterium tumefaciens* containing plasmids with the lipase and/or FAD4 nucleic acids engineered for expression in plants. Bacteria were inactivated by ethanol dehydration prior to bombardment. A low level of transient expression of the lipase and/or FAD4 protein can be observed 24-48 hours following DNA delivery. In addition, stable transformants containing the lipase and/or FAD4 nucleic acids are recovered following bombardment with either *E. coli* or *Agrobacterium tumefaciens* cells. It is contemplated that particles may contain DNA rather than be coated with DNA. Hence particles may increase the level of DNA delivery but are not, in and of themselves, necessary to introduce DNA into plant cells.

An advantage of microprojectile bombardment, in addition to being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension can be concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Using techniques set forth here in one may obtain up to 1000 or more foci of cells transiently expressing a desirable trait (e.g., as detected by expression of a marker gene). The number of cells in a focus which express the exogenous gene product 48 hours post bombardment often range, for example, from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of one or more lipase and/or FAD4 nucleic acid(s) to recipient cells by any of the methods discussed above (e.g., in an expression vector), the transformed cells can be identified for further culturing and plant regeneration. As mentioned above, to improve the ability to identify transformants, one may desire to employ a selectable or screenable marker gene as, or in addition to, the lipase and/or FAD4 nucleic acids. In this case, one would then generally assay the potentially transformed cell population by exposing the cells to a selective agent or agents, or one would screen the cells for the desired marker gene trait. Alternatively, the introduced (e.g., transgenic) nucleic acids can be detected and/or characterized by use of a nucleic acid probe to detect the presence of an expression cassette and/or expressed RNA. The introduced nucleic acids can also be detected and/or evaluated by sequencing.

Selection:

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

For example, to use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/11 bialaphos or about 1-3 mM glyphosate can be employed, it is proposed that ranges of at least about 0.1-50 mg/l bialaphos or at least about 0.1-50 mM glyphosate may be useful. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at inhibiting concentrations that cause 100% inhibition followed by screening of growing tissue for expression of a screenable marker gene such as luciferase would allow one to recover transformants from cell or tissue types that are not amenable to selection alone. In one example, embryogenic Type II callus of *Zea mays* L. can be selected with sub lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that express the desired trait(s). In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the lipase and/or FAD4 nucleic acids into the genome of the inbred plants. This process is referred to as backcross conversion. When a number of crosses to the recurrent inbred parent have been completed, a product of the backcross conversion process that is substantially isogenic with the recurrent inbred parent except for the presence of the introduced lipase and/or FAD4 nucleic acids is generated. Such a plant is self-pollinated at least once in order to produce a homozygous backcross converted inbred plant line containing the lipase and/or FAD4 nucleic acids. Progeny of these plants are true breeding.

Alternatively, seed from transformed plants regenerated from transformed tissue cultures is grown in the field and self-pollinated to generate true breeding plants.

Seed from the fertile transgenic plants can be evaluated for the presence and/or expression of the lipase and/or FAD4 nucleic acids (or the lipase and/or FAD4 protein products). Transgenic plant and/or seed tissue can be analyzed for lipase and/or FAD4 expression using standard methods such as SDS polyacrylamide gel electrophoresis, liquid chromatography (e.g., HPLC) or other means of detecting a lipase and/or FAD4 protein.

Once a transgenic seed expressing the lipase and/or FAD4, and having an increase in oil in the plant tissue is identified, the seed can be used to develop true breeding plants. The true breeding plants are used to develop a line of plants with an increase in the percent of oil in the plant tissues while still maintaining other desirable functional agronomic traits. Adding the trait of increased oil/decreased carbohydrate production to the plant can be accomplished by back crossing with this trait and with plants that do not exhibit these traits and studying the pattern of inheritance in segregating generations.

Those plants expressing the target trait in a dominant fashion are preferably selected. Back crossing is carried out by crossing the original fertile transgenic plants with a plant from an inbred line exhibiting desirable functional agronomic characteristics while not necessarily expressing the trait of an increased percent of oil in the plant. The resulting progeny are then crossed back to the parent that expresses the increased oil/decreased carbohydrate trait. The progeny from this cross will also segregate so that some of the progeny carry the traits and some do not. This back crossing is repeated until an inbred line with the desirable functional agronomic traits, and with expression of the trait involving an increase in oil and/or a decrease in carbohydrate in the vegetative tissues of the plant. Such expression of the increased percentage of oil or decreased percentage of carbohydrate in plant tissues can be expressed in a dominant fashion.

Subsequent to back crossing, the new transgenic plants can be evaluated for an increase in the weight percent of oil (TAG) incorporated into vegetative tissues of the plant. This can be done, for example, by thin layer chromatography (TLC), gas chromatography, gas chromatography-flame ionization detector (GC-FID), electrospray ionization mass spectrometry (ESI-MS), mass spectroscopy, nuclear magnetic resonance (NMR), high pressure liquid chromatography (HPLC), and/or infrared spectral analysis of plant tissue or by other available methods of detecting and quantifying oils in harvested plant tissues. The new transgenic plants can also be evaluated for a battery of functional agronomic characteristics such as lodging, kernel hardness, yield, resistance to disease, resistance to insect pests, drought resistance, and/or herbicide resistance.

Plants that can be generated by these methods include but are not limited to oil and/or starch plants (canola, potatoes, cassava, lupins, oilseeds, olive, palm, peanut, rape, rapeseed, safflower, sorghum, soybean, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), fiber-producing plants (cotton, flax), softwood, hardwood and other woody plants (e.g., those used for paper production such as poplar species, pine species, and eucalyptus). Examples of plants and/or plant cells that can be modified as described herein include alfalfa (e.g., forage legume alfalfa), algae, avocado, barley, broccoli, Brussels sprouts, cabbage, camelina, canola, cassava, cauliflower, coconut, cole vegetables, collards, corn, crucifers, flax, grain legumes, grasses (e.g., forage grasses), jatropa, kale, kohlrabi, maize, miscanthus, mustards, nut sedge, oats, oil firewood trees, oilseeds, olive, palm, peanut, potato, radish, rape, rapeseed, rice, rutabaga, safflower, sorghum, soybean, sugar beets, sugarcane, sunflower, switchgrass, tobacco, tomato, turnips, and wheat. In some embodiments, the plant is a *Brassicaceae* or other Solanaceae species. In some embodiments, the plant or cell can be a maize plant or cell. In some embodiments, the plant is not a species of *Arabidopsis*, for example, in some embodiments, the plant is not *Arabidopsis thaliana*.

Determination of Stably Transformed Plant Tissues:

To confirm the presence of the lipase and/or FAD4 nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant. In some embodiments, the amount of oil in plant tissues is quantified. Such a quantified oil content can be compared to a control plant, for example, a control plant of the same species that has not be modified to express the lipase and/or FAD4 protein.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from the introduced lipase and/or FAD4 nucleic acids. RT-PCR also be used to reverse transcribe expressed RNA into DNA, using enzymes such as reverse transcriptase, and then this DNA can be amplified through the use of PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

Southern blotting, northern blotting and PCR may be used to detect the lipase and/or FAD4 nucleic acid in question. Expression may also be evaluated by specifically identifying the presence or absence of protein products of the introduced lipase and/or FAD4 nucleic acids, by assessing the level of lipase and/or FAD4 mRNA and/or protein expressed, or evaluating the phenotypic changes brought about by their expression.

Assays for the production and identification of specific proteins may make use of physical chemical, structural, functional, or other properties of the proteins. Unique physical chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to confirm the identity of the lipase and/or FAD4 protein expressed such as evaluation by nucleic acid or amino acid sequencing following purification. The Examples of this application also provide assay procedures for detecting lipase and/or FAD4 activity. Other procedures may be additionally used.

The expression of a lipase and/or FAD4 gene product can also be determined by evaluating the phenotypic results of its expression. These assays also may take many forms including but not limited to analyzing changes in the chemical composition, morphology, or physiological properties of the plant. Chemical composition of plant tissues may be altered by expression of the lipase and/or FAD4 protein(s).

Kits

A kit is provided that can include a transgenic seed containing lipase and/or FAD4 nucleic acids, as well as instructions for cultivating the seeds, as well the use of any other material or reagent not included in the kit. The kit can also include a medium for growth of the seeds, or for grow of seedlings, or for induction of expression of the lipase and/or FAD4 nucleic acids to generate lipase and/or FAD4 proteins. Such a medium can also include sugar or a source of sugar. The kit can also include fertilizer. Instructions can include text on when and how to induce expression of the lipase and/or FAD4. Variations that can be implemented can also be described in the instructions.

Any of the lipase and/or FAD4 nucleic acids, polypeptides and/or related nucleic acids and/or polypeptides described herein can be included in a kit. In some embodiments, the kits can include a container that includes a nucleic acid, or a mixture of nucleic acids. Such a nucleic acid or mixture of nucleic acids can be used, for example, to transform plant cells and/or generate transgenic plants. The nucleic acid(s) can encode a lipase and/or FAD4 protein.

The kits can also include more than one container. For example, the kits can include two or more containers, where one container includes a lipase and/or FAD4 nucleic acid, and another container includes other nucleic acids of interest, or other components for transformation of plant cells. For example, the kit can include a container with a lipase and/or FAD4 nucleic acid, where the lipase and/or FAD4 nucleic acid can be part of an expression cassette or an expression vector.

The kits may also include one or more containers of buffers, such as buffers to dilute or stabilize the lipase and/or FAD4 nucleic acids, or transcription buffers, or hybridization buffers, or buffers for measuring lipase and/or FAD4 activity or compounds for manipulating the nucleic acids, and/or components for isolating the resultant expression cassette that may be integrated into a plant genome.

The kits can also contain substrates for measuring lipase and/or FAD4 activities. For example, the kits can contain lipase substrates such as PG and/or MGDG.

The components of the kits may be packaged either in aqueous media or in lyophilized form. The containers can be vials, test tubes, flasks, bottles, syringes or other container means, into which a component may be placed, and suitably aliquoted.

Where there is more than one component in the kit, the kit also will generally contain a second, third or other additional container into which the additional components may be separately placed. However, various combinations of components may also be included in one container. The kits of the present invention also will typically include a means for containing the nucleic acids, and any other reagent containers in close confinement for commercial sale. Such containers may include injection or blow-molded plastic packages into which the desired vials are retained.

When the components of the kit are provided in one and/or more liquid solutions, the liquid solution is an aqueous solution, for example, a sterile aqueous solution. The nucleic acids can also be provided as an alcohol precipitate or as dried powder(s). When reagents and/or components are provided as a dry powder, the powder can be reconstituted by the addition of a suitable solvent. It is envisioned that the solvent may also be provided in another container.

In some embodiments, nucleic acids are provided in dried form or suspended in an appropriate buffer or solvent. It is contemplated that 0.1, 1, 5, 10, 20, 30, 40, 50, 60, 70, 80, 90, 100, 120, 120, 130, 140, 150, 160, 170, 180, 190, 200, 300, 400, 500, 600, 700, 800, 900, 1000 µg or nucleic acid can be provided in kits of the invention.

The kits can also include a means for containing the vials in close confinement for commercial sale, such as, e.g., injection and/or blow-molded plastic containers into which the desired vials are retained.

Such kits may also include components that preserve or maintain the nucleic acids or that protect against their degradation. Such components may be DNAse-free or RNAse free. The kits may include containers of DNase or RNase inhibitors. Such kits generally will comprise, in suitable means, distinct containers for each individual reagent or solution.

A kit will also include instructions for employing the kit components as well the use of any other reagent not included in the kit. Instructions may include variations that can be implemented.

PLIP1 Prefers 18:3/16:1$^{\Delta 3t}$-PG as Natural Substrate

Figure 1B:
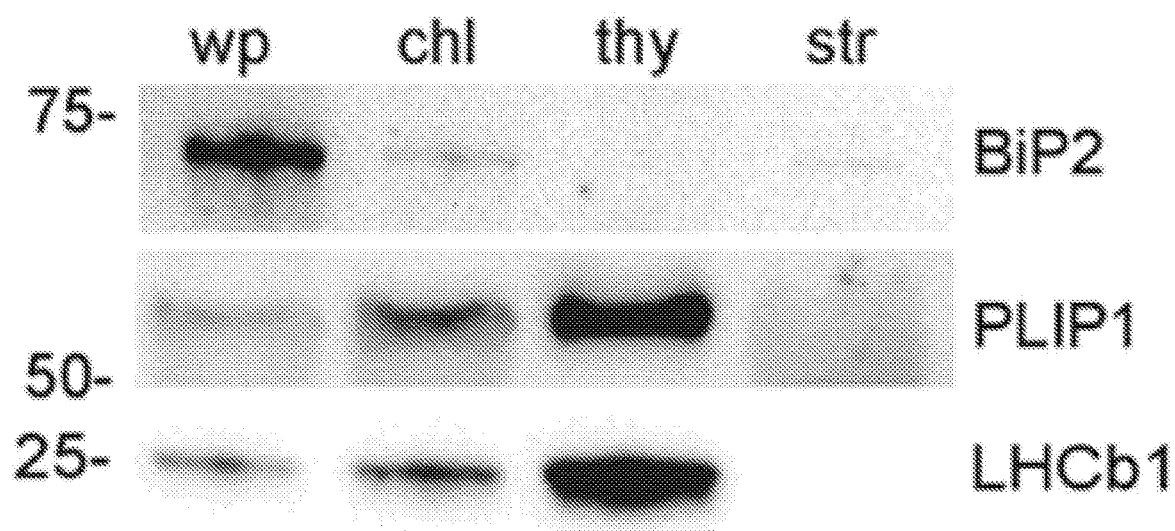
Figure 1C:
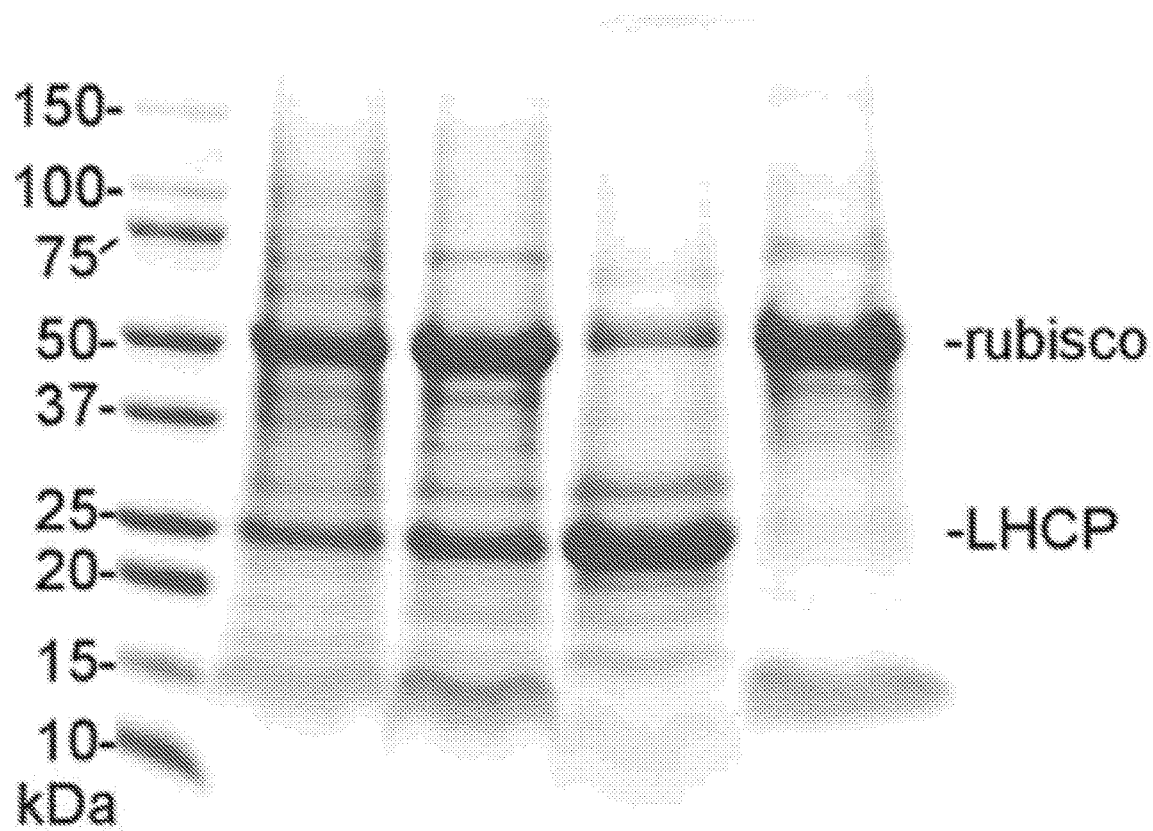

Recombinant lipases are notoriously difficult to produce and to study in vitro. PLIP1 is no exception as its production in E. coli led to membrane degradation, which confirmed its general lipase activity, but made PLIP1 challenging to purify (FIG. 1E-F). Furthermore, while recombinant PLIP1 was specifically acting on the glyceryl sn-1 position, it could use a range of polar lipids found in plants and bacteria in vitro (FIG. 2G-2H). Notably, it did not act on TAG and had very little activity on the two glycolipids DGDG and sulfolipid found in the chloroplast, but high activity towards PG and MGDG. Because the full spectrum of all possible combinations of glycerolipid molecular species occurring in chloroplasts was impractical to test in vitro, the in vivo specificity of PLIP1 was evaluated by overproducing the protein in chloroplasts, which the inventors had determined was the location of PLIP1 in plant cells using multiple independent approaches (FIG. 1). This allowed testing PLIP1 lipase activity in a quasi-native environment with the caveat that PLIP1 is normally not abundant in leave chloroplasts and more likely active in chloroplasts of developing embryos based on the gene's expression profile and the loss-of-function phenotype visible in seeds (FIG. 4). However, leaf chloroplasts are much more readily accessible for assays than embryo chloroplasts and we assumed that findings on PLIP1 activity would be transferable between the two tissues, which was ultimately confirmed. Based on the in vivo analysis of PLIP1, 18:3/16:1$^{\Delta 3t}$-PG emerged as the most likely in vivo substrate for PLIP1, which was corroborated in vitro using a native, leaf-isolated molecular species mixture of PG (FIG. 2D-2F). It should be noted that in the over expression lines, effects on MGDG and PC were observed in addition to PG (FIGS. 3B and 3C). This could be directly due to the activity of PLIP1 on MGDG, or caused by secondary effects related to acyl exchange and acyl transfer in case of PC, which is not in the thylakoid membranes and should not be directly accessible to PLIP1.

PLIP1 Location Limits Availability of Likely Substrates In Vivo

To explain the observed PLIP1 substrate preference in vivo, one might invoke the presence of factors in its native environment that are simply not present in vitro. Another, more likely, explanation might be the limited accessibility of certain lipid molecular species to PLIP1 due to the specific membrane location of the PLIP1, assuming that specific membrane leaflets or lateral subdomains might have a specific lipid composition. The inventors now have some clarity on the location of PLIP1, its likely peripheral association with thylakoid membranes based on fractionation, chloroplast import, and protease protection experiments, and its dual processing (FIG. 1). Fractionation showed that PLIP1 is associated with thylakoid membranes, while import and protease protection assays were consistent with three possible suborganellar locations for PLIP1: stroma, thylakoid or the stroma leaflet of the inner envelope membrane (FIG. 1). PLIP1 is not predicted to contain transmembrane domains, but must be a peripheral membrane protein to gain access to its substrate. Most likely, PLIP1 is a peripheral thylakoid protein, but PLIP1 also can transiently be free in the stroma or PLIP1 can even access to the inner envelope membrane. Double processing of PLIP1 as observed can be interpreted as first generating an intermediate during protein import into the stroma, while the second processing possibly releases the majority of the mature protein from the thylakoid fraction into the soluble stroma fraction. A conserved twin-arginine motif is generally required for importing proteins into thylakoids (Robinson and Bolhuis, 2001; Goosens and van Dijl, 2016), but PLIP1 is missing a canonical motif, although it contains two sets of twin-arginine in its transit peptide usually part of such a motif. Therefore, PLIP1 may peripherally attach to the thylakoid membrane but is likely prevented from being further imported into thylakoid lumen.

For the likely substrate of PLIP1, $18:3/16:1^{\Delta 3t}$-PG, we only know that it is exclusively present in chloroplasts, where the FAD4 desaturase required for its synthesis is located as well (Gao et al., 2009). However, the presence of $18:3/16:1^{\Delta 3t}$-PG in a specific suborganellar membrane, leaflet, or lateral membrane domain is not known. All we can conclude based on our localization of PLIP1 is that $18:3/16:1^{43t}$-PG must be present in the stroma leaflet of the thylakoid or envelope membranes to be accessible to PLIP1.

PLIP1 is Involved in TAG Biosynthesis in Developing Embryos

Figures 4A, 4B:
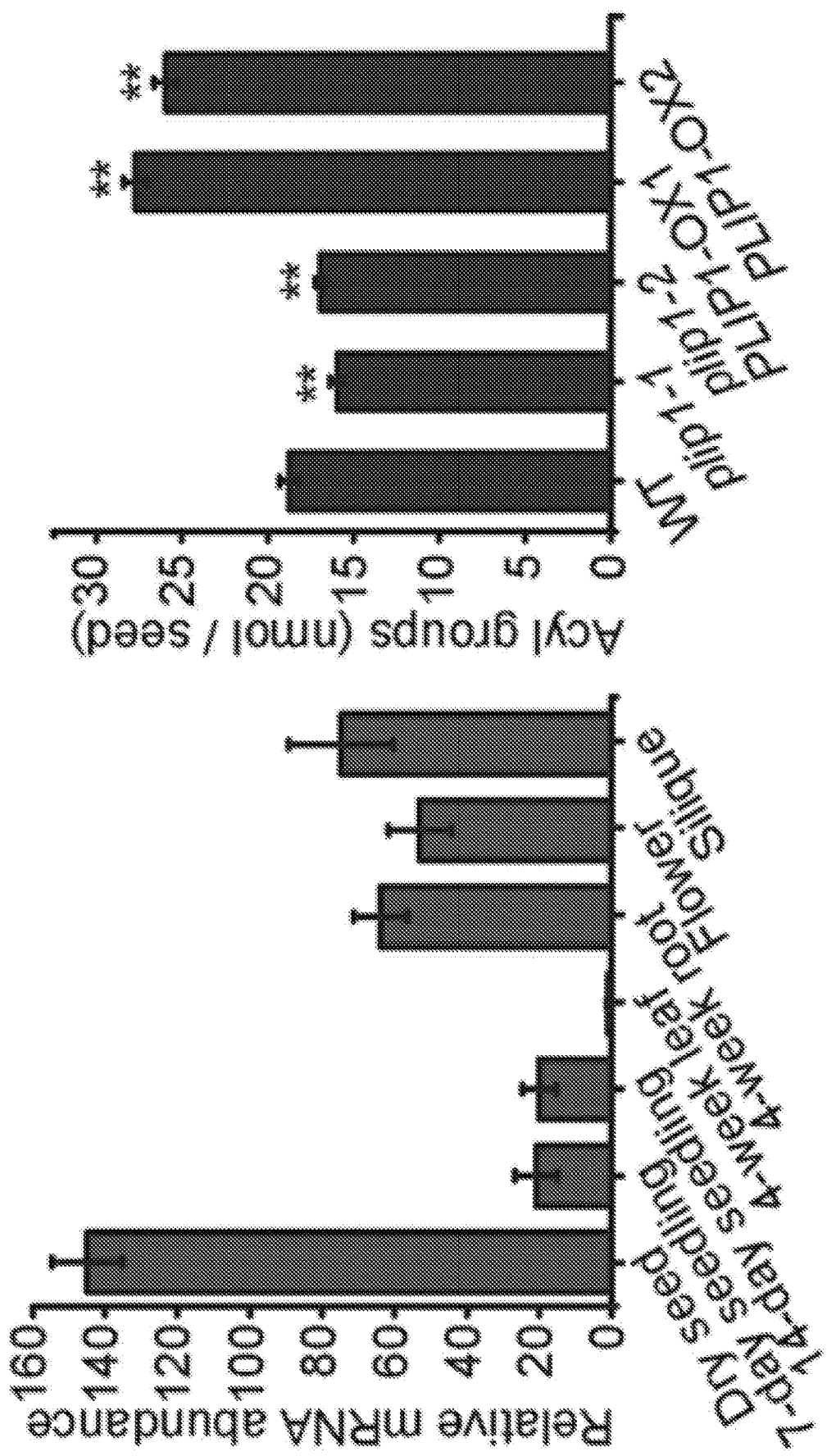
FIG. 4A-4E illustrates the effects of PLIP1 on seed oil biosynthesis and germination.
Figures 4C, 4D:
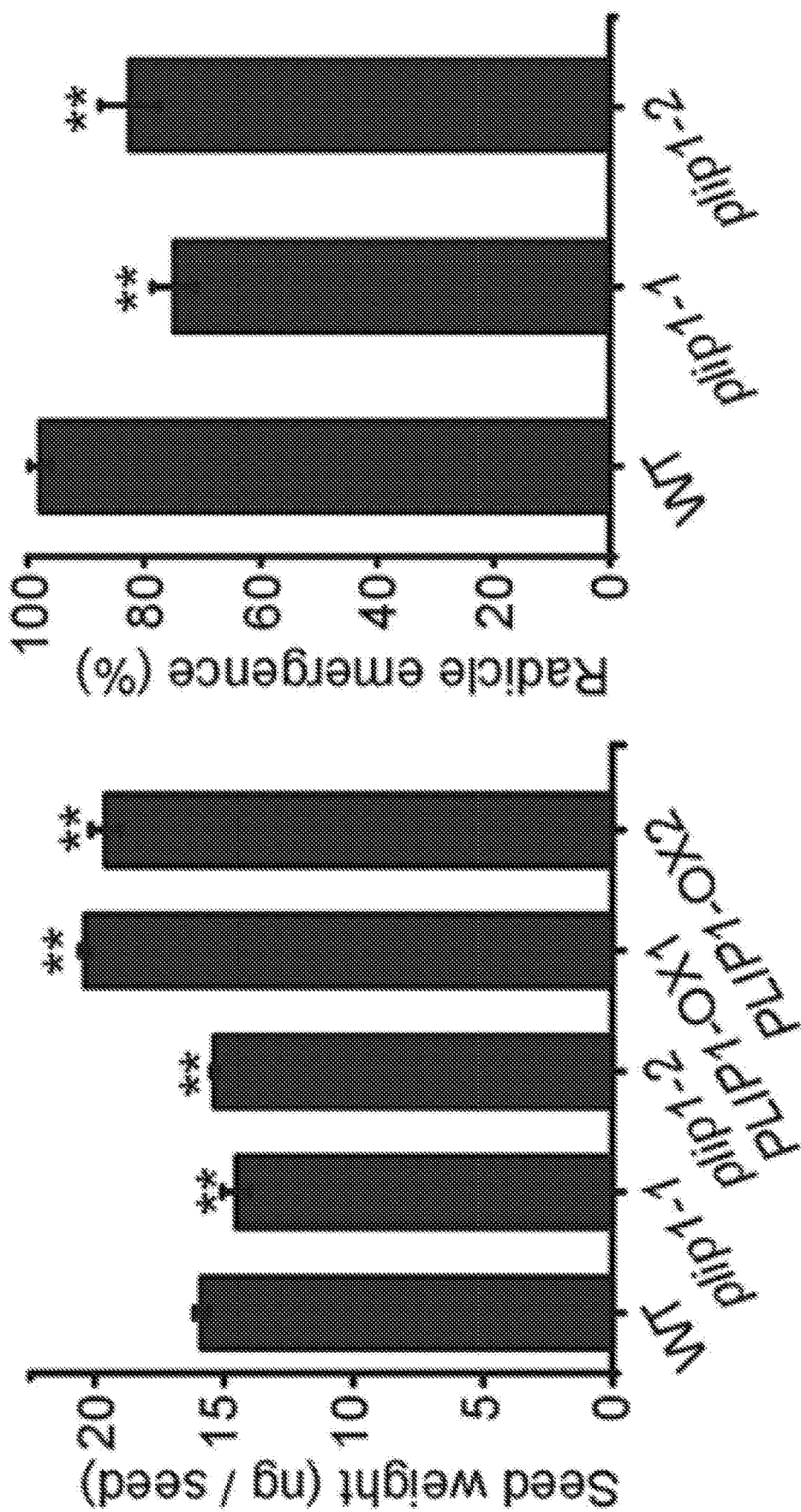

PG is required for proper embryo development. The development of embryos in a pgp1, pgp2 double mutant affected in PG biosynthesis in chloroplasts, mitochondria and the endoplasmic reticulum is delayed and maturing seeds shrink during desiccation, resulting subsequently in compromised germination (Tanoue et al., 2014). Originally, it was proposed that the chloroplast-specific molecular lipid species, $18:3/16:1^{\Delta 3t}$-PG, is critical for the function of the photosynthetic membrane, but its complete replacement with 18:3/16:0-PG in the *Arabidopsis* fad4 mutant had only mild effects on leaf photosynthesis (Browse et al., 1985; McCourt et al., 1985). Therefore, the fact that PLIP1 preferentially releases 18:3 from $18:3/16:1^{\Delta 3t}$-PG, might point towards previously unrecognized roles for this lipid, especially in seeds, where PLIP1 is most highly expressed (FIG. 4A). In fact, with increased expression of PLIP1, seed TAG content increased, while decreased PLIP1 expression in T-DNA insertional lines reduced seed TAG content (FIG. 4), corroborating a possible involvement of PLIP1 in seed TAG biosynthesis. Furthermore, decreased TAG in plip1 seeds lead to decreased germination (FIG. 4D).

Figure 3A:
FIG. 3A-3J illustrates in vivo PLIP1 activity.
Figure 3C:
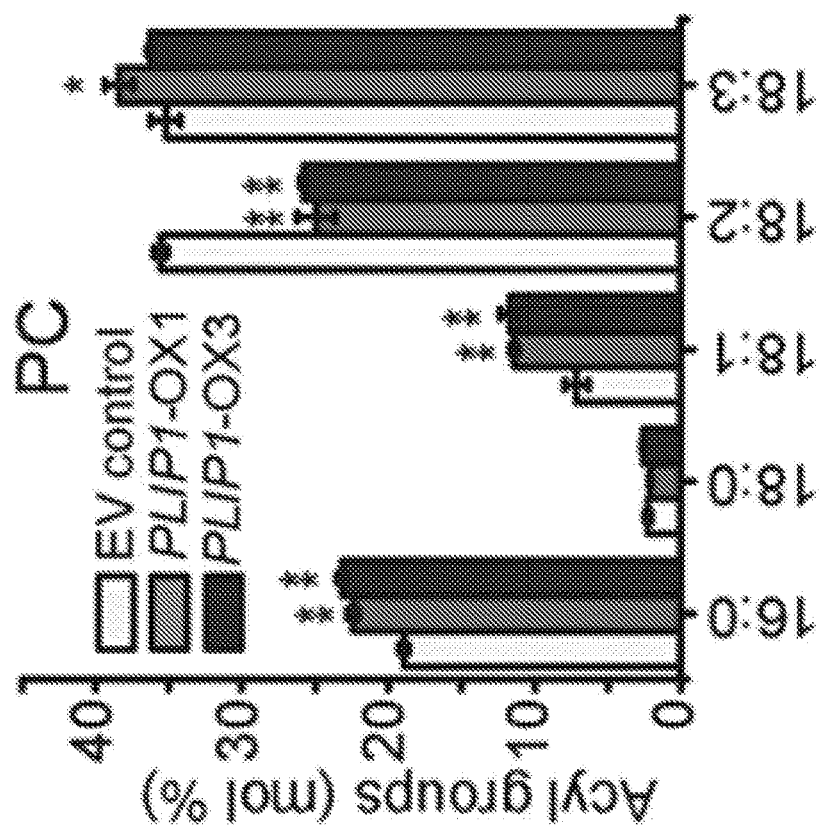
Figure 3B:
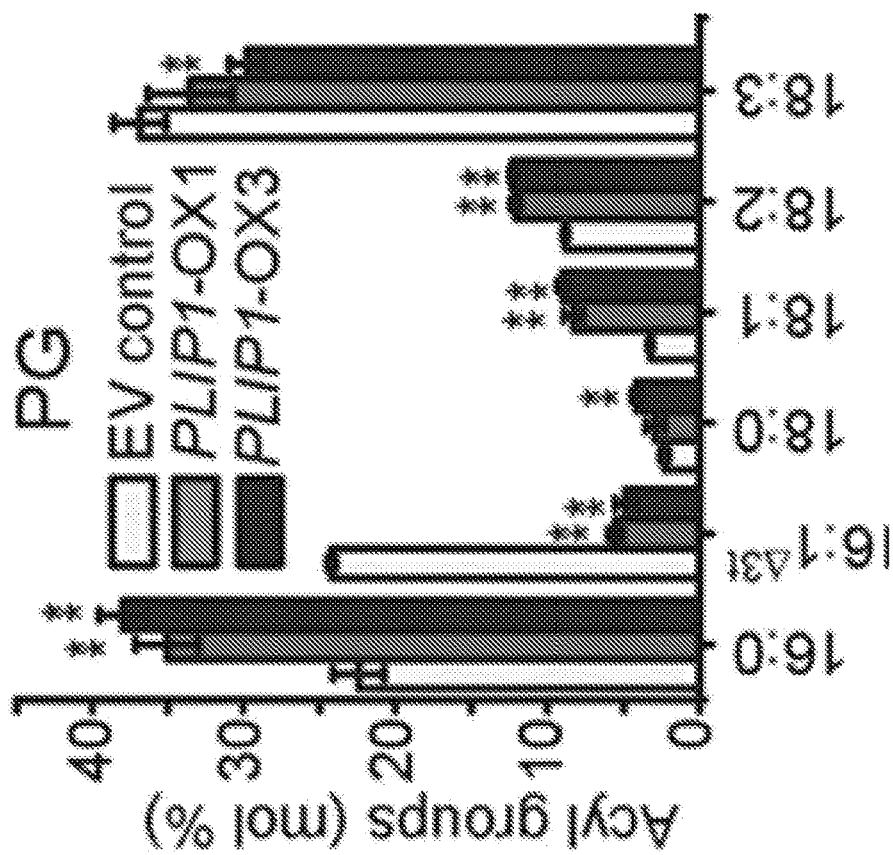
Figure 5A:
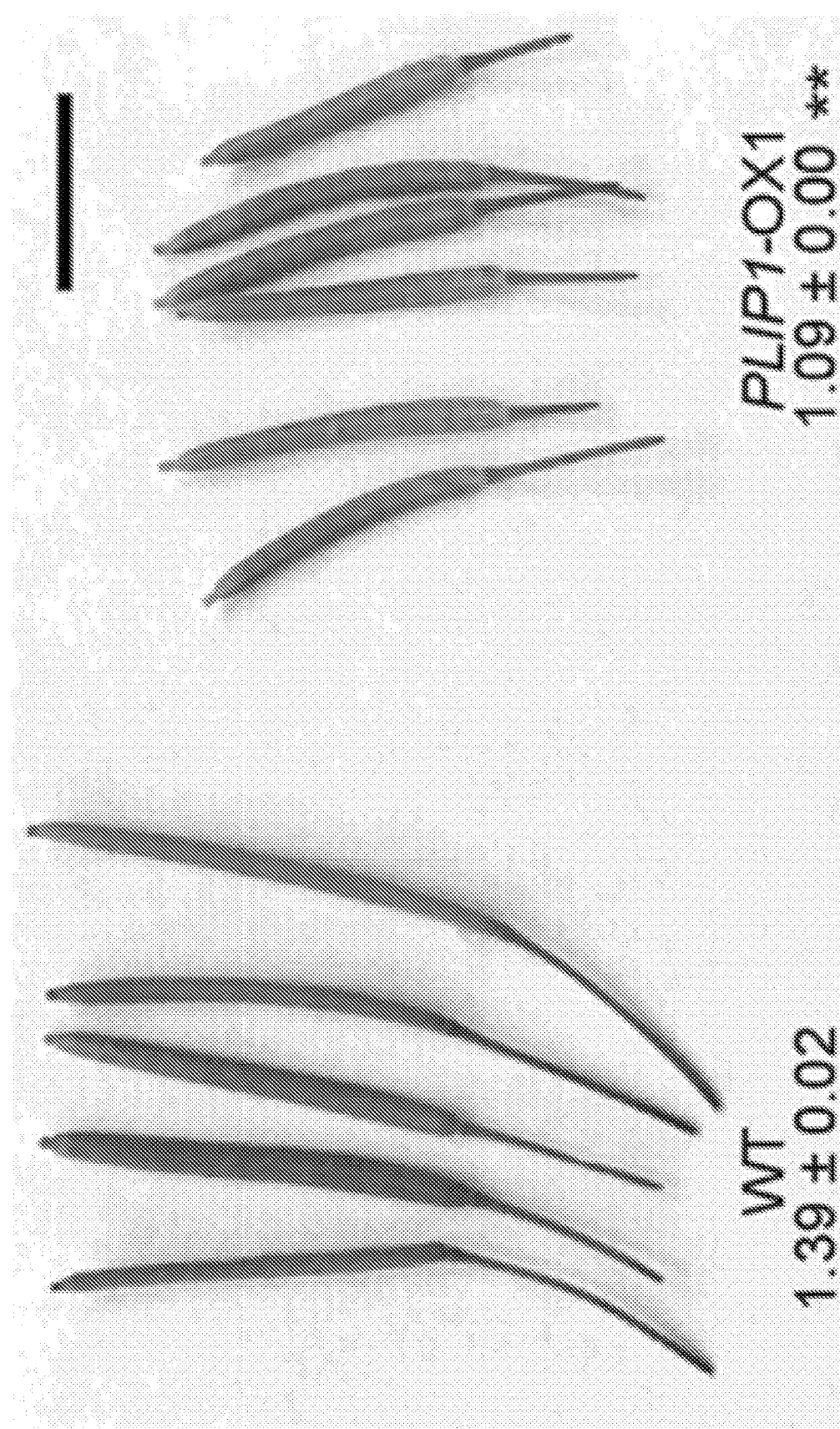
FIG. 5A-5C illustrate the phenotype of PLIP1-OX1 embryos.
Figure 5B:
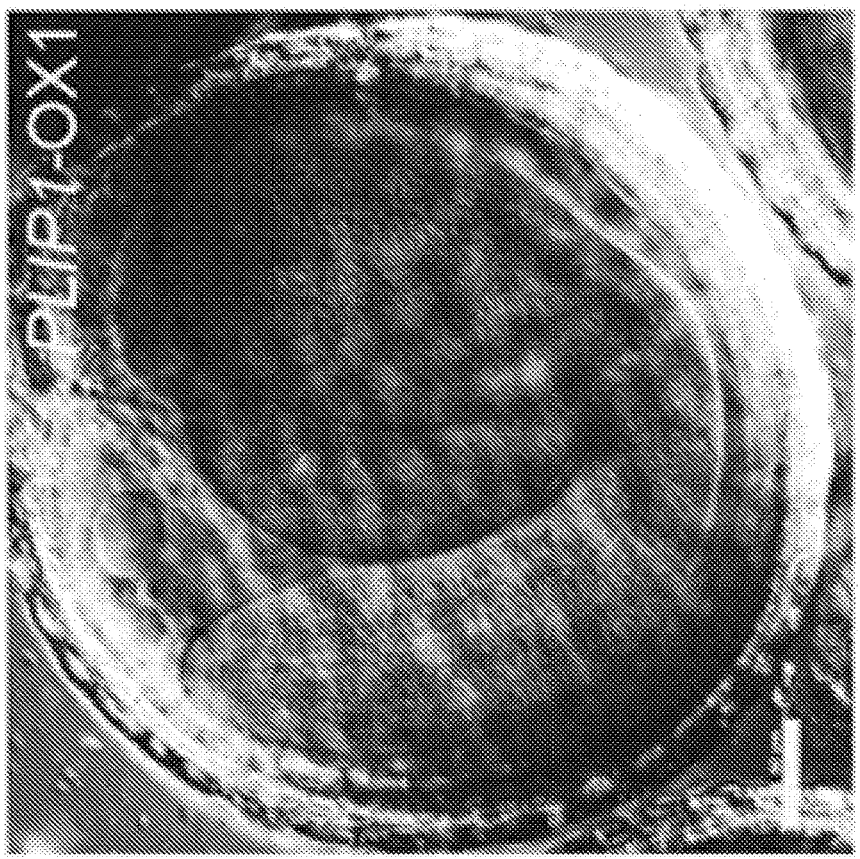
Figure 5B:
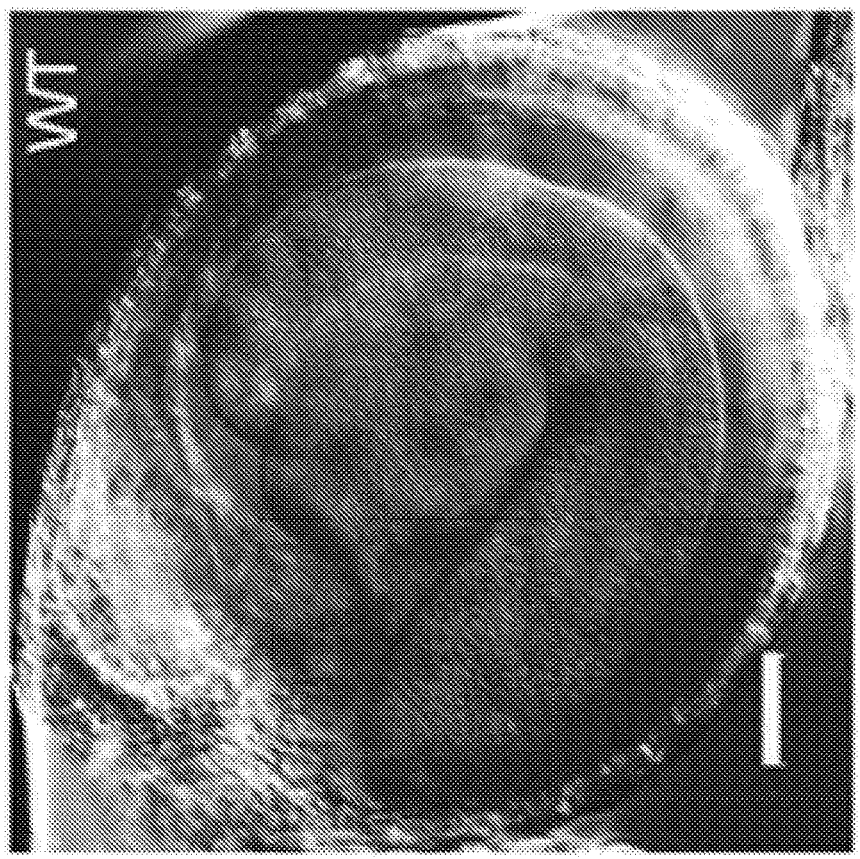
Figure 5C:
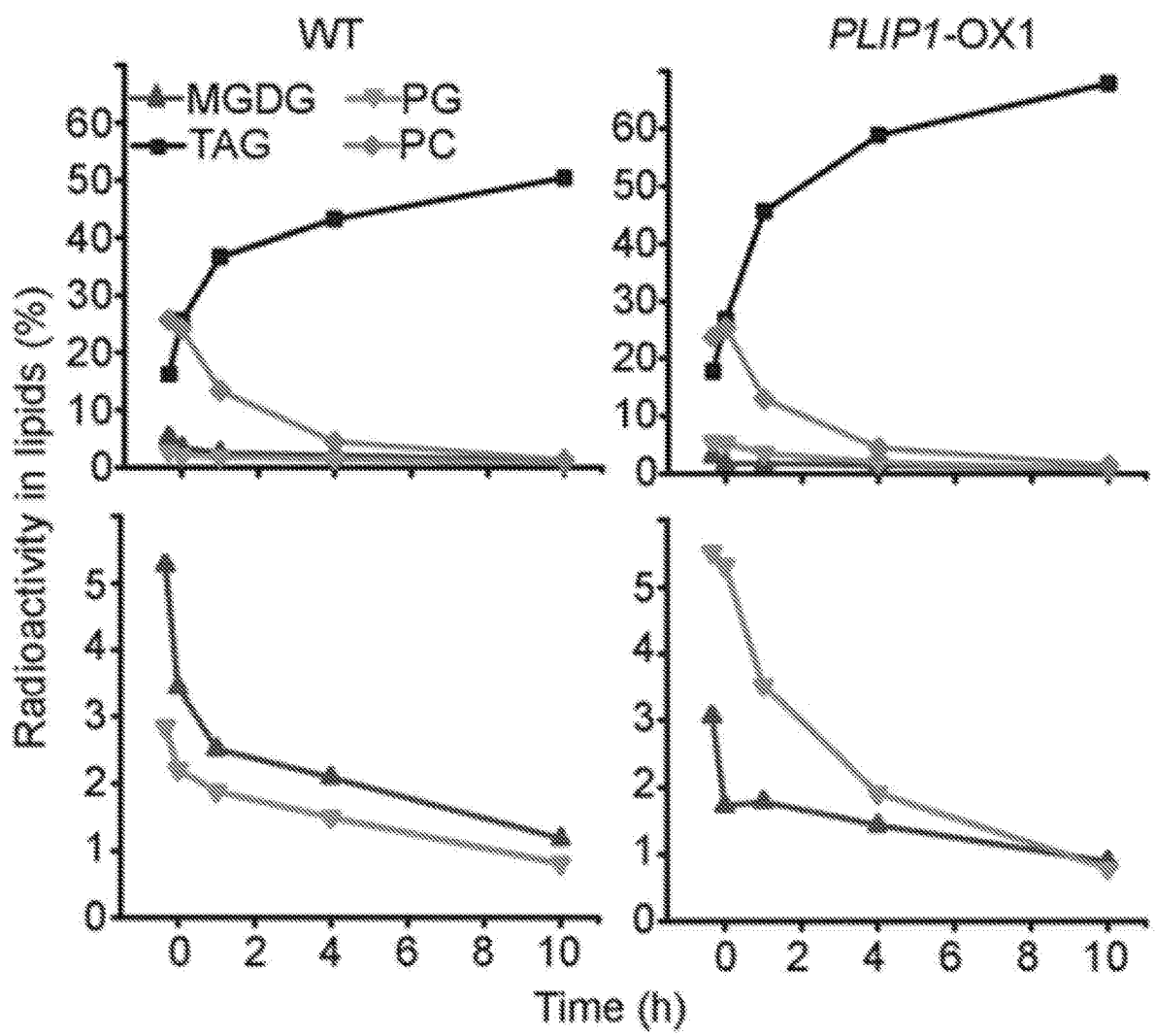

During the labeling experiment on isolated embryos, saturating substrate levels were provided (FIG. 5C). Therefore, higher carbon incorporation into TAG in PLIP1-OX seeds reflects an increased capacity for TAG biosynthesis in individual embryos, despite the reduced plant growth and the decreased overall seed yield of the plants (FIG. 3A). Interestingly, this increased rate of incorporation into TAG was also observed for leaves of the PLIP1-OX lines (FIG. 3H). Furthermore, given the preference of PLIP1 for $18:3/16:1^{\Delta 3t}$-PG, the recapitulation of the plip1 low-TAG seed phenotype in the fad4 mutant lacking $18:3/16:1^{\Delta 3t}$-PG supports the role of PLIP1 in seed TAG biosynthesis and provides a possible function for this unusual lipid molecular species.

Figure 6:
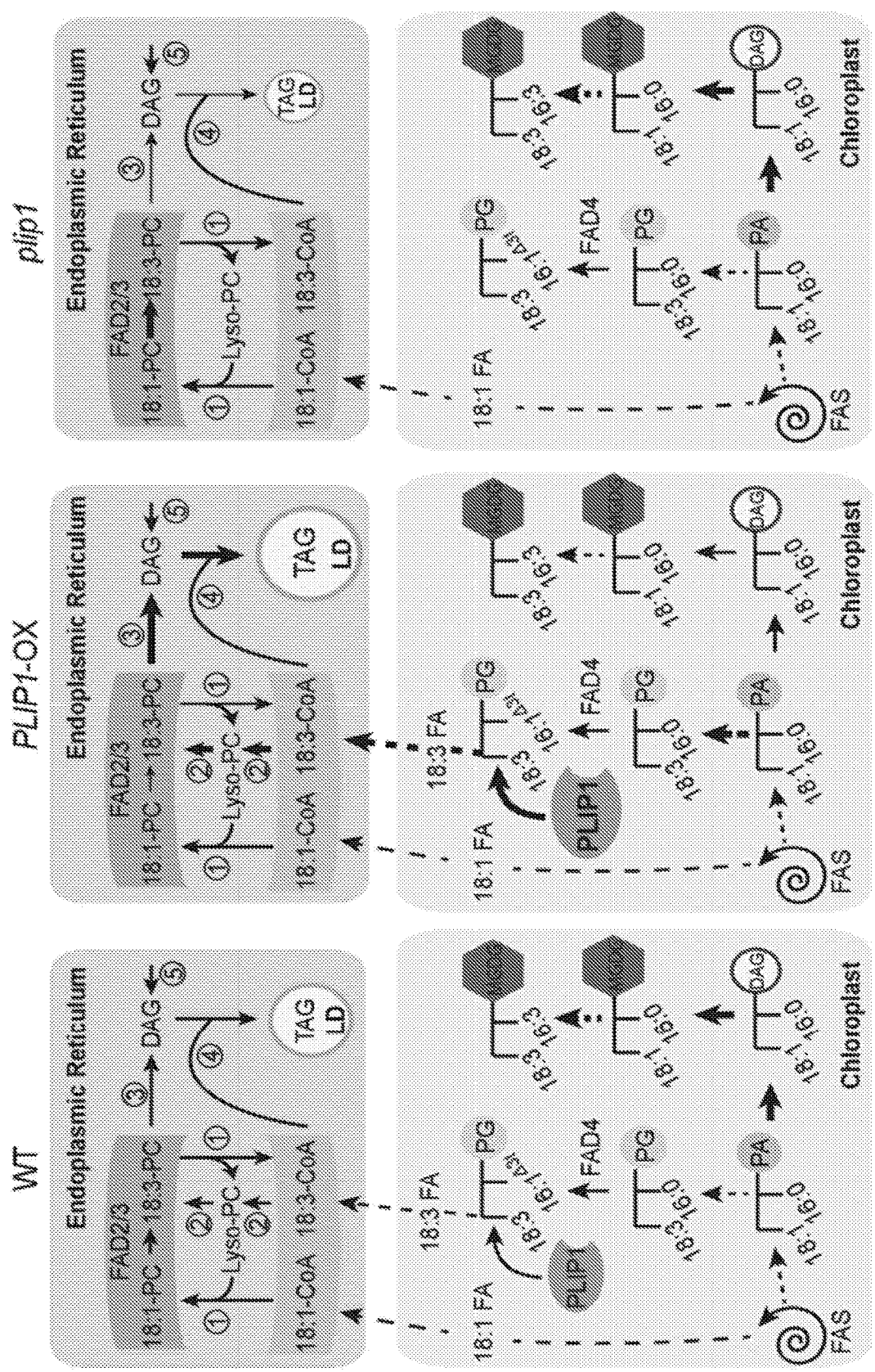
FIG. 6 shows a model of PLIP1 function in triacylglycerol biosynthesis. The left panel depicts the wild type (WT), the middle panel the PLIP1-overexpression lines, and the right panel the plip1 mutant. The thickness of the arrows indicates the relative fluxes in the three different lines. Reactions or sets of reactions are numbered as follows: 1. In WT (left panel) acyl exchange on phosphatidylcholine (PC) involving desaturation of acyl groups by FAD2/3 provides one mechanism to introduce polyunsaturated fatty acids (FAs) into diacylglycerol (DAG). 2. A second, parallel mechanism to introduce PUFAs into DAG involves PLIP1. In the chloroplast, PLIP1 hydrolyzes $18:3/16:1^{\Delta 3t}$-phosphatidylglycerol (PG) at the sn-1 glyceryl position and releases 18:3 (carbon: double bonds). 18:3 is exported to the Endoplasmic Reticulum and incorporated into the acyl-CoA pool and PC before entering DAG. 3. A head group exchange mechanism leads to DAG formation from PC containing polyunsaturated FAs. 4. Triacylglycerol (TAG), which accumulates in lipid droplets (LDs), is formed by the action of DAG-acyltransferases, which can introduce an additional 18:3 into TAG from the acyl-CoA pool. 5. DAG can also be formed by de novo assembly through the Kennedy pathway, which, however, is thought to play a minor role in the synthesis of TAGs in seeds. In the chloroplast, biosynthesis of PG and monogalactosyldiacylglycerol (MGDG) share the precursor phosphatidic acid (PA), with more PA being shuttled to MGDG biosynthesis in the wild type. In PLIP1-OX lines (middle panel), both PG biosynthesis and degradation are accelerated, resulting in increased export of 18:3 and its direct incorporation into PC (reactions 2). Direct incorporation of 18:3 competes with polyunsaturated FA formation by the acyl-editing pathway of PC involving FAD2/3 (reactions 1), but leads to increased flux of 18:3 into the end product TAG. Due to increased PG turnover in chloroplasts of PLIP1-OX lines, PA is preferably shuttled into PG biosynthesis, which subsequently reduces its availability for MGDG assembly in the plastid visible in changes in the MGDG acyl composition. In the plip1 mutant (right panel), the PLIP1-dependent pathway is deficient, resulting in decreased TAG biosynthesis. Without the competing effect of PLIP1 on the acyl exchange reactions and FAD2/3, more 18:1 is converted to 18:3 explaining the altered acyl composition of TAG and other extraplastidic lipids.
Figure 7A:
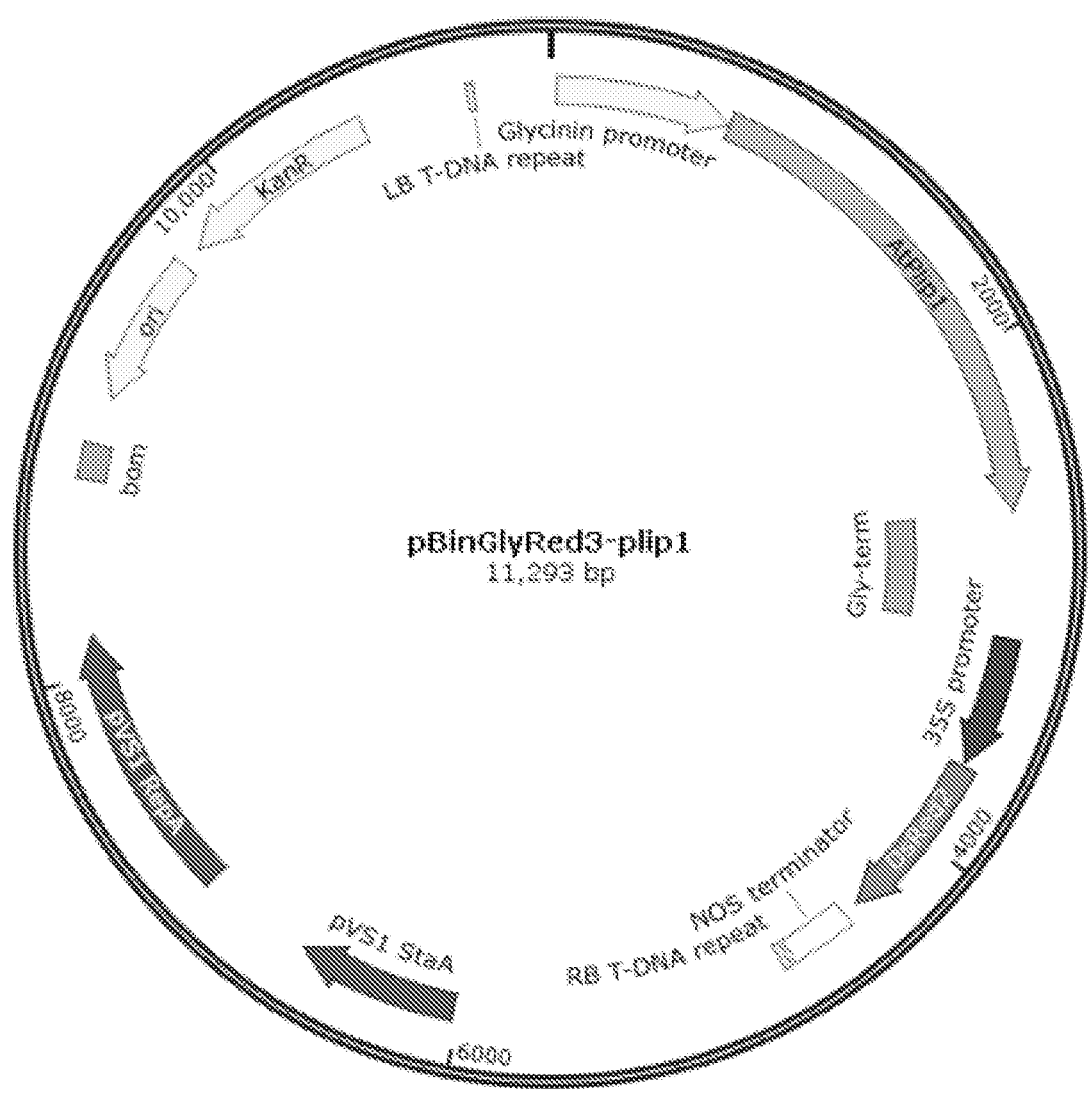
FIG. 7A-7D illustrates examples of expression vectors.
Figure 7B:
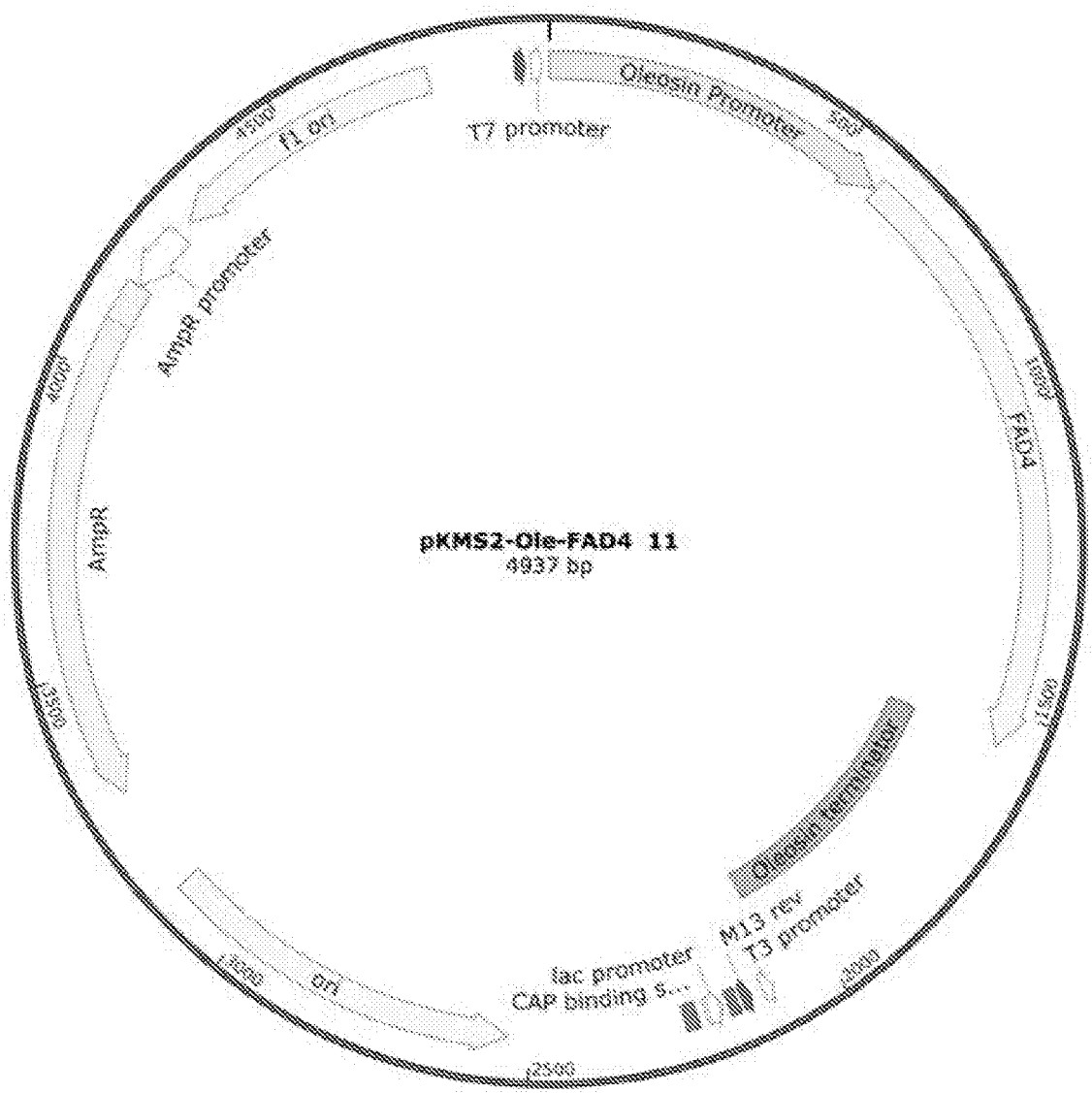
Figure 7C:
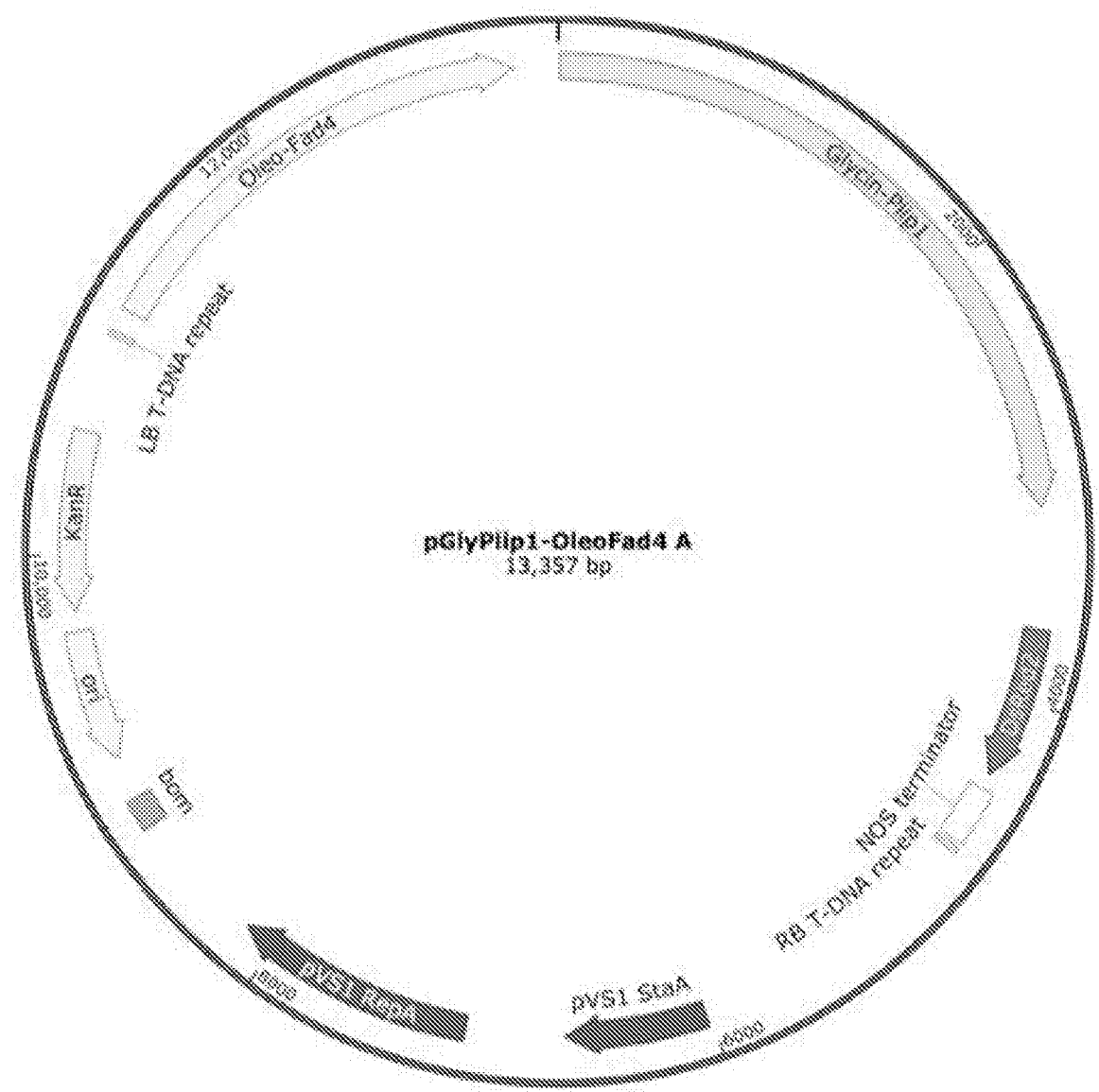
Figure 7D:

PLIP1 Enables Channeling of Acyl Groups from Plastid $18:3/16:1^{\Delta 3t}$-PG to TAG at the Endoplasmic Reticulum How can PLIP1, a lipase, be a component of a mechanisms directing FAs synthesized in the plastid into TAG lipid droplets in the cytosol during embryogenesis? A large body of evidence suggests that PC is a critical precursor for TAG biosynthesis in developing seeds. As shown in FIG. 6, at least two pathways, acyl editing of PC (FIG. 6, reaction 1) followed by transfer of 18:3 from the acyl-CoA pool to TAG (FIG. 6, Reaction 4) and head group exchange generating DAG with 18:3 acyl groups (FIG. 6, reaction 3), contribute to the incorporation of polyunsaturated FAs into TAG during seed development (Bates et al., 2012; Li-Beisson et al., 2013). However, even in the rod1, lpcat1, lpcat2 triple mutant carrying the strongest known alleles at each locus, which in combination should completely disrupt acyl editing and head group exchange, the capacity of seeds to produce 18:3-containing TAG is only cut by half (Bates et al., 2012). Therefore, other mechanisms likely exist for incorporating polyunsaturated FAs into ER lipids and TAGs. The inventors hypothesized that PLIP1 provides an additional acyl editing mechanism to resupply the cytosolic 18:3-CoA pool as depicted in FIG. 6, Reaction 2. Whenever PLIP1 is highly abundant in vegetative tissues or seeds, the turnover of plastid PG accelerates (FIG. 3 and FIG. 5). The PG pool size does not change, but the PG acyl composition does, which is indicative of acyl-editing of plastid PG. Importantly carbon flux and specifically 18:3 flux from PG to PC are increased in PLIP1 overexpression lines, which is evident from the pulse-chase labeling experiments (FIG. 5) and reflected in the compositional changes of bulk PC, respectively (FIG. 4). Restoration of the low 18:3-PC lipid phenotype of the fad3-2 mutant by overexpression of PLIP1 (FIG. 3F) corroborates this hypothesis. This result is consistent with a competition between PLIP1 providing 18:3 acyl groups incorporated into PC by acyl exchange from the acyl-CoA pool and desaturation of acyl groups directly on PC by ER desaturases followed by head group exchange and 18:3 DAG production.

PLIP1 Takes Part in Acyl Group Export from Chloroplasts

The hypothesis outlined above (FIG. 6) also implies that PLIP1 activity leads to acyl export from the plastid. Assuming that PLIP1 acts at the stroma surface of the thylakoids or the inner envelope membrane, additional chloroplast proteins are likely necessary to direct acyl groups from chloroplast $18:3/16:1^{\Delta 3t}$-PG into TAGs. Recently, chalcone isomerase-like chloroplast proteins were shown to be FATTY ACID BINDING PROTEINS (FAP), which may be associated with chloroplast fatty acid export (Ngaki et al., 2012). The expression pattern of FAPs resembles that of PLIP1, and all FAPs are located in the stroma of chloroplasts. One of the FAPs, FAP1 shows high proclivity for binding 18:3. Therefore, it seems possible that 18:3 released by PLIP1 from $18:3/16:1^{\Delta 3t}$-PG is bound by FAP, thereby sequestering it to avoid cytotoxicity of free FAs or to mediate FA transfer to the chloroplast envelope membrane. Another protein possibly involved is FATTY ACID EXPORT1 (FAX1), a likely acyl group or FA transporter of the inner envelope membrane of plastids (Li et al., 2015). In the fax1 mutant, of the four thylakoid lipids PG levels are increased the most, especially $18:3/16:1^{\Delta 3t}$-PG, and levels of PC are decreased. Also, TAG biosynthesis, especially its poly unsaturated FA content correlates with the presence of FAX1 in reproductive tissues. Hence it seems possible that PLIP1, FAP and FAX1 work together to channel plastid synthesized acyl groups through $18:3/16:1^{\Delta 3t}$-PG into PC outside the plastid and ultimately into TAG during seed development.

Movement of de novo synthesized lipid groups through the chloroplast membrane lipid pool has been previously observed in *Chlamydomonas*, in which PGD1 is a lipase specific for newly synthesized 18:1/18:1-MGDG, while 18:3/16:4 MGDG is resistant to its activity (Li et al., 2012). In this case PGD1 expression is induced following N-deprivation and participates in the channeling of acyl groups into TAG biosynthesis under those conditions. Although plants synthesize TAG in vegetative tissues under stress (Moellering et al., 2010), they generally produce bulk TAG in developing embryos. PLIP1 is too distantly related to PGD1 to be an orthologue and *Chlamydomonas* does not contain PC, while *Arabidopsis* lacks 18:3/16:4-MGDG. However, both lipases point towards a common theme, the need for channeling of newly synthesized acyl groups through the chloroplast lipid pool prior to incorporation into extraplastidic TAGs. The specific substrate selectivity of these two lipases also partially explains the existence of unusual molecular species of chloroplast lipids, 18:3/16:4 MGDG in *Chlamydomonas* and $18:3/16:1^{\Delta 3t}$-PG in *Arabidopsis* and most other plants and algae. It seems likely that unusual acyl groups tag specific molecular species for specific purposes. In case of 18:3/16:4 MGDG in *Chlamydomonas* it is tagged as structural thylakoid membrane lipid resistant to PGD1, while in case of $18:3/16:1^{\Delta 3t}$-PG in *Arabidopsis* it is the preferred substrate for PLIP1 leading to 18:3 acyl export, rather than having a specific function related to photosynthetic light capture and conversion as previously assumed. *Chlamydomonas* also contains $18:3/16:1^{\Delta 3t}$-PG and genomes of plants and algae encode many more potential plastid-targeted lipases. Therefore, it is likely that acyl hydrolysis catalyzed by specific plastid lipases and their respective native substrates is a common process in maintaining photosynthetic membrane homeostasis while enabling the exchange and export of acyl groups for the synthesis of extraplastidic lipids or as precursors for retrograde signaling molecules.

Definitions

As used herein, "isolated" means a nucleic acid or polypeptide has been removed from its natural or native cell. Thus, the nucleic acid or polypeptide can be physically isolated from the cell, or the nucleic acid or polypeptide can be present or maintained in another cell where it is not naturally present or synthesized. The isolated nucleic acid or the isolated polypeptide can also be a nucleic acid or protein that is modified but has been introduced into a cell where it is or was naturally present. Thus, a modified isolated nucleic acid or an isolated polypeptide expressed from a modified isolated nucleic acid can be present in a cell along with a wild copy of the (unmodified) natural nucleic acid and along with wild type copies of the (natural) polypeptide.

As used herein, a "native" nucleic acid or polypeptide means a DNA, RNA or amino acid sequence or segment that has not been manipulated in vitro, i.e., has not been isolated, purified, mutated, and/or amplified.

The term "transgenic" when used in reference to a plant or leaf or vegetative tissue or seed for example a "transgenic plant," "transgenic leaf," "transgenic vegetative tissue," "transgenic seed," or a "transgenic host cell" refers to a plant or leaf or tissue or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "transgene" refers to a foreign gene that is placed into an organism or host cell by the process of transfection. The term "foreign nucleic acid" or refers to any nucleic acid (e.g., encoding a promoter or coding region) that is introduced into the genome of an organism or tissue of an organism or a host cell by experimental manipulations, such as those described herein, and may include nucleic acid sequences found in that organism so long as the introduced gene does not reside in the same location, as does the naturally occurring gene.

The term "host cell" refers to any cell capable of replicating and/or transcribing and/or translating a heterologous nucleic acid. Thus, a "host cell" refers to any eukaryotic or prokaryotic cell (e.g., plant cells, algal cells, bacterial cells, yeast cells, *E. coli*, insect cells, etc.), whether located in vitro or in vivo. For example, a host cell may be located in a transgenic plant, or located in a plant part or part of a plant tissue or in cell culture.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the term "plant" is used in its broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. In some instances, the plant part can include vegetative tissues of the plant.

Vegetative tissues or vegetative plant parts do not include plant seeds, and instead include non-seed tissues or parts of a plant. The vegetative tissues can include reproductive tissues of a plant, but not the mature seeds.

The term "seed" refers to a ripened ovule, consisting of the embryo and a casing.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location, or are associated with portions of the chromosome not found in nature (e.g., the heterologous nucleic acids are expressed in tissues where the gene is not normally expressed).

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and of a particular enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter element," "promoter," or "promoter sequence" refer to a DNA sequence that is located at the 5' end of the coding region of a DNA polymer. The location of most promoters known in nature is 5' to the transcribed region. The promoter functions as a switch, activating the expression of a gene. If the gene is activated, it is said to be transcribed, or is participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific.

The term "tissue specific" as it applies to a promoter refers to a promoter that can direct selective expression of a nucleic acid of interest to a specific type of tissue (e.g., vegetative tissues) in the relative absence of expression of the same nucleic acid of interest in a different type of tissue (e.g., seeds). Tissue specificity of a promoter may be evaluated by, for example, operably linking a reporter gene and/or a reporter gene expressing a reporter molecule, to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleic acid of interest in a specific type of cell in the relative absence of expression of the same nucleic acid of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleic acid of interest whose expression is controlled by the promoter. A labeled (e.g., peroxidase conjugated) secondary antibody that is specific for the primary antibody can bind to the sectioned tissue and specific binding detected (e.g., with avidin/biotin) by microscopy.

Promoters may be "constitutive" or "inducible." The term "constitutive" when made in reference to a promoter means that the promoter can direct transcription of an operably linked nucleic acid in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098; herein incorporated by reference), and ubi3 promoters (see e.g., Garbarino and Belknap, Plant Mol. Biol. 24:119-127 (1994); herein incorporated by reference). Such promoters have been used successfully to direct the expression of heterologous nucleic acid sequences in transformed plant tissue.

In contrast, an "inducible" promoter is one that can direct a level of transcription of an operably linked nucleic acid in the presence of a stimulus (e.g., heat shock, chemicals, light, etc.) that is different from the level of transcription of the operably linked nucleic acid in the absence of the stimulus.

The term "vector" refers to nucleic acid molecules that transfer DNA segment(s). Transfer can be into a cell, cell to cell, et cetera. The term "vehicle" is sometimes used interchangeably with "vector." The vector can, for example, be a plasmid. But the vector need not be plasmid.

The following non-limiting Examples illustrate how aspects of the invention have been developed and can be made and used.

Example 1: Materials and Methods

This Example describes some of the materials and methods employed in the development of the invention.

Plant Material and Growth Conditions

Experiments were performed with *Arabidopsis thaliana* ecotype Columbia (Col-0). Seeds of T-DNA insertion lines SALK_102149 (plip1-1) and SALK_147687 (plip1-2) were obtained from the *Arabidopsis* Biological Resource Center, Ohio State University. Lines overexpressing PLIP1 (or PLIP1$^{S422A}$) were generated by subcloning the coding sequence of PLIP1 or PLIP1$^{S422A}$ (see below for their origin) into pEarleyGate 101 (YFP at the C-terminus) (Earley et al., 2006), followed by introducing constructs into Col-O plants by *Agrobacterium tumefaciens*-mediated floral dip (Clough and Bent, 1998). Transformed seeds were initially screened for resistance to Basta, followed by confirmation by RT-PCR. Primers used for genotyping of T-DNA insertion lines or for RT-PCR analysis of overexpression lines are given in Table 1. *Arabidopsis* seeds were vernalized at 4° C. in the dark for two days before being sown on soil, and grown under 100 µE m$^{-2}$s$^{-1}$ in a 16 h light (22° C.) and 8 h dark (20° C.) cycle. Alternatively, sterilized and vernalized seeds were sown onto phytoagar plates containing 1× Murashige and Skoog (MS) growth medium (Murashige and Skoog, 1962) and 1% sucrose under 100 µE m$^{-2}$s$^{-1}$ in the same light/dark cycle at 22° C. (Wang et al., 2016).

Quantitative Real-Time PCR

Total RNA was isolated from leaves of 4-week-old *Arabidopsis* plants grown on soil as previously described (Wang et al., 2016) using an RNeasy Plant Mini kit (Qiagen). Total RNA (600 ng) was used to synthesize complementary DNA using SuperScript III Reverse Transcriptase (Invitrogen). qRT-PCR was performed using the SYBR Green PCR Core Reagents mix (Life Technologies) based on the manufacturer's instructions. The $2^{-\Delta\Delta Ct}$ calculation was used to determine the relative mRNA levels. Table 1 lists the primers used. Reference primers were as previously described (Robinson and Bolhuis, 2001).

TABLE 1

Primer sequences

| Primer Name | Sequence | SEQ ID NO: |
|---|---|---|
| PEG_PLIP1 F | CACCATGGCGTTTAATACGGCTATG | 35 |
| PEG101_PLIP1 R | GACACGTGTCATGATCTCCTCGG | 36 |
| PEG104_PLIP1 R | TTAGACACGTGTCATGATCTCCTCG | 37 |
| BamHI_PLIP1 F | TCGGATCCATGGCGTTTAATACGGCTATG | 38 |
| PLIP1_XhoI R | GACTCGAGTTAGACACGTGTCATGATCTCC | 39 |
| pET41a_His del F | ATGTATATCTCCTTCTAAAGTAAACAAA | 40 |
| pET41a_His del R | ATGGCGTTTAATACGGCTATG | 41 |
| PLIP1_TP_Q5 F | GCCGAGGAGATCATGACACGTGTC | 42 |
| PLIP1_TP_Q5 R | ACGAACAGACACAGCAAGAATGCG | 43 |
| PLIP1_S422A F | AGTCTCTCATTAATAGTGAATTTGATGCTTATC | 44 |
| PLIP1_S422A R | GCCTCCAAGAGCATGACCCGTG | 45 |
| PLIP1_D483A F | GAGCCTTTTCGTGTAATTATCCTGACCA | 46 |
| PLIP1_D483A R | GTGGGACGATAGCTCTATGCATCA | 47 |
| PLIP1_qPCR F | AGTTCTATAATCCCAAGTCCGA | 48 |
| PLIP1_qPCR R | CTCCTTATCTCAAGCAGCCT | 49 |
| TIP-41_like qPCR F | GTGAAAACTGTTGGAGAGAAGCAA | 50 |
| TIP-41_like qPCR R | TCAACTGGATACCCTTTCGCA | 51 |
| PDF2 qPCR F | TAACGTGGCCAAAATGATGC | 52 |
| PDF2 qPCR R | GTTCTCCACAACCGCTTGGT | 53 |
| LBb1.3 | ATTTTGCCGATTTCGGAAC | 54 |

TABLE 1-continued

Primer sequences

| Primer Name | Sequence | SEQ ID NO: |
|---|---|---|
| plip1-1 LP | AGATTCTAGCGGAGCTTGGTC | 55 |
| plip1-1 RP | GCCTCTTCAAACCAAATCTCC | 56 |
| plip1-2 LP | TTATTACCGGAGCGACAACAC | 57 |
| plip1-2 RP | TCCAATAACGGTTAAGCAACG | 58 |
| fad3-2 genotype F | GTCACGATGAGAAGTTGCCTTGG | 59 |
| fad3-2 genotype R | CAATGTCGTGATGAATGTTGTTAAAGAAT | 60 |

Confocal Laser Scanning Microscopy

Imaging of YFP fusions was performed on leaves of 4-week-old *Arabidopsis* grown on soil using an Olympus FluoView 1000 confocal laser scanning microscope (Olympus) with excitation at 514 nm and emissions at 600 nm. Chlorophyll autofluorescence was visualized using excitation at 633 nm and emission at 700 nm. Images were merged and pseudocolored using Olympus FluoView 1000 confocal microscope software (Olympus).

Protein Extraction and Immunoblot Analysis

Intact chloroplasts were isolated from 4-week-old *Arabidopsis* plants grown on MS medium essentially according to (Aronsson and Jarvis, 2002; Roston et al., 2011), followed by sub-fractionation into stroma and thylakoid according to (Keegstra and Yousif, 1986; Roston et al., 2012) with minor modifications. In brief, isolated intact chloroplasts were pelleted and ruptured by resuspension in hypertonic solution (0.6 M sucrose in TE buffer) and the suspension was homogenized with a Dounce tissue homogenizer. After incubation on ice for 10 min, bulk thylakoid fractions were harvested by three 1500×g 5-min centrifugations at 4° C. Supernatants were subjected to another 100,000×g 2-h centrifugation at 4° C. to remove envelope membranes, and the final supernatants were harvested as the stroma fraction. Total protein from each fraction was extracted using a Plant Total Protein Extraction Kit (Sigma) according to the manufacturer's instructions, and protein was quantified using the Bio-Rad Bradford assay. Appropriate amounts of extracted organellar or total cellular protein were separated by SDS-PAGE (4-20% gradient, Bio-Rad), transferred to polyvinylidene fluoride membranes (Bio-Rad) and subjected to immunoblot analysis using primary antisera in 1:1000 to 1:5000 dilutions in TBST buffer (137 mM NaCl; 20 mM Tris base pH 7.5; 0.5% Tween-20). Secondary anti-rabbit or anti-chicken IgG antibodies were diluted 1:10,000. Positive immunoreactions were visualized using the Horseradish Peroxidase reaction with SuperSignal West Dura Extended Duration Substrate (Thermo Scientific), and the chemiluminescent signal was captured using the ChemiDoc™ imaging system (Bio-Rad) according to the manufacturer's instructions.

Recombinant Protein and Antiserum Production

The PLIP1 sequence was amplified from *Arabidopsis* wild-type cDNA (see above under RT-PCR procedure) and inserted into pGEM-T-EASY plasmid (Promega). It was then subcloned into the pET41a plasmid through BamHI and XhoI restriction sites. The PLIP1$^{S422A}$ point mutation construct was generated with a Q5 Site-Directed Mutagenesis Kit (New England Biolabs). Constructs were confirmed by sequencing. Final pET41a-PLIP1 and pET41a-PLIP1$^{S422A}$ constructs were transformed into BL21 (DE3) *E. coli* strains for protein production. Cultures grown in LB medium (containing 0.1% glucose) were inoculated with fresh *E. coli* colonies and grown to log phase ($OD_{260}$ 0.8) at 37° C. Protein production was then induced by adding isopropyl-3-β-thiogalactopyranoside (IPTG) to the final concentration of 0.2 mM, and the culture was transferred to 14° C. Cells were harvested after 3 h of induction. Cultures were harvested and sonicated to lyse cells. Supernatant was collected after centrifugation at 10,000×g for 30 min, and subjected to another 1-h centrifugation at 100,000×g to remove the majority of membrane bound PLIP1. The finally harvested supernatant was used to extract and purify PLIP1 recombinant proteins using a Ni-NTA column as described (Lu and Benning, 2009), except with a modified washing buffer (50 mM Tris HCl, pH 7.5; 600 mM NaCl; 40 mM imidazole). Purified protein was concentrated using an Amicon Ultra-15 Centrifugal Filter (Millipore, UFC901024) and recovered with 1×PBS buffer. The protein was quantified using the Bio-Rad Bradford assay, before the protein was aliquoted and stored at −20° C. with 30% glycerol.

Recombinant PLIP1$^{422}$ was produced in *E. coli* and purified with a Ni-NTA column as described above. Purified protein was separated by SDS-PAGE and the corresponding band of PLIP1$^{42}$ was isolated. Protein was recovered by immersing gel bands into 1×PBS buffer at 4° C. overnight with gentle agitation. Recovered proteins were concentrated with an Amicon Ultra-15 Centrifugal Filter to a final purity above 98%. Antisera were raised in rabbits by Cocalico Biologicals, Inc. using their standard protocol.

Chloroplast Import Assay

The N-terminal 6×His tag and TEV cleavage site of pET41a-PLIP1 were removed using a Q5 Site-Directed Mutagenesis Kit (New England Biolabs) and the construct was confirmed by sequencing prior to use for import assays. The FtsH8 gene was used as control. Isolation of pea chloroplasts, import assays and post-import trypsin treatment were done as previously described (Xu et al., 2005).

PLIP1 Lipase Assay

Commercial lipid substrates were purchased from Avanti Polar Lipids Inc. For each PLIP1 lipase reaction, 60 μg lipids were used. The organic solvent was removed under an $N_2$ stream, and the lipids were resuspended in 300 μL reaction buffer (0.1 M PBS, pH 7.4; 4.2 mM Anzergent 3-12 (Anatrace)) and dispersed by sonication for 3×10 s on ice (Misonix; Sonicator 3000 with microprobe; power setting 1.5). Then, 0.5 μg protein in 20 μL 1×PBS with 30% glycerol was added to each reaction. The mixture was sonicated again for 10 s with the same parameters mentioned above and incubated at ambient temperature (~22° C.) for 1.5 h or as indicated for time courses. The reaction was stopped by lipid extraction, followed by lipid analysis with TLC and gas chromatography as described below.

To prepare tobacco phosphatidylglycerol (PG) substrates, total lipids were isolated from 4-week-old plant leaves and resolved by polar thin layer chromatography (TLC). The phosphatidylglycerol bands were isolated and lipids were recovered from silica powder by extraction with chloroform-methanol (1:1 by volume).

Lipid Analysis

Lipid extraction, TLC of polar and neutral lipids, transesterification, and gas chromatography were done as described in (Wang and Benning, 2011). Polar lipids were analyzed on activated ammonium sulfate-impregnated silica gel TLC plates (TLC Silica gel 60; EMD Chemical, Germany) using a solvent system consisting of acetone, toluene and water (91:30:7-7.5 by volume). The water amount adjusted according to ambient humidity (in general, 7 for summer; 7.5 for winter). This solvent system was also used for separation of lyso-lipids derived from monogalactosyldiacylglycerol, (MGDG) and phosphatidylglycerol during in vitro lipase assays. For triacylglycerol (TAG) quantification, lipids were resolved by TLC on DC-Fertigplatten SIL G-2 (MACHEREY-NAGEL, Germany) using a solvent system consisting of petroleum ether, ether and acetic acid (80:20:1 by volume). For total fatty acid analysis of dry seeds, 3 h transesterification was conducted directly on a number of seeds as specified. Lipids were visualized on TLC plates by brief exposure to iodine vapor. To separate lyso-lipids from phosphatidylcholine (PC), phosphatidylethanolamine (PE), or phosphatidylinositol (PI), a solvent system consisting of chloroform, methanol, glacial acetic acid and water (65:35:8:5 by volume) was used. To separate lyso-PS from PS, the running solvent consisted of chloroform, methanol and ammonium hydroxide (28-30% $NH_3$ in water) (65:25:5 by volume). To separate lyso-lipids from digalactosyldiacylglycerol, (DGDG) and sulfoquinovosyldiacylglycerol (SQDG) the running solvent contained chloroform, methanol, glacial acetic acid and water (85:20:10:4 by volume).

Pulse-Chase Labeling

For leaf labeling experiments, detached leaves from 4-week-old soil-grown plants were incubated in non-radioactive medium (25 mM MES-KOH, pH 5.7; 0.01% Triton X-100) under light (~40 $\mu E\ m^{-2}s^{-1}$) at ambient temperature for 1 h. Radiolabeling was initiated by adding sodium [$^{14}C$]-acetate (specific activity 100 mCi/mmol in ethanol; American Radiolabeled Chemicals, Inc.) to the medium to provide 1 µCi/mL followed by a 1-hour incubation with gentle agitation. The leaves were then washed twice in non-radioactive medium prior to incubation in non-radioactive medium for another 48 hours. At various time points after application of the label, samples were harvested and the metabolism was halted by immediate lipid extraction. Lipids were extracted and separated by TLC as described above, and radioactivity in each lipid fraction was analyzed using a scintillation counter (MicroBeta Trilux, Perkin Elmer) with 3 ml of scintillator solution (4a20, Research Products International Corporation) for 1 min per sample, or using phosphorimaging (FBCS 810, Fisher Biotech) with quantification by Quantity One (V 4.6.6).

Embryo labeling experiments were done as described (Bates et al., 2012). Briefly, the newly opened flowers of 4-week-old soil-grown plants were tagged, and nine days later, siliques were harvested for embryo isolation. For each time point, a 100 µL volume of embryos was collected from approximately 50 siliques, and pre-incubated in non-radioactive buffer (5 mM MES, pH 5.8; 0.5% sucrose; 0.5×MS) under light (~40 $\mu E\ m^{-2}s^{-1}$) for 20 min with gentle agitation at room temperature. Labeling was initiated by removing the old medium and replacing it with the same medium containing 5 µCi sodium [$^{14}C$] acetate. Pulse labeling lasted for one hour, followed by washing and replacing with non-radioactive medium to start the chase. Samples were collected at indicated time points, and the reaction was quenched by immediate lipid extraction as described above.

Observation of Embryo Morphology

Siliques were harvested nine days after flowering and subsequently cleared with a clearing solution (chloral hydrate:glycerol:water=8:2:1) according to (Herr Jr, 1993). Developing embryos were dissected from siliques after clearance and observed under a Nikon C2 microscope.

Accession Number

Sequences can be found in the *Arabidopsis* TAIR database (see website at www.arabidopsis.org/) under the following accession numbers: At3g61680 for PLIP1, At2g29980 for FAD3, At4g27030 for FAD4, At5g42020 for BIP2, At1g06430 for FTSH8.

The At3g61680 sequence for the PLIP1 protein is shown below as SEQ ID NO:1.

```
  1 MAFNTAMAST SPAAANDVLR EHIGLRRSLS GQDLVLKGGG IRRSSSDNHL

51 CCRSGNNNNR ILAVSVRPGM KTSRSVGVFS FQISSSIIPS PIKTLLFETD

101 TSQDEQESDE IEIETEPNLD GAKKANWVER LLEIRRQWKR EQKTESGNSD

151 VAEESVDVTC GCEEEEGCIA NYGSVNGDWG RESFSRLLVK VSWSEAKKLS

201 QLAYLCNLAY TIPEIKGEDL RRNYGLKFVT SSLEKKAKAA ILREKLEQDP

251 THVPVITSPD LESEKQSQRS ASSSASAYKI AASAASYIHS CKEYDLSEPI

301 YKSAAAAQAA ASTMTAVVAA GEEEKLEAAR ELQSLQSSPC EWFVCDDPNT

351 YTRCFVIQGS DSLASWKANL FFEPTKFEDT DVLVHRGIYE AAKGIYEQFL

401 PEITEHLSRH GDRAKFQFTG HSLGGSLSLI VNLMLISRGL VSSEAMKSVV

451 TFGSPFVFCG GEKILAELGL DESHVHCVMM HRDIVPRAFS CNYPDHVALV

501 LKRLNGSFRT HPCLNKNKLL YSPMGKVYIL QPSESVSPTH PWLPPGNALY
```

-continued

```
551 ILENSNEGYS PTALRAFLNR PHPLETLSQR AAYGSEGSVL RDHDSKNYVK

601 AVNGVLRQHT KLIVRKARIQ RRSVWPVLTS AGRGLNESLT TAEEIMTRV
```

The At2g29980 sequence for the FAD3 protein is shown below as SEQ ID NO:61.

```
  1 MVVAMDQRTN VNGDPGAGDR KKEERFDPSA QPPFKIGDIR AAIPKHCWVK

51 SPLRSMSYVV RDIIAVAALA IAAVYVDSWF LWPLYWAAQG TLFWAIFVLG

101 HDCGHGSFSD IPLLNSVVGH ILHSFILVPY HGWRISHRTH HQNHGHVEND

151 ESWVPLPERV YKKLPHSTRM LRYTVPLPML AYPLYLCYRS PGKEGSHFNP

201 YSSLFAPSER KLIATSTTCW SIMFVSLIAL SFVFGPLAVL KVYGVPYIIF

251 VMWLDAVTYL HHHGHDEKLP WYRGKEWSYL RGGLTTIDRD YGIFNNIHHD

301 IGTHVIHHLF PQIPHYHLVD ATKAAKHVLG RYYREPKTSG AIPIHLVESL

351 VASIKKDHYV SDTGDIVFYE TDPDLYVYAS DKSKIN
```

The At4g27030 sequence for the FAD4 protein is shown below as SEQ ID NO:28.

```
  1 MAVSLPTKYP LRPITNIPKS HRPSLLRVRV TCSVTTTKPQ PNREKLLVEQ

51 RTVNLPLSND QSLQSTKPRP NREKLVVEQR LASPPLSNDP TLKSTWTHRL

101 WVAAGCTTLF VSLAKSVIGG FDSHLCLEPA LAGYAGYILA DLGSGVYHWA

151 IDNYGDESTP VVGTQIEAFQ GHHKWPWTIT RRQFANNLHA LAQVITFTVL

201 PLDLAFNDPV FHGFVCTFAF CILFSQQFHA WAHGTKSKLP PLVVALQDMG

251 LLVSRRQHAE HHRAPYNNNY CIVSGAWNNV LDESKVFEAL EMVFYFQLGV

301 RPRSWSEPNS DWIEETEISN NQA
```

The At5g42020 sequence for the BIP2 protein is shown below as SEQ ID NO:62.

```
  1 MARSFGANST VVLAIIFFGC LFAFSTAKEE ATKLGSVIGI DLGTTYSCVG

51 VYKNGHVEII ANDQGNRITP SWVGFTDSER LIGEAAKNQA AVNPERTVFD

101 VKRLIGRKFE DKEVQKDRKL VPYQIVNKDG KPYIQVKIKD GETKVFSPEE

151 ISAMILTKMK ETAEAYLGKK IKDAVVTVPA YFNDAQRQAT KDAGVIAGLN

201 VARIINEPTA AAIAYGLDKK GGEKNILVFD LGGGTFDVSV LTIDNGVFEV

251 LSTNGDTHLG GEDFDHRIME YFIKLIKKKH QKDISKDNKA LGKLRRECER

301 AKRALSSQHQ VRVEIESLFD GVDLSEPLTR ARFEELNNDL FRKTMGPVKK

351 AMDDAGLQKS QIDEIVLVGG STRIPKVQQL LKDFFEGKEP NKGVNPDEAV

401 AYGAAVQGGI LSGEGGDETK DILLLDVAPL TLGIETVGGV MTKLIPRNTV

451 IPTKKSQVFT TYQDQQTTVS IQVFEGERSL TKDCRLLGKF DLTGVPPAPR

501 GTPQIEVTFE VDANGILNVK AEDKASGKSE KITITNEKGR LSQEEIDRMV

551 KEAEEFAEED KKVKEKIDAR NALETYVYNM KNQVSDKDKL ADKLEGDEKE

601 KIEAATKEAL EWLDENQNSE KEEYDEKLKE VEAVCNPIIT AVYQRSGGAP

651 GAGGESSTEE EDESHDEL
```

The At1g06430 sequence for the FTSH8 protein is shown below as SEQ ID NO:63.

```
  1 MAASSACLLG NGLSVYTTKQ RFQKLGLDRT SKVTVVKASL DEKKHEGRRG

51 FFKLLLGNAA AGVGLLASGN ANADEQGQGV SSSRMSYSRF LEYLDKGRVE

101 KVDLYENGTI AIVEAVSPEL GNRIQRVRVQ LPGLSQELLQ KLRAKNIDFA

151 AHNAQEDQGS PILNLIGNLA FPVILIGGLF LLSRRSSGGM GGPGGPGFPL

201 QIGQSKAKFQ MEPNTGVTFD DVAGVDEAKQ DFMEVVEFLK KPERFTAVGA

251 RIPKGVLLVG PPGTGKTLLA KAIAGEAGVP FFSISGSEFV EMFVGVGASR

301 VRDLFKKAKE NAPCIVFVDE IDAVGRQRGT GIGGGNDERE QTLNQLLTEM

351 DGFEGNTGVI VVAATNRADI LDSALLRPGR FDRQVSVDVP DVKGRTDILK

401 VHSGNKKFES GVSLEVIAMR TPGFSGADLA NLLNEAAILA GRRGKTAISS

451 KEIDDSIDRI VAGMEGTVMT DGKSKSLVAY HEVGHAICGT LTPGHDAVQK

501 VTLIPRGQAR GLTWFIPSDD PTLISKQQLF ARIVGGLGGR AAEEVIFGES

551 EVTTGAVSDL QQITGLAKQM VTTFGMSEIG PWSLMDSSEQ SDVIMRMMAR

601 NSMSEKLAND IDTAVKTLSD KAYEIALSQI RNNREAMDKI VEILLEKETM

651 SGDEFRAILS EFTEIPPENR VASSTSTSTP TPASV
```

Example 2: PLIP1 is a Chloroplast Thylakoid Associated Protein

The *Arabidopsis* genome encodes approximately 300 putative lipases (Li-Beisson et al., 2013; Troncoso-Ponce et al., 2013; Kelly and Feussner, 2016), among which 46 were included in the Chloroplast 2010 Project, aimed at assigning functions to nearly all plastid localized proteins (Lu et al., 2008; Ajjawi et al., 2010). The inventors hypothesized that some of these putative chloroplast lipases may play roles in the maintenance of photosynthetic membranes and perhaps have specialized roles in tissues with high demands on lipid metabolism such as developing seeds that accumulate TAG.

One of the predicted chloroplast lipase genes, At3g61680, encodes a protein with a conserved Lipase 3 domain and a strongly predicted transit peptide, was subsequently named PLIP1. With its Lipase 3 domain, this *Arabidopsis* protein has similarities to a bona fide lipase of *Chlamydomonas*, PGD1, involved in the turnover of chloroplast MGDG, leading to the export of acyl groups and their incorporation into TAG following nutrient deprivation (Li et al., 2012), although the two proteins do not share sequence similarity outside the Lipase 3 domain and are not orthologues.

To experimentally verify the subcellular location of PLIP1, the PLIP1 coding sequence derived from an *Arabidopsis* wild-type (Col-0) cDNA was spliced at its 3'-end (creating a C-terminal fusion) to the open reading frame of yellow fluorescent protein (YFP). When the PLIP1-YFP construct was stably expressed in wild type under the control of the cauliflower mosaic virus (CaMV) 35S promoter, the YFP and chlorophyll signals overlapped (FIG. 1A). Although transgenic lines used in this experiment had constitutive expression of PLIP1-YFP, only about 10 to 15% of mesophyll chloroplasts showed YFP signals.

To corroborate the suborganellar location of PLIP1, intact chloroplasts were isolated from 4-week-old wild-type seedlings, and further fractionated into thylakoid membranes and stroma. Immunoblot analysis of PLIP1 showed increasing signal intensity from whole plant tissue to intact chloroplasts and thylakoids, consistent with an association of PLIP1 with the thylakoids (FIG. 1B). Fractionation quality was controlled for by including marker proteins for each fraction. The thylakoid protein Light Harvesting Complex b1 (LHCb1) showed a similar intensity pattern as PLIP1. To exclude contamination with endoplasmic reticulum (ER) associated proteins, the ER specific marker BiP2 was also included (FIG. 1B). The fractionation of the stroma-specific rubisco large subunit and the thylakoid-specific light-harvesting chlorophyll a/b-binding protein (LHCP) are visible on a Coomassie Brilliant Blue-stained SDS-PAGE gel (FIG. 1C).

The PLIP1 gene is predicted to encode a 71,735-D protein for which a molecular or biochemical function had not been experimentally determined. Based on the ARAMEMNON database, PLIP1 is not predicted to contain any transmembrane domains (Schwacke et al., 2003). These data indicate that PLIP1 is a peripheral thylakoid membrane protein. To learn more about its suborganellar location and processing enroute, the PLIP1 cDNA was translated in vitro in the presence of labeled methionine. During the import of the translation product into isolated pea chloroplasts, the PLIP1 precursor was processed into a smaller intermediate protein which was present in both stroma and chloroplast membrane fractions. In addition, the trypsin resistance of PLIP1 indicated that it is inside the chloroplast (FIG. 1D). Interestingly, the intermediate PLIP1 form was further processed into a smaller mature protein, which mainly was associated with the stroma fraction. As a control for proper fractionation and import, thylakoid lumen localized FtsH8 (Rodrigues et al., 2011) was processed and imported into the thylakoids with a pattern that is different from PLIP1, suggesting that PLIP1 is probably not imported into the thylakoid lumen, but attaches to the outside leaflet of thylakoid membranes and can be released into the stroma with additional processing. Summing all the localization data up, PLIP1 is likely a thylakoid membrane associated protein.

Example 3: PLIP1 is a Phospholipase $A_1$ with a Preference for Unsaturated Acyl Groups PLIP1 is annotated as a TAG lipase in *Arabidopsis* (see TAIR website at arabidopsis.org). An in vitro lipase assay was developed to verify PLIP1 activity and determine its enzymatic properties. However, expression of the recombinant PLIP1 purified from *E. coli* that expressed the recombinant 6xHis-PLIP1 construct was very low as detected by immunoblotting against the His tag. Analysis of transgenic *E. coli*-derived lipid extracts by thin-layer chromatography (TLC) showed that, when PLIP1 was expressed, PG and phosphatidylethanolamine (PE), the two major polar lipids of *E. coli*, were degraded leading to the accumulation of free FAs (FIG. 1E). This observation indicated that PLIP1 is a lipase that releases acyl groups from PG and PE.

Lipases belong to a group of serine esterases with a lipase signature motif, an Asp-His-Ser triad, with some exceptions having only a Ser-Asp dyad. In all cases Ser serves as the active site residue participating in the reaction mechanism (Brady et al., 1990; Winkler et al., 1990; Richmond and Smith, 2011; Kelly and Feussner, 2016). Alignment of the PLIP1 protein sequence with those of classic lipases using NCBI's conserved domain database (Marchler-Bauer et al., 2015) identified two potential catalytic residues, $Asp^{483}$ and $Ser^{422}$. Replacing these two residues with Ala, respectively, abolished PLIP1 lipase activity, when the respective mutant proteins were abundantly produced in *E. coli*, as PG and PE were not degraded (FIG. 1F). Taken together, these data indicate that PLIP1 is a lipase with a catalytic dyad with $Ser^{22}$ as the catalytic residue. Taking advantage of the enhanced production of nonfunctional $PLIP1^{S422A}$ in *E. coli* as compared to the wild-type enzyme, the mutant protein was purified and an antibody was raised in rabbits to specifically detect PLIP1.

Figure 2A:
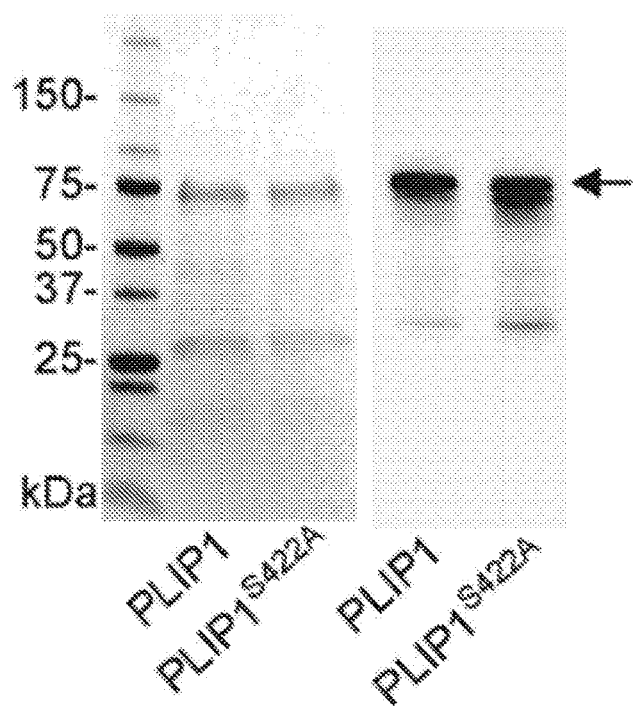
Figure 2B:
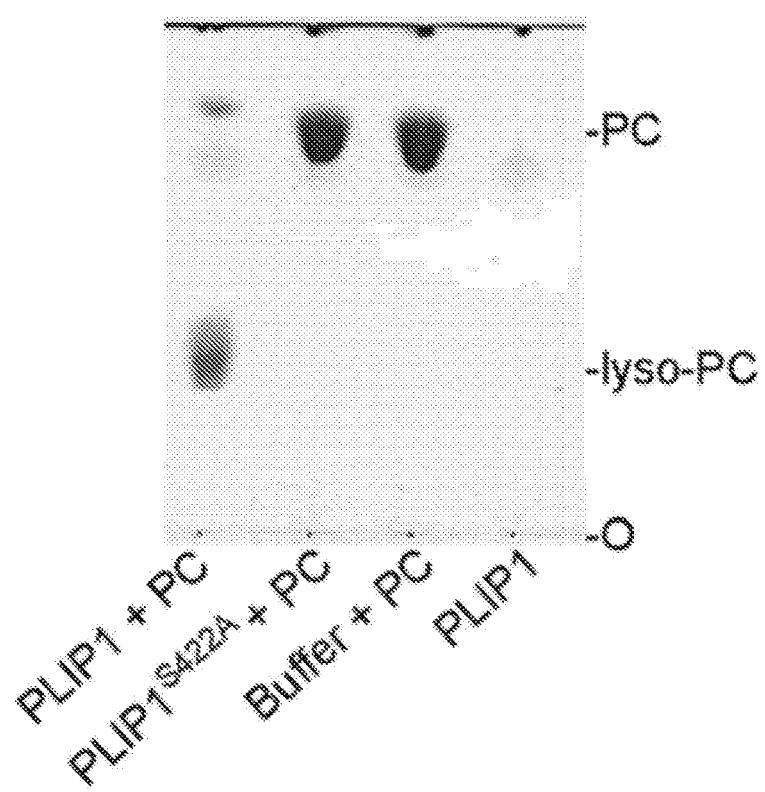

To develop an in vitro lipase assay, recombinant PLIP1 and $PLIP1^{S422A}$ were produced in *E. coli*, and then were affinity-purified from the soluble fraction (FIG. 2A). Anzergent 3-12 was chosen as the solubilizing detergent from a series of other reagents, because of its high compatibility with PLIP1 enzyme activity and because it was not co-chromatographing with native plant membrane lipids during subsequent TLC analysis. In the final optimized system, in vitro lipase activity of PLIP1 was observed on a wide range of substrates (FIG. 2G-2H). As an example, which is shown in FIG. 2B, phosphatidylcholine (PC) was provided to PLIP1 and $PLIP1^{S422A}$. At the end of the reaction, lipids were extracted and separated by TLC. Lipase activity based on the production of lyso-PC was only observed when PLIP1 was present, but not when the $PLIP1^{S422A}$ was present (FIG. 2B).

To survey PLIP1 substrate preference in vitro, most plant glycerolipids were offered to PLIP1, including galactoglycerolipids, phospholipids, as well as TAG (FIG. 2H). High enzyme activity was detected for all tested phospholipids and MGDG. Given the plastid location of PLIP1, possible native substrates were limited to PG and MGDG. Low activities detected for SQDG, DGDG and TAG indicated that these are not likely substrates of PLIP1 (FIG. 2H). Based on these results, despite its conserved Lipase 3 domain, PLIP1 is apparently not a TAG lipase.

PLIP1 in vitro activity with PC and other glycerolipids as substrates always resulted in lyso-lipid products, indicating that PLIP1 can only hydrolyze one of the two acyl-glyceryl ester bonds in glycerolipids. To investigate which glyceryl position PLIP1 prefers, two PCs with reversed acyl compositions were offered to PLIP1. At the end of the reaction, lipids were extracted, lyso-PC was isolated by TLC, and FA methyl esters derived from the lyso-lipid were analyzed by liquid-gas chromatography.

Figure 2C:
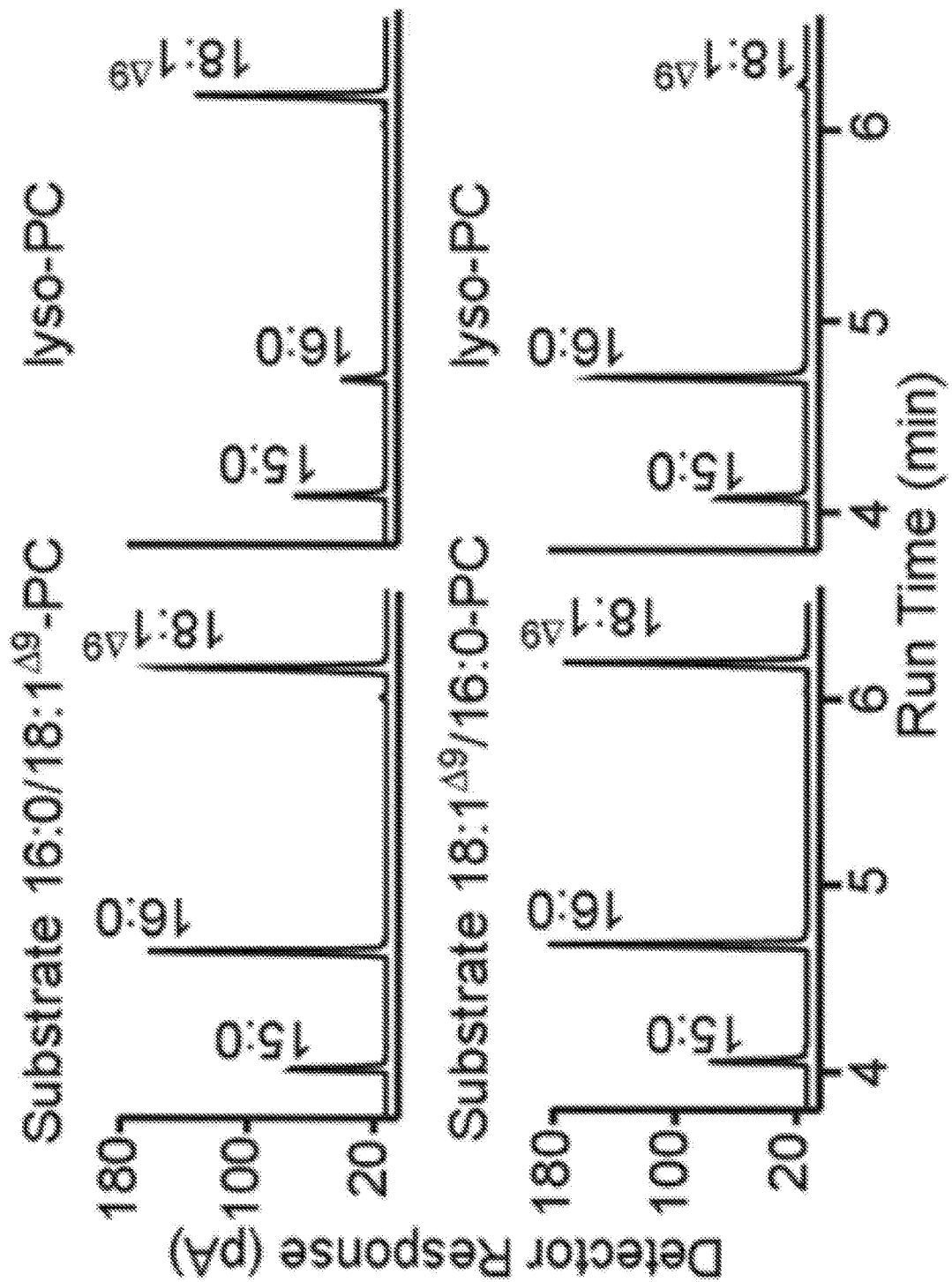
Figure 2E:
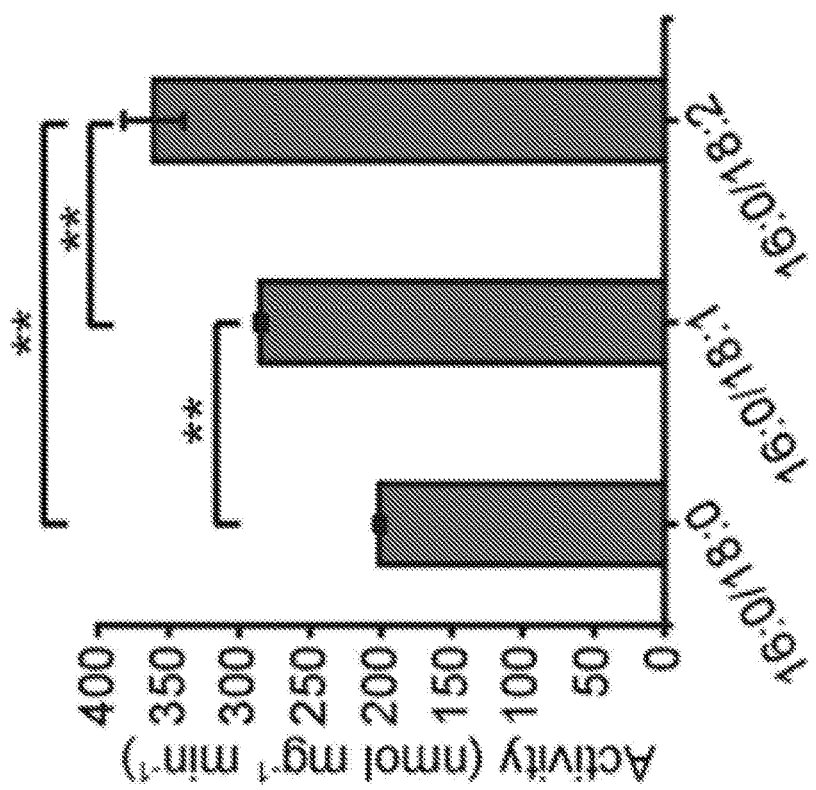
Figure 2D:
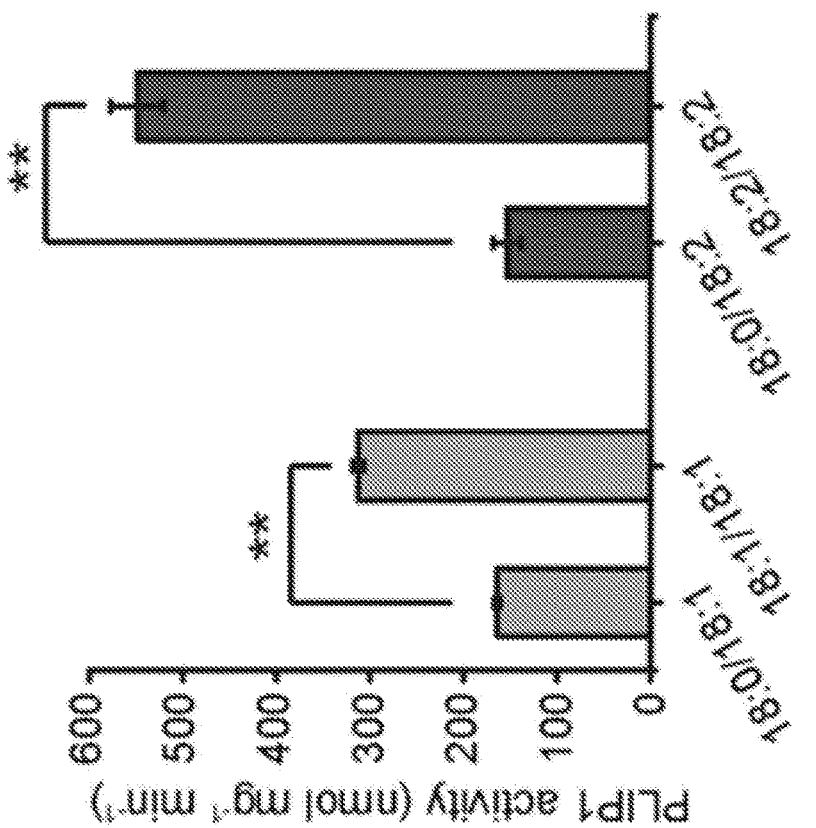

FIG. 2C shows that for PC with a composition of $18:1^{\Delta 9}$/16:0 (sn-1/sn-2), $18:1^{\Delta 9}$ was selectively cleaved and 16:0 was retained in the lyso-product. The result was reversed with PC containing $16:0/18:1^{\Delta 9}$ because the lyso-product contained $18:1^{\Delta 9}$. Therefore, PLIP1 is a lipase that prefers the sn-1 glyceryl position of the respective glycerolipid.

To determine a possible acyl group preference of PLIP1 at the sn-1 glyceryl position, PLIP1 was offered different combinations of pure PC molecules carrying the same acyl groups at the sn-2, but acyl groups with different degree of saturation levels at the sn-1 position (FIG. 2D). Comparing 18.0/18:1 with 18:1/18:1, PLIP1 enzyme activity was approximately twice as high for 18:1/18:1-PC. When comparing 18:0/18:2 with 18:2/18:2, PLIP1 activity was nearly four times elevated for 18:2/18:2-PC. Therefore, PLIP1 is a phospholipase $A_1$ with a preference for more unsaturated acyl groups.

Example 4: $18:3/16:1^{\Delta 3t}$-PG is the Native Substrate of PLIP1

The in vitro assays in combination with its established chloroplast location narrowed down possible native PLIP1 substrates to MGDG and PG (FIG. 2H). However, given the complexity of native plant acyl compositions, this limited survey based on an in vitro lipase assay alone could only provide a first approximation of the likely PLIP1-preferred substrate in vivo. To assess PLIP1 activity in its native biological context, *Arabidopsis* transgenic lines were prepared and used for PLIP1 localization as described in previous Examples.

In total, 30 independent PLIP1-YFP (PLIP1-OX) and 14 $PLIP1^{S422A}$-YFP ($PLIP1^{S422A}$-OX) overexpression *Arabidopsis* transgenic lines were generated and three PLIP1-OX *Arabidopsis* transgenic lines were selected as representatives. As shown in FIG. 3A, the PLIP1-OX lines had smaller rosettes and fewer leaves, which were slightly pale yellow, whereas $PLIP1^{S422A}$-OX plants were indistinguishable from wild-type and empty vector control plants.

On a fresh weight basis, the total leaf acyl group content of the smaller PLIP1-OX plants was not reduced (Table 2).

TABLE 2

Leaf acyl group content in different genotypes

| Genotypes | Acyl Groups (µg/mg FW) |
|---|---|
| Col-0 | 3.48 ± 0.067 |
| plip1-1 | 3.51 ± 0.076 |
| plip1-2 | 3.51 ± 0.063 |
| EV control | 3.55 ± 0.055 |
| $PLIP1^{S422A}$-OX1 | 3.53 ± 0.055 |
| $PLIP1^{S422A}$-OX2 | 3.59 ± 0.049 |
| PLIP1-OX1 | 3.56 ± 0.062 |
| PLIP1-OX2 | 3.54 ± 0.063 |
| PLIP1-OX3 | 3.56 ± 0.067 |

Acyl group contents are determined by the measurement of total leaf fatty acid methyl esters. Plants were grown on soil for 4 weeks. Four independent samples were averaged and the SD is indicated. FW, fresh weight.

A comparison of the relative abundance of polar lipids and the acyl group composition of individual polar lipids of empty vector control plants and two PLIP1-OX lines is shown in FIG. 3. In PLIP1-OX lines, lipids associated with chloroplasts (MGDG, PG and DGDG) decreased, while lipids mostly associated with the ER (PC, PE and PI) increased, indicating a decreased ratio of plastid-to-extraplastidic membranes in PLIP1-OX lines. Acyl group analysis of individual membrane lipids showed the greatest changes for PG (FIG. 3B). Specifically, the ratio of 16:0 to $16:1^{\Delta 3t}$ was increased in PLIP1-OX lines. For 18-carbon acyl groups, which are primarily present at the sn-1 position of plastid PG, polyunsaturated 18:3 decreased with a con-current increase in relative abundance of 18:1 and 18:2. Based on these changes in the molecular composition of PG, 18:3/16:1P'-PG is a preferred substrate of PLIP1 in its native environment.

MGDG, the most abundant lipid in chloroplasts, also showed a subtly decreased ratio of 16:3 to 18:3 in PLIP1-OX lines. For ER lipids, a decrease in 18:2 and an increase in 18:1 was observed for PC (FIG. 3C), as well as for PE and PI. PLIP1 is located in the chloroplast and is spatially separated from ER lipids. Observation of the ER lipid alteration shown, for example in FIG. 3C, indicated that turnover of chloroplast lipids can affect the synthesis of ER lipids (assuming that lipid precursors are transported from the chloroplast to ER). The other two photosynthetic membrane lipids, DGDG and SQDG showed very minor changes in their molecular compositions in PLIP1-OX lines, which was consistent with the low activity of PLIP1 on DGDG and SQDG in vitro (FIG. 2G-2H).

Example 5: Overexpression of PLIP1 Accelerates Recycling of 18:3/16:1$^{\Delta 3t}$-PG Acyls Groups and their Transfer to PC The analysis of PLIP1-OX lines described above represents the lipid composition at steady-state. However, lipid metabolism is a dynamic process, and pulse-chase labeling is an effective way of probing the dynamics of lipid metabolism and movement of acyl groups through different lipid pools and between organelles (Xu et al., 2008; Li et al., 2012). Therefore, pulse-chase labeling was employed of membrane lipids using [$^{14}$C]-acetate, which can be readily converted to acyl groups in plastids by the FA synthase complex.

Figure 3D:
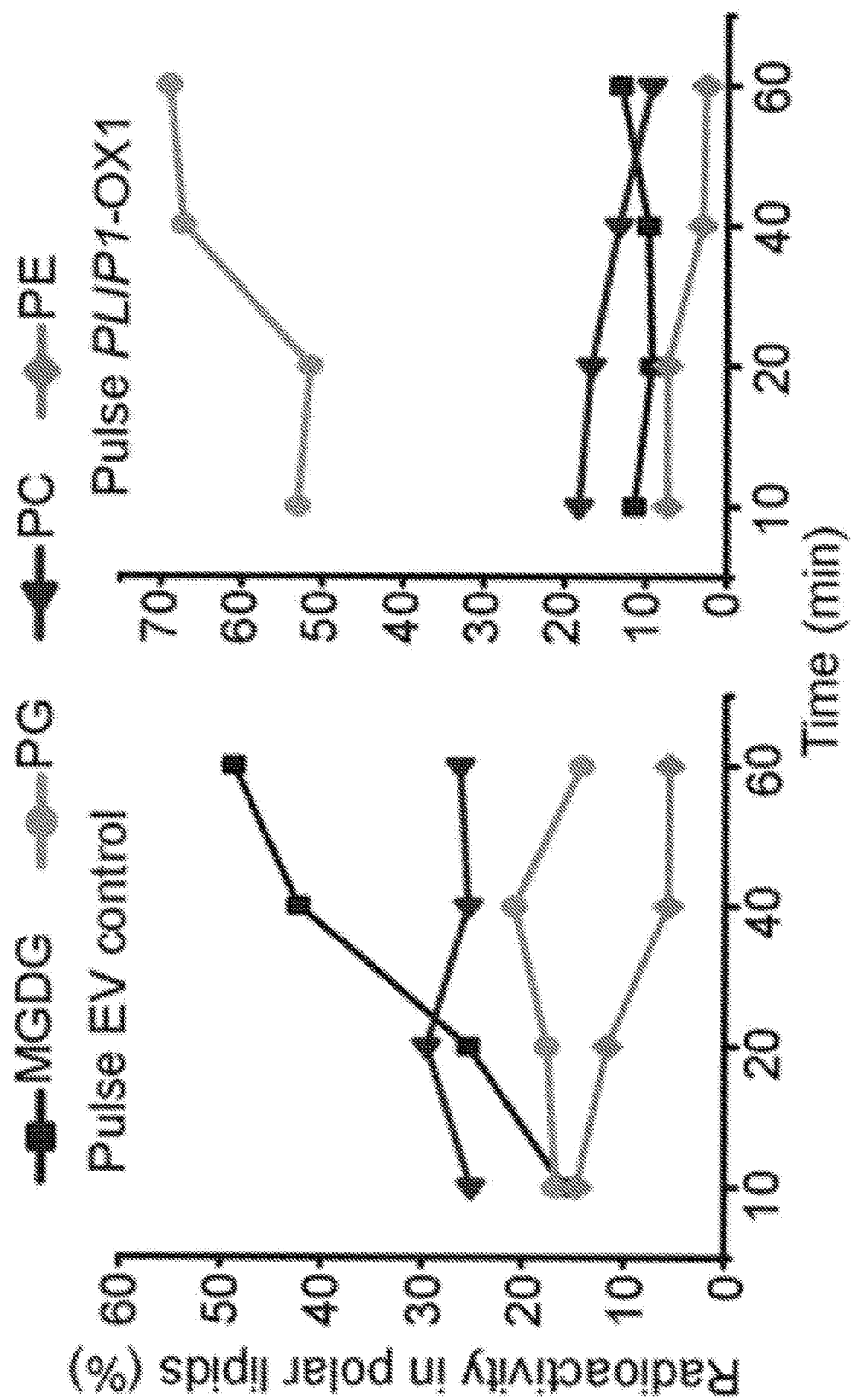
Figure 3E:
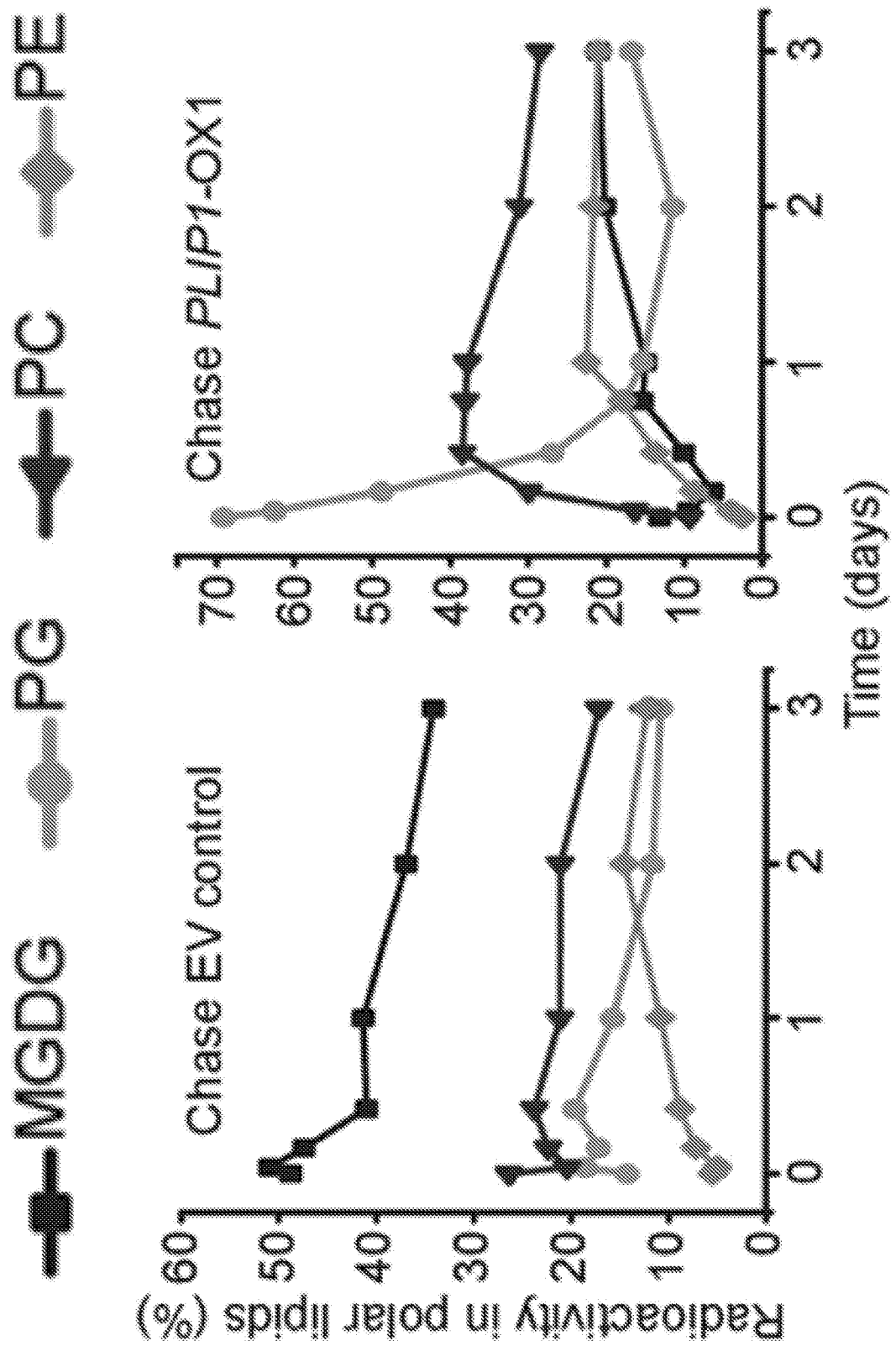

The pulse phase of the experiment is shown in FIG. 3D. These results show that MGDG, PG and PC contain the majority of the label in empty vector (EV) control leaves with PG accounting for approximately 15% of the label after 1 hour. However, in PLIP1-OX1 plants, incorporation of label into PG accounted for nearly 70% of total label at the end of the pulse phase. This result indicates that incorporation of de novo synthesized acyl groups into PG is greatly accelerated in PLIP1-OX lines. During the chase phase (FIG. 3E), PG rapidly lost most of the label (within a day), and the label concomitantly increased in PC and to a smaller extent in PE in the PLIP1-OX1 line. The EV control line showed less drastic changes in labeling during the chase phase. The rapid increase and subsequent loss of PG label in PLIP1-OX1 during the pulse and chase phases, respectively, indicates that a rapid acyl exchange occurs preferably on PG in these lines. These results support a conclusion that PG is the preferred PLIP1 substrate in its native environment.

The most notable acyl group change observed in PLIP1-OX lines was the increased 16:0-to-16:1$^{\Delta 3t}$ ratio in PG (FIG. 3B). However, 16-carbon FAs only exist at the sn-2 position of plastid PG. This indicates that acyl groups at the glycerol sn-2 position affect PLIP1 catalyzed hydrolysis at the glyceryl sn-1 position of PG. To test this possibility, purified recombinant PLIP1 was provided with a set of commercial PCs with 16:0 at the glyceryl sn-1 position, but 18-carbon acyl groups of different saturation levels at the glyceryl sn-2 position. The highest enzyme activity was observed for PC with 18:2 at the sn-2 position, followed by 18:1 with lowest activity for 18:0 (FIG. 2E), indicating that unsaturated sn-2 acyl groups enhance PLIP1 activity. Therefore, it follows that 16:1$^{\Delta 3t}$ should be favored over 16:0 at the sn-2 position of PG.

To test the hypothesis that 16:1$^{\Delta 3t}$ is favored over 16.0 at the sn-2 position of PG, plant derived PG composed of species containing 16:0 or 16:1$^{\Delta 3t}$ at the glyceryl sn-2 position was extracted from tobacco leaves and offered to PLIP1 in vitro. Total PG was degraded while lyso-PG was produced over time. The fraction of 16:1$^{\Delta 3t}$ in lyso-PG increased over time, while 16:0 decreased (FIG. 2F), indicating that 16:1$^{\Delta 3t}$-PG is preferred by PLIP1 under these conditions when native PG substrate is offered. The opposite pattern between 16:0 and 16:1$^{\Delta 3t}$ was observed in retained PG. Therefore, 18:3/16:1$^{\Delta 3t}$-PG is the native substrate of PLIP1 based on data gathered from the above described combination of in vitro and in vivo experiments.

Another interesting observation was noted during the chase phase of the labeling experiment: the sequential labeling of PG and PC points towards a precursor-product relationship between these two lipids, which was consistent with the decreased plastid-to-extraplastidic lipid ratio observed during steady-state lipids analysis of PLIP1-OX lines. The data indicated that 18:3 released from 18:3/16:1$^{\Delta 3t}$-PG was exported from the plastid and incorporated into PC. PC is known for its intermediate role in acyl editing involving desaturation of PC-acyl groups (18:1 to 18:2 and 18:3) followed by acyl exchange (Bates et al., 2007).

Figure 3F:
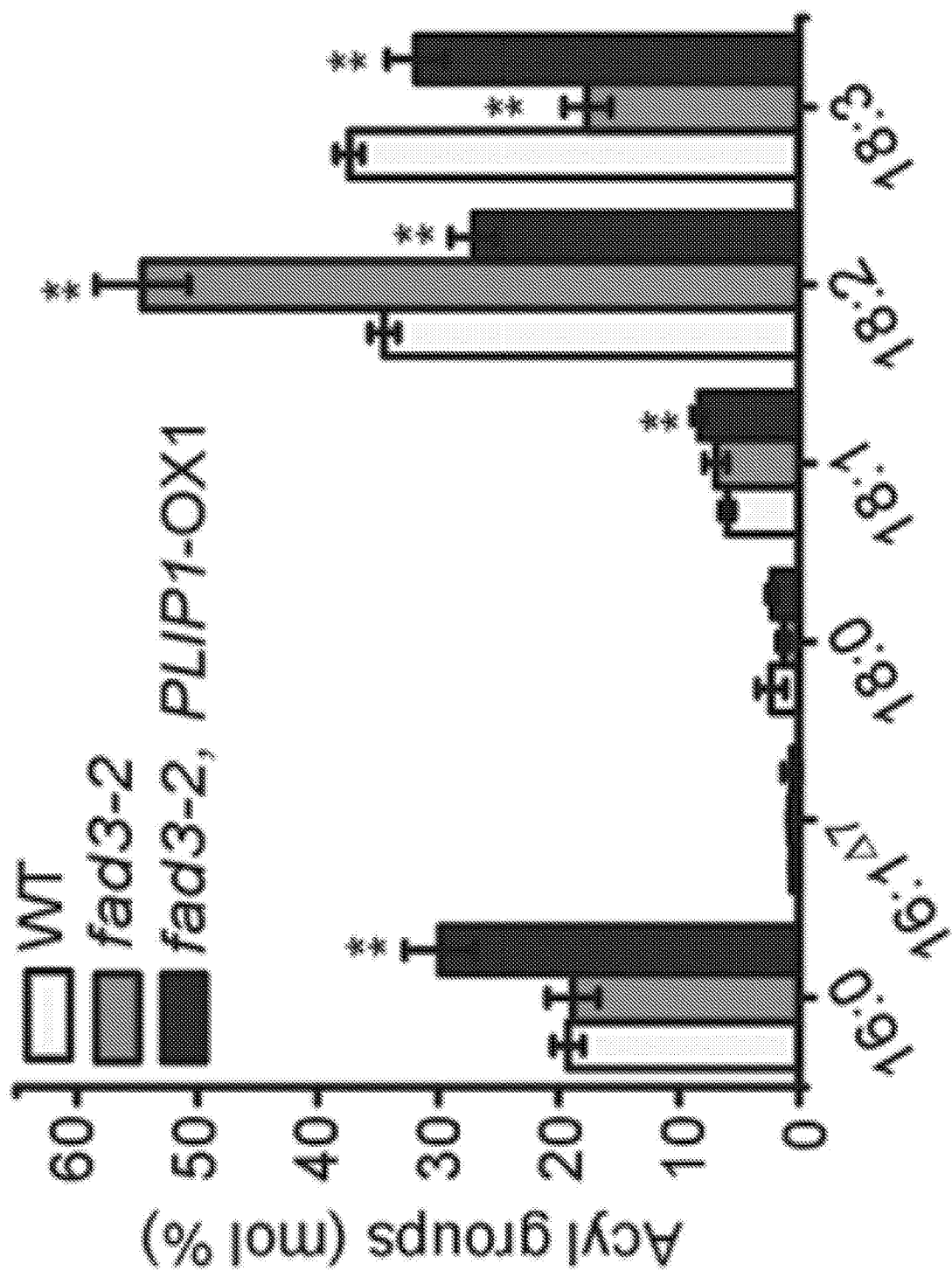
Figures 3G, 3H:
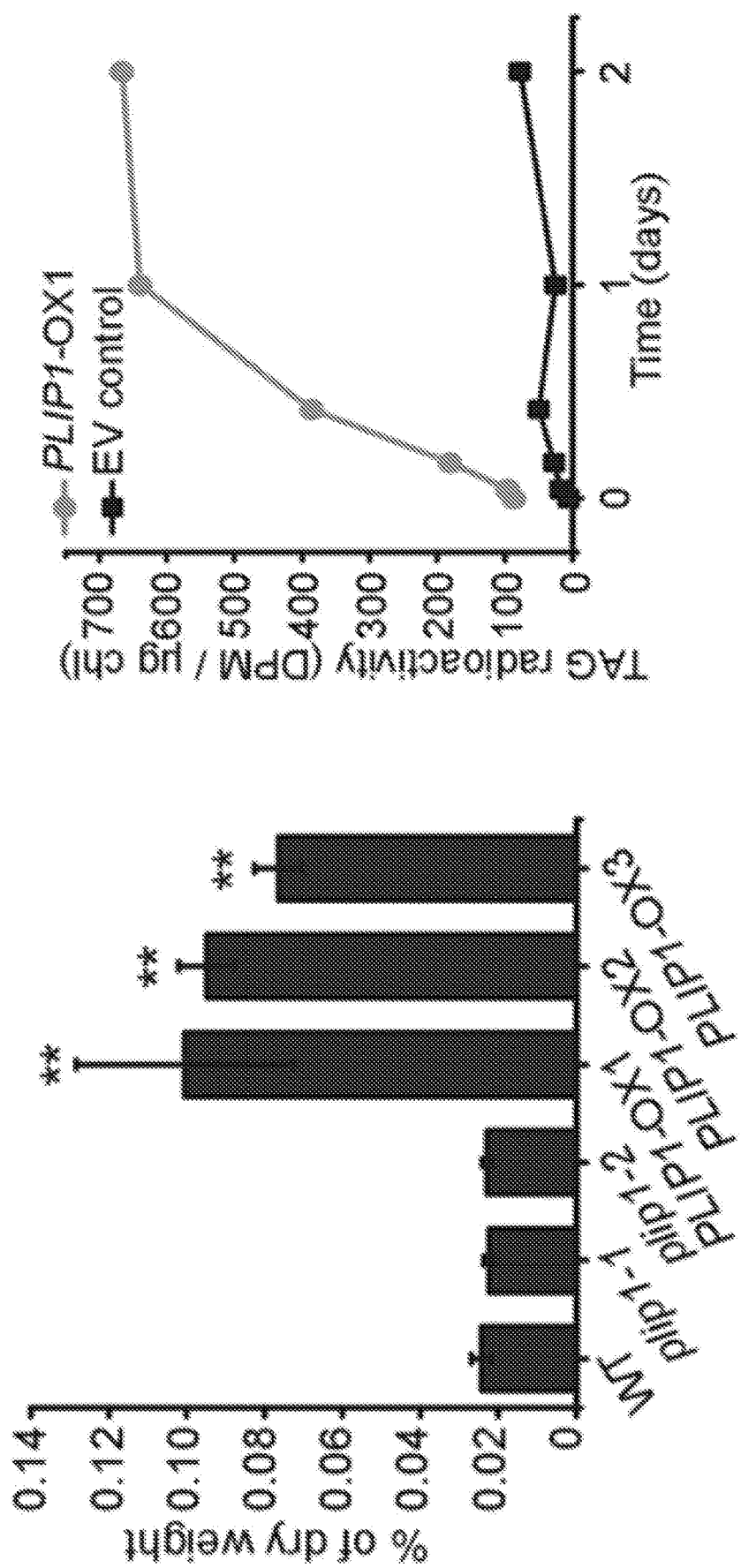

The inventors reasoned that the decreased 18:2 content of PC in PLIP1-OX lines might be due to the increased competition for incorporation of plastid derived 18:3 into PC with the activity of ER desaturases FAD2 and FAD3 generating 18:3 from 18:1 and 18:2 bound to PC. To test this hypothesis, a PLIP1-OX1 plant was crossed to a fad3-2 mutant plant, which is deficient in the desaturation of 18:2 to 18:3 for ER lipids (PC, PI and PE). The inventors expected that PLIP1 overexpression might rescue the fad3-2 defect. The fad3-2 mutant had a decreased 18:3 content in ER lipids, while the overexpression of PLIP1 in the fad3-2 mutant background partially reversed this phenotype by increasing 18:3 in ER lipids PC, PI and PE (FIG. 3F). These 18:3 acyl groups must have been derived from the chloroplast where the FAD7/8 desaturases (Li-Beisson et al., 2013) catalyze the lipid-linked desaturation of acyl groups from 18:2 to 18:3. This increase in 18:3 in PC is paralleled by a decrease in 18:3/16:1$^{\Delta 3t}$-PG. Taken together, these data indicate that in PLIP1-OX lines 18:3 increasingly moves from plastid 18:3/16:1$^{\Delta 3t}$-PG to PC, which interferes with desaturation of acyl groups on PC and the PC-based acyl editing process.

Example 6: Overexpression of PLIP1 Increases TAG Content in Leaf Tissues

Accelerated recycling of the PG pool and exporting of 18:3 to PC only resulted in a minor increase of the amount of PC in leaves (FIG. 3), indicating that PC is an intermediate, not an end product.

Figure 3I:
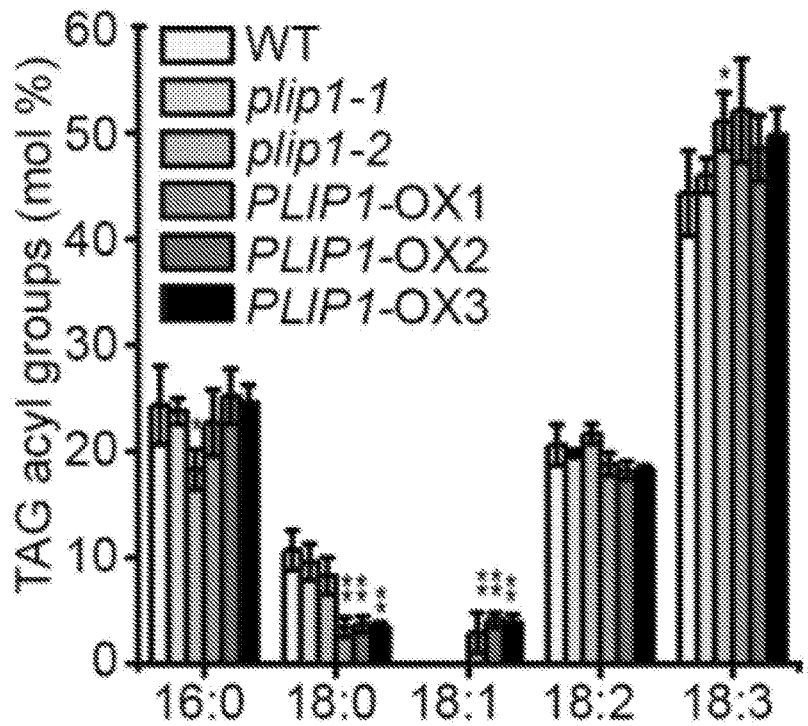
Figure 3J:
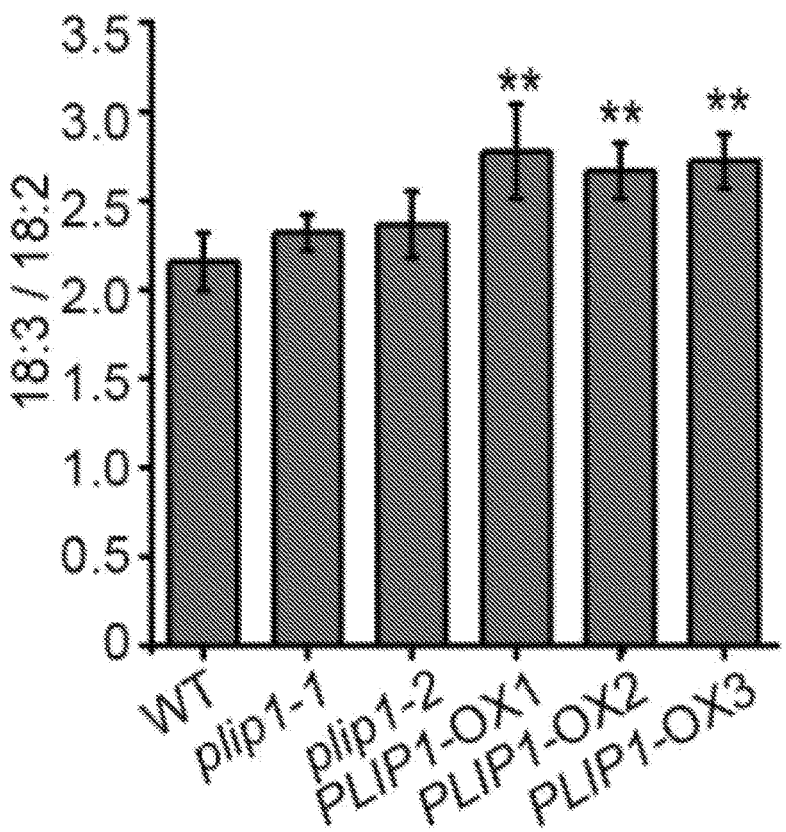

To explore the ultimate fate of exported acyl groups in PLIP1-OX lines, TAG was analyzed from lyophilized whole rosettes of 4-week-old Arabidopsis plants. PLIP1-OX lines contained five to six-fold more TAG than WT and plip1 mutant lines (FIG. 3G). Labeling of PLIP1-OX lines with [$^{14}$C]-acetate (FIG. 3H) confirmed that TAG labeling in PLIP1-OX1 leaves during the first day of the chase was much higher than for the EV control plants and then stabilized. Interestingly, acyl group analysis of TAG in leaves also showed a pattern of decreased 18:2 and increased 18:1 and 18:3 (FIG. 3I-3J), similar to the leaf PC acyl group composition found in PLIP1-OX lines. The trends were clearer when the ratios between 18:3 and 18:2 were calculated (FIG. 3I-3J). Similar acyl group compositions of PC and TAG in leaves indicated a precursor-and-product relationship, respectively. Taken together, the polar lipid and TAG labeling data (FIG. 3), and the rapid turnover of PG followed by increased label incorporation into PC and TAG within the first day of the chase, supported the hypothesis that label moves from PG-to-PC-to-TAG in leaves of the PLIP1-OX lines.

Example 7: PLIP1 is Involved in TAG Synthesis During Embryogenesis

The analysis of PLIP1, thus far, has focused on its biochemical function in vitro and in vivo using overexpression lines. Querying the native tissue-specific and developmental expression of PLIP1, the highest gene expression was detected primarily in seeds and in the reproductive tissues, including flowers and siliques (FIG. 4A). Considering the fact that PLIP1 encodes a lipase that has high expression during embryogenesis, the inventors postulated that PLIP1 might play a role in seed lipid metabolism, which is dominated by the synthesis of TAG. In fact, towards the end of seed development, over 90% of total acyl groups are stored in TAG (Li et al., 2006; Li-Beisson et al., 2013).

To explore the physiological function of PLIP1 during embryogenesis, two independent T-DNA insertion *Arabidopsis* lines were obtained (Alonso et al., 2003). The T-DNA allele corresponding to SALK_102149 was designated as plip1-1, and the second corresponding to SALK_147687 as plip1-2. The T-DNA insertions were in the 3' and 5' UTRs, respectively. Quantitative RT-PCR analysis indicated that both lines carry leaky alleles. Under normal growth conditions, the two plip1 mutant alleles were physiologically indistinguishable from the wild-type plants (WT). Lipid analysis also showed no changes in vegetative tissues. However, in dry seeds, where PLIP1 has high expression levels, insertion lines showed an approximate 10% reduction of total seed acyl group content indicative of a decrease in TAG, while overexpression lines had a 40-50% increased seed acyl group content (FIG. 4B). Altered seed TAG amounts were consistent with seed weight changes; plip1 mutants had smaller seeds, while the seeds of overexpression lines were larger (FIG. 4C). Concomitant with the decreased seed oil content, germination of the plip1 mutant seeds was also compromised (FIG. 4D). However, it must be noted that mature PLIP1-OX lines had shorter and bushier inflorescences and that seed yield was decreased by approximately 60% for the PLIP1-OX lines. Thus, overall oil yield was not increased in the PLIP1-OX plants. Nevertheless, the plip1 mutant phenotype indicated that PLIP1 might play a role in TAG synthesis during embryogenesis.

Figure 4E:
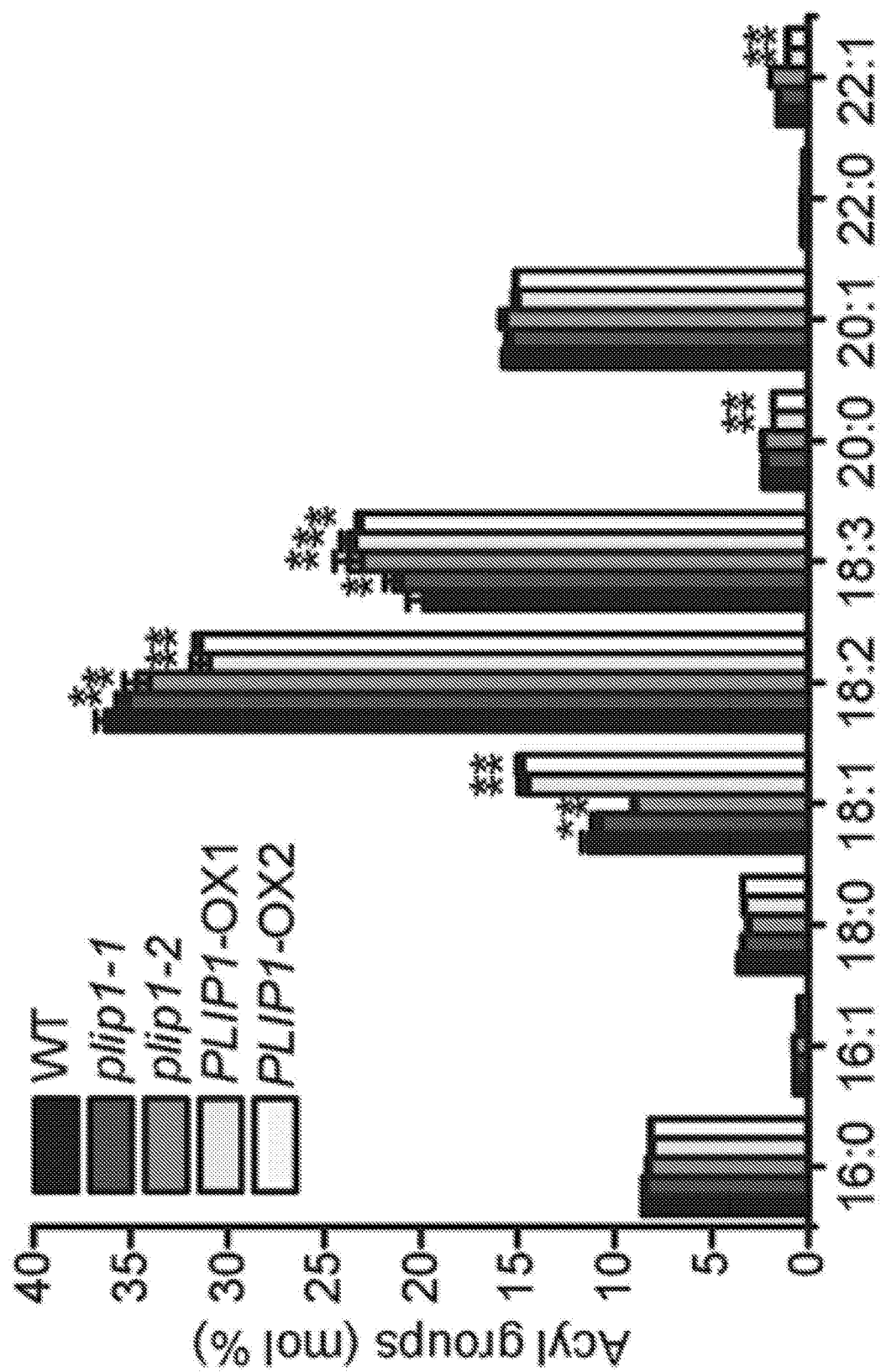

To gain more information on how the plastid-located PLIP1 contributes to TAG synthesis during embryogenesis, TAG acyl groups were analyzed in dry seeds. In the insertional mutants, especially in the slightly stronger plip1-2 allele, 18:3 increased relative to 18:1 (FIG. 4E). For the two PLIP1-OX lines, 18:2 FA decreased, while 18:3 and 18:1 increased, a pattern that resembled the leaf PC acyl group profile (FIG. 3C). This indicated that increased TAG may be derived from increased flux of acyl groups through PC in the overexpression lines. From the lipid analysis in vegetative tissues above (FIG. 3), the inventors hypothesized that PLIP1 in developing embryos contributes to TAG synthesis by catalyzing the turnover of PG increasing the flux of acyl groups into PC and ultimately TAG.

As discussed above, 18:3/16:1$^{\Delta 3t}$-PG is likely the native substrate of PLIP1 and 16:1$^{\Delta 3t}$ only exists at the sn-2 position of plastid PG. FAD4 is the enzyme in *Arabidopsis* that specifically introduces trans-double bonds into the 16:0 acyl chain of PG (Gao et al., 2009). If our hypothesis that PLIP1 contributes to embryonic TAG biosynthesis is correct, removal of 16:1$^{\Delta 3t}$-PG should result in a similar seed phenotype as observed for the plip1 mutants. To test this hypothesis, two FAD4 knockout lines, fad4-2 and fad4-3 (Gao et al., 2009), were characterized. Observations indicated that 16:1$^{\Delta 3t}$ was not detected in PG in either fad4-2 or fad4-3 leaf tissues. Similar to the plip1 mutants, fad4-2 and fad4-3 showed a close to 10% reduction in total seed acyl group content, reduced seed weight, but no altered seed yield. The fad4-2 and fad4-3 mutants also had altered seed acyl group profiles, specifically decreased 18:2 and increased 18:3 content, similar to the changes in plip1-2 seed acyl group composition (FIG. 4E). Taken together, these observations indicate that acyl groups in plastid 18:3/16:1$^{\Delta 3t}$-PG contribute to TAG biosynthesis during embryogenesis and that this requires PLIP1 activity.

Example 8: Overexpression of PLIP1 Increases PG Recycling and TAG Synthesis During Embryogenesis To determine whether increased turnover of plastid PG is responsible for increased TAG biosynthesis during embryogenesis in PLIP1-OX lines, siliques were harvested nine days after flowering from WT and PLIP1-OX plants and embryos were isolated. Embryos at this developmental stage have robust lipid metabolism (Le et al., 2010; Bates et al., 2012). However, siliques of the same age collected from PLIP1-OX1 plants were shorter than those from WT (FIG. 5A), which raised the concern that embryos from PLIP1-OX1 and WT might be at different developmental stages. However, upon closer examination, WT and PLIP1-OX1 had nearly mature embryos with fully developed cotyledons and radicals (FIG. 5B), indicating they were at similar developmental stage and likely metabolically comparable. Therefore, [$^{14}$C]-acetate pulse-chase labeling was performed on isolated embryos. Pulse time pointes were collected after 20 and 60 minutes and are shown before time 0 of the chase start on the X axis, followed by three chase time points (FIG. 5C). Compared to PC and TAG, plastid lipids PG and MGDG were not highly labeled, during embryogenesis, likely due to their small pool size; therefore, an expanded view for PG is shown in the lower graph of FIG. 5C. PLIP1-OX1 had higher incorporation of label into PG and increased turnover during the chase phase as was observed for the equivalent experiment done on leaves (FIG. 5C). The altered labeling patterns between PG and MGDG resembled those observed in leaf labeling assays (FIGS. 3D and 3E). The most strongly labeled lipids were TAG and PC reflecting their end-product status (TAG) or large pool size (PC) in developing seeds. However, the much smaller PG pool (mostly in the chloroplast as 16:1$^{\Delta 3t}$-PG) seemed to be more metabolically active in PLIP1-OX1 than in WT. Incorporation of label into PG during the pulse under the conditions tested was faster than could be captured by the earliest sampling time points. The rate and extent of incorporation into TAG was increased in the PLIP1-OX1 line consistent with increased total acyl group content in these seeds, while the PC pool was similarly labeled in the WT and overexpression lines.

Example 9: Transgenic Camelina Expressing PLIP1 and PLIP1/FAD4

This Example describes generation of transgenic camelina (false flax) that express increased levels of PLIP1 and/or PLIP1/FAD. Camelina was selected as a transgenic host because it is a crop that can produce much more oil than *Arabidopsis*, it is an oil seed plant that is transformable, and transformation of Camelina is typically easier than transformation of an oil seed plant such as Canola. Another reason for using Camelina is that it has a relatively short life cycle of about 3 months.

An example, of a vector for recombinant expression of PLIP1 is shown in FIG. 7. The PLIP1 gene is under control of seed specific promoter, and a red fluorescence marker DsRED was used for selection of transformants. Another expression vector that included PLIP1 and hygromycin resistance coding regions was created. A further expression vector was made that included a FAD4 coding region downstream of the seed specific Oleosin promoter. An expression vector with Glycin-PLIP1 and Oleosin-FAD4 expression cassettes was also prepared. See FIG. 7A-7D.

At least twenty camelina plants from ten independent PLIP1 transgenic events and the control empty vector lines were grown. There was no apparent growth difference between the empty vector control and the PLIP1 transgenic lines. No life-cycle differences were observed in the PLIP1 transgenic lines, and no differences were observed in germination rates compared to wild type. However, all transgenic plants were maturing faster than usual. T2 seeds were harvested.

REFERENCES

Ajjawi, I., Lu, Y., Savage, L. J., Bell, S. M., and Last, R. L. (2010). Large-scale reverse genetics in *Arabidopsis*: case studies from the Chloroplast 2010 Project. Plant Physiol 152, 529-540.

Alonso, J. M., Stepanova, A. N., Leisse, T. J., Kim, C J., Chen, H., Shinn, P., Stevenson, D. K., Zimmerman, J., Barajas, P., Cheuk, R., Gadrinab, C., Heller, C., Jeske, A., Koesema, E., Meyers, C. C., Parker, H., Prednis, L., Ansari, Y., Choy, N., Deen, H., Geralt, M., Hazari, N., Hornm, E., Karnes, M., Mulholland, C., Ndubaku, R., Schmidt, I., Guzman, P., Aguilar-Henonin, L., Schmid, M., Weigel, D., Carter, D. E., Marchand, T., Risseeuw, E., Brogden, D., Zeko, A., Crosby, W. L., Berry, C. C., and Ecker, J. R. (2003). Genome-wide insertional mutagenesis of *Arabidopsis thaliana*. Science 301, 653-657.

Andersson, M. X., and Dörmann, P. (2009). Chloroplast Membrane Lipid Biosynthesis and Transport. In The Chloroplast, A. S. Sandelius and H. Aronsson, eds (Berlin, Heidelberg: Springer Berlin Heidelberg), pp. 125-158.

Aronsson, H., and Jarvis, P. (2002). A simple method for isolating import-competent *Arabidopsis* chloroplasts. FEBS Lett 529, 215-220.

Bates, P. D., Ohlrogge, J. B., and Pollard, M. (2007). Incorporation of newly synthesized fatty acids into cytosolic glycerolipids in pea leaves occurs via acyl editing. J Biol Chem 282, 31206-31216.

Bates, P. D., Fatihi, A., Snapp, A. R., Carlsson, A. S., Browse, J., and Lu, C. (2012). Acyl editing and headgroup exchange are the major mechanisms that direct polyunsaturated fatty acid flux into triacylglycerols. Plant Physiol 160, 1530-1539.

Benning, C. (2009). Mechanisms of lipid transport involved in organelle biogenesis in plant cells. Annu Rev Cell Dev Biol 25, 71-91.

Benning, C. (2010). The Anionic Chloroplast Membrane Lipids: Phosphatidylglycerol and Sulfoquinovosyldiacylglycerol. In The Chloroplast: Biochemistry, Molecular Biology and Bioengineering., C. A. Rebeiz, C. Benning, H. Bohnert, H. Daniell, B. Green, K. Hoober, H. Lichtenthaler, A. Portis, and B. Tripathy, eds (Netherlands: Springer), pp. 171-184.

Boudière, L., Michaud, M., Petroutsos, D., Rébeillé, F., Falconet, D., Bastien, O., Roy, S., Finazzi, G., Rolland, N., Jouhet, J., Block, M. A., and Maréchal, E. (2014). Glycerolipids in photosynthesis: Composition, synthesis and trafficking. Biochim Biophys Acta, Bioenerg 1837, 470-480.

Brady, L., Brzozowski, A. M., Derewenda, Z. S., Dodson, E., Dodson, G., Tolley, S., Turkenburg, J. P., Christiansen, L., Huge-Jensen, B., Norskov, L., Thim, L., and Menge, U. (1990). A serine protease triad forms the catalytic centre of a triacylglycerol lipase. Nature 343, 767-770.

Browse, J., McCourt, P., and Somerville, C. R. (1985). A mutant of *Arabidopsis* lacking a chloroplast-specific lipid. Science 227, 763-765.

Browse, J., McConn, M., James, D., Jr., and Miquel, M. (1993). Mutants of *Arabidopsis* deficient in the synthesis of alpha-linolenate. Biochemical and genetic characterization of the endoplasmic reticulum linoleoyl desaturase. J Biol Chem 268, 16345-16351.

Clough, S. J., and Bent, a. F. (1998). Floral dip: a simplified method for *Agrobacterium*-mediated transformation of *Arabidopsis thaliana*. Plant Journal 16, 735-743.

Earley, K. W., Haag, J. R., Pontes, O., Opper, K., Juehne, T., Song, K., and Pikaard, C. S. (2006). Gateway-compatible vectors for plant functional genomics and proteomics. Plant Journal 45, 616-629.

Gao, J., Ajjawi, I., Manoli, A., Sawin, A., Xu, C., Froehlich, J. E., Last, R. L., and Benning, C. (2009). FATTY ACID DESATURASE4 of *Arabidopsis* encodes a protein distinct from characterized fatty acid desaturases. Plant Journal 60, 832-839.

Goosens, V. J., and van Dijl, J. M. (2016). Twin-Arginine Protein Translocation. Curr Top Microbiol Immunol.

Herr Jr, J. (1993). Clearing techniques for the study of vascular plant tissues in whole structures and thick sections. Tested studies for laboratory teaching 5, 63-84.

Hurlock, A. K., Roston, R. L., Wang, K., and Benning, C. (2014). Lipid trafficking in plant cells. Traffic 15, 915-932.

Ishiguro, S., Kawai-Oda, A., Ueda, J., Nishida, I., and Okada, K. (2001). The DEFECTIVE IN ANTHER DEHISCIENCE gene encodes a novel phospholipase A1 catalyzing the initial step of jasmonic acid biosynthesis, which synchronizes pollen maturation, anther dehiscence, and flower opening in *Arabidopsis*. Plant Cell 13, 2191-2209.

Keegstra, K., and Yousif, A. E. (1986). Isolation and Characterization of Chloroplast Envelope Membranes. Methods Enzymol 118, 316-325.

Kelly, A. A., and Feussner, I. (2016). Oil is on the agenda: Lipid turnover in higher plants. Biochim Biophys Acta.

Kobayashi, K., Endo, K., and Wada, H. (2016). Roles of Lipids in Photosynthesis. Subcell Biochem 86, 21-49.

Le, B. H., Cheng, C., Bui, A. Q., Wagmaister, J. A., Henry, K. F., Pelletier, J., Kwong, L., Belmonte, M., Kirkbride, R., Horvath, S., Drews, G. N., Fischer, R. L., Okamuro, J. K., Harada, J J., and Goldberg, R. B. (2010). Global analysis of gene activity during *Arabidopsis* seed development and identification of seed-specific transcription factors. Proc Natl Acad Sci USA 107, 8063-8070.

Li-Beisson, Y., Shorrosh, B., Beisson, F., Andersson, M. X., Arondel, V., Bates, P. D., Baud, S., Bird, D., Debono, A., Durrett, T. P., Franke, R. B., Graham, I. A., Katayama, K., Kelly, A. A., Larson, T., Markham, J. E., Miquel, M., Molina, I., Nishida, I., Rowland, O., Samuels, L., Schmid, K. M., Wada, H., Welti, R., Xu, C., Zallot, R., and Ohlrogge, J. (2013). Acyl-lipid metabolism. *Arabidopsis Book* 11, e0161.

Li, N., Gugel, I. L., Giavalisco, P., Zeisler, V., Schreiber, L., Soill, J., and Philippar, K. (2015). FAX1, a novel membrane protein mediating plastid fatty acid export. PLoS Biol 13, e1002053.

Li, X., Moellering, E. R., Liu, B., Johnny, C., Fedewa, M., Sears, B. B., Kuo, M. H., and Benning, C. (2012). A Galactoglycerolipid Lipase Is Required for Triacylglycerol Accumulation and Survival Following Nitrogen Deprivation in *Chlamydomonas reinhardtii*. Plant Cell.

Li, Y., Beisson, F., Pollard, M., and Ohlrogge, J. (2006). Oil content of *Arabidopsis* seeds: the influence of seed anatomy, light and plant-to-plant variation. Phytochemistry 67, 904-915.

Lu, B., and Benning, C. (2009). A 25-amino acid sequence of the *Arabidopsis* TGD2 protein is sufficient for specific binding of phosphatidic acid. J Biol Chem 284, 17420-17427.

Lu, Y., Savage, L. J., Ajjawi, I., Imre, K. M., Yoder, D. W., Benning, C., Dellapenna, D., Ohlrogge, J. B., Osteryoung, K. W., Weber, A. P., Wilkerson, C. G., and Last, R. L. (2008). New connections across pathways and cellular processes: industrialized mutant screening reveals novel associations between diverse phenotypes in *Arabidopsis*. Plant Physiol 146, 1482-1500.

Marchler-Bauer, A., Derbyshire, M. K., Gonzales, N. R., Lu, S., Chitsaz, F., Geer, L. Y., Geer, R. C., He, J., Gwadz, M., Hurwitz, D. I., Lanczycki, C. J., Lu, F., Marchler, G. H., Song, J. S., Thanki, N., Wang, Z., Yamashita, R. A., Zhang, D., Zheng, C., and Bryant, S. H. (2015). CDD: NCBIs conserved domain database. Nucleic Acids Res 43, D222-226.

McCourt, P., Browse, J., Watson, J., Arntzen, C J., and Somerville, C. R. (1985). Analysis of Photosynthetic Antenna Function in a Mutant of *Arabidopsis thaliana* (L.) Lacking trans-Hexadecenoic Acid. Plant Physiol 78, 853-858.

Moellering, E. R., Muthan, B., and Benning, C. (2010). Freezing tolerance in plants requires lipid remodeling at the outer chloroplast membrane. Science 330, 226-228.

Murashige, T., and Skoog, F. (1962). A revised medium for rapid growth and bio assays with tobacco tissue cultures. Physiol. Plant. 15, 473-497.

Ngaki, M. N., Louie, G. V., Philippe, R. N., Manning, G., Pojer, F., Bowman, M. E., Li, L., Larsen, E., Wurtele, E. S., and Noel, J. P. (2012). Evolution of the chalcone-isomerase fold from fatty-acid binding to stereospecific catalysis. Nature 485, 530-533.

Richmond, G. S., and Smith, T. K. (2011). Phospholipases A(1). Int J Mol Sci 12, 588-612.

Robinson, C., and Bolhuis, A. (2001). Protein targeting by the twin-arginine translocation pathway. Nat Rev Mol Cell Biol 2, 350-356.

Rodrigues, R. A., Silva-Filho, M. C., and Cline, K. (2011). FtsH2 and FtsH5: two homologous subunits use different integration mechanisms leading to the same thylakoid multimeric complex. Plant J 65, 600-609.

Roston, R., Gao, J., Xu, C., and Benning, C. (2011). *Arabidopsis* chloroplast lipid transport protein TGD2 disrupts membranes and is part of a large complex. Plant Journal 66, 759-769.

Roston, R. L., Gao, J., Murcha, M. W., Whelan, J., and Benning, C. (2012). TGD1, -2, and -3 proteins involved in lipid trafficking form ATP-binding cassette (ABC) transporter with multiple substrate-binding proteins. J Biol Chem 287, 21406-21415.

Scherer, G. F., Ryu, S. B., Wang, X., Matos, A. R., and Heitz, T. (2010). Patatin-related phospholipase A: nomenclature, subfamilies and functions in plants. Trends Plant Sci 15, 693-700.

Schwacke, R., Schneider, A., van der Graaff, E., Fischer, K., Catoni, E., Desimone, M., Frommer, W. B., Flugge, U. I., and Kunze, R. (2003). ARAMEMNON, a novel database for *Arabidopsis* integral membrane proteins. Plant Physiol 131, 16-26.

Tanoue, R., Kobayashi, M., Katayama, K., Nagata, N., and Wada, H. (2014). Phosphatidylglycerol biosynthesis is required for the development of embryos and normal membrane structures of chloroplasts and mitochondria in *Arabidopsis*. FEBS Lett 588, 1680-1685.

Troncoso-Ponce, M. A., Cao, X., Yang, Z., and Ohlrogge, J. B. (2013). Lipid turnover during senescence. Plant Sci 205-206, 13-19.

Wang, G., Ryu, S., and Wang, X. (2012). Plant phospholipases: an overview. Methods Mol Biol 861, 123-137.

Wang, K., Hersh, H. L., and Benning, C. (2016). SENSITIVE TO FREEZING2 Aides in Resilience to Salt and Drought in Freezing-Sensitive Tomato. Plant Physiol 172, 1432-1442.

Wang, X. (2004). Lipid signaling. Curr Opin Plant Biol 7, 329-336.

Wang, Z., and Benning, C. (2011). *Arabidopsis thaliana* polar glycerolipid profiling by thin layer chromatography (TLC) coupled with gas-liquid chromatography (GLC). J Vis Exp.

Winkler, F. K., D'Arcy, A., and Hunziker, W. (1990). Structure of human pancreatic lipase. Nature 343, 771-774.

Xu, C., Fan, J., Cornish, A. J., and Benning, C. (2008). Lipid trafficking between the endoplasmic reticulum and the plastid in *Arabidopsis* requires the extraplastidic TGD4 protein. Plant Cell 20, 2190-2204.

Xu, C., Fan, J., Froehlich, J. E., Awai, K., and Benning, C. (2005). Mutation of the TGD1 chloroplast envelope protein affects phosphatidate metabolism in *Arabidopsis*. Plant Cell 17, 3094-3110.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:

1. An expression system comprising at least one expression cassette comprising a promoter operably linked to a heterologous nucleic acid segment encoding a plastid-specific lipase.

2. The expression system of statement 1, wherein the lipase has at least 90%, or at least 91%, or at least 93%, or at least 95%, or at least 96%, or at least 97%, or at least 98%, or at least 99% sequence identity to SEQ ID NO: 1, 3-12, 14-21, 23-27, 64-70 or 71.

3. The expression system of statement 1 or 2, further comprising at least one expression cassette comprising a promoter operably linked to a nucleic acid segment encoding a FAD4.

4. The expression system of statement 1, 2, or 3, wherein the FAD4 has at least 90%, or at least 91%, or at least 93%, or at least 95%, or at least 96%, or at least 97%, or at least 98%, or at least 99% sequence identity to any of SEQ ID NOs: 28, 30-33, or 34.

5. The expression system of statement 1-3 or 4, wherein the nucleic acid encoding the lipase has at least 90%, or at least 91%, or at least 93%, or at least 95%, or at least 96%, or at least 97%, or at least 98%, or at least 99% sequence identity to SEQ ID NO: 2, SEQ ID NO:13, or SEQ ID NO: 22.

6. The expression system of statement 1-4 or 5, wherein the nucleic acid encoding the FAD4 has at least 90%, or at least 91%, or at least 93%, or at least 95%, or at least 96%, or at least 97%, or at least 98%, or at least 99% sequence identity to SEQ ID NO:29.

7. The expression system of statement 1-5 or 6, wherein the promoter operably linked to a heterologous nucleic acid segment encoding a lipase is an inducible promoter, a tissue-specific promoter, or a developmentally regulated promoter.

8. A plant cell comprising the expression system of statement 1-6 or 7.

9. The plant cell of statement 8, wherein the plant cell is not an *Arabidopsis thaliana* plant cell.

10. The plant cell of statement 8 or 9, wherein the plant cell is a food plant cell, vegetable oil plant cell, seed oil plant cell, forage plant cell, or fodder plant cell.

11. The plant cell of statement 8, 9, or 10, wherein the plant cell is a monocot or dicot.

12. The plant cell of statement 8-10 or 11, wherein the plant cell is an alfalfa, algae, avocado, barley, broccoli, Brussels sprout, cabbage, camelina, canola, cassava, cauliflower, coconut, cole vegetables, collard, corn, crucifers, flax, grain legumes, forage grasses, jatropa, kale, kohlrabi, maize, miscanthus, mustards, nut sedge, oats, oil firewood trees, oilseeds, olive, palm, peanut, potato, radish, rapeseed, rice, rutabaga, safflower, sorghum, soybean, sugar beets, sugarcane, sunflower, switchgrass, tobacco, tomato, turnips, or wheat plant cell.

13. A seed comprising the expression system of statement 1-6 or 7.

14. The seed of statement 13, wherein the seed is not an *Arabidopsis thaliana* seed.

15. The seed of statement 13 or 14, wherein the seed is a food plant seed, vegetable oil plant seed, seed oil plant seed, forage plant seed, or fodder plant seed.

16. The seed of statement 13, 14, or 15, wherein the seed is a monocot or dicot.

17. The seed of statement 13-15 or 16, wherein the seed is an alfalfa, algae, avocado, barley, broccoli, Brussels sprouts, cabbage, camelina, canola, cassava, cauliflower, coconut, cole vegetables, collards, crucifers, flax, grain legumes, forage grasses, jatropa, kale, kohlrabi, maize, miscanthus, mustards, nut sedge, oats, oil firewood trees, oilseeds, olive, palm, peanut, potato, radish, rice, rutabaga, safflower, sorghum, soybean, sugar beets, sugarcane, sunflower, switchgrass, tobacco, tomato, turnip, or wheat seed.

18. The seed of statement 13-16 or 17, wherein the seed has about 0.5% to about 60%, or about 0.5% to about 50%, or about 0.5% to about 40%, or about 0.5% to about 30%, or about 0.5% to about 25%, or about 1% to about 20%, or about 2% to about 18%, or about 3% to about 15%, or about 5% to about 15% oil content.

19. The seed of statement 13-17 or 18, wherein the seed has at least about 1.2-fold, at least about 1.5-fold, least about 2-fold, at least about 3-fold, at least about 4-fold, at least about 5-fold, at least about 7-fold, at least about 10-fold, at least about 12-fold, at least about 15-fold more oil, as measured by percent oil per dry weight, than a seed of the same species that has not been modified to contain the expression system.

20. A plant comprising the expression system of statement 1-6 or 7.

21. The plant of statement 20, wherein the plant is not an *Arabidopsis thaliana* plant.

22. The plant of statement 20 or 21, wherein the plant is a food plant, vegetable oil plant, seed oil plant, forage plant, or fodder plant.

23. The plant of statement 20, 21 or 22, wherein the plant is a monocot or dicot.

24. The plant of statement 20-22 or 23, wherein the plant is an alfalfa, algae, avocado, barley, broccoli, Brussels sprout, cabbage, camelina, canola, cassava, cauliflower, coconut, cole vegetables, collards, corn, crucifers, flax, grain legumes, forage grasses, jatropa, kale, kohlrabi, maize, miscanthus, mustards, nut sedge, oats, oil firewood trees, oilseeds, olive, palm, peanut, potato, radish, rapeseed, rice, rutabaga, safflower, sorghum, soybean, sugar beets, sugarcane, sunflower, switchgrass, tobacco, tomato, turnips, or wheat plant.

25. The plant of statement 20-23 or 24, wherein the plant tissues of the plant have about 0.5% to about 40%, or about 0.5% to about 35%, or about 0.5% to about 30%, or about 0.5% to about 25%, or about 0.5% to about 20%, or about 1% to about 18%, or about 2% to about 15%, or about 3% to about 15%, or about 5% to about 15% oil or lipid content.

26. The plant of statement 20-24 or 25, wherein the seed has at least about 1.2-fold, at least about 1.5-fold, least about 2-fold, at least about 3-fold, at least about 4-fold, at least about 5-fold, at least about 7-fold, at least about 10-fold, at least about 12-fold, or at least about 15-fold, more oil in its plant tissues, as measured by percent oil per dry weight, than a plant of the same species that has not been modified to contain the nucleic acid, expression cassette, or expression vector.

27. A method of generating oil comprising isolating tissues or seeds from the plant of any of statements 20-25 or 26 and extracting oil from the tissues or seeds.

28. The method of statement 27, further comprising cultivating the seed of statement 13-18 or 19 to generate the plant.

29. A method comprising cultivating the seed of statements 1-6 or 7.

30. The method of statement 29, further comprising generating at least one line of plants comprising a heterologous nucleic acid segment encoding a lipase with at least 90% amino acid sequence identity to any of SEQ ID NOs: 1, 3-12, 14-21, 23-27, 64-70 or 71.

31. The method of statement 30, wherein the at least one line of plants is generated by transforming one or more plant cells with the expression system of any of statements 1-6, or 7 to generate one or more transgenic plant cells; generating one or more transgenic plants from the one or more transgenic plant cells; and clonally or vegetatively propagating at least one line of transgenic plants.

32. The method of statement 29, 30 or 31, wherein the plant is not an *Arabidopsis thaliana* plant.

33. The method of statement 29-31 or 32, wherein the plant is a food plant, vegetable oil plant, seed oil plant, forage plant, or fodder plant.

34. The method of statement 29-32 or 33, wherein the plant is a monocot or dicot.

35. The method of statements 28-33 or 34, wherein the plant is an alfalfa, algae, avocado, barley, broccoli, Brussels sprouts, cabbage, camelina, canola, cassava, cauliflower, coconut, cole vegetables, collards, crucifers, flax, grain legumes, forage grasses, jatropa, kale, kohlrabi, maize, miscanthus, mustards, nut sedge, oats, oil firewood trees, oilseeds, olive, palm, peanut, potato, radish, rice, rutabaga, safflower, sorghum, soybean, sugar beets, sugarcane, sunflower, switchgrass, tobacco, tomato, turnips, or wheat plant.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It is apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a catalyst" or "a ligand" includes a plurality of such compounds, catalysts or ligands, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. An expression system comprising at least one expression cassette comprising a promoter operably linked to a heterologous nucleic acid segment encoding a lipase having at least 95% sequence identity to SEQ ID NO:1.

2. The expression system of claim 1, further comprising at least one expression cassette comprising a promoter operably linked to a heterologous nucleic acid segment encoding a FAD4.

3. The expression system of claim 2, wherein the FAD4 has at least 95% amino acid sequence identity to any of SEQ ID NOs: 28, 30-33 or 34.

4. The expression system of claim 1, wherein the promoter is an inducible promoter, a tissue-specific promoter, a seed-specific promoter, or a developmentally regulated promoter.

5. A plant cell or plant seed comprising the expression system of claim 1.

6. The plant cell or plant seed of claim 5, wherein the seed has about 0.5% to about 60% percent dry weight oil.

7. The plant cell or plant seed of claim 5, wherein the seed has at least 1.2-fold more lipid than a seed of the same species that has not been modified to contain the expression system.

8. A plant comprising the expression system of claim 1.

9. The plant of claim 8, wherein vegetative tissues of the plant have about 0.5% to about 60% oil content.

10. The plant of claim 8, wherein the vegetative tissues of the plant have at least 1.2-fold more lipid than vegetative tissues of a plant of the same species that has not been modified to contain the expression system.

11. A method of generating oil, comprising isolating tissues or seeds from the plant of claim 8 and extracting oil from the tissues or seeds.

12. A method, comprising (a) transforming a plant cell with the expression system of claim 1, (b) generating a plant from the plant cell, and cultivating the plant to provide a mature plant.

13. The method of claim 12 further comprising extracting oil from the tissues or seeds of the mature plant.

14. The plant cell or plant seed of claim 5, further comprising at least one expression cassette comprising a promoter operably linked to a heterologous nucleic acid segment encoding a FAD4.

15. The plant of claim 8, further comprising at least one expression cassette comprising a promoter operably linked to a heterologous nucleic acid segment encoding a FAD4.

16. The method of claim 12, further comprising transforming a plant cell with at least one expression cassette comprising a promoter operably linked to a heterologous nucleic acid segment encoding a FAD4.

\* \* \* \* \*